(12) United States Patent
Silverman et al.

(10) Patent No.: US 9,951,014 B2
(45) Date of Patent: Apr. 24, 2018

(54) MAMMALIAN AND BACTERIAL NITRIC OXIDE SYNTHASE INHIBITORS

(71) Applicant: Northwestern University, Evanston, IL (US)

(72) Inventors: Richard B. Silverman, Winnetka, IL (US); Qing Jing, Morton Grove, IL (US); Soosung Kang, Incheon (KR); Heng-Yen Wang, Evanston, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 14/932,587

(22) Filed: Nov. 4, 2015

(65) Prior Publication Data

US 2016/0122302 A1    May 5, 2016

Related U.S. Application Data

(60) Provisional application No. 62/075,001, filed on Nov. 4, 2014, provisional application No. 62/089,044, filed on Dec. 8, 2014, provisional application No. 62/185,267, filed on Jun. 26, 2015.

(51) Int. Cl.
| | |
|---|---|
| *A61K 31/444* | (2006.01) |
| *C07D 213/73* | (2006.01) |
| *C07D 401/14* | (2006.01) |
| *C07D 401/10* | (2006.01) |
| *C07D 401/12* | (2006.01) |
| *C07D 471/04* | (2006.01) |
| *C07D 401/04* | (2006.01) |
| *C07D 401/06* | (2006.01) |
| *A61K 31/44* | (2006.01) |

(52) U.S. Cl.
CPC ............ *C07D 213/73* (2013.01); *A61K 31/44* (2013.01); *A61K 31/444* (2013.01); *C07D 401/04* (2013.01); *C07D 401/06* (2013.01); *C07D 401/10* (2013.01); *C07D 401/12* (2013.01); *C07D 401/14* (2013.01); *C07D 471/04* (2013.01)

(58) Field of Classification Search
CPC ..... A61K 31/44; A61K 31/444; C07D 213/73
USPC .................................................. 514/340, 352
See application file for complete search history.

(56) References Cited

U.S. PATENT DOCUMENTS

| | | | |
|---|---|---|---|
| 7,470,790 B2 | 12/2008 | Silverman et al. | |
| 8,278,084 B2 * | 10/2012 | Silverman et al. .. | C07D 401/14 435/184 |
| 8,557,552 B2 | 10/2013 | Silverman et al. | |
| 8,932,842 B2 | 1/2015 | Silverman et al. | |

(Continued)

FOREIGN PATENT DOCUMENTS

| | | |
|---|---|---|
| WO | 9910339 A1 | 3/1999 |
| WO | 0050400 A1 | 8/2000 |

OTHER PUBLICATIONS

Huang et al, Journal of Medicinal Chem (2013), vol. 56, pp. 3024-3032.*

(Continued)

*Primary Examiner* — Craig D Ricci
*Assistant Examiner* — Janet L. Coppins
(74) *Attorney, Agent, or Firm* — Andrus Intellectual Property Law, LLP

(57) ABSTRACT

Compounds and related methods for inhibition of mammalian and bacterial nitric oxide synthase.

16 Claims, 22 Drawing Sheets

(56) References Cited

U.S. PATENT DOCUMENTS

| | | |
|---|---|---|
| 9,120,750 B2 | 9/2015 | Silverman et al. |
| 9,242,957 B2 | 1/2016 | Silverman et al. |
| 2002/0045656 A1 | 4/2002 | Chenard et al. |
| 2002/0151572 A1 | 10/2002 | Lowe et al. |
| 2004/0229911 A1 | 11/2004 | Saltarelli et al. |
| 2013/0040359 A1 | 2/2013 | Silverman et al. |
| 2014/0221366 A1 | 8/2014 | Heinrich et al. |

OTHER PUBLICATIONS

Jing et al, Bioorganic & Medinal Chemistry (2013), vol. 21, pp. 5323-5331.*

Gusarov, I. et al., "NO mediated cytoprotection: instant adaption to oxidative stress in bacteria", Proc. Natl. Acad. Sci. USA 102,13855-13860 (2005).

Gusarov, I. et al., "Endogenous nitric oxide protects bacteria against a wide spectrum of antibiotics", Science 325, 1380-1384 (2009).

Chen, V. et al., "Spatial relationship between L-arginine and heme binding sites of endothelial nitric-oxide synthase", J Biol Chem 271(52): 33293-33300 (1996).

Roman, L. et al., "High-level expression of functional rat neuronal nitric oxide synthase in *Escherichia coli*", Proc Natl Acad Sci USA 92(18): 8428-8432 (1995).

Martasek P, et al. (1996) Characterization of bovine endothelial nitric oxide synthase expressed in *E. coli*. Biochem Biophys Res Commun 219(2):359-365.

Delker, S. et al., "Role of zinc in isoform-selective inhibitor binding to neuronal nitric oxide synthase", Biochemistry 49, 10803-10810 (2010).

Huang, H. et al., "Structure-guided design of selective inhibitors of neuronal nitric oxide synthase", J. Med. Chem. 56, 3024-3032 (2013).

Huang, H. et al., "Potent and selective double-headed thiophene-2-carboximidamide inhibitors of neuronal nitric oxide synthase for the treatment of melanoma", J. Med. Chem. 57, 686-700 (2014).

Jing, Q. et al., "Chiral Linkers to Improve Selectivity of Double-Headed Neuronal Nitric Oxide Synthase Inhibitors" Bioorg. Med. Chem.

Xue, F. et al., "Symmetric double-headed aminopyridines, a novel strategy for potent and membrane-permeable inhibitors of neuronal nitric oxide synthase", J. Med. Chem. 54, 2039-2048 (2011).

Huang, H. et al., "Selective monocationic inhibitors of neuronal nitric oxide synthase. Binding mode insights from molecular dynamics simulations", J. Am. Chem. Soc. 134, 11559-11572 (2012).

Jing, Q. et al., "In search of potent and selective inhibitors of neuronal nitric oxide synthase with more simple structures", Bioorg. Med. Chem. (2013).

Xue, F. et al., "Concise Route to the Chiral Pyrrolidine Core of Selective Inhibitors of Neuronal Nitric Oxide", Org. Lett. 11, 5194-5197 (2009).

Holden, J. et al., "Identification of Redox Partners and Development of a Novel Chimeric Bacterial Nitric Oxide Synthase for Structure Activity Analyses", J. Biol. Chem (2014).

Kang et al., "Nitric Oxide Synthase Inhibitors That Interact with Both Heme Propionate and Tetrahydrobiopterin Show High Isoform Selectivity", J. Med Chem., 53, 5272-9 (2014).

Cinelli et al., "Simplified 2-Aminoquinoline-Based Scaffold for Potent and Selective Neuronal Nitric Oxide Synthase Inhibitions", J. Med. Chem., 57, 1513-30 (2014).

Holden et al., "Structural and biological studies on bacterial nitric oxide synthase inhibitors", Proc. Natl. Acad. Sci. USA, 110, 18127 (2013).

Holden, bNOS1, "Structure-Based Design of Bacterial Nitric Oxide Synthase Inhibitors", J. Med. Chem. Submitted (2014).

Li, H. et al., "Structures of human constitutive nitric oxide Synthases", Acta Crystallogr, 2014, D70, 2667 2674.

Jing, Q. et al., "Combination of chiral linkers with thiophenecarboximidamide heads to improve the selectivity of inhibitors of neuronal nitric oxide synthase", Bioorg. Med. Chem. Lett., 2014, 24, 4504-4510.

Kang, S. et al., "Nitric oxide synthase inhibitors that interact with both heme propionate and H4B show high isoform selectivity", J. Med. Chem., 2014, 57, 4382 4396.

Surry, D. S. et al., "Dialkylbiaryl phosphines in Pd-catalyzed amination: a user's guide", Chem. Sci., 2011, 2, 27 50.

Anagnostopoulos, C. et al, "Requirements for Transformation in Bacillus Subtilis", Journal of Bacteriology, 81, 741 (1961).

Pant, K. et al., "Structure of a nitric oxide synthase heme protein from Bacillus subtilis", Biochemistry, 41, 11071 11079.

Li, H. et al., "The novel binding mode of N-alkyl-N'-hydroxyguanidine to neuronal nitric oxide synthase provides mechanistic insights into NO biosynthesis", Biochemistry, 41, 13868-13875 (2002).

Raman, C. S. et al., "Crystal structure of constitutive endothelial nitric oxide synthase: a paradigm for pterin function involving a novel metal center", Cell, 95, 939-950 (1998).

Kale, L. et al., "NAMD2: Greater scalability for parallel molecular dynamics", J Comput Phys, 151, 283-312 (1999).

Mackerell, A.D. et al., "Extending the treatment of backbone energetics in protein force fields: Limitations of gas-phase quantum mechanics in reproducing protein conformational distributions in molecular dynamics simulations", J Comput Chem, 25, 1400-1415 (2004).

Madrona, Y. et al., "P450cin active site water: implications for substrate binding and solvent accessibility", Biochemistry 52, 5039-5050 (2013).

Vanommeslaeghe, K. et al., "CHARMM General Force Field: A Force Field for Drug-Like Molecules Compatible with the CHARMM All-Atom Additive Biological Force Fields", J Comput Chem, 31, 671-690 (2010).

Miyamoto, S. et al., "Settle—an Analytical Version of the Shake and Rattle Algorithm for Rigid Water Models", J Comput Chem, 13, 952-962 (1992).

Humphrey, W. et al., "VMD: visual molecular dynamics", Journal of molecular graphics, 14, 33-38, 27-38 (1996).

Minakata, S. et al., "Functionalization of 1h-Pyrrolo[2,3-B]Pyridine", B Chem Soc Jpn, 65, 2992-2997 (1992).

Minakata, S. et al, "Regioselective Functionalization of 1h-Pyrrolo[2,3-B]Pyridine Via Its N-Oxide", Synthesis-Stuttgart, 661-663 (1992).

Walia, A. et al., "Microwave-assisted protection of primary amines as 2,5-dimethylpyrroles and their orthogonal deprotection", J. Org. Chem., 2013, 78, 10931-10937.

Labby, K. J. et al., "Intramolecular hydrogen bonding: A potential strategy for more bioavailable inhibitors of neuronal nitric oxide synthase", Bioorg. Med. Chem., 2012, 20, 2435 2443.

Hevel, J. M. et al., "Nitric-oxide synthase assays", Methods Enzymol., 1994, 233, 250 258.

Li, H. "The mobility of a conserved tyrosine residue controls isoform-dependent enzyme-inhibitor interactions in nitric oxide synthases", Biochemistry, 2014, 53, 5272-5279.

McPhillips, T. M. et al., "Blu-Ice and the Distributed Control System: software for data acquisition and instrument control at macromolecular crystallography beamlines", J. Synchrotron Radiat., 2002, 9, 401-406.

Otwinowski, Z. et al., "Processing of X-ray diffraction data collected in oscillation mode" Methods Enzymol., 1997, 276, 307-326.

Leslie, A.G.W. et al., "Processing diffraction data with Mosflm." In Evolving Methods for Macromolecular crystallography, 2007, 245, 41-51.

Springer, Dordrecht; Kabsch, W. XDS. Acta Crystallogr. 2010, D66, 125-132.

Evans, P.R. "Scaling and assessment of data quality", Acta Crystallogr, 2006, D62, 72 82.

Murshudov, G. N. et al., "Refinement of macromolecular structures by the maximum-likelihood method", Acta Crystallogr., 1997, D53, 240-255.

Emsley, P. et al., "Coot: model-building tools for molecular graphics", Acta Crystallogr., 2004, D60, 2126-2132.

(56) References Cited

OTHER PUBLICATIONS

Adams, P. D. et al., "PHENIX: a comprehensive Python-based system for macromolecular structure solution", Acta Crystallogr., 2010, D66, 213-221.
Winn, M. D. et al, "Use of TLS parameters to model anisotropic displacements in macromolecular refinement", Acta Crystallogr., 2001, D57, 122-133.
Kishii, N. et al., "The extraction and transport of metal ions by 6,6'-diamino-2,2'-bipyridine Derivatives", Journal of the Chemical Society, Dalton transactions, 1985, No. 2, pp. 373-378.
Holden, J. K. et al., "Nitric Oxide Synthase as a Target for Methicillin-Resistant *Staphylococcus aureus*", Chemistry & biology, Jun. 18, 2015, vol. 22, No. 6, pp. 785-792.
International Search Report and Written Opinion for PCT/US2015/059061 dated Aug. 19, 2016, 20 pages.
Cinelli, M. A. et al., "Simplified 2-Aminoquinoline-Based Scaffold for Potent and Selective Neuronal Nitric Oxide Synthase Inhibition", Journal of Medicinal Chemistry, Jan. 28, 2014, vol. 57, No. 4, pp. 1513-1530.
Holden, J. K. et al., "Structure-Based Design of Bacterial Nitric Oxide Synthase Inhibitors", Journal of Medicinal Chemistry, Dec. 18, 2014, vol. 58, No. 2, pp. 994-1004.
Wegener et al., "Nitric Oxide Synthase Inhibitors as Antidepressants", Pharmaceuticals, 2010, 3, 273-299.
International Search Report and Written Opinion for PCT/2014/021366, dated Jul. 24, 2014, 9 pages.

\* cited by examiner

Figure 5A
Figure 5B
Figure 5C
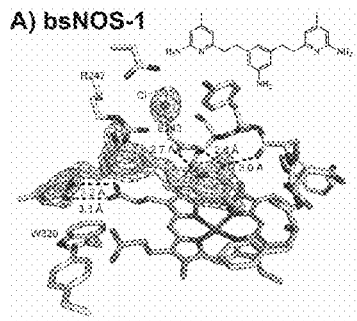
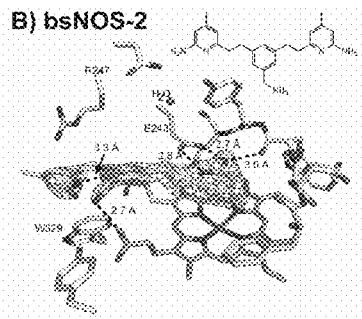
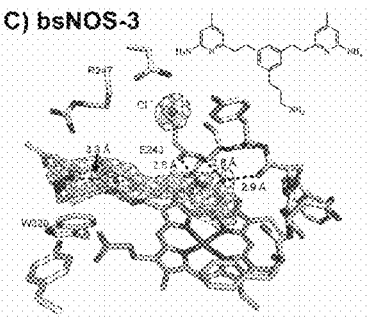
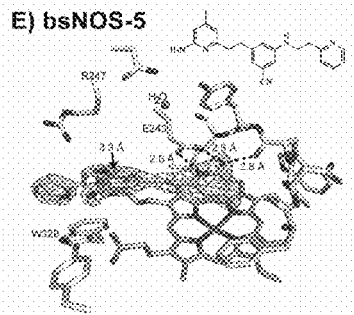
Figure 5D
Figure 5E
Figure 5F Figure 6A
Figure 6B
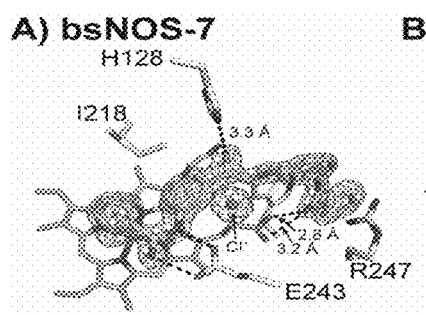
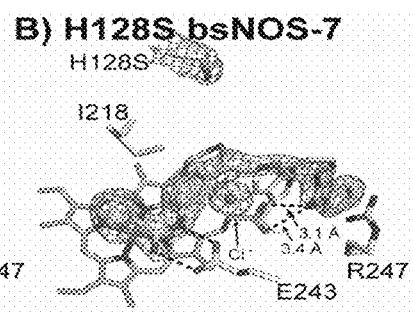
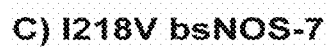
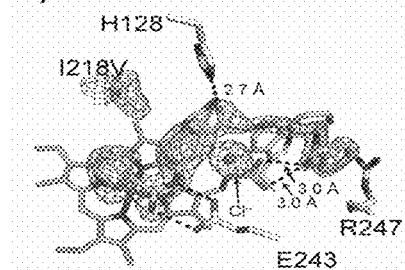
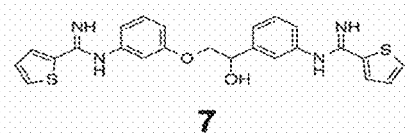
Figure 6C
Figure 6D Figure 7A
Figure 7B
Figure 7C
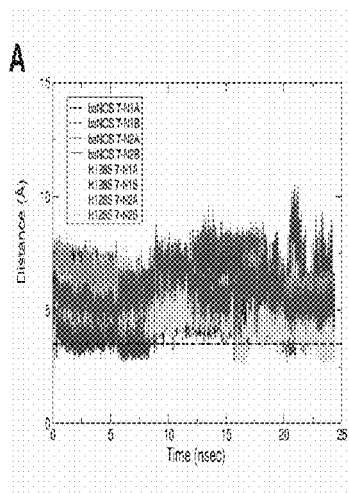
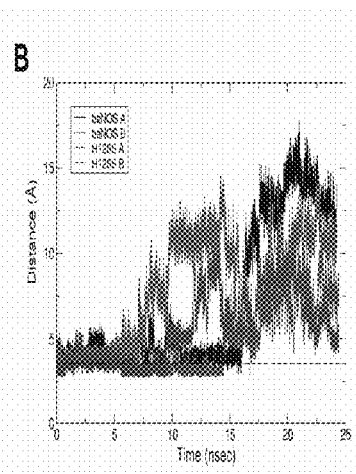
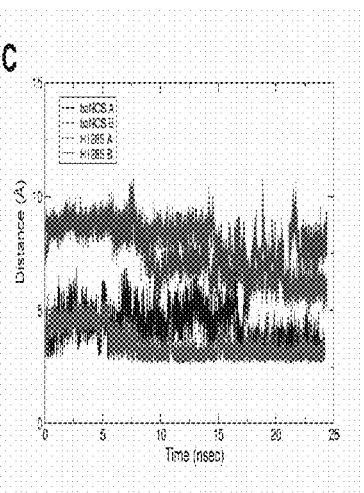

Figure 12A          Figure 12B
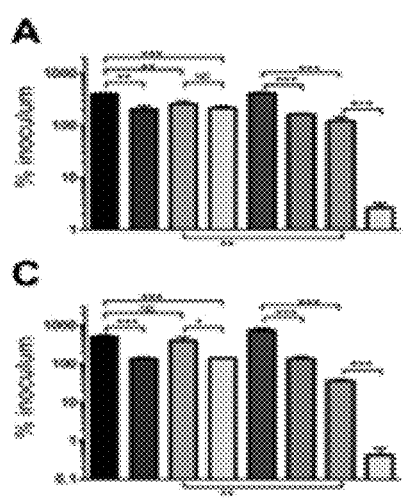
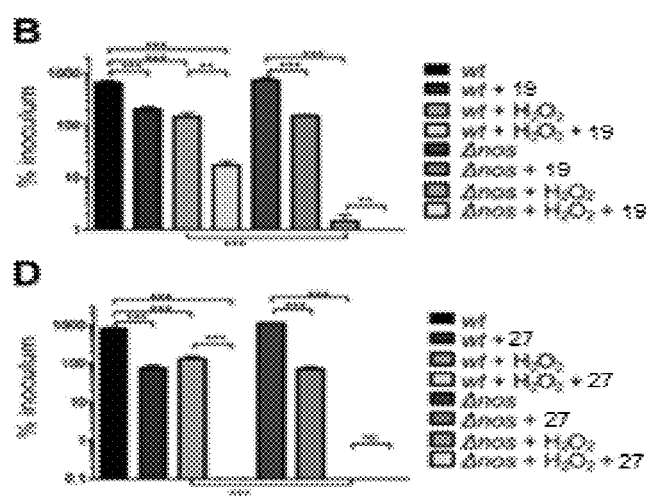
Figure 12C          Figure 12D Figure 14A  Figure 14B  Figure 14C
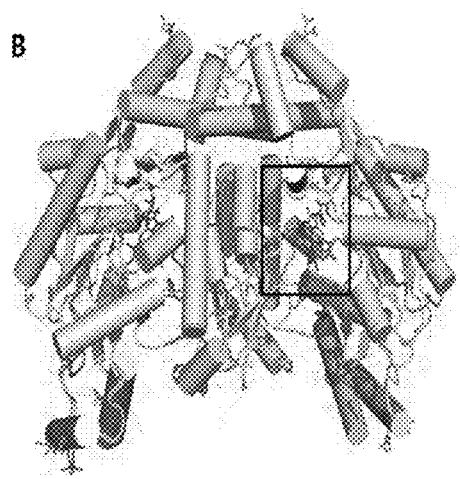
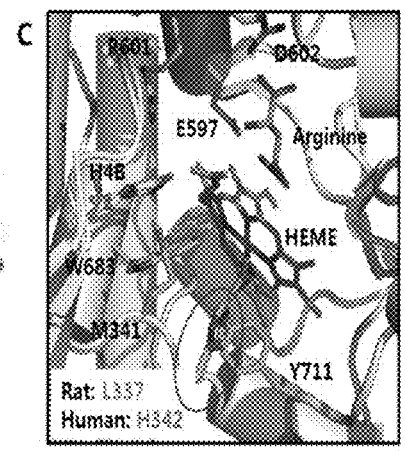

Figure 16A
Figure 16B
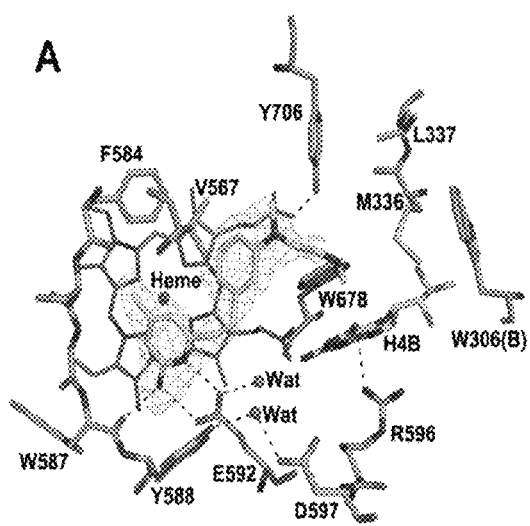
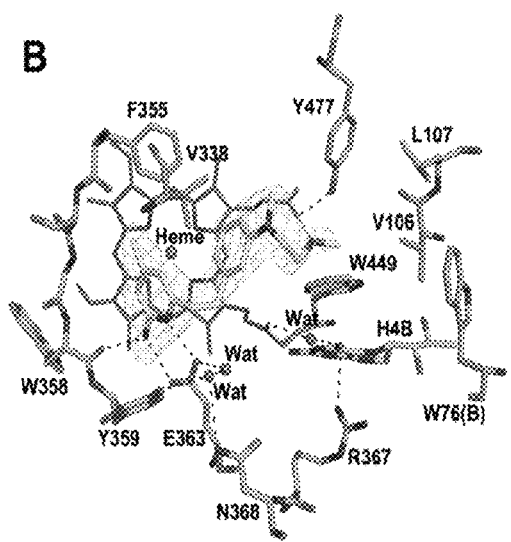

Figure 21A
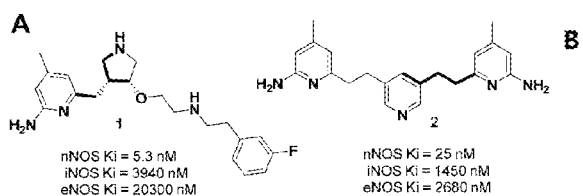
Figure 21B
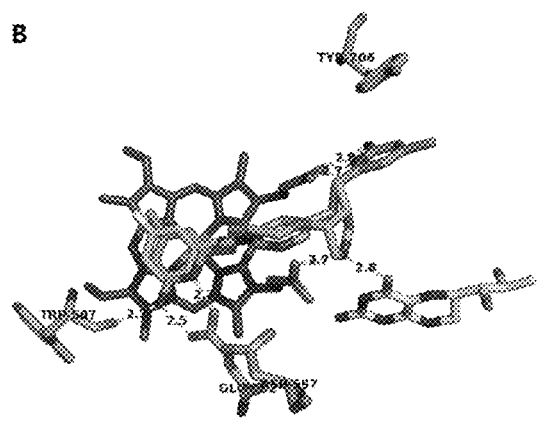
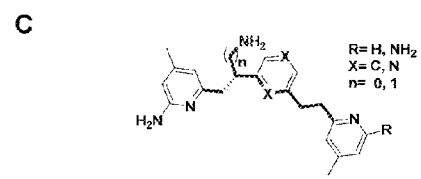
Figure 21C

MAMMALIAN AND BACTERIAL NITRIC OXIDE SYNTHASE INHIBITORS

This application claims priority to and the benefit of application Ser. No. 62/075,001 filed Nov. 4, 2014, Application Ser. No. 62/089,044 filed Dec. 8, 2014 and application Ser. No. 62/185,267 filed Jun. 26, 2015—each of which is incorporated herein by reference in its entirety.

This invention was made with government support under GM049725 awarded by the National Institutes of Health. The government has certain rights in the invention.

BACKGROUND OF THE INVENTION

NO is a highly reactive free radical produced by the hemethiolate monooxygenase nitric oxide synthase (NOS, mNOS=mammalian NOS, bNOS=bacterial NOS). NOS generates NO by oxidizing L-Arg and is found in both mammals and some bacteria. While mNOS is a multi-domain protein composed of both oxygenase and reductase domains, bNOS from the genus Bacillus and Staphylococcus contains only an oxygenase domain. X-ray crystal structures determined for both bNOS and mNOS oxygenase domains reveals a near identical tertiary structure and active site except that bNOS lacks the N-terminal fragment that contains the $Zn^{2+}$ binding motif observed in mNOS.

In mammalian systems, NO functions as an essential signaling molecule and is involved in a variety of physiological functions ranging from blood pressure homeostasis to neural cell communication and host defense. There are three mNOS isoforms: endothelial NOS (eNOS), inducible NOS (iNOS) and neuronal NOS (nNOS). Owing to the pathological consequences of the over or under production of NO, significant effort has been made toward the development and characterization of isoform selective mNOS inhibitors, which has resulted in the development of many unique inhibitors.

One of the major issues in the design of bNOS inhibitors is its structural similarity to mNOS isoforms. Direct comparison of the mammalian and bacterial NOS structures/sequences reveals several key differences that could be exploited for a bNOS inhibitor design effort. The first key difference is between the domain architecture of the NOS isoforms. Each mNOS is a multi-domained protein composed of both a reductase and oxygenase domain whose activity is regulated by calmodulin. In sharp contrast, bNOS is only composed of an oxygenase domain and is not regulated by calmodulin. Since bNOS is not covalently linked to its redox partners like mNOS, bNOS must utilize redox partners for activity. A second key difference is amino acid variances between the NOS active sites. For example, both bNOS and endothelial NOS (eNOS) have an Asn residue that directly interacts with the L-Arg substrate while this residue is Asp in nNOS and inducible NOS (iNOS). The active site Asp/Asn difference provided the initial structural underpinning for the design of nNOS selective inhibitors. Despite this difference in electrostatics between bNOS and nNOS, inhibitors that target the Asn residue might be detrimental if they also inhibit the critical eNOS isoform. Additional active site differences in bNOS include His128 (mammalian equivalent is Ser) and Ile218 (mammalian equivalent is Val). The slightly bulkier Ile adjacent to the $O_2$ binding site has been shown to decrease the NO release rates in bNOS. The last key difference between mNOS and bNOS is present at the pterin cofactor-binding site. Since bNOS lacks the N-terminal $Zn^{2+}$ binding motif present in mNOS, the pterin binding site is more exposed in bNOS, resulting in weaker micromolar binding affinity in bNOS vs. the stronger nanomolar affinity in mNOS. While the physiologically relevant bNOS cofactor that binds to the bNOS pterin site remains unknown, inhibitors that target this site are an attractive avenue for structure-based drug design.

In Gram-positive bacteria, bNOS produced NO has been found to modulate macromolecules by nitrosylation, to function as a commensal molecule, to protect against oxidative stress, and to detoxify antimicrobials (See, e.g., Gusarov, I. and Nudler, E. NO-mediated cytoprotection: instant adaption to oxidative stress in bacteria. Proc. Natl. Acad. Sci. USA 102, 13855-13860 (2005); and Gusarov, I., Shatalin, K., Starodubtseva, M. and Nudler, E. Endogenous nitric oxide protects bacteria against a wide spectrum of antibiotics. Science 325, 1380-1384 (2009)). Although the biological function of NO varies among bacterial organisms, the unique ability of NO to protect the pathogens Staphylococcus aureus and Bacillus anthracis against oxidative and antibiotic-induced oxidative stress by activation of catalase and by suppression of damaging Fenton chemistry implicates bNOS as a potential therapeutic target (Gusarov, supra). Moreover, commonly used antibiotics for the treatment of Gram-positive pathogens—like beta-lactams and vancomycin—elicit antibacterial function by generation of reactive oxygen species. Together, these data suggest that inhibition of bNOS will attenuate bacterial survival against antibiotic induced oxidative stress. Owing to the essential role NO plays in mammals, development of a bNOS-specific inhibitor ideally should take advantage of subtle differences between bNOS and mNOS.

To do so first requires identification of NOS inhibitors that demonstrate antimicrobial-like properties within a bacterial system under oxidative stress and characterization of the inhibitor-binding mode for structure-based inhibitor development. Studies on the effects of inhibitors on bNOS have thus far been limited to the finding that nonselective NOS inhibitor $N^G$-methyl-L-arginine generates greater sensitivity to $H_2O_2$-induced oxidative stress in B. anthracis. Accordingly, there is an ongoing search in the art for NOS inhibitors that decrease bacterial viability in the presence of an antimicrobial agent or otherwise under conditions inducing oxidative stress.

As bacterial pathogens acquire resistance to commonly used antibiotics, it has become clear that novel therapeutic strategies are required to combat serious infections. In particular, there is an urgent need for the development of new pharmaceuticals that target methicillin-resistant Staphylococcus aureus (MRSA). MRSA, a Gram-positive pathogen resistant to common antibiotics like isoxazoyl penicillins and β-lactams, was first reported in 1961 and remains one of the most costly bacterial infections worldwide. MRSA has remained a major threat to public health in part due to the emergence of community-associated strains, its varying epidemiology, and drug resistance. In recent years, the threat of MRSA has been compounded by reports of vancomycin resistant strains, as this agent is often considered the drug of last resort. Therefore, characterization and exploitation of alternative bacterial drug targets is essential for future successful management of MRSA infections.

Recent gene deletion experiments in S. aureus, B. anthracis and B. subtilis have implicated bacterial nitric oxide synthase (bNOS) as a potential drug target, as it provides the bacterial cell a protective defense mechanism against oxidative stress and select antibiotics. The growth of B. subtilis was found to be severely perturbed in response to combination therapy with an active site NOS inhibitor and an established antimicrobial.

While such evidence suggests bNOS as a potential therapeutic target for improving the efficacy of antimicrobials, design and development of a potent bNOS inhibitor is complicated by the active site structural homology shared with the three mammalian NOS (mNOS) isoforms. Especially considering the critical role of mammalian iNOS in pathogen clearance, bNOS inhibitors must be isoform specific to circumvent short-circuiting critical mammalian NO functions. Recent structure-based studies suggest that bNOS specificity can be achieved through targeting the pterin-binding site, as the bNOS and mNOS pterin binding sites are quite different.

SUMMARY OF THE INVENTION

In part, the present invention can be directed to compounds of a formula

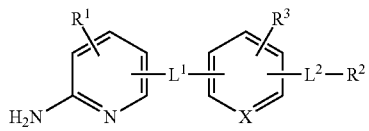

wherein $R^1$ can be selected from H, alkyl and amino moieties; $L^1$ can be a divalent linker moiety selected from a covalent bond, alkylene and substituted alkylene moieties, such alkylene substituents as can be selected from oxa (—O—), aza (—NH—), alkyl and cycloalkyl (R) substituted aza (—NR—), hydroxy, aminoalkyl, and amino substituents and combinations thereof; $R^3$ can be selected from H, alkyl, halo (e.g., F, Cl and Br), haloalkyl, cyano and amino moieties and combinations thereof; X can be selected from CH, $CR^3$ and N; $L^2$ can be a divalent linker moiety selected from alkylene and substituted alkylene moieties, such alkylene substituents as can be selected from aza (—NH—) or (—N—), alkyl and cycloalkyl (R) and substituted aza (—NR—) substituents; and $R^2$ can be a moiety selected from amino, substituted amino and optionally-substituted cycloalkyl, heterocycloalkyl, aryl and heteroaryl moieties, such substituents as can be selected from amino, halo, alkyl, cycloalkyl and heterocycloalkyl substituents and divalent alkylene and heteroatom-substituted alkylene substituents, and salts of such compounds.

In certain non-limiting embodiments, such a compound can be of a formula

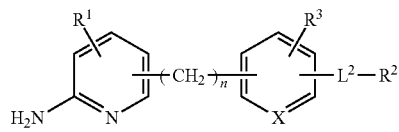

wherein n can be 1-3 and $L^2$, X and $R^{1-3}$ can be as provided above or discussed elsewhere herein. In certain such embodiments, n can be 2, $L^2$ can be —$(CH_2)_m$—, —NH$(CH_2)_m$— or $N(R)(CH_2)_m$—, where m can be 0-4, R can be selected from alkyl and cycloalkyl (e.g., cyclopropyl) moieties, and $R^2$ can be selected from amine, mono- and di-substituted amine moieties and optionally-substituted aryl and heteroaryl moieties.

In certain such embodiments, such a compound can be of a formula

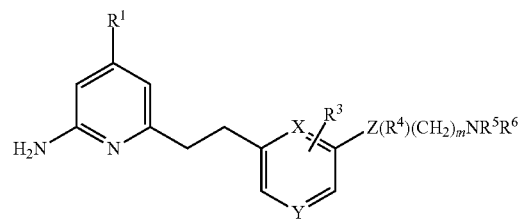

wherein $R^1$ can be selected from H and methyl moieties; X and Y are independently selected from CH, $CR^3$ and N, providing both X and Y are not N; $R^3$ can be as selected from moieties provided above or discussed elsewhere herein; Z can be selected from N, NH and CH; m can be an integer selected from 0-3 and $R^4$, $R^5$ and $R^6$ can be independently selected from H and moieties provided above or discussed elsewhere herein and moieties; or where m is 0, $R^6$ can be selected from H and moieties provided above or discussed elsewhere herein, and $R^4$ and $R^5$ can be independently divalent alkylene moieties to provide together with $NR^6$ and Z, respectively, a heterocycloalkyl moiety (e.g., without limitation, a piperidinyl or a piperazinyl moiety). Without limitation, Y can be N, or X can be CH and Y can be $CR^3$.

In part, the present invention can also be directed to a method inhibiting, modulating or otherwise affecting a nitric oxide synthase. Such a method can comprise providing a compound of this invention, e.g., without limitation, one or more of the preceding compounds whether or not part of a pharmaceutical composition, and administering an effective amount of such a compound for contact with a nitric oxide synthase, such compounds as can include but are not limited to those illustrated by the following examples, referenced figures and/or accompanying synthetic schemes. Structural analogs of such compounds can be prepared using techniques of the sort described herein or in the references incorporated herein, or straight-forward variations thereof. Such analogous compounds are limited only by commercial or synthetic availability of corresponding starting materials and reagents, such techniques, variations, starting materials and reagents as would be understood by those skilled in the art made aware of this invention. In certain such embodiments, such a compound and/or combination thereof can be present in an amount at least partially sufficient to increase human (and rat) nNOS binding affinity and selectively inhibit human/rat neuronal nitric oxide synthase over inducible and endothelial isoforms. Such a method can thereby inhibit, modulate or otherwise affect production of nitric oxide.

In certain other embodiments, $L^1$ can be a covalent bond, such a compound as can be of a formula

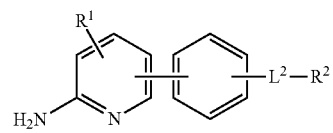

where $L^2$ and $R^2$ can be as provided above or described elsewhere herein. In certain such embodiments, such a compound can be of a formula

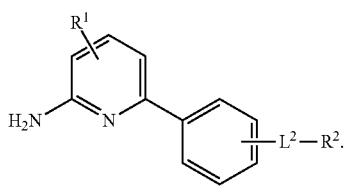

Regardless, various compounds of or useful in conjunction with the methods of this invention are without stereochemical or configurational limitation. As illustrated and discussed below, several such compounds and/or their intermediates are available as single enantiomers, racemic mixtures from which isomers can be resolved, or diastereomers from which the corresponding enantiomers can be separated. Accordingly, any stereocenter can be (S) or (R) with respect to any other stereocenter(s). As another separate consideration, various compounds can be present as an acid salt, either partially or fully protonated. In certain such embodiments, the counter ion can be a conjugate base of a protic acid. Further, it will be understood by those skilled in the art that any one or more of the compounds of this invention can be provided as part of a pharmaceutical composition comprising a pharmaceutically-acceptable carrier component for use in conjunction with a treatment method or medicament.

In part, the present invention can also be directed to a method of binding a nitric oxide synthase inhibitor compound to a bacterial nitric oxide synthase. Such a method can comprise providing one or more of the preceding compounds; and contacting such compound(s) with a cellular medium comprising bacterial nitric oxide synthase. Without limitation, such a method can comprise induction of oxidative stress within such a cellular medium. In certain embodiments, such stress can be induced by administration of an antimicrobial agent. In certain such embodiments, an agent can be selected from antimicrobial compounds of the sort disclosed herein or as would otherwise be known to those skilled in the art made aware of this invention. Without limitation, acriflavine can be used in conjunction with the present methodology.

In part, the present invention can also be directed to a method of modulating, impacting, inhibiting and/or otherwise affecting a bacterial nitric oxide synthase. Such a method can comprise providing a gram-positive bacterium expressing a nitric oxide synthase; contacting such a bacterium with a compound of the sort described above or discussed elsewhere herein; and optionally administering to such a bacterium an antimicrobial agent inducing oxidative stress in such a bacterium. Such a method can thereby modulate or otherwise affect production of bacterial nitric oxide. In certain embodiments, such a bacterium can be $S.$ $aureus$. In certain such embodiments, such a compound can selectively modulate or inhibit bNOS over mNOS. Without limitation, such an antimicrobial agent can be selected from acriflavine and other antimicrobial agents of the sort discussed herein or as would otherwise be understood by those skilled in the art made aware of this invention.

In part, the present invention can also be directed to a method of inhibiting bacterial growth. Such a method can comprise providing a gram-positive bacterium expressing a nitric oxide synthase; contacting such a bacterium with a compound selected from compounds of this invention; and administering to such a bacterium and antimicrobial agent capable of inducing oxidative stress therein. Without limitation, such a bacterium can be $S.$ $aureus$ and, in particular, a methicillin-resistant strain thereof. Such a method can thereby inhibit bacterial growth and survival. In particular, as described below, such a method can selectively inhibit growth or viability of MRSA. Without limitation, acriflavine can be utilized as an antimicrobial agent in conjunction with such a method.

In part, the present invention can also be directed to a method of modulating, inhibiting and/or otherwise affecting a bacterial nitric oxide synthase. Such a method can comprise providing a compound demonstrating inhibitory activity against mammalian nitric oxide synthase, such a compound selected from compounds of a formula

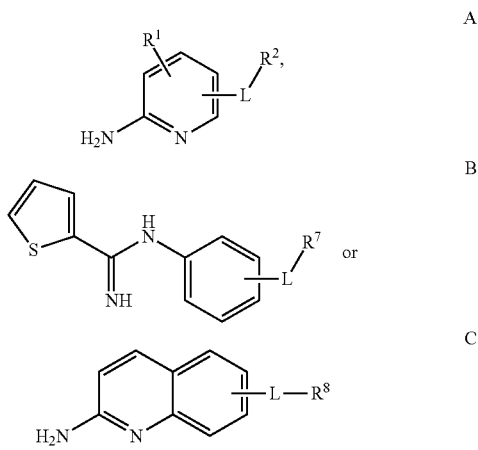

wherein $R^1$ can be selected from H, alkyl and amino moieties; L can be a divalent linker moiety selected from substituted and unsubstituted alkylene, alkylenearylalkylene, alkyleneheteroarylalkylene, alkylenepyrrolidinylalkylene moieties, such alkylene component substituents as can be independently selected from alkyl, hydroxy, amino, aminoalkyl, oxa (—O—) and aza (—NH—) and alkyl and cycloalkyl (R) substituted aza (—NR—) substituents and combinations thereof; and such aryl, heteroaryl and pyrrolidinyl component substituents as can be independently selected from alkyl, amino, aminoalkyl and cyano substituents and combinations thereof; $R^2$ and $R^8$ can be independently selected from aryl, substituted aryl, heteroaryl, substituted heteroaryl, fused aryl, substituted fused aryl, fused heteroaryl and substituted fused heteroaryl moieties, such substituents as can be selected from alkyl, halo (e.g., F, Cl and Br), and amino substituents and combinations thereof; and $R^7$ can be a moiety selected from aryl, substituted aryl, heteroaryl, substituted heteroaryl, fused aryl, substituted fused aryl, fused heteroaryl and substituted fused heteroaryl moieties and thiopheneimidamidophenyl moieties, such substituents as can be selected from alkyl, halo (e.g., F, Cl, Br) and amino substituents and combinations thereof, and a salt of such a compound or combinations of such compounds and/or salts; and providing a cellular medium comprising a bacterium expressing a nitric oxide synthase and contacting such a medium/bacterium with such a compound.

In certain embodiments, such a compound can be of a formula

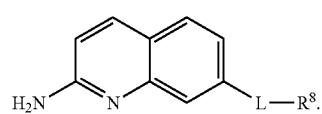

Without limitation, L can be a divalent aza-substituted alkyl moiety. In certain such embodiments L can be —$(CH_2)_m NH(CH_2)_n$—, where m and n can independently be an integer selected from 1-3. Regardless, $R^8$ can be selected from phenyl and substituted phenyl moieties, such substituents as can be selected from alkyl, halo and amino substituents and combinations thereof.

Without limitation, such a method can comprise induction of oxidative stress within such a cellular medium. In certain embodiments, such stress can be induced by administration of an antimicrobial agent. In certain such embodiments, an agent can be selected from antimicrobial compounds of the sort disclosed herein or as would otherwise be known to those skilled in the art made aware of this invention. Without limitation, acriflavine can be used in conjunction with the present methodology.

In part, the present invention can be directed to a method of modulating, impacting, inhibiting and/or otherwise affecting a bacterial nitric oxide synthase. Such a method can comprise providing a gram-positive bacterium expressing a nitric oxide synthase; contacting such a bacterium with a compound of the sort described above or discussed elsewhere herein; and optionally administering to such a bacterium an antimicrobial agent inducing oxidative stress in said bacterium. Such compounds can include but are not limited to those illustrated by the following examples, figures and/or accompanying synthetic schemes. Structural analogs of such compounds can be prepared using techniques of the sort described herein or in the references incorporated herein, or straight-forward variations thereof. Such analogous compounds are limited only by commercial or synthetic availability of corresponding starting materials and reagents, such techniques, variations, starting materials and reagents as would be understood by those skilled in the art made aware of this invention. Such a method can thereby modulate or otherwise affect production of nitric oxide in such a bacterium. Without limitation, such an antimicrobial agent can be selected from acriflavine and other antimicrobial agents of the sort discussed herein or as would otherwise be understood by those skilled in the art made aware of this invention.

BRIEF DESCRIPTION OF THE DRAWINGS

FIGS. 5A-F. Active site view of bsNOS-inhibitor bound crystal structures with the inhibitor. Inhibitor-protein H-bond distances are represented as black lines. The $2F_o$-$F_c$ maps are shown for A) 1 contoured at 1.8σ, B) 2 contoured at 1.4σ, C) 3 contoured at 1.2σ, D) 4 contoured at 1.8σ, E) 5 contoured at 2.0σ and F) 6 contoured at 1.3σ.

FIGS. 6A-D. Neither His128 nor I218 provides binding specificity of 7 to bsNOS. A) WT bsNOS-7 with $2F_o$-$F_c$ map contoured at 2.0σ reveals a 3.3 Å H-bond interaction between His128 and the hydroxyl group of 7. B) H128S-bsNOS-7 crystal structure with $2F_o$-$F_c$ map contoured at 1.5σ. C) I218V-bsNOS-7 crystal structure with $2F_o$-$F_c$ map contoured at 1.8σ. D) 2D chemical structure of 7.

FIGS. 7A-C. Molecular dynamics simulation of 7 bound to bsNOS and H128S-bsNOS reveals inhibitor is only tightly bound to active site Glu-243. A) The distance measured between active site Glu-243 and the imine group of 7 bound to the active site is constant over time. The dotted line indicates 3.5 Å. B) The distance measured between heme propionate D and the imine group bound to pterin site of 7 over time with the dotted line indicating a distance of 3.5 Å. C) The distance measured between the hydroxyl group of 7 and α-carbon of residue 128.

FIGS. 12A-D. NOS inhibitors and peroxide work to eliminate *S. aureus* over time. Colonies of *S. aureus* observed after A) 30 min and B) 60 min exposure to 200 μM 19 and/or 5 mM $H_2O_2$. Similarly, *S. aureus* viability was also measured at C) 30 min and D) 60 min following exposure to 200 μM 27 and/or 5 mM $H_2O_2$. Error bars represent the mean±SD of 3 replicates. Students t test gives *P<0.001, P<0.01 and *P<0.05.

FIGS. 14A-C. Crystal structure overlays of rat (PDB: 1OM4, cyan) and human (PDB:4D1N, green) nNOS heme domains. Nonidentical pairs within the heme domain are summarized in (A) and highlighted with side chains shown in (B) and identical sequences shown as a gray cartoon, heme in pink, and arginine in orange. (C) zoom-in view of the substrate (arginine) binding site, where the only non-identical pair H342 (human)—L337(rat) is located near Y711 (red circle). All structural figures were prepared with PyMol (www.pymol.org).

FIGS. 16A-B. Structure of compound 10a bound to nNOS (A) or eNOS (B). The omit Fo-Fc electron density for the inhibitor is shown at the 2.5 σ contour level. Major hydrogen bonds are depicted with dashed lines.

FIGS. 21A-C. (A) Chemical structures of leads 1 and 2 and inhibitory activities; (B) Overlay of inhibitors 1 and 2 complexed with nNOS, showing heme, $H_4B$, and key residues in the active site; (C) Scaffold derived from compounds 1 and 2.

DETAILED DESCRIPTION OF CERTAIN EMBODIMENTS

Figure 1:
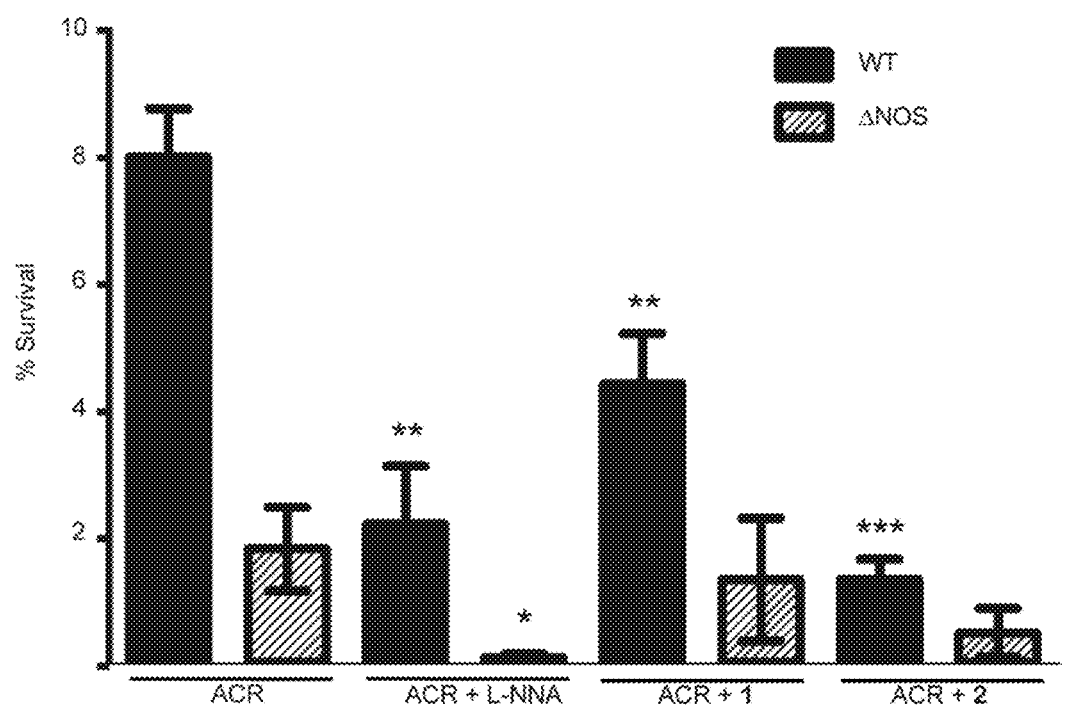
FIG. 1. NOS inhibitors and their effect on *B. subtilis* survival and growth. Bacterial survival of *B. subtilis* wt and Δnos strains decreases in the presence of 2 mM ACR and NOS inhibitors. The concentrations were 500 μM for L-NNA and 1 and 250 μM for 2 indicating that 2+ACR is more effective and inhibiting growth at 250 μM inhibitor than L-NNA+ACR at 500 μM inhibitor. Student's t test gives *P<0.001, P<0.01, *P<0.05.
Figure 2A:
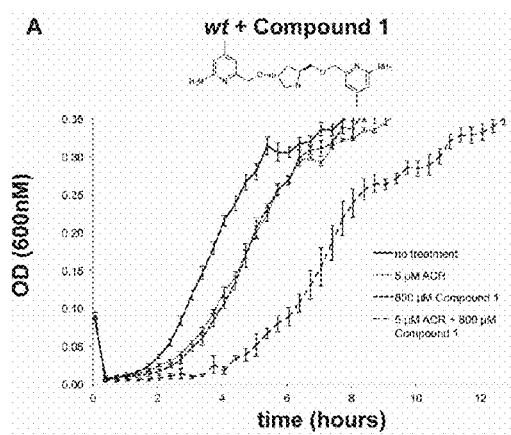
FIGS. 2A-D. The effect of ACR and compounds 1 (A and C) and 2 (B and D) on bacterial growth in both wt and Δnos *B. subtilis*. Error bars represent the mean±the SEM of at least three replicates.
Figure 2B:
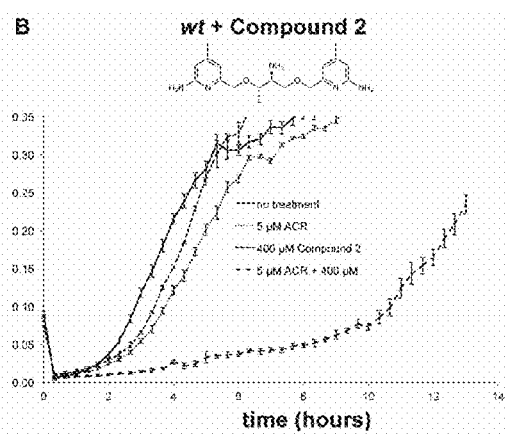
Figure 2C:
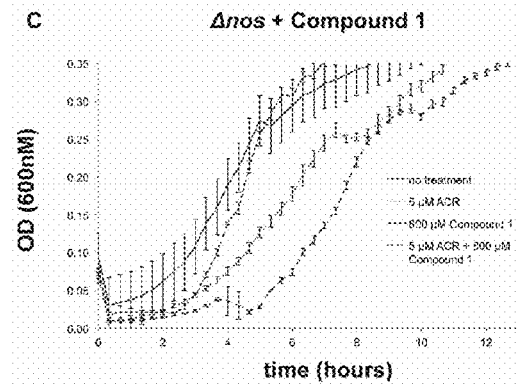
Figure 2D:
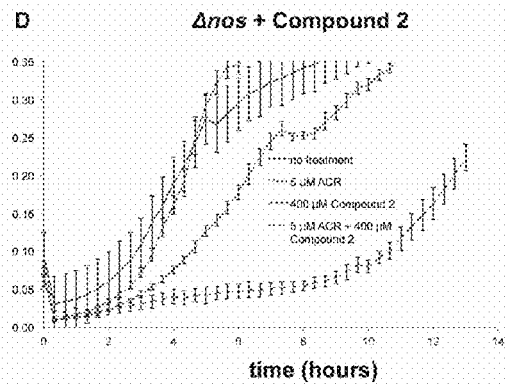
Figure 3:
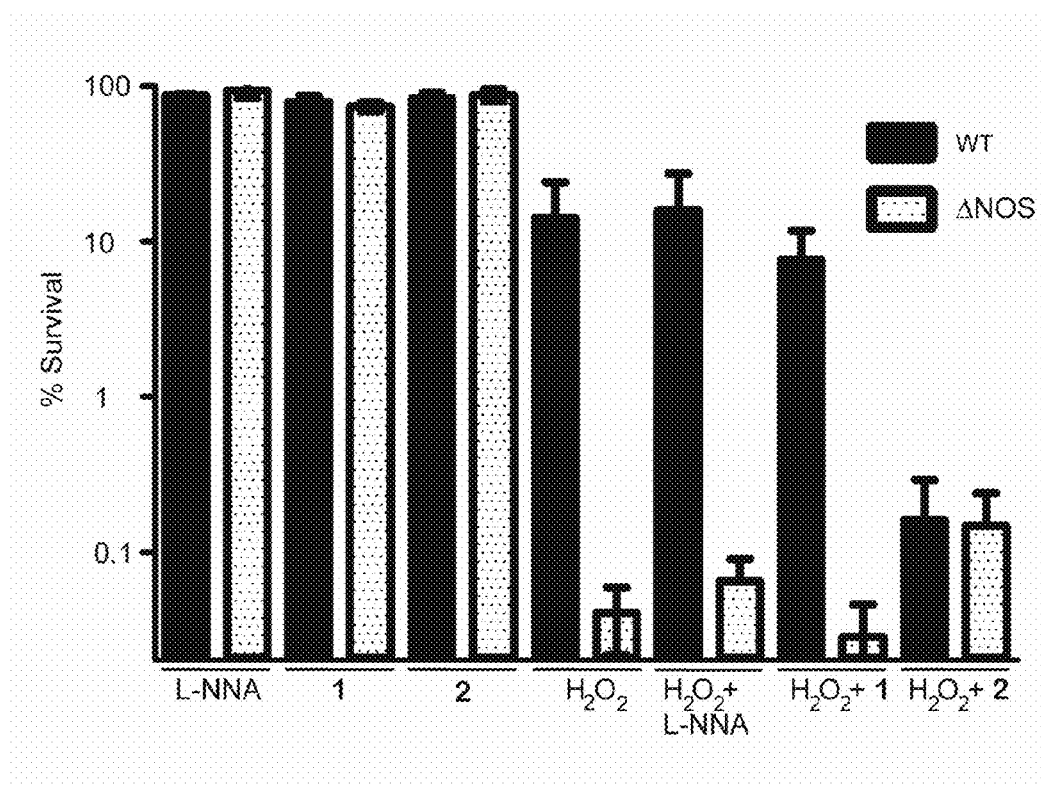
FIG. 3. Bacterial survival of *B. subtilis* WT and ΔNOS strains decreases in the presence of $H_2O_2$, relative to untreated cells. Co-addition of NOS inhibitors and $H_2O_2$ lowers bacterial survival for the WT strain. Error bars represent mean±the SEM of at least three replicates.

To demonstrate various non-limiting embodiments of this invention, bacterial oxidative stress was induced to *B. subtilis*, a non-pathogenic model organism for *B. anthracis*, by addition of either $H_2O_2$ or the antimicrobial agent acriflavine (ACR). (Reference is made to Tables 1-4, examples 1-16, FIGS. 1-9 and the compounds separately numbered therein and discussed below.) Direct comparison of wt and Δnos *B. subtilis* treated with ACR (FIG. 1) revealed the Δnos *B. subtilis* strain to have a decreased % survival in comparison to the untreated cells, as previously observed. NOS inhibitors that enhance the toxicity of oxidative stress on wt *B. subtilis* were identified from a library of inhibitors that were designed to target nNOS. (See, Silverman, R. B. (2009) Design of selective neuronal nitric oxide synthase inhibitors for the prevention and treatment of neurodegenerative diseases *Acc Chem Res* 42, 439-451; and Poulos, T. L. and Li, H. (2013) Structural basis for isoform-selective inhibition in nitric oxide synthase *Acc Chem Res* 46, 390-398.) Initially, inhibitors were identified that bound the bsNOS active site based on an imidazole displacement analysis outlined below. From the NOS inhibitors identified to bind bsNOS, 10 NOS inhibitors were screened for the ability to delay *B. subtilis* growth in the presence of oxidative stress. (See, examples, below). From an initial screen, two NOS inhibitors, compounds 1 and 2 (FIG. 2), were demonstrated to have antimicrobial-like properties with varying potencies. Further analysis revealed 2 significantly lowers the % survival of wt ACR (FIG. 1) and wt $H_2O_2$ treated cells (FIG. 3) and is more potent than 1. The non-selective NOS inhibitor $N^\omega$-nitro-L-arginine (L-NNA) was also tested, and it was found that bacterial % survival decreased in the presence of ACR (FIG. 3). Interestingly, L-NNA has trivial effects on bacterial survival in the presence of $H_2O_2$, similar to 1 (FIG. 3).

While induction of oxidative stress was demonstrated using ACR and $H_2O_2$, various other antimicrobial agents known in the art, currently or hereafter, can be used in conjunction with this invention. Such agents include but are not limited to 5-chloro-7-iodo-8-hydroxyquinoline, 8-hydroxyquinoline, 8-hydroxy-5-nitroquinoline, novobiocin, acriflavine, 9-aminoacridine, prochlorperazine, chlorpromazine, penimepicycline, sisomicin, gentamicin, cephaloridine, 7-aminocephalosporanic acid, cefotaxime, cefuroxime, ampicillin, moxalactam, 6-aminopenicillanic acid, amoxicillin and azlocillin. (See, Gusarov, supra.) Likewise, various other compounds known to inhibit mammalian nitric oxide synthase can be utilized, such compounds including but not limited to those disclosed and/or taught by the references incorporated herein. (See, e.g., Table 2 at Example 4 and the incorporated references listed therewith.)

From the above results it is clear that NOS inhibitors decrease the % survival of oxidatively stressed *B. subtilis*. To corroborate the additive effect of oxidative stress with NOS inhibitors on bacterial survival, *B. subtilis* growth was monitored over time in the presence of the antimicrobial agent ACR and/or NOS inhibitor (FIG. 2). Both untreated wt and Δnos *B. subtilis* growth curves revealed nearly identical growth rates. *B. subtilis* strains co-cultured with 1 or 2 demonstrated a slightly delayed growth but equal in both wt and Δnos cells relative to untreated cells. Most importantly, Δnos cells treated with ACR result in a dramatic shift in growth relative to wt treated with ACR. Moreover, cells co-treated with ACR and either 1 or 2 showed a severely delayed growth relative to the ACR treated cell. Compound 2 is the more potent inhibitor because it is more effective at 400 μM than 1 is at 800 μM (FIG. 2).

The effect of the more potent inhibitor, 2, on Δnos, suggests 2 to function promiscuously within *B. subtilis*. Based on the wild type results (FIG. 2B), it might be expected that Δnos exhibits the same growth pattern in the presence of ACR alone as wild type in the presence of ACR+2. This, however, is not the case. ACR does not inhibit Δnos growth to the extent one might have expected and the addition of 2+ACR has a dramatic effect on growth (FIG. 2D). This suggests that 2 may be hitting some other non-NOS target or encouraging ACR mediated oxidative stress through a currently unknown mechanism. If the former, this hypothetical non-NOS target cannot be very important in wt *B. subtilis* since 1 and 2 have little effect on % survival (FIG. 3) and bacterial growth (FIG. 2) in the absence of oxidative stress. Therefore, a significant part of the ability of 1 and 2 to block bacterial growth in wt *B. subtilis* is consistent with blocking NO production, which increases the susceptibility to antibiotic-induced oxidative stress.

The imidazole displacement shift from low- to high-spin was used to estimate the spectral dissociation constant, $K_S$ for bsNOS, eNOS, and nNOS (Table 1). Both inhibitors bind to bsNOS with similar affinities to eNOS and nNOS with 2 being an especially good inhibitor. This correlates well with 2 being especially effective at inhibiting bacterial growth.

TABLE 1

Comparison of calculated $K_s$ values.

| Ligand | bsNOS | eNOS | nNOS |
| --- | --- | --- | --- |
| L-Arg 1 $K_S$ (μM) | 0.76 | 1.00[a] | 0.72[b] |
| L-NNA 1 $K_S$ (μM) | 1.33 | 0.10[c] | 0.04[b] |
| Compound 1 $K_S$ (μM) | 4.44 | 2.10 | 0.14 |
| Compound 2 $K_S$ (μM) | 1.05 | 1.70 | 0.36 |

The calculated $K_s$ values were derived from the measured $K_{s, app}$ values. Experiments were performed as described below.
[a]Data from Berka, V., Chen, P. F., and Tsai, A. L. (1996) Spatial relationship between L-arginine and heme binding sites of endothelial nitric-oxide synthase *J Biol Chem* 271(52): 33293-33300.
[b]Data from Roman, L. J., Sheta, E. A., Martasek, P., Gross, S. S., Liu, Q., and Masters, B. S. (1995) High-level expression of functional rat neuronal nitric oxide synthase in *Escherichia coli Proc Natl Acad Sci USA* 92(18): 8428-8432.
[c]Data from Martasek P, et al. (1996) Characterization of bovine endothelial nitric oxide synthase expressed in *E. coli. Biochem Biophys Res Commun* 219(2): 359-365.

X-ray data were collected on single crystals soaked in $H_4B$ and NOS inhibitor. bsNOS crystals contain one monomer of bsNOS per asymmetric unit, and the functional dimer is generated by the 2-fold crystallographic symmetry axis, as previously observed. The $C_\alpha$ RMSD between the inhibitor bound crystal structures and the search model (PDB 2FBZ) for residues 2-137 and 146-363 is 0.315 Å; residues 138-145 were excluded because of sequence differences between our crystal structures and the search model. On the basis of the low RMSD, it was concluded that surface mutations E25A/E26A/E316A, selected for reasons outlined below, did not affect the overall structure.

Figure 4A:
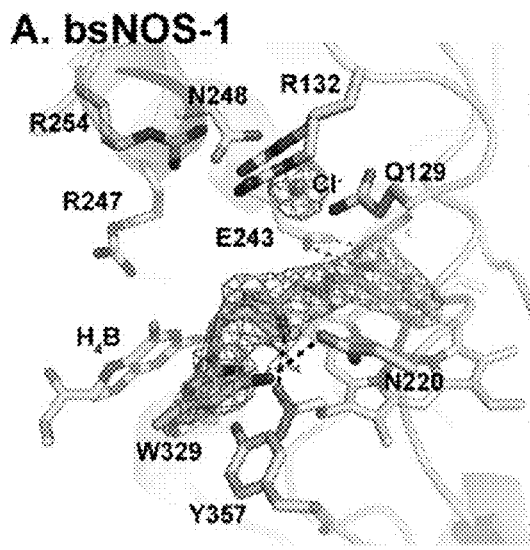
FIGS. 4A-D. Active site structure of A) bsNOS-1 complex with $2F_o$-$F_c$ electron density map contoured at 1.5σ; B) bsNOS-2 complex with $2F_o$-$F_c$ electron density contoured at 1.0σ; C) *Rattus norvegicus* nNOS-1 complex with the 2Fo-Fc electron density map contoured at 1.0σ; D) nNOS-2 complex.
Figure 4B:
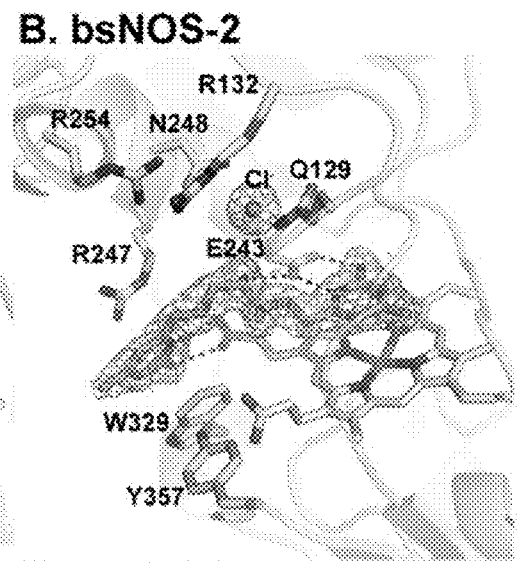

Electron density maps for both 1 and 2 clearly establish that an aminopyridine group is positioned on the distal face of the heme active site to hydrogen bond with the protein-derived Glu243 residue (FIGS. 4A and 4B). In the bsNOS-1 structure the pyrrolidine ring is positioned within 2.7 Å to H-bond to heme-propionate D. While the 2Fo-Fc map contoured at 1.5σ reveals density for the second aminopyridine group, the B-factors for this group are relatively high in comparison to the rest of the molecule, indicating less specific binding of the second aminopyridine group. As modeled, the amine on the second aminopyridine group is positioned within 3.1 Å of Asp220 for a potential H-bond (FIG. 4A). The second aminopyridine is also modeled as binding within van der Waals contact radii of Tyr357. The cofactor $H_4B$ also is present in the bsNOS-1 crystal structure and is bound at the previously characterized bacterial pterin site.

While 2 binds to Glu243 in a near identical orientation and position as 1, the second aminopyridine group of 2 displaces the $H_4B$ molecule to form two stabilizing H-bonds (2.8 Å and 2.9 Å) with heme propionate A (FIG. 4B). Unlike 1, the electron density for 2 is well defined for the entire inhibitor. The improved electron density corresponds to a lower $K_S$ for 2, 1.05 μM, compared to 1, 4.44 μM. (FIG. 4). The binding mode of 2 is further stabilized by the cation-π interaction with the nearby Arg247, a H-bond (2.9 Å) between the primary amine and Glu243, and a H-bond (3.0 Å) between the primary amine and the heme propionate A (FIG. 2B).

A consistent finding in these and other bsNOS crystal structures (not shown) is the presence of a large solvent molecule located where the carboxyl group of the substrate, L-Arg, would be located. Modeling a Cl⁻ anion at this position accounts best for the electron density. In the eNOS-2 structure there is an acetate ion located in approximately the same position. Electrostatic stabilization results from the nearby Arg254 and Arg132, both of which are conserved in eNOS and bsNOS (FIG. 4). However, nNOS has no anion at this position (FIG. 4D). This is very likely because bsNOS Asn248 (also Asn in eNOS) is replaced with Asp in nNOS. Asn248 is about 3.2 Å from the Cl⁻ anion, so an Asp at this position would result in weaker electrostatic stabilization of an anion.

Figure 4C:
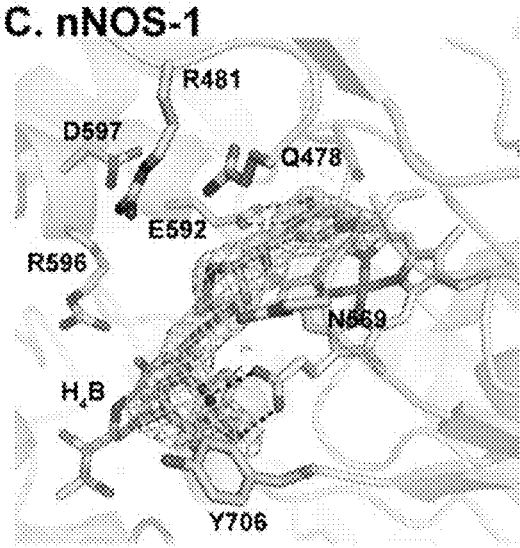
Figure 4D:
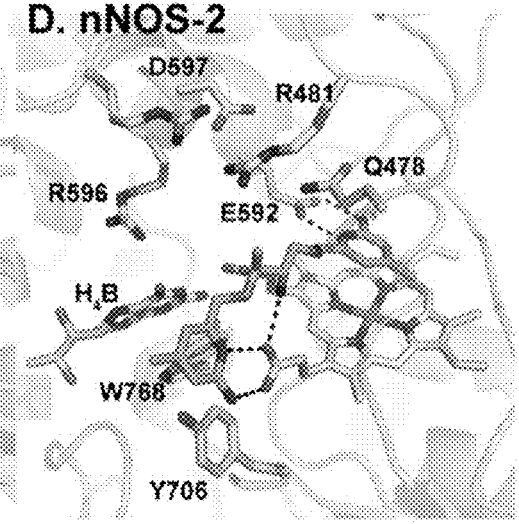

With the structures of 2 bound to eNOS and nNOS known, the crystal structure of the nNOS-1 complex was also determined (FIG. 4C). There are two major differences. First, the pyrrolidine ring in nNOS points "up" toward Asp597, while in bNOS the pyrrolidine ring points "down" toward heme propionate D. Second, Tyr706 is displaced in nNOS, which allows the second aminopyridine to H-bond with heme propionate D. Normally, this tyrosine H-bonds with heme propionate D, but it was observed in other double headed NOS inhibitors that this tyrosine readily moves to enable inhibitors to H-bond with heme propionate D, which happens more often in nNOS than eNOS. The structure of the eNOS-1 complex was also determined (not shown), and the main difference is that Tyr477 (corresponds to Tyr706 in nNOS) is not displaced. It, therefore, appears that Tyr706 is able to move more freely in nNOS than either eNOS or bsNOS. There are substantial sequence differences between NOS isoforms near Tyr706, but, unfortunately, several residues in this region are not well resolved in nNOS and eNOS electron density maps, so it is difficult to provide a structural basis for the observed enhanced susceptibility of Tyr706 to be displaced in nNOS.

FIG. 4D shows the nNOS-2 complex. Here there is an even more dramatic difference. Relative to bsNOS, the inhibitor flips 180° in nNOS so that the aminopyridine that is situated near the active site Glu in bsNOS H-bonds with heme propionate D in nNOS, which requires movement of Tyr706. This enables the primary amino group in nNOS to H-bond with heme propionate D. This large difference in binding mode of 2 is attributed to the displacement of the $H_4B$ cofactor in bsNOS but not in nNOS. The actual physiological cofactor in bsNOS remains an open question, but the binding of pterins to bsNOS is fairly weak, in the 10-20 μM range, compared to mNOS, which is in the nM range. Therefore, $H_4B$ is more easily displaced in bsNOS than in mNOS. As a result, inhibitors targeting the pterin binding pocket might be selective to bNOS over mNOS.

With consideration of the preceding, because NOS inhibitors that bind both the active and pterin binding sites could allow for further design of bNOS inhibitor specificity, several NOS inhibitors compounds (1-7) were identified by solving crystal structures that target both the active and pterin binding sites of *B. subtilis* NOS (bsNOS). (Compound 1 was preliminarily considered and is listed as compound 4 in Table 4, below. For purpose of this comparative analysis, and with respect to examples 10-16, it will be referenced as compound 1.) From initial analysis of NOS inhibitors (1-4) two additional inhibitors (5 and 6) that also targeted the active and pterin binding sites were then designed and synthesized. Further characterization of inhibition was carried out using inhibitor binding assays, enzyme assays, molecular dynamics simulations, and bacterial assays to provide a structural framework for the continued design of isoform-selective bNOS inhibitors that function as antimicrobials. (See Examples 12-14)

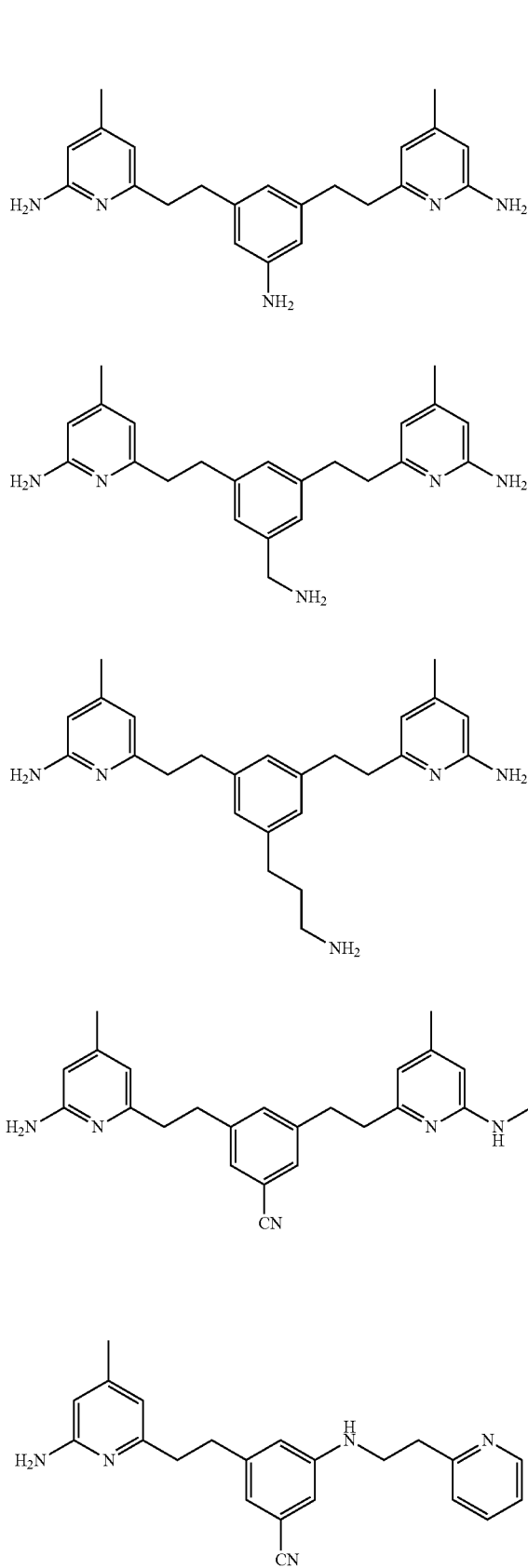

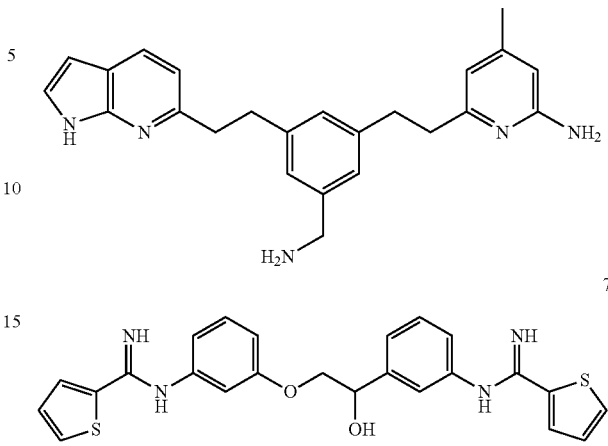

Inhibitors 1-3 were initially designed to target nNOS and the structures of mNOS-1,2,3 have previously been reported. The structures of bsNOS with inhibitors 1-6 revealed that each compound interacts with the active site Glu-243 and heme propionate D through a series of H-bonds between the aminopyridine functional groups (FIG. 5A-D). While 1 and 2 only differ in the amine substituent at the para-position of the aromatic ring linker, it is clear that linker composition between the aminopyridine groups dictates the orientation of the inhibitor and the rotameric position of Arg-247. For example, in 1 Arg-247 reorients to form a π-cation interaction with the aromatic ring of the linker. This alternative rotamer was also observed with 4. In sharp contrast, the linkers of 2 and 3 are parallel to the heme group, and Arg-247 is observed in its native position. In the case of 2 the parallel orientation (relative to the heme group) of the aromatic ring within the linker is likely a result of the H-bond formed between the linker's primary amine and heme propionate A.

Considering that a cyano substituent within the linker of 4 results in a π-cation interaction with Arg-247 and a H-bond between heme propionate D and the aminopyridine functional group, it was anticipated that inhibitor binding to the pterin site could be further improved by addition of a secondary amino group to form an additional H-bond with heme propionate D and the cyano conjugated ring to maintain the π-cation interaction with Arg-247. These observations led to the synthesis of 5, whose linker unexpectedly adopted a parallel orientation to the heme group but maintained the π-cation interaction with Arg-247 (FIG. 5E). To further improve inhibitor binding to the pterin site of bsNOS compound 6 was also synthesized. The design of 6 was based on the crystal structure of 2. The goal was to develop an inhibitor that formed a stable π-π stacking interaction with Trp-329 by replacing one of the aminopyridine groups of 2 with a pyrrolopyridine. The pyrrolopyridine should also be able to H-bond with heme propionate D. As observed with 2, compound 6 does indeed form a H-bond with the heme propionate and undergoes a π-π stacking interaction with Trp-329.

To further characterize inhibitor binding at the NOS active site we measured the spectral binding constant, $K_S$, for each inhibitor to both bsNOS and iNOS. On the basis of the measured $K_S$ for each inhibitor, binding to both bsNOS and iNOS was in the low μM range (Table 2). In addition, $K_S$ was also measured for bsNOS in the presence and absence of H$_4$B. It was anticipated that the K$_S$ of inhibitors targeting the pterin site to increase in the presence of H$_4$B, as inhibitor binding would be weakened owing to competition with the pterin molecule. However, in the case of inhibitors that tightly bind to the pterin site, for example 1, only a two-fold difference in binding was observed (Table 2), which was considered to be a negligible difference since the K$_S$ of ligands L-NNA and NOHA—two ligands that do not bind to the pterin site—resulted in a 3.4 and 1.2 fold difference in binding, respectively. Another interpretation is that the binding affinity of 1 to the pterin site is significantly stronger then the binding affinity of H$_4$B and that 1 is able to easily displace H$_4$B. If this is true, for tight binders the K$_S$ should remain unchanged in the presence or absence of H$_4$B. In contrast, for inhibitors that are transiently associated with the pterin site, as is observed with 5 and 6, it is not surprising that a negligible change in K$_S$ was also observed upon addition of H$_4$B owing to the weak non-covalent interactions observed at the pterin site. Regardless, from the crystal structures (FIG. 5) it is apparent that compounds 1-6 may serve as templates for structure-based drug design against bNOS, as all molecules do bind to the pterin-binding site.

TABLE 2

Imidazole displacement assay used to calculate the spectral binding constants (K$_S$) in the absence (−) and presence (+) of 50 μM H$_4$B.

| | K$_S$ (μM) | | |
|---|---|---|---|
| Compound | bsNOS (−H$_4$B) | bsNOS (+H$_4$B) | iNOS (+H$_4$B) |
| 1 | 0.91 ± 0.08 | 1.9 ± 0.1 | 2.9 ± 0.4 |
| 2 | 15 ± 3 | 47 ± 2 | 33 ± 8 |
| 3 | 16 ± 1 | 19 ± 1 | 19 ± 4 |
| 4 | 12 ± 1 | 19 ± 2 | 6.1 ± 0.6 |
| 5 | 39 ± 2 | 34 ± 4 | 16 ± 6 |
| 6 | 10 ± 2 | 12 ± 4 | 21 ± 8 |
| 7 | 13 ± 2 | 80 ± 19 | 93 ± 77 |
| N-omega-nitro-L-arginine (NOHA) | 1.32 ± 0.04[8] | 4.4 ± 0.3 | n.d. |
| N-omega-hydroxy-L-arginine (L-NNA) | 3.2 ± 0.5[9] | 1.9 ± 0.1 | n.d. |

Thiophenecarboximidamide inhibitors are expected to exhibit improved pharmacological properties over aminopyridine inhibitors but form similar complexes with Nnos. Accordingly, binding of compound 7 to bsNOS was investigated. Similar to 1-6, crystal structure analysis of 7 revealed that the inhibitor also bound at both the active and pterin sites (FIG. 6A). Since 7 is an asymmetric inhibitor with both ends of 7 being composed of a thiophenecarboximidamide, the noncovalent interactions that allow for the unique binding mode and orientation of 7 to bsNOS were examined in more detail. From the crystal structures it was hypothesized that the inhibitor orientation observed in bsNOS-7 resulted from the 3.2 Å H-bond formed with His-128 and/or the hydrophobic contact shared between Ile-218 and one of the inhibitor aromatic rings. The observation of a 3.2 Å H-bond between 7 and His-128 (FIG. 6A) was of particular interest because the corresponding residue in mNOS is a Ser. Similarly, it is feasible that the hydrophobic contact between Ile-218 and 7 would favor 7 to bind the aromatic ring lacking a polar substituent to form better nonpolar interactions with the larger Ile-218 side chain. However, site directed mutagenesis of bsNOS revealed that neither the H128S (FIG. 6B) nor the I218V mutants (FIG. 6C) resulted in an alternative bsNOS-7 binding mode. In fact, I218V-bsNOS resulted in a more stable H-bond, 2.7 Å vs. 3.3 Å for WT, with His-128. Together these data suggest that the binding mode of 7 results from the ability of 7 to bind in the pterin pocket in order for 7 to optimally interact with both the pterin and active sites, and this is likely observed in bsNOS because pterin binding is weak. The importance of 7 binding to the pterin site is evidenced by the 6-fold decrease in affinity in the presence of H4B (Table 2).

To further probe the binding mode of 7 to bsNOS and investigate the H-bond contribution of His-128 to the binding mode, MD simulations were run for 25 ns. After allowing the system to equilibrate for 4.5 ns, the ligand was allowed to freely move. In both WT and H128S MD simulations 7 retains its interactions with the active site Glu-243 (FIG. 7A) and is loosely bound to heme propionate D (FIG. 7B), suggesting that the H-bond formed between 7 and Glu-243 is strong and the H-bond between 7 and heme propionate D is weak. In fact, the bond distance between 7 and heme propionate D exceeded 3.5 Å for 96.4% of the bsNOS MD trajectory. Moreover, comparison of the MD trajectories for bsNOS and H128S-bsNOS suggests that the H-bond between 7 and His128 is also transient and does not contribute toward the binding mode of 7. Distance measurements between the α-carbon of residue 128 and the hydroxyl group of 7 reveal His128 to function only by sterically restricting the movement of 7, as the atom distances range from 2.6 Å to 7.6 Å for bsNOS-7 and 4.7 Å to 10.7 Å for H128S-bsNOS-7 (FIG. 7C). This is not surprising as His is a much bulkier residue then Ser.

Interestingly, in both WT and H128S MD simulations, the thiophenecarboximidamide head group of 7 initially bound at the pterin site was observed to rotate in and out of the pterin pocket. This rotation of the thiophenecarboximidamide rendered the pterin-binding site temporarily solvent exposed. More specifically, direct measurement of the bond distance between heme propionate D and the imine of 7 throughout the MD simulation revealed the distance between heme propionate D and the imine of 7 to be non-uniform within each chain of the bsNOS dimer (FIG. 7B). Together these data provide additional support that binding of 7 to the pterin site is relatively weak.

Both the aminopyridine and thiophenecarboximidamide based inhibitors bind and inhibit the three mNOS isoforms (Table 3). Considering 1-4 were originally designed to target nNOS, it is not surprising that 1-4 also inhibit nNOS in the low nM range. Interestingly, a comparison of Ki's for 2 and 6, with 6 having a bulkier pyrrolopyridine group then the aminopyridine present in 2, suggests the bulkier pyrrolopyridine group lowers the specificity toward the mNOS isoforms. Specifically, the potency of 6 toward nNOS decreased >4 fold as compared to the potency of 2 toward nNOS. Hence, the introduction of a bulkier group that also binds to the bNOS pterin site has the potential to lower inhibitor affinity to the mNOS isoforms.

TABLE 3

K$_i$ values of inhibitors 1-7 with the mammalian NOS isoforms.

| | K$_i$ (nM) | | |
|---|---|---|---|
| Inhibitor | nNOS | eNOS | iNOS |
| 1 | 85[a] | 4950[a] | 3400[a] |
| 2 | 53[b] | 11700[b] | 6310[b] |
| 3 | 540[b] | 12100[b] | 32500[b] |
| 4 | 196 | 11806 | 14410 |

TABLE 3-continued

K$_i$ values of inhibitors 1-7 with the mammalian NOS isoforms.

| Inhibitor | K$_i$ (nM) | | |
|---|---|---|---|
| | nNOS | eNOS | iNOS |
| 5 | 1267 | 1557 | 12750 |
| 6 | 220 | 52726 | 7098 |
| 7 | 819[c] | 10100[c] | 5200[c] |

[a]Delker, S. L., Xue, F., Li, H., Jamal, J., Silverman, R. B., and Poulos, T. L. (2010) Role of zinc in isoform-selective inhibitor binding to neuronal nitric oxide synthase, *Biochemistry* 49, 10803-10810.
[b]Huang, H., Li, H., Martasek, P., Roman, L. J., Poulos, T. L., and Silverman, R. B. (2013) Structure-guided design of selective inhibitors of neuronal nitric oxide synthase, *J. Med. Chem.* 56, 3024-3032.
[c]Huang, H., Li, H., Yang, S., Chreifi, G., Martasek, P., Roman, L. J., Meyskens, F. L., Poulos, T. L., and Silverman, R. B. (2014) Potent and selective double-headed thiophene-2-carboximidamide inhibitors of neuronal nitric oxide synthase for the treatment of melanoma, *J. Med. Chem.* 57, 686-700.

Figure 8:
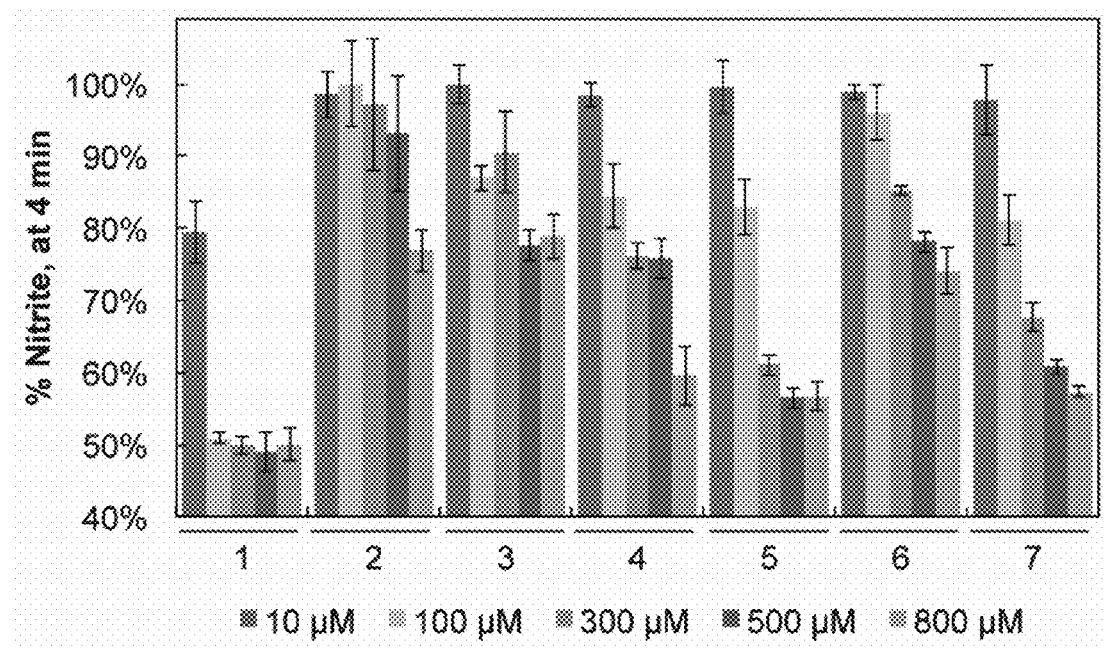
FIG. 8. % Nitrite detected as a function of bBidomain activity in the presence of NOS inhibitors at varying concentrations. On the basis of a single time point analysis, 1 is the most potent bNOS inhibitor. Error bars represent the mean±the SEM for three separate experiments.

With the use of the recently described bBiDomain and YumC system for bNOS activity/inhibition measurements, the potency of each inhibitor was evaluated at varying concentrations using a single time point approach. (Table 4) At all concentrations evaluated, compound 1 was the most potent with 49.2±1.2% nitrite detected at an inhibitor concentration of 300 μM. The increased potency of 1, compared to 2-7, is likely because 1 is able to form two separate 3.3 Å H-bonds with heme propionate D (FIG. 5A), which accounts for an additional 1-3 kcal/mol in binding energy. Unlike 1, compounds 2-6 are unable to form a strong H-bond with the heme propionate D (FIG. 5). On the basis of this limited data set, it is clear that formation of a strong H-bond with heme propionate D improves inhibitor potency for molecules that target the pterin site. Moreover, of the compounds evaluated here, it also is clear that inhibitor potency needs to be dramatically improved, as only one of these compounds lowered enzyme activity below 50% (FIG. 8). The relatively weak potency observed might be the result of the inclusion of 50 μM H$_4$B in the enzyme assay, as these inhibitors must compete with H$_4$B. Moreover, because the physiological pterin group and its concentration within either *S. aureus* or *B. anthracis* is unknown, the actual in vivo potency may be substantially different from these in vitro results. Even so, the relative inhibitor potency of each inhibitor can be utilized therapeutically and/or as a tool to guide inhibitor design.

TABLE 4

Chemical structures, pseudonyms and corresponding K$_S$ values of NOS inhibitors initially screened against *B. subtilis* and evaluated for antimicrobial properties. From the 10 NOS inhibitors initially screened, compounds 1 and 2 demonstrated antimicrobial properties.

| Name | Chemical Structure | KS (μM) | Reported |
|---|---|---|---|
| 1 | 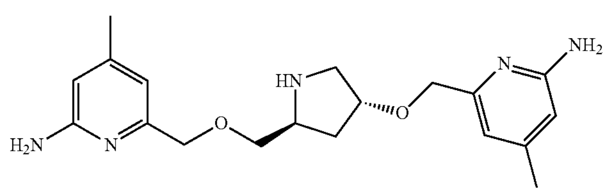 [SMILES: Cc1cc(N)nc(COC[C@@H]2C[C@@H](OCc3cc(C)cc(N)n3)CN2)c1] | 4.44 | this study |
| 2 | 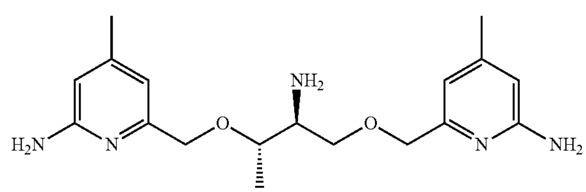 [SMILES: Cc1cc(N)nc(COC[C@H](N)[C@H](C)OCc2cc(C)cc(N)n2)c1] | 1.05 | (1) |
| 3 | 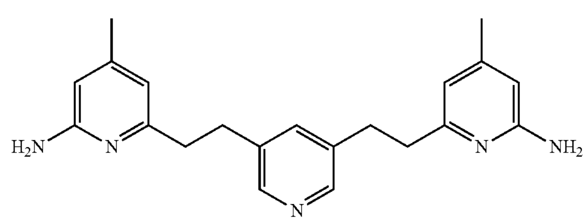 [SMILES: Cc1cc(N)nc(CCc2cncc(CCc3cc(C)cc(N)n3)c2)c1] | 1.26 | (2) |
| 4 | 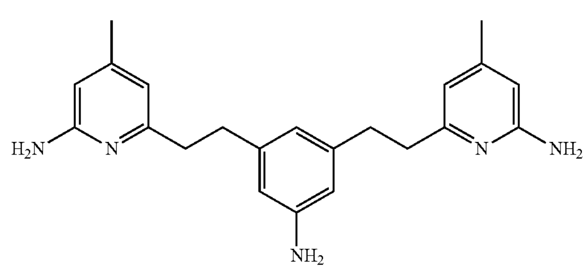 [SMILES: Cc1cc(N)nc(CCc2cc(N)cc(CCc3cc(C)cc(N)n3)c2)c1] | 0.99 | (2) |

TABLE 4-continued

*Chemical structures, pseudonyms and corresponding $K_S$ values of NOS inhibitors initially screened against B. subtilis and evaluated for antimicrobial properties. From the 10 NOS inhibitors initially screened, compounds 1 and 2 demonstrated antimicrobial properties.*

| Name | Chemical Structure | KS (μM) | Reported |
|------|-------------------|---------|----------|
| 5 | 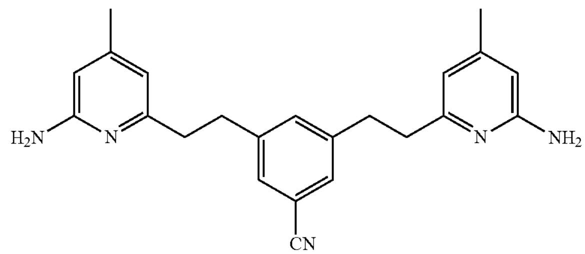 [SMILES: Cc1cc(N)nc(CCc2cc(C#N)cc(CCc3cc(C)cc(N)n3)c2)c1] | 0.24 | (3) |
| 6 | 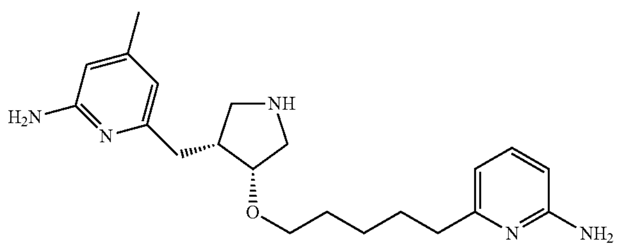 [SMILES: Cc1cc(N)nc(C[C@@H]2CNC[C@@H]2OCCCCCc2cccc(N)n2)c1] | 1.24 | (4) |
| 7 | 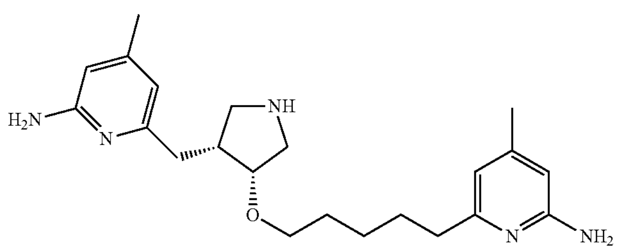 [SMILES: Cc1cc(N)nc(CCCCCO[C@H]2CNC[C@H]2Cc2cc(C)cc(N)n2)c1] | 0.32 | (4) |
| 8 | 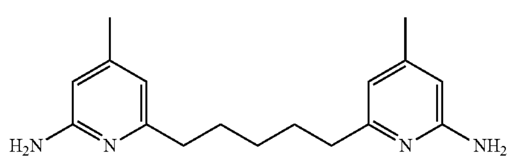 [SMILES: Cc1cc(N)nc(CCCCCc2cc(C)cc(N)n2)c1] | N/A | (5) |
| 9 | 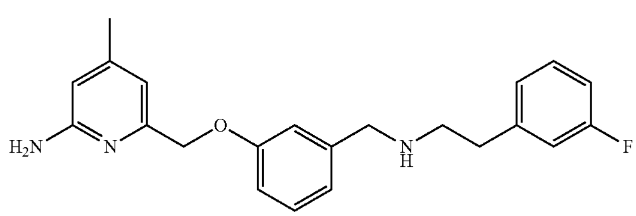 [SMILES: Cc1cc(N)nc(COc2cccc(CNCCc3cccc(F)c3)c2)c1] | N/A | (5) |

TABLE 4-continued

Chemical structures, pseudonyms and corresponding $K_S$ values of NOS inhibitors
initially screened against *B. subtilis* and evaluated for antimicrobial properties. From the 10
NOS inhibitors initially screened, compounds 1 and 2 demonstrated antimicrobial properties.

| Name | Chemical Structure | KS (µM) | Reported |
|---|---|---|---|
| 10 | [structure] | 1.89 | this study |

(1) Jing, Q., Li, H., Chreifi, G., Roman, L. J., Martásek, P., Poulos, T. L., Silverman, R. B. Chiral Linkers to Improve Selectivity of Double-Headed Neuronal Nitric Oxide Synthase Inhibitors. *Bioorg. Med. Chem.*, submitted;
(2) Xue, F., Delker, S. L., Li, H., Fang, J., Martásek, P., Roman, L. J., Poulos, T. P., Silverman, R. B. (2011) Symmetric double-headed aminopyridines, a novel strategy for potent and membrane-permeable inhibitors of neuronal nitric oxide synthase, *J. Med. Chem.* 54, 2039-2048;
(3) Huang, H., Li, H., Martásek, P., Roman, L. J., Poulos, T. L., and Silverman, R. B. (2013). Structure-guided design of selective inhibitors of neuronal nitric oxide synthase, *J. Med. Chem.* 56, 3024-3032;
(4) Huang, H., Ji, H., Li, H., Jing, Q., Jansen Labby, K., Martásek, P., Roman, L. J., Poulos, T. L., and Silverman, R. B. (2012) Selective monocationic inhibitors of neuronal nitric oxide synthase. Binding mode insights from molecular dynamics simulations, *J. Am. Chem. Soc.* 134, 11559-11572;
(5) Jing, Q., H., Li, Fang, J., Roman, L. J., Martásek, P., Poulos, T. L., Silverman, R. B. (2013) In search of potent and selective inhibitors of neuronal nitric oxide synthase with more simple structures, *Bioorg. Med. Chem.* (in press); and
(6) Xue, F., Gu, W., Silverman, R. B. (2009) Concise Route to the Chiral Pyrrolidine Core of Selective Inhibitors of Neuronal Nitric Oxide, *Org. Lett.* 11, 5194-5197, each of which is incorporated herein in its entirety.

Such compounds and various other compounds and related compositions, as can be utilized in conjunction with the methods of this invention, are described or inferred in U.S. Pat. Nos. 8,278,084 and 8,557,552 and co-pending application Ser. No. 13/573,654 filed Oct. 1, 2012 and Ser. No. 14/199,599 filed Mar. 6, 2014—each of which is incorporated herein by reference in its entirety.

Figure 9A:
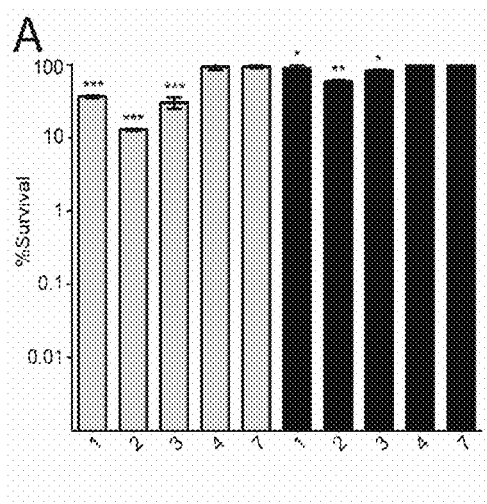
FIGS. 9A-B. NOS inhibitors influence the % survival of *B. subtilis*. A) *B. subtilis* treated with NOS inhibitors. Significance calculated using the Student's t test between the measured CFU of *B. subtilis* treated with and without NOS inhibitors for each strain separately. B) Bacterial survival of *B. subtilis* wt and Δnos decreases in the presence of 800 μM ACR and 500 μM NOS inhibitors. Significance calculated for each strain separately using the Student's t test between the calculated % survival of ACR treated cells and % survival of ACR+NOS inhibitor treated cells. Error bars represent the mean±the SEM of at least three replicates. Student's t test gives *p<0.01, p<0.05, *p<0.1.
Figure 9B:
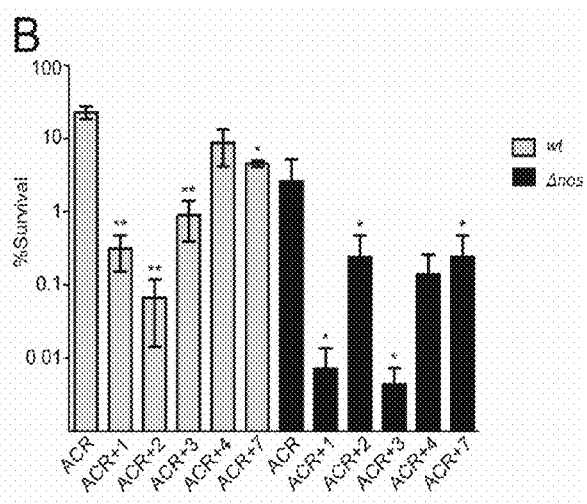

Just as some NOS inhibitors developed for selective inhibition of nNOS worked synergistically with the antibiotic ACR, to inhibit the growth of *B. subtilis*—and there was a good correlation between the binding affinity of a NOS inhibitor to bsNOS and its ability to work synergistically with ACR in bacterial killing—it was expected that inhibitor 1 would be effective at bacterial growth inhibition, and this indeed is the case (FIG. 9). Of the inhibitors tested, 1 is the most effective at working synergistically with ACR to block growth. With ACR alone bacterial growth is 23% of control. In the presence of inhibitor 1 growth is 36% of control, but together with ACR the inhibition is close to 99%, clearly indicating a strong synergistic effect. While the correlation between being an effective bsNOS and a bacterial growth inhibitor are strong, 2 is an outlier. Inhibitor 2 does not bind as tightly to bsNOS nor is it as effective at blocking bsNOS activity, but it is, nevertheless, a good inhibitor of bacterial growth. Given that both 1 and 2 can inhibit bacterial growth on their own suggests that these compounds block bsNOS to render the bacteria more susceptible to ACR but may also influence additional non-bsNOS target(s).

Although the physiological pterin cofactor for bNOS remains unknown, NO production by bNOS requires the presence of a pterin group. Because of this pterin group factor relating to activity and the significant differences in the pterin binding sites between mNOS and bNOS, inhibitors that target the pterin site may provide the key to unlocking the design and development of potent bNOS inhibitors. By taking a structure-based approach toward the identification of NOS inhibitors, several chemical scaffolds were identified that inhibit bsNOS by binding to both the active and pterin sites. Several of these structures resulted in unexpected rotameric positions of active site residue Arg-247. These alternate rotameric positions can, in turn, be considered for future structure-based drug design. Moreover, while the crystal structures and $K_S$ analysis provide definitive support for each molecule binding at the active site, MD simulations suggest inhibitor binding to the pterin site for 7 is transient and, therefore, weak. Unlike 7, more effective inhibitors can have an aminopyridine moiety in the pterin pocket where it can form better stacking interactions with Trp329 and also form more optimal H-bonds with the heme propionate.

As discussed above and as relates to certain other embodiments of this invention, bacterial infections associated with MRSA are a major economic burden to hospitals and confer high rates of morbidity and mortality amongst those infected. (Reference is made to Tables 5-8, schemes 1-5, examples 17-39, FIGS. 10-12 and the compounds separately numbered therein and discussed below.) Exploitation of novel therapeutic targets is thus necessary to combat MRSA infections. In accordance with certain non-limiting embodiments of this invention, two NOS inhibitors that function as antimicrobials against MRSA were identified and characterized. Illustrating the utility of various other embodiments, these data provide the first evidence that NOS inhibitors have the potential to work synergistically with antibiotic-induced oxidative stress to enhance MRSA killing. Crystal structures show that each inhibitor binds near an active site Ile residue that is Val in the mammalian NOS isoforms. Since conversion of this Ile to Val decreases inhibitor binding by about 6-fold, the greater hydrophobic interactions in the bacterial NOS active site may be a factor for consideration in the design of specific bacterial NOS inhibitors.

In order to quickly identify potent bNOS inhibitors a wide variety of NOS inhibitors were screened using a novel chimeric protein recently reported for bNOS activity analysis. (See, Holden, J. K., Lim, N., and Poulos, T. L. (2014) Identification of Redox Partners and Development of a Novel Chimeric Bacterial Nitric Oxide Synthase for Structure Activity Analyses. *J. Biol. Chem.*) From this high-throughput analysis it was possible to identify, in particular, two potent and chemically distinct NOS inhibitors. Crystal structure and binding analysis revealed that both inhibitors bind to a hydrophobic patch within the bNOS active site. Moreover, both of these compounds were found to function as antimicrobials against *S. aureus*, suggesting that the NOS inhibitors reported herein represent the first bNOS isoform specific inhibitors identified with antimicrobial properties. Representative compounds tested are provided in Table 5, below.

TABLE 5

Tested compounds and the $K_S$ values

| Molecules | $K_S$ (µM) | Structure | note |
|---|---|---|---|
| 0 | 1.32 ± 0.04 | L—NNA | |
| 1 | 0.91 ± 0.08 | 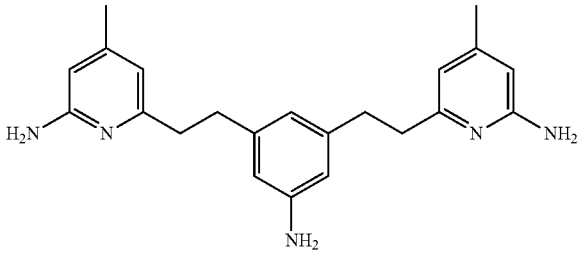 | Ref6 |
| 2 | 121 ± 12 | 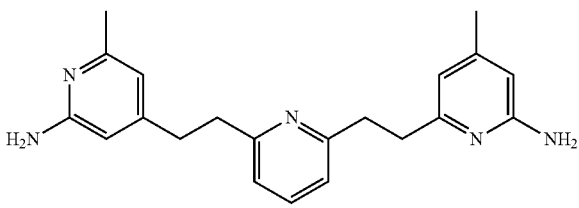 | Ref6 |
| 3 | 15 ± 3 | 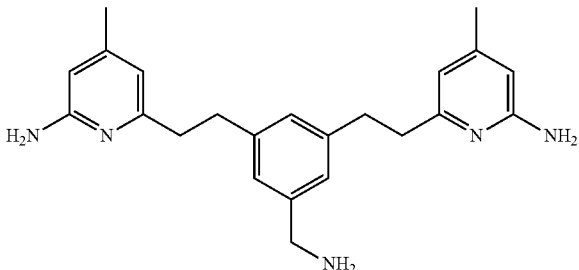 | Ref1 |
| 4 | 16 ± 1 | 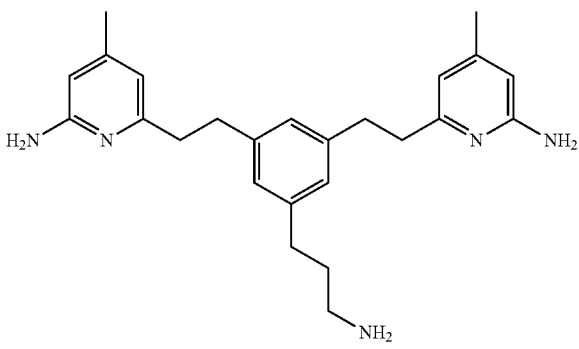 | Ref1 |
| 5 | 12 ± 1 | 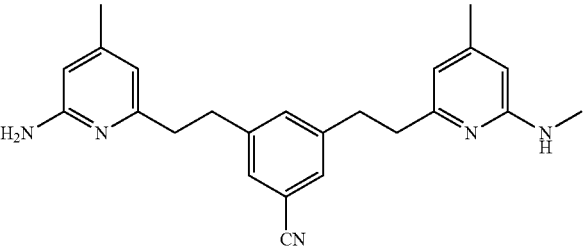 | Ref10 |

TABLE 5-continued
Tested compounds and the $K_S$ values
| Molecules | $K_S$ (μM) | Structure | note |
|---|---|---|---|
| 6 | 39 ± 2 | 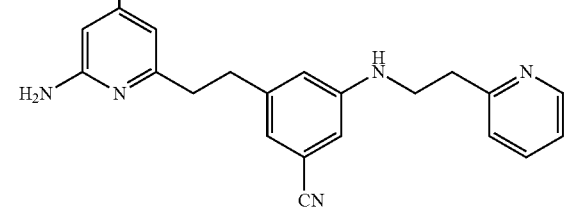 | Ref10 |
| 7 | 6.0 ± 2.4 | 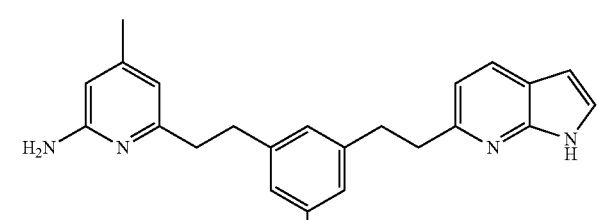 | Ref10 |
| 8 | 10 ± 2 | 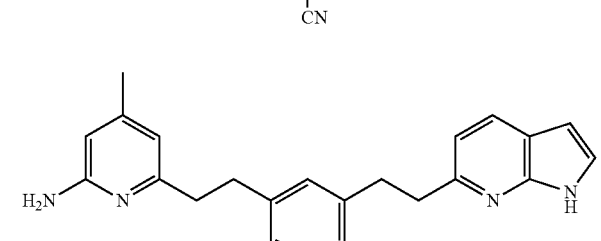 | Ref10 |
| 9 | 13 ± 2 | 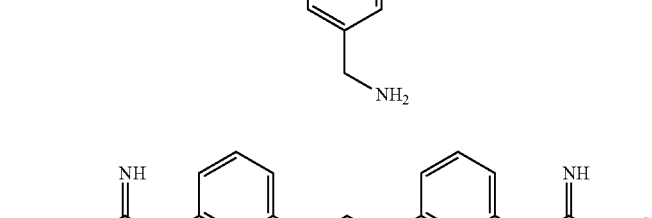 | Ref4 |
| 10 | 4.4 ± 0.1 | 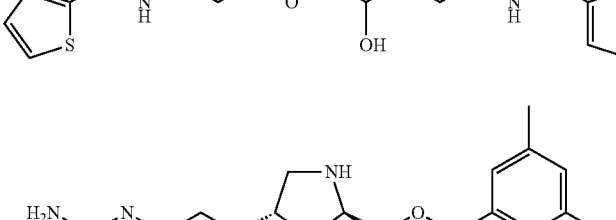 | Ref9 |
| 11 | 1.1 ± 0.1 | 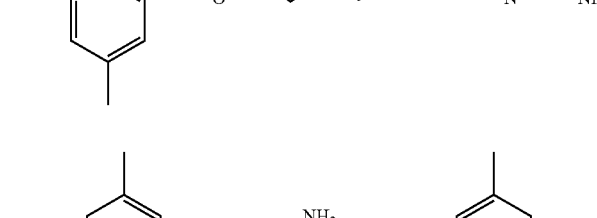 | Ref5 |

TABLE 5-continued

Tested compounds and the $K_S$ values

| Molecules | $K_S$ (μM) | Structure | note |
|---|---|---|---|
| 12 | 0.44 | 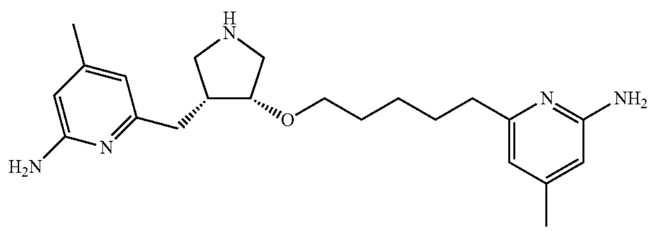 [SMILES: Cc1cc(N)nc(CCCCCO[C@H]2CNC[C@H]2Cc2cc(C)cc(N)n2)c1] | Ref2 |
| 13 | 25 ± 1 | 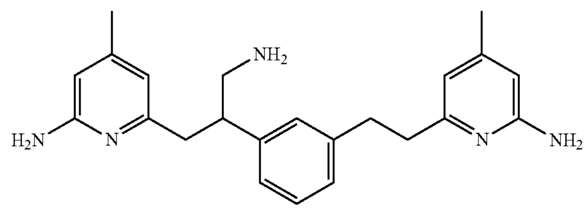 [SMILES: Cc1cc(N)nc(CCc2cccc(C(CN)Cc3cc(C)cc(N)n3)c2)c1] | Ref7 |
| 14 | 23 ± 2 | 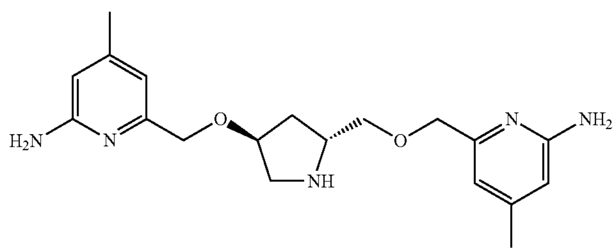 [SMILES: Cc1cc(N)nc(COC[C@H]2C[C@H](OCc3cc(C)cc(N)n3)CN2)c1] | Ref4 |
| 15 | 119 ± 25 | 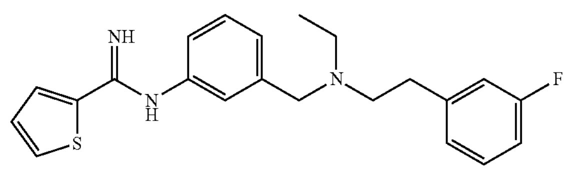 [SMILES: CCN(CCc1cccc(F)c1)Cc1cccc(NC(=N)c2cccs2)c1] | Ref3 |
| 16 | 95 ± 20 | 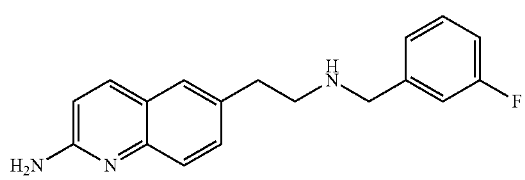 [SMILES: Nc1ccc2cc(CCNCc3cccc(F)c3)ccc2n1] | Ref8 |
| 17 | 420 ± 130 | 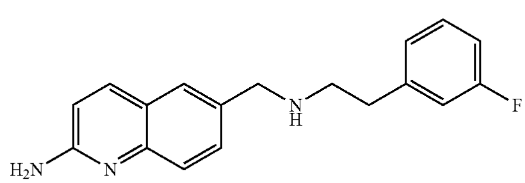 [SMILES: Nc1ccc2cc(CNCCc3cccc(F)c3)ccc2n1] | Ref8 |
| 18 | 0.97 ± 0.04 | 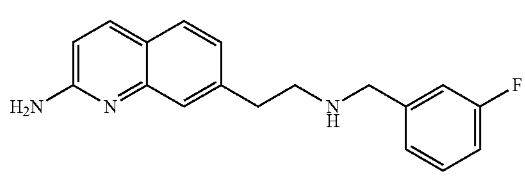 [SMILES: Nc1ccc2ccc(CCNCc3cccc(F)c3)cc2n1] | Ref8 |

TABLE 5-continued

Tested compounds and the $K_S$ values

| Molecules | $K_S$ (μM) | Structure | note |
|---|---|---|---|
| 19 | 3.6 ± 0.8 | 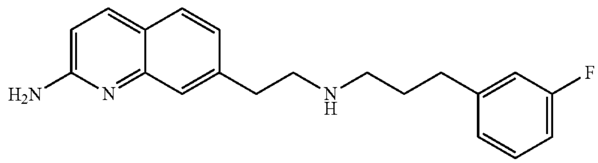 [SMILES: Nc1ccc2ccc(CCNCCCc3cccc(F)c3)cc2n1] | Ref8 |
| 20 | 6.7 ± 0.7 | 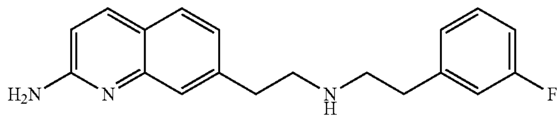 [SMILES: Nc1ccc2ccc(CCNCCc3cccc(F)c3)cc2n1] | Ref8 |
| 21 | 3.2 ± 0.1 | 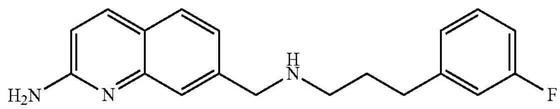 [SMILES: Nc1ccc2ccc(CNCCCc3cccc(F)c3)cc2n1] | Ref8 |
| 22 | 62 ± 25 | 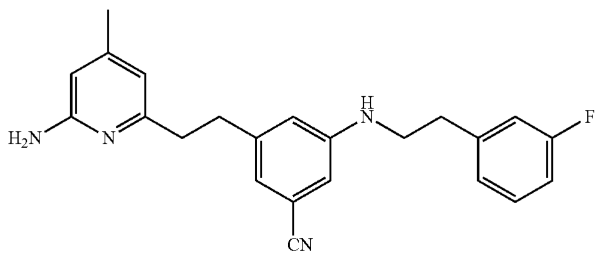 [SMILES: Cc1cc(N)nc(CCc2cc(C#N)cc(NCCc3cccc(F)c3)c2)c1] | This study |
| 23 | 9.6 ± 1.3 | 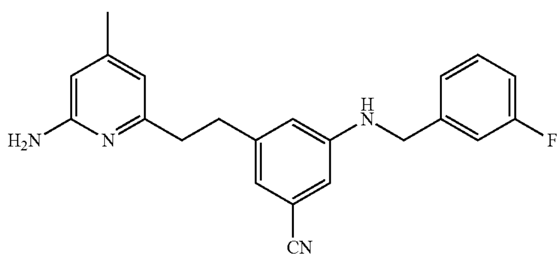 [SMILES: Cc1cc(N)nc(CCc2cc(C#N)cc(NCc3cccc(F)c3)c2)c1] | This study |
| 24 | 29 ± 4 | 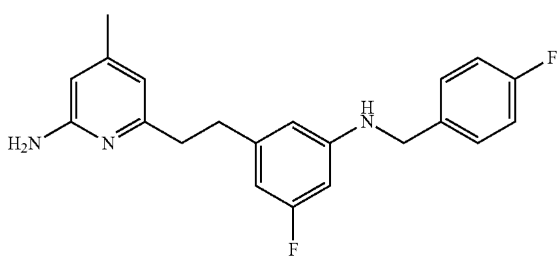 [SMILES: Cc1cc(N)nc(CCc2cc(F)cc(NCc3ccc(F)cc3)c2)c1] | This study |
| 25 | 19 ± 5 | 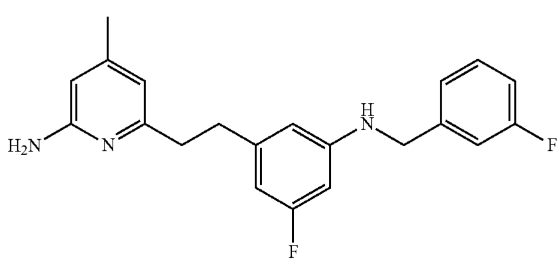 [SMILES: Cc1cc(N)nc(CCc2cc(F)cc(NCc3cccc(F)c3)c2)c1] | This study |

TABLE 5-continued
Tested compounds and the $K_S$ values
| Molecules | $K_S$ (μM) | Structure | note |
|---|---|---|---|
| 26 | 6.3 ± 0.3 | 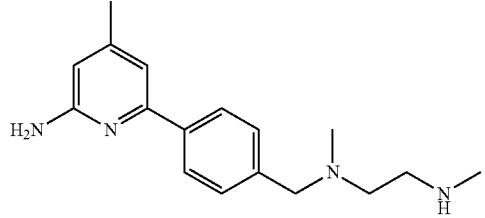 [SMILES: CNCCN(C)Cc1ccc(-c2cc(C)cc(N)n2)cc1] | This study |
| 27 | 8.9 ± 2.0 | 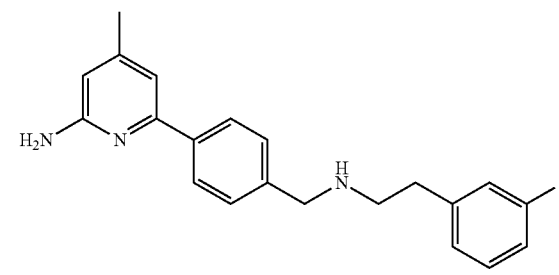 | This study |
| 28 | 3.2 ± 0.1 | 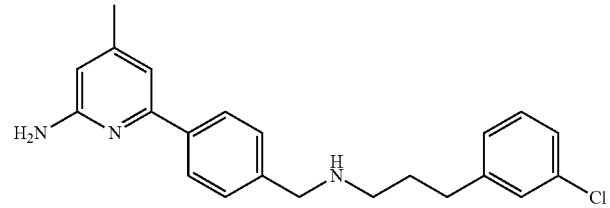 [SMILES: Cc1cc(N)nc(-c2ccc(CNCCCc3cccc(Cl)c3)cc2)c1] | This study |
| 29 | 1.5 ± 0.3 | 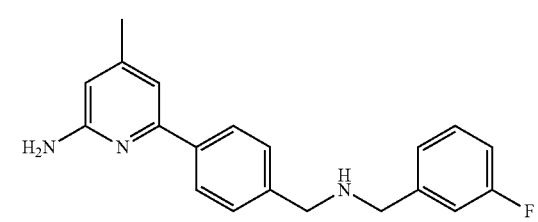 [SMILES: Cc1cc(N)nc(-c2ccc(CNCc3cccc(F)c3)cc2)c1] | This study |
| 30 | 22 ± 1 | 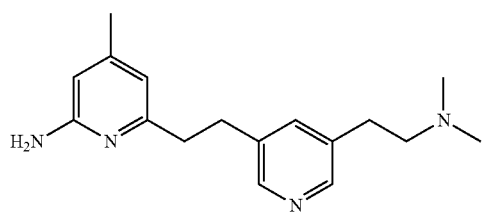 [SMILES: Cc1cc(N)nc(CCc2cncc(CCN(C)C)c2)c1] | This study |
| 31 | 94 ± 22 | 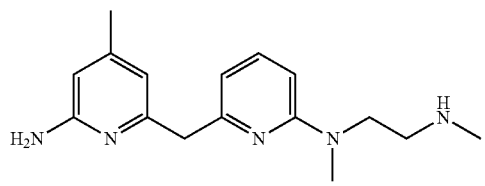 [SMILES: CNCCN(C)c1cccc(Cc2cc(C)cc(N)n2)n1] | This study |

TABLE 5-continued

Tested compounds and the $K_S$ values

| Molecules | $K_S$ (μM) | Structure | note |
|---|---|---|---|
| 32 | 1.6 ± 0.6 | 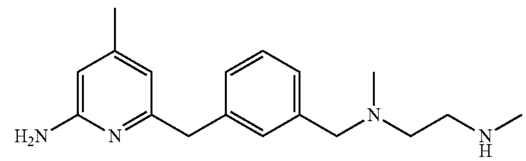 [SMILES: CNCCN(C)Cc1cccc(Cc2cc(C)cc(N)n2)c1] | This study |

Ref1: Huang et al (2013) J. Med. Chem. 56, 3124-32
Ref2: Huang et al (2012) J. Am. Chem. Soc. 134, 11559-72
Ref3: Huang et al (2014) J. Med. Chem. 57, 686-700
Ref4: Qing et al (2014) ACS Med. Chem. Lett. 5, 56-60
Ref5: Qing et al (2013) Bioorg. Med. Chem. Lett. 23, 5674-9
Ref6: Delker et al (2010) Biochemistry 49, 10803-10
Ref7: Kang et al (2014) J. Med Chem. 53, 5272-9.
Ref8: Cinelli et al (2014) J. Med. Chem. 57, 1513-30; and co-pending application Ser. No. 61/964,645 filed Jan. 10, 2014, the entirety of which is incorporated herein by reference.
Ref9: Holden et al (2013) Proc. Natl. Acad. Sci. USA 110, 18127
Ref10: Holden bNOS1 (2014) J. Med. Chem. submitted.
Each of Refs1-10 are incorporated hereby in its entirety.

Diverse molecules (1-21) were collected from previous NOS studies and several new molecules (22-32) were synthesized. This library (1-32), representative of various other compounds in accordance with this invention, includes aminopyridine derivatives (aminopyridinyl-2-ethyl, aminopyridinyl-2-benzyl, aminopyridinyl-2-phenyl), 7-azaindoles, thiopheneamidine, and 2-aminoquinoline. Compounds 22-32 generally have arylalkyl side chains or $N^1,N^2$-dimethylethane-1,2-diamine tail; using these molecules, the binding pocket near the heme binding site and possibly exposed to the solvent (water) was examined to determine whether the site is advantageous for bacterial NOS.

Compounds 22-25 were synthesized using the previously established methods (Scheme 1); dibromophenethyl derivatives III-V were prepared by coupling of benzylbromide (I-II) with lithiated pyrrolyl-4,6-lutidine. Intermediate III underwent microwave-assisted Rosenmund-von Braun reaction with CuCN to introduce a nitrile moiety (IV). Buchwald-Hartwig reaction of IV and V with several aryl amines using $Pd_2(dba)_3$ and Dave-phos gave P22-P25. The 2,5-dimethylpyrrole protecting group was removed with $NH_2OH.HCl$ using a microwave to generate final products 22-25.

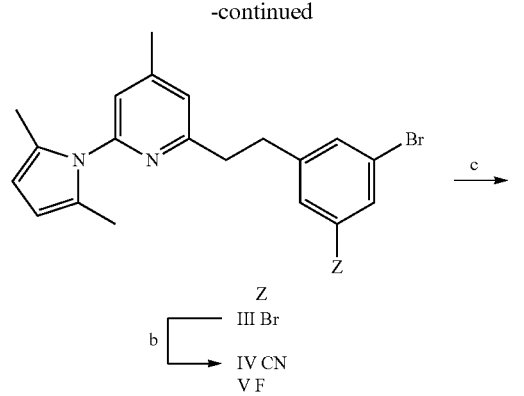

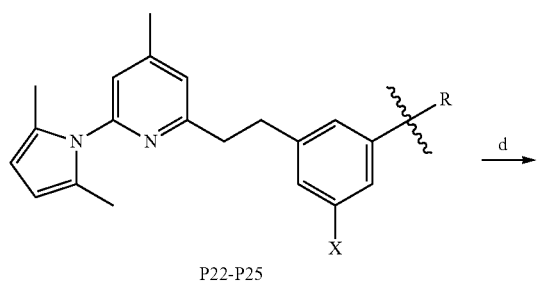

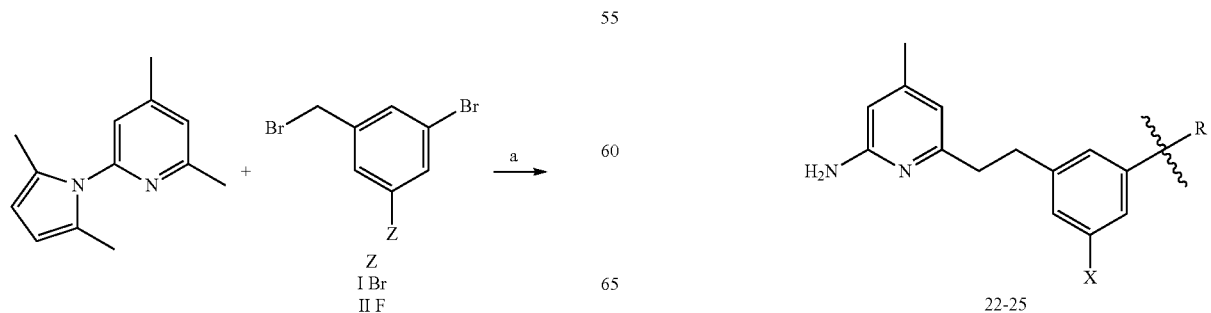

X = F, CN

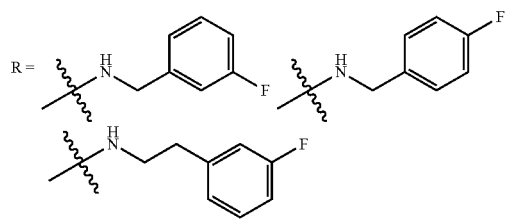

Scheme 1. Reagents and conditions: a) (i) BuLi, 0° C., 30 min, THF; (ii): I or II, 81-86%; b) CuCN, DMF, microwave, 220° C., 20 min, 57%; c) amine, Pd$_2$(dba)$_3$, Dave-Phos, NaOtBu, THF, 1,4-dioxane, 5~10 h, 100° C., 69-90%; d) NH$_2$OH(HCl) 5 eq, EtOH, H$_2$O, microwave, 120° C., 25 min, 60-80%.

Compound 26-29 were prepared using the synthetic pathway shown in Scheme 2. Palladium-catalysed Suzuki cross coupling between pyridinylbromide and phenylboronic acid yielded VI. To install an amine tail in 26-29, the aromatic nitrile moiety of VI was converted into requisite benzaldehyde. This was accomplished with DIBALH. Benzaldehyde VII was then condensed with several amines by reductive amination to give the corresponding benzylamines P26-P29. The 2,5-dimethylpyrrole protecting group on P26-P29 was removed with NH$_2$OH.HCl using a microwave to generate final products 26-29.

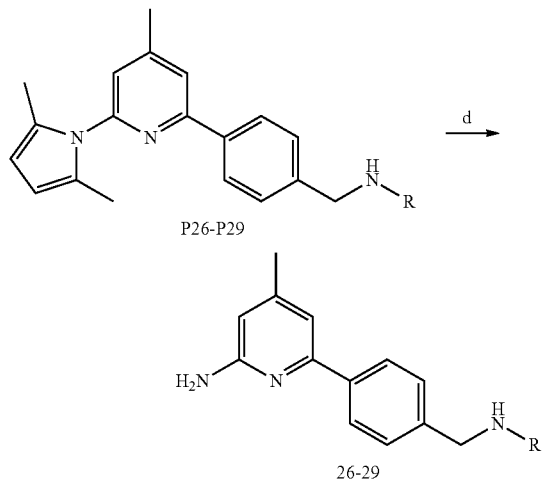

Scheme 2. a) Pd(PPh$_3$)$_4$, Na$_2$CO$_3$, toluene, 12 h, 100° C., 71%; b) DIBAL, CH$_2$Cl$_2$, 51% c) NaBH(OAc)$_3$, AcOH, CH$_2$Cl$_2$, room temperature, 12 h, 62%, d) NH$_2$OH(HCl) 5 eq, EtOH, H$_2$O, microwave, 120° C., 25 min, 60-80%.

To synthesize 30, Sonogashira coupling between VIII and IX were employed as shown Scheme 3. Hydrogen reduction of acetylene and nitrile moieties of X with Raney-Nickel yielded the desired aryl ethylamine XI. Treatment of formaldehyde with NaBH(OAc)$_3$ and following deprotection of 2,5-dimethylpyrrole gave the N-dimethylated product 30.

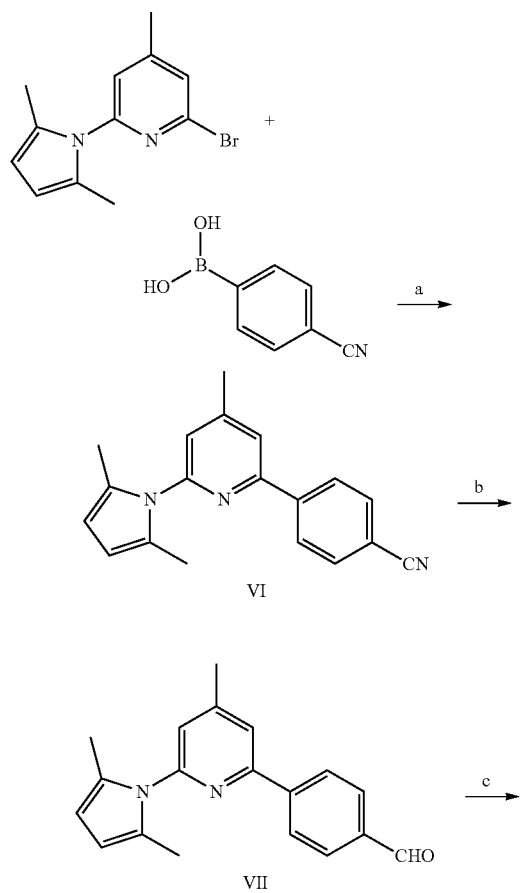

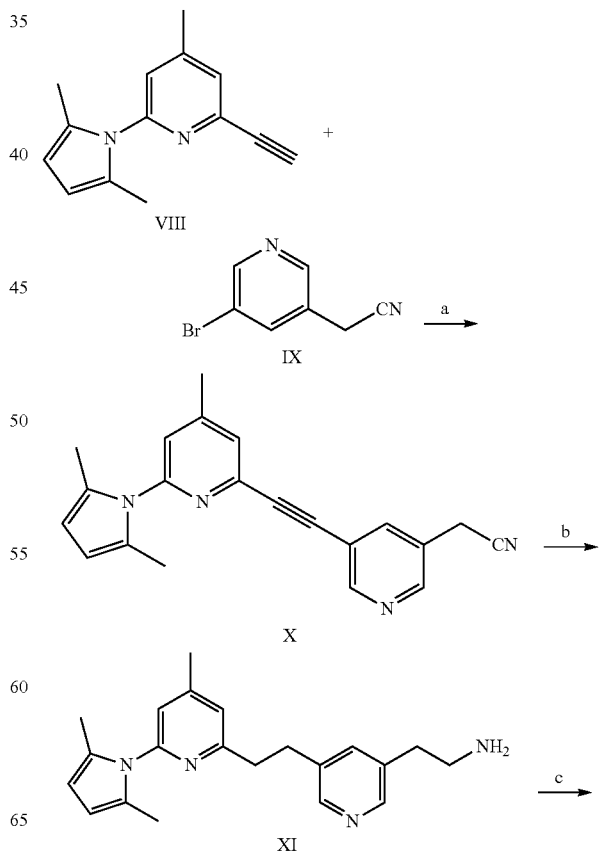

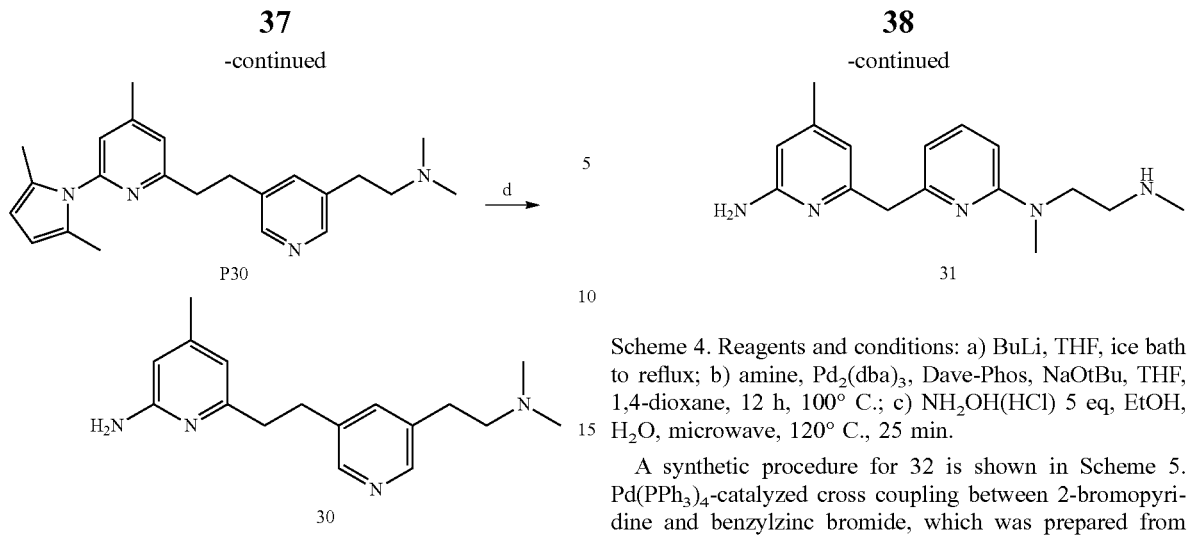

Scheme 3. Reagents and conditions: a) Pd(PPh$_3$)$_2$Cl$_2$, CuI, PPh$_3$, DEA, DMF; b) Raney-Ni, H$_2$, MeOH/EtOH; c) formaldehyde (35%), NaBH(OAc)$_3$, MeOH/CH$_2$Cl$_2$; d) NH$_2$OH (HCl) 5 eq, EtOH, H$_2$O, microwave, 120° C., 25 min.

With reference to Scheme 4, the methylene-linked bis (pyridine) derivative 31 was synthesized from lithiated 2-(2,5-dimethyl-1H-pyrrol-1-yl)-4,6-dimethylpyridine addition into 0.5 equivalents of 2,6-dichloropyridine as nucleophilic component. (See, Mohr, F., Binfield, S. A., Fettinger, J. C., and Vedernikov, A. N. A Practical, Fast, and High-Yielding Aziridination Procedure Using Simple Cu(II) Complexes Containing N-Donor Pyridine-Based Ligands *J. Org. Chem.* 2005, 70, 4833-4839.) Although branched byproducts are produced, two equivalents of the lithiated pyridine were used because compound XII includes an acidic methylene unit. Buchwald-Hartwig reaction with N$^1$,N$^2$-dimethylethane-1,2-diamine and deprotection of dimethylpyrrole gave final product 31.

Scheme 4. Reagents and conditions: a) BuLi, THF, ice bath to reflux; b) amine, Pd$_2$(dba)$_3$, Dave-Phos, NaOtBu, THF, 1,4-dioxane, 12 h, 100° C.; c) NH$_2$OH(HCl) 5 eq, EtOH, H$_2$O, microwave, 120° C., 25 min.

A synthetic procedure for 32 is shown in Scheme 5. Pd(PPh$_3$)$_4$-catalyzed cross coupling between 2-bromopyridine and benzylzinc bromide, which was prepared from BnBr and Zn, afforded 2-benzylpyridine (XIII). Similar to the synthesis of 26-29, N$^1$,N$^2$-dimethylethane-1,2-diamine tail was installed after conversion the carboxylate of XIII into benzaldehyde with DIBAL.

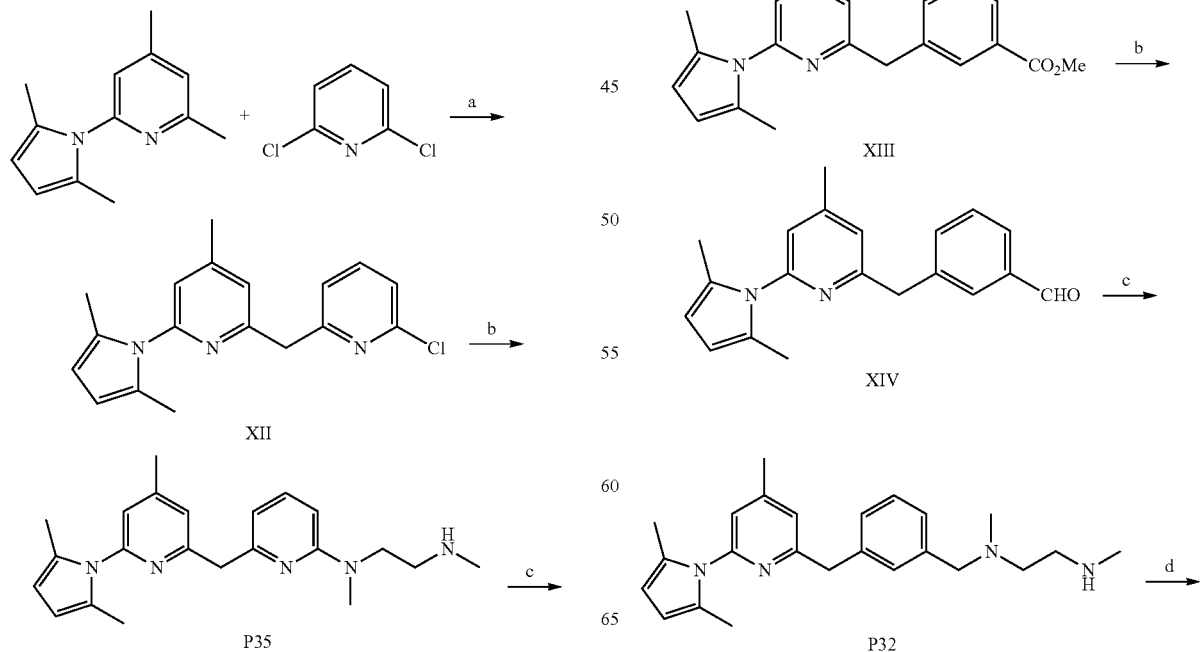

-continued

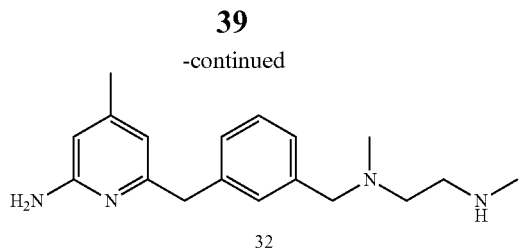

32

Scheme 5. Reagents and condition. a) Zn dust, Pd(PPh$_3$)$_4$, THF, room temperature, 12 h; b) DIBAL, toluene; c) NaBH(AcO)$_3$, AcOH, CH$_2$Cl$_2$, room temperature, 12 h; d) NH$_2$OH (HCl) 5 eq, EtOH, H$_2$O, microwave, 120° C., 25 min.

Figure 10:
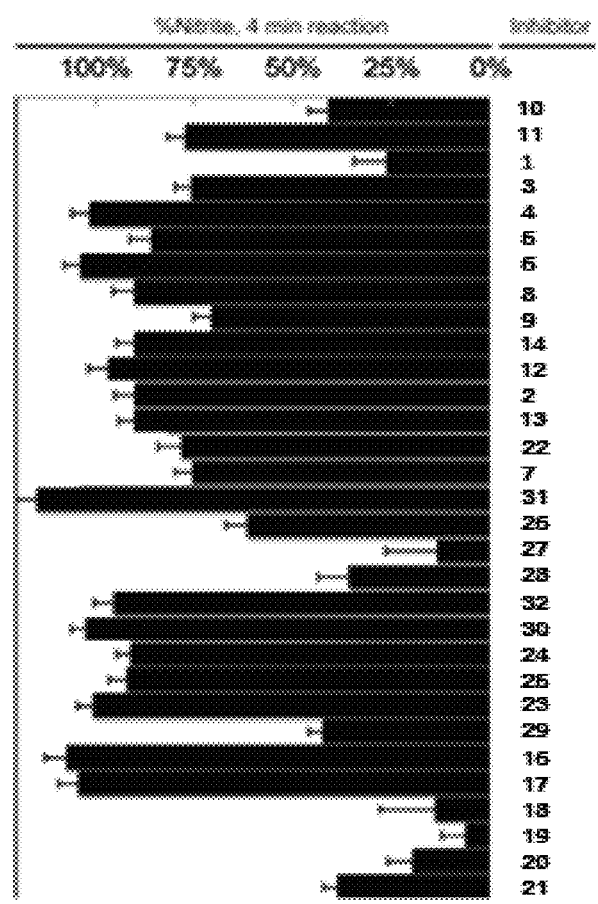
FIG. 10. NOS inhibitors have varying potency and binding affinity towards the active site. Nitrite concentrations were measured after 4 min incubation. Error bars represent the SEM for three separate experiments.

Rapid identification of molecular fragments that function as potent bNOS inhibitors is a necessary step towards the design and characterization of future bNOS inhibitors. In order to carry this out we adapted a previously reported bNOS activity assay to screen through a series of NOS inhibitors using a single time point approach (FIG. 10). Concurrently, the K$_S$ for each inhibitor was measured using the imidazole displacement assay (FIG. 10). While all inhibitors were observed to bind bsNOS within the μM range, the most potent bsNOS inhibitors identified from the activity analysis were also calculated to K$_S$ values within the low μM to nM range. By using the single time point approach in combination with the imidazole displacement assay, it was possible to identify compounds that were both potent inhibitors and tight binders to the active site. Since L-NNA is an excellent inhibitor analog of the NOS substrate L-Arg, the potency of L-NNA at 40.9±5.3% nitrite (FIG. 10) was established as an arbitrary threshold for identifying designer molecules with increased potency. Using L-NNA as a threshold of potency, several NOS inhibitors were classified as potent bNOS inhibitors. This group includes three aminoquinoline inhibitors, two 6-benzyl aminopyridine inhibitors, and two aminopyridine inhibitors. Of the two aminopyridine inhibitors, 11 was previously described as a NOS inhibitor with antimicrobial properties. Because the binding of aminopyridine inhibitors to bNOS was previously characterized, the most potent aminoquinoline and 6-benzyl-aminopyridine based inhibitors, 19 and 27, respectively, were selected for further analysis. Compounds 19 and 27 were also the two most potent inhibitors of the 40 NOS inhibitors evaluated, using the bNOS single time point analysis at 6.1% nitrite and 13.2% nitrite, respectively.

Compounds 19 and 27 were next assayed separately against purified NOS isoforms at varying concentrations. Even though the IC$_{50}$s for both mNOS and bNOS were measured by complimentary methods, both methods allowed for an excellent comparison of inhibitor potency, as IC$_{50}$ was used to calculate K$_i$ from the Cheng-Prusoff equation. From the K$_i$ analysis (Table 6), it is clear that both 19 (69.7 nM) and 27 (502 nM) function as potent bNOS inhibitors and demonstrate excellent selectivity over both iNOS and eNOS (Table 6). Unfortunately, neither 19 nor 27 demonstrated significant isoform selectivity for bNOS over mammalian nNOS. This difference in isoform selectivity may be clinically acceptable, but only if the inhibitor demonstrates poor blood-brain barrier permeability, as mammalian nNOS is primarily expressed in neuronal tissue.

TABLE 6

Inhibition of NOS isoforms by inhibitors 31 and 23. The bBiDomain construct was used to estimate the K$_i$ for bNOS.

| Inhibitor | K$_i$ bBiDomain (nM) | K$_i$ nNOS (nM) | K$_i$ iNOS (nM) | K$_i$ eNOS (nM) |
|---|---|---|---|---|
| 27 | 502 | 525 | 6440 | 2870 |
| 19 | 69.7 | 164 | 31900 | 7250 |

To better understand the structural basis for inhibitor potency and selectivity inhibitor bound crystal structures of 27 and 19 were solved (FIG. 11, Table 7). While the compounds are chemically very different, both 27 and 19 bound to the active site Glu-243 through a series of H-bonds. In addition, binding of 27 and 19 was further stabilized by H-bonds between the secondary amine of each inhibitor and the heme propionate groups. Direct comparison of the bsNOS-19 and the previously reported nNOS-19 revealed the binding mode of 19 to be unchanged between the two NOS isoforms. However, the binding mode in bsNOS is further stabilized by the hydrophobic contact between the Ile-218 residue and the aminoquinoline group of 19. Because Ile-218 is within van deer Waals contact of 19 and the analogous residue in nNOS is Val-567, data suggest that slight differences in hydrophobicity between Ile and Val allow for improved binding of 19 to bsNOS.

Figure 11A:
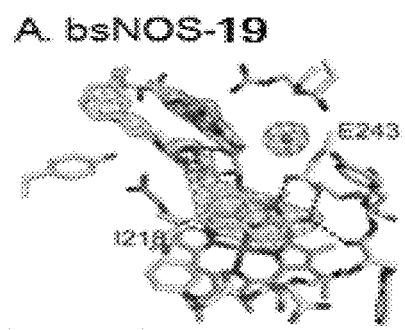
FIGS. 11A-D. Inhibitor bound NOS crystal structures with select side chains colored white, heme group colored salmon and both the active site inhibitor and $H_4B$ molecule colored yellow. Both 19 and 27 make hydrophobic contact with bsNOS I218; yet I218 does not influence the binding mode of inhibitor. A) 19 bound to bsNOS with $2F_o$-$F_c$ map contoured at 1.8σ. B) 19 bound to nNOS (PDB 4CAO). C) 27 bound to bsNOS with $2F_o$-$F_c$ map contoured at 1.8σ. D) 27 bound to I218V bsNOS with $2F_o$-$F_c$ map contoured at 1.8σ.
Figure 11B:
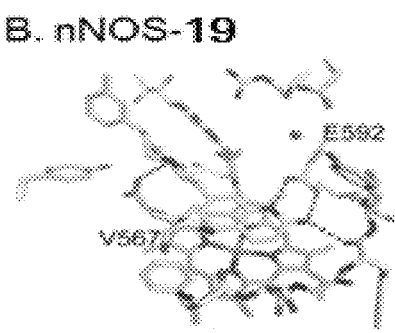
Figure 11C:
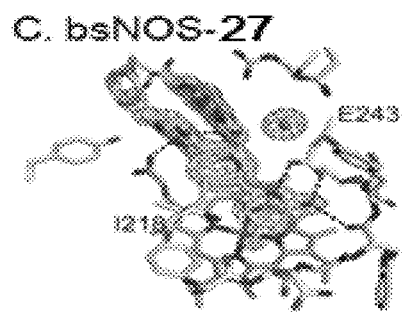
Figure 11D:
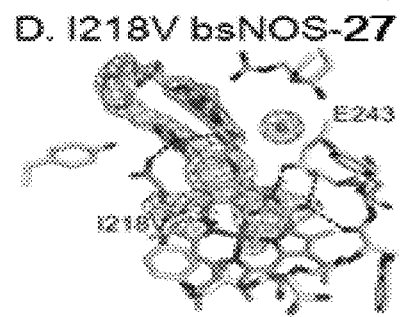

Similar to 19, crystal structure analysis of 27 demonstrates the inhibitor-binding mode to be further stabilized by the hydrophobic contact between the inhibitor and Ile-218 (FIG. 11C). Unable to obtain crystal structures of 31 to mNOS, Ile-218 was mutated to a Val residue in bsNOS. Interestingly, the mutant crystal structure revealed the inhibitor-binding mode to be unchanged, as compared to the wild-type enzyme. To evaluate the contribution of Ile-218 to the inhibitor-binding mode, inhibitor binding was measured using the imidazole displacement assay. From this analysis, the inhibitor binding of both 19 and 27 was found to be ~5-6 fold tighter to Ile-218 over I218V (Table 8). Between the crystal structures and binding assay results, data suggest that the increased hydrophobicity of Ile-218 over the analogous mNOS Val residue improves inhibitor binding to bNOS. Considering that Ile-218 is conserved across all bNOS enzymes, future inhibitors designed to target bNOS may well continue to exploit Ile-218 by using the scaffolds of 19 and 27.

TABLE 7

Data collection and refinement statistics for *B. subtilis* NOS-inhibitor bound structures.

| PDB Code | bsNOS-19 | bsNOS-27 | I218V bsNOS-27 |
|---|---|---|---|
| Data Collection | | | |
| Wavelength (Å) | 0.976484 | 0.918370 | 0.999746 |
| Space group | P2$_1$2$_1$2 | P2$_1$2$_1$2 | P2$_1$2$_1$2 |

TABLE 7-continued

Data collection and refinement statistics for *B. subtilis* NOS-inhibitor bound structures.

| PDB Code | bsNOS-19 | bsNOS-27 | I218V bsNOS-27 |
|---|---|---|---|
| Cell dimensions | | | |
| a, b, c (Å) | 80.9 94.7 62.8 | 80.5 94.8 62.8 | 80.6 95.0 61.6 |
| α, β, γ (°) | 90 90 90 | 90 90 90 | 90 90 90 |
| Total Observations | 168110 (6783) | 456677 (22720) | 147923 (10525) |
| Unique | | | |
| Observations | 32128 (2261) | 70341 (3408) | 34480 (2411) |
| Resolution (Å) | 49.62-2.02 (2.07-2.02) | 37.06-1.55 (1.58-1.55) | 48.94-1.96 (2.01-1.96) |
| $R_{merge}$ | 0.128 (0.570) | 0.052 (2.522) | 0.135 (1.518) |
| $R_{PIM}$ | 0.078 (0.530) | 0.033 (1.599) | 0.096 (1.074) |
| $CC_{1/2}$ | 0.997 (0.834) | 1.000 (0.528) | 0.992 (0.558) |
| I/σI | 10.1 (1.6) | 18.0 (0.6) | 7.3 (1.0) |
| Completeness (%) | 99.5 (97.5) | 99.8 (99.8) | 99.6 (100.0) |
| Multiplicity | 5.2 (3.0) | 6.5 (6.7) | 4.3 (4.4) |
| Wilson B-factor | 29.788 | 22.417 | 21.444 |

*Values in parentheses are for highest-resolution shell.

TABLE 8

Calculated $K_S$ by imidazole displacement for NOS inhibitors to bsNOS.

| Compound | WT – $K_S$ (μM) | I218V – $K_S$ (μM) |
|---|---|---|
| L-Arg | 4.8 ± 0.1 (25) | 2.0 ± 0.2 (25) |
| 19 | 3.6 ± 0.8 | 18 ± 2 |
| 27 | 8.8 ± 2.0 | 58 ± 4 |

To evaluate the antibacterial potential of NOS inhibitors 19 and 27 on bacterial growth, the highly virulent CA-MRSA strain UAMS118 representative of the USA300 clonal linage, and a previously engineered isogenic NOS deletion mutant were utilized. Since previous experiments have shown bacterial Δnos strains to be more susceptible to $H_2O_2$-mediated killing, the effect of NOS inhibitors and $H_2O_2$ was evaluated on *S. aureus* (FIG. 12). Results both confirm previous findings that the Δnos strain is more susceptible to $H_2O_2$-mediated killing compared to the wild-type strain, and further demonstrate that co-treatment of *S. aureus* with $H_2O_2$ and either 19 or 27 significantly increases the $H_2O_2$-mediated killing of the bacteria. Together these data suggest that survival of MRSA can be significantly lowered in the presence of oxidative stress when a NOS inhibitor impairs bacterial NO production. These results are consistent with previous results indicating that blockade of NO signaling increases bacterial susceptibility to oxidative stress, and indicate that 19 and 27 can function as antimicrobials. Considering that many existing antibiotics function through an oxidative mechanism, bNOS inhibitors like 19 and 27 could function to increase the killing efficiency of such agents. Despite the combined effect of NOS inhibitors and $H_2O_2$ on *S. aureus* survival, bacteria treated with 19 or 27 alone at 200 μM also showed reduced bacterial survival over time. The decreased survival observed for both WT and the Δnos strains as a result of 19 or 27 treatments implies that both molecules have off-target effects to limit bacterial growth.

While induction of oxidative stress can be demonstrated using $H_2O_2$, various other antimicrobial agents known in the art, currently or hereafter, can be used in conjunction with this invention. Such agents include but are not limited to 5-chloro-7-iodo-8-hydroxyquinoline, 8-hydroxyquinoline, 8-hydroxy-5-nitroquinoline, novobiocin, acriflavine, 9-aminoacridine, prochlorperazine, chlorpromazine, penimepicycline, sisomicin, gentamicin, cephaloridine, 7-aminocephalosporanic acid, cefotaxime, cefuroxime, ampicillin, moxalactam, 6-aminopenicillanic acid, amoxicillin and azlocillin. (See, Gusarov, I., Shatalin, K., Starodubtseva, M. and Nudler, E. Endogenous nitric oxide protects bacteria against a wide spectrum of antibiotics. *Science* 325, 1380-1384 (2009)). Likewise, various other compounds known to inhibit mammalian nitric oxide synthase can be utilized, such compounds including but not limited to those disclosed and/or taught by the references incorporated herein.

Figure 13:
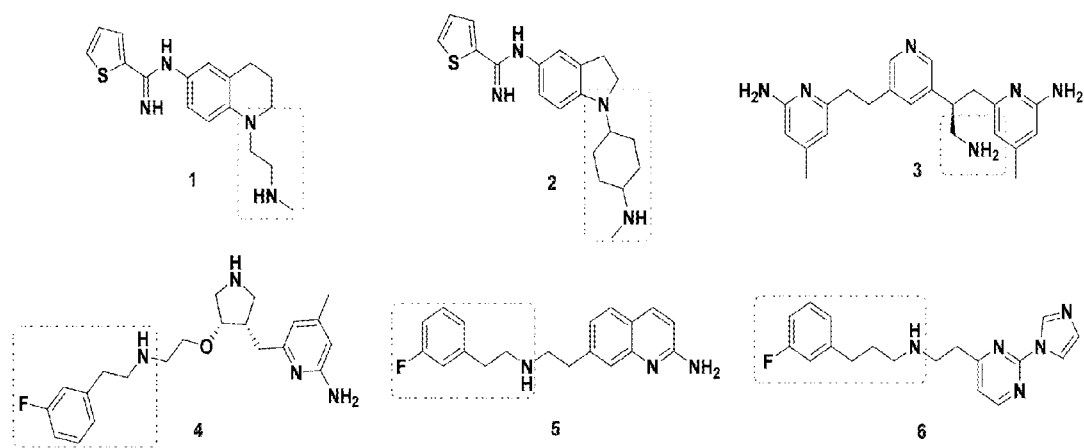
FIG. 13. Structures of recent nNOS inhibitors, which share common pharmacophores (Prior Art).
Figure 15:
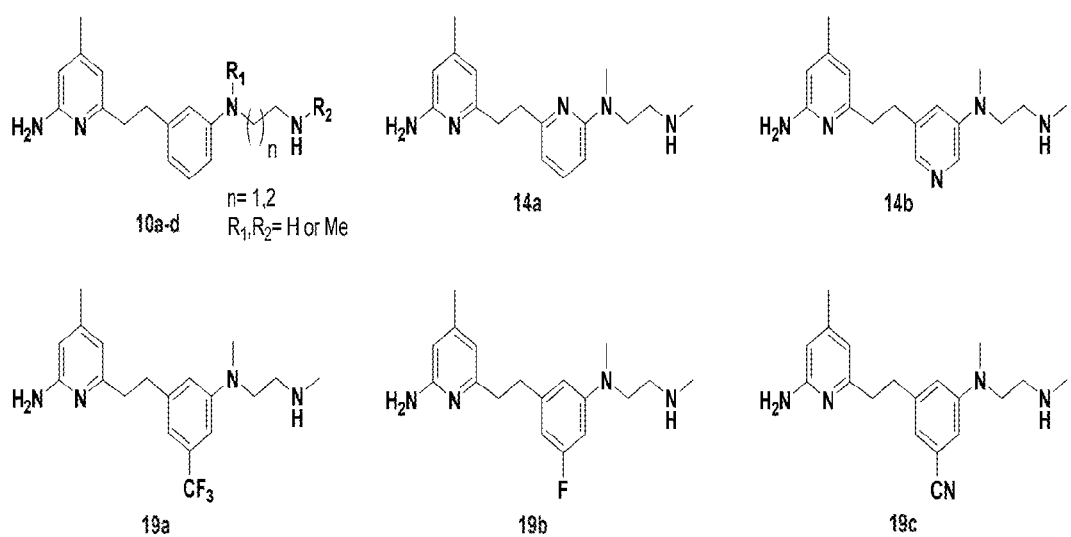
FIG. 15. Structures of selected synthesized $N^1,N^2$-dimethylethylenediamine derivatives in accordance with certain embodiments of this invention.

More generally, with regard to mNOS, many nNOS inhibitors have been reported (FIG. 13), but development of selective inhibitors of nNOS against iNOS and eNOS remains a challenge because the active sites of NOSs are nearly identical among all three isoforms. For historical reasons, rat nNOS and bovine eNOS have been used for crystallographic studies. In these studies, it was concluded that a guanidine isostere such as 2-aminopyridine and 2-aminoquinoline, or an iron-binding motif such as 2-imidazolylpyrimidine, achieved the NOS active site recognition via hydrogen bonds with an active site glutamate residue or by a direct ligation bond to the heme iron. In addition, the 3-fluorophenethyl moiety of 4-6 was thought useful for additional selectivity by occupying a peripheral hydrophobic pocket along the substrate access channel. A unique nNOS selective induced-fit conformational change has also been observed in which Tyr706 of rat nNOS is more readily rotated out to adopt an out-rotamer conformation, while the corresponding Tyr477 in bovine eNOS remained in an in-rotamer position. The out-rotamer conformation provides better H-bonding (salt-bridge) between the protein (heme propionates) and inhibitors, thus increasing nNOS potency and selectivity over eNOS.

The design of rat nNOS-selective inhibitors has been useful for success in preclinical studies, leading to clinical studies. However, because drugs are typically designed for human disease treatment, it is imperative to attain high potency for human targets. If drug candidates are excellent human target inhibitors, but weak lower animal target inhibitors, they will never have acceptable efficacy to advance to clinical trials. Likewise, if they are excellent lower animal target inhibitors, but weak human target inhibitors, they will fail in clinical trials. Therefore, it is imperative to identify target inhibitors that have comparable and high potency for both lower animal and human targets.

Because the primary sequence of rat nNOS is almost identical (>93%) to human nNOS and the nNOS active site for each mammalian species is highly conserved, an inhibitor binding to rat nNOS was thought to reflect the binding behaviors to human nNOS. However, it has been observed that compounds that were developed based on the rat nNOS crystal structure often displayed 5- to 10-fold weaker inhibitory activity toward human nNOS. Recently, efforts succeeded in obtaining a crystal structure of human nNOS. (Li, H.; Jamal, J.; Plaza, C.; Pineda, S. H.; Chreifi, G.; Jing, Q.; Cinelli, M. A.; Silverman, R. B.; Poulos, T. L. Structures of human constitutive nitric oxide Synthases. *Acta Crystallogr.* 2014. D70, 2667-2674.) An active site overlay of human nNOS with rat nNOS (FIG. 14B) showed that the active site structures of the two mammalian nNOSs are identical, and the only difference is in the peripheral pocket, where Leu337 of rat nNOS is replaced by a histidine (His342) in human nNOS (FIG. 14C). The human peripheral pocket containing a histidine is relatively more narrow and more polar; consequently, it prefers inhibitors to have a less bulky and more hydrophilic tail. That may explain why previous nNOS selective compounds fit well into the rat NOS Leu337 hydrophobic pocket but displayed decreased potency against human nNOS.

As can relate to the development of certain other embodiments of this invention, compounds 1 and 2 (FIG. 13), having an amidine and a methylamine tail with a tetrahydroquinoline or indoline core, recently reported by other research groups, display good potency toward human nNOS. (Reference is made to Tables 9-12, schemes 6-14, examples 40-106, FIGS. 13-20 and the compounds separately numbered therein and discussed below.) Although 3-dimensional structural information of these compounds with nNOS were not reported, previous crystallographic experience indicates that the thiophene-carboximidamide moiety should occupy the substrate binding pocket over the heme, and the tetrahydroquinoline or indole core should share the binding site with the middle aromatic ring of 3 near the C and D ring propionates (See, (a) Huang, H.; Li, H.; Yang, S.; Chreifi, G.; Martásek, P.; Roman, L. J.; Meyskens, F. L.; Poulos, T. L.; Silverman, R. B. Potent and selective double-headed thiophene-2-carboximidamide inhibitors of neuronal nitric oxide synthase for the treatment of melanoma. *J. Med. Chem.* 2014, 57, 686-700. (b) Jing, Q.; Li, H.; Roman, L. J.; Martásek, P.; Poulos, T. L.; Silverman, R. B. Combination of chiral linkers with thiophenecarboximidamide heads to improve the selectivity of inhibitors of neuronal nitric oxide synthase. *Bioorg. Med. Chem. Lett.* 2014, 24, 4504-4510). The N-methyl substituted alkylamine chains from the core should improve the selectivity and potency by interacting with residues peripheral to the active site.

It was recently reported a double-headed aminopyridine compound (3, FIG. 13) that uses its methylamine group to interact with both heme propionate A and the H$_4$B, thereby displacing a water molecule. Although the same binding mode was maintained in both nNOS and eNOS, different electrostatic environments in the active site of nNOS and eNOS resulted in distinct isoform binding affinity, leading to good isoform selectivity. (Kang, S.; Tang, W.; Li, H.; Chreifi, G.; Martásek, P.; Roman, L. J.; Poulos, T. L.; Silverman, R. B. Nitric oxide synthase inhibitors that interact with both heme propionate and H$_4$B show high isoform selectivity. *J. Med. Chem.* 2014, 57, 4382-4396.)

On the basis of these observations new human nNOS selective and potent compounds were designed via hybridization of the potent molecular fragment of compound 3 (the 2-aminopyridine attached to an aromatic ring) and the human nNOS adaptable alkylamine fragment from compound 1, with the goal of displacing the H$_4$B conserved water molecule. It is possible that the alkylamine fragment of compound 1 corresponds to the alkylamine tail of compound 3. To avoid the Leu337/His342 difference between rat nNOS and human nNOS in the hydrophobic cleft one of the aromatic heads of compound 3 was removed and substituted with an alkylamine chain. The other aminopyridine ring of 3 was retained as an isostere of guanidine, and the middle aromatic linker and $N^1$ or $N^2$-methyl substituted ethylenediamine tail were varied. Because substitution on the middle aromatic ring provided bioactivity during previous exploration with symmetric molecules, the middle aromatic linker was substituted with cyano, fluorine, trifluoromethyl, and substituted by pyridine. (Huang, H.; Li, H.; Martásek, P.; Roman, L. J.; Poulos, P. L.; Silverman, R. B. Structure-guided design of selective inhibitors of neuronal nitric oxide synthase. *J. Med. Chem.* 2013, 56, 3024-3032.) The molecules in FIG. 15, having a truncated side chain and various substitutions of the middle aromatic ring, were synthesized and their inhibitory potencies were determined in vitro. Crystal structures of the promising compounds were obtained using either rat nNOS or human nNOS, as well as bovine eNOS. As a result, the present invention provides a modified scaffold, as compared to previous aminopyridine derivatives, for improved potency against human nNOS for investigation of its influence on the binding mode, and a foundation for further design of potent, selective, and bioavailable inhibitors for human nNOS.

All compounds described here were prepared from various aryl bromides in three steps: a coupling reaction, a Buchwald-Hartwig amination, and pyrrole deprotection (Schemes 6-8). The coupling reaction of an aryl bromide (8, 11a-b, 15a-c) and lithiated pyrrolyl-4,6-dimethylpyridine, which was prepared by addition of BuLi to pyrrolyl-4,6-dimethylpyridine (7), gave an arylethylpyridine intermediate (9, 12a-b, 16a-c). One bromine atom in dibromo intermediate 16c was converted to the nitrile (17) by microwave assisted cyanation with CuCN. Next, Buchwald-Hartwig amination of 9, 12a-b, 16a-b, and 17 with N,N-dimethyldiamine was performed using a catalytic amount of Pd$_2$(dba)$_3$ and DavePhos. (Surry, D. S.; Buchwald, S. L. Dialkylbiaryl phosphines in Pd-catalyzed amination: a user's guide. *Chem. Sci.* 2011, 2, 27-50.) Sterically hindered ligand DavePhos was more efficient than BINAP and DPPF at coupling with a secondary amine. Finally, the pyrrole protecting group on the aminopyridine was removed from 9, 13a-b, and 18a-c by microwave-aided hydrolysis to give final compounds 10a-d, 14a-b, and 19a-c in good yields. Because the Buchwald-Hartwig products of 9a-d produced mainly the desired amine intermediates, those intermediates were passed through a 2-cm silica gel pad and used in the next deprotection step without further purification or characterization. Purification of these final polar compounds was performed by flash column chromatography using C-18 prepacked cartridges. (Analogous synthetic procedures are outlined in Schemes 9-10, to provide compounds 21a-e and 23a-i. Alternate synthetic procedures are outlined in Schemes 11-14, to provide separately numbered compounds.)

Scheme 6.<sup>a</sup>

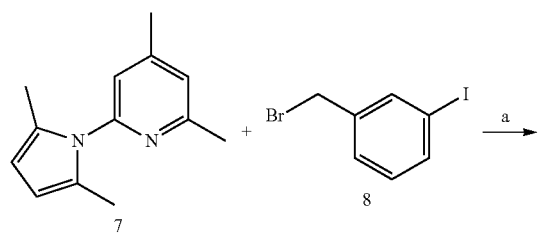

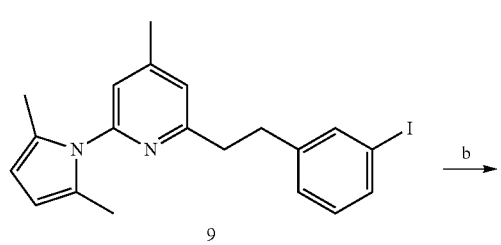

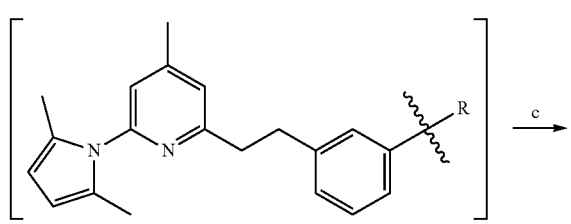

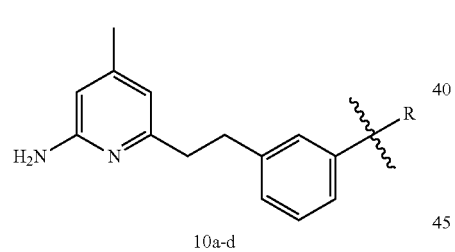

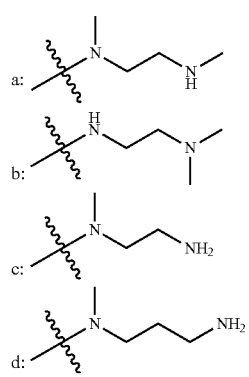

<sup>a</sup>Reagents and conditions: (a) (i) 7, BuLi, 0° C., 30 min, THF; (ii): 8, 94%; (b) Pd₂(dba)₃, DavePhos, NaOtBu, diamine a-d, THF, 1,4-dioxane, 5~10 h, 100° C.; (c) conc-HCl, EtOH, microwave, 120° C., 20 min. two-step yield: 31-48%.

Scheme 7.<sup>a</sup>

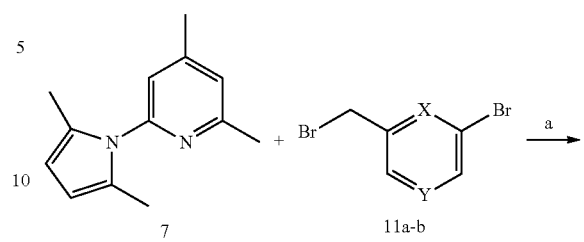

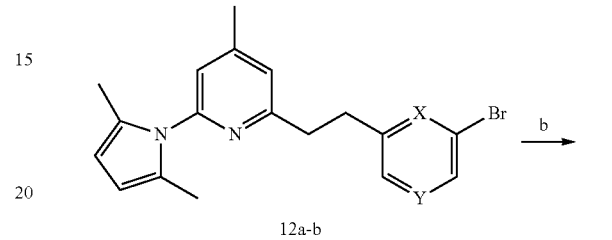

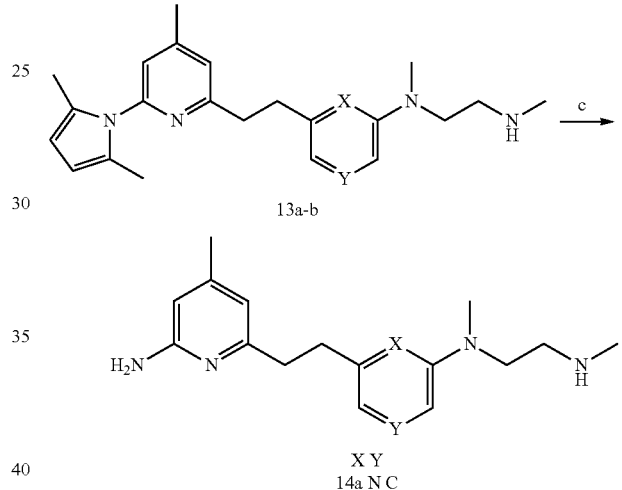

| X | Y |
|---|---|
| 14a | N C |
| 14b | C N |

<sup>a</sup>Reagents and conditions:
(a) (i) 7, BuLi, 0° C., 30 min, THF;
(ii): 11a-b, 89-91%;
(b) N¹, N²-dimethylethane-1,2-diamine (2 equiv), Pd₂(dba)₃, DavePhos, NaOtBu, THF, 1,4-dioxane, 5~10 h, 100° C., 87-91%;
(c) NH₂OH•HCl (5 equiv), EtOH, H₂O, microwave, 120° C., 30 min, 65-70%.

Scheme 8.<sup>a</sup>

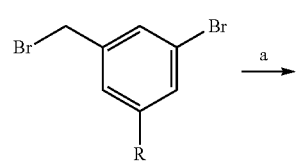

15a CF₃
15b F
15c Br

-continued

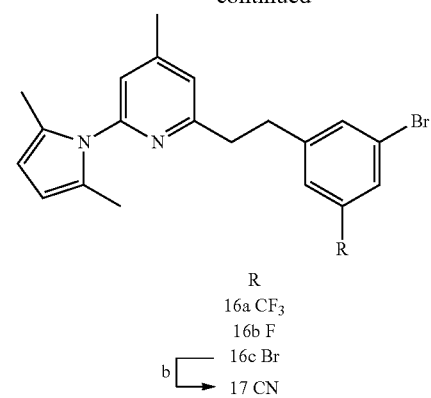

R
16a CF$_3$
16b F
16c Br
b ⎣→ 17 CN

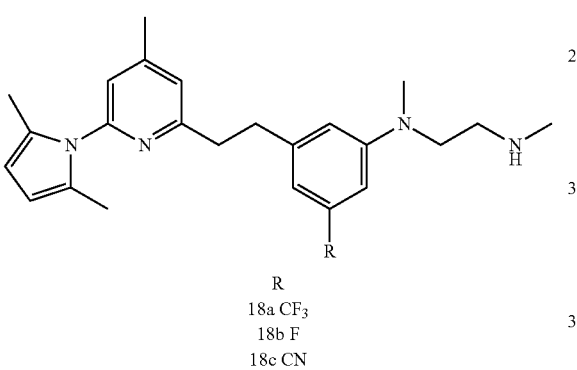

R
18a CF$_3$
18b F
18c CN d ↓

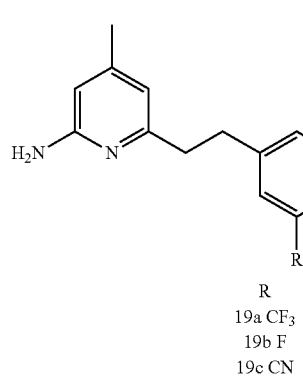

R
19a CF$_3$
19b F
19c CN

[a]Reagents and conditions:
(a) (i) 7, BuLi, 0° C., 30 min, THF;
(ii): 15a-c, 81-86%;
(b) CuCN, DMF, microwave, 220° C., 20 min, 57%;
(c) N$^1$, N$^2$-dimethylethane-1,2-diamine (2 equiv), Pd$_2$(dba)$_3$, DavePhos, NaOtBu, THF, 1,4-dioxane, 5 h, 100° C., 75%;
(d) NH$_2$OH•HCl (5 equiv), EtOH, H$_2$O, microwave, 120° C., 30 min, 62-81%.

Scheme 9.[a]

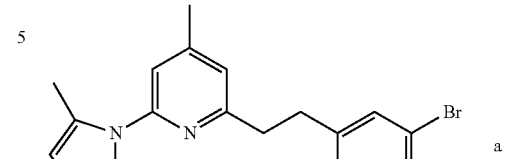

17

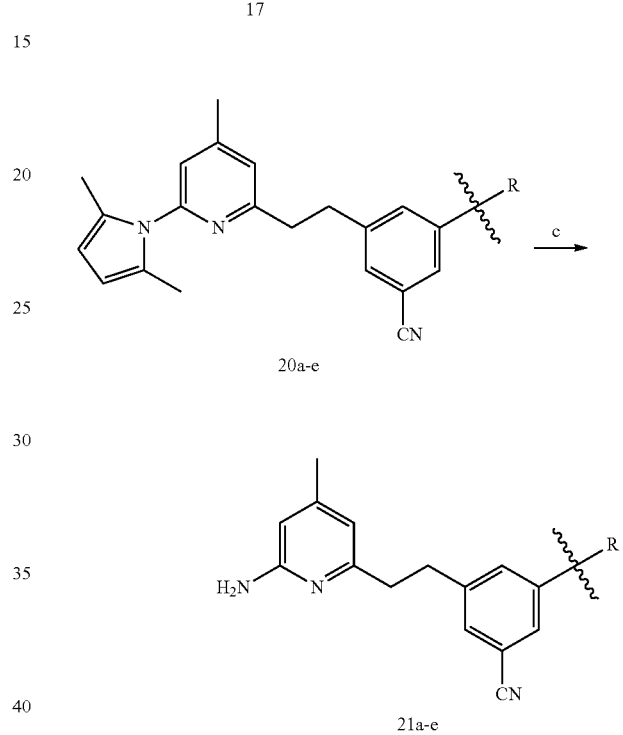

20a-e 21a-e

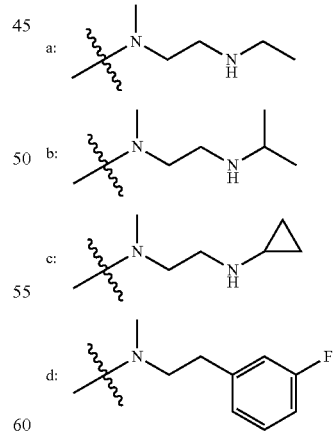

[a]Reagents and condition:
(a) 21, amine (2 eq), Pd$_2$(dba)$_3$, Dave-Phos, NaOtBu, THF, 1,4-dioxane, 5~10 h, 100° C., 69-90%;
(b) NaH, MeI, THF 61%;
(c) NH$_2$OH(HCl) 5 eq, EtOH, H$_2$O, microwave, 120° C., 25 min, 60-80%.

Scheme 10.[a]
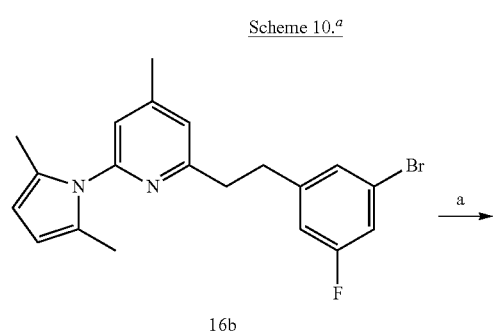
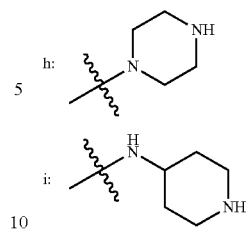
[a]Reagents and condition:
(a) 19, amine (2 eq), Pd₂(dba)₃, Dave-Phos, NaOtBu, THF, 1,4-dioxane, 5~10 h, 100° C., 28-93%;
(b) NH₂OH(HCl) 5 eq, EtOH, H₂O, microwave, 120° C., 25 min, 60-80%.
Scheme 11.
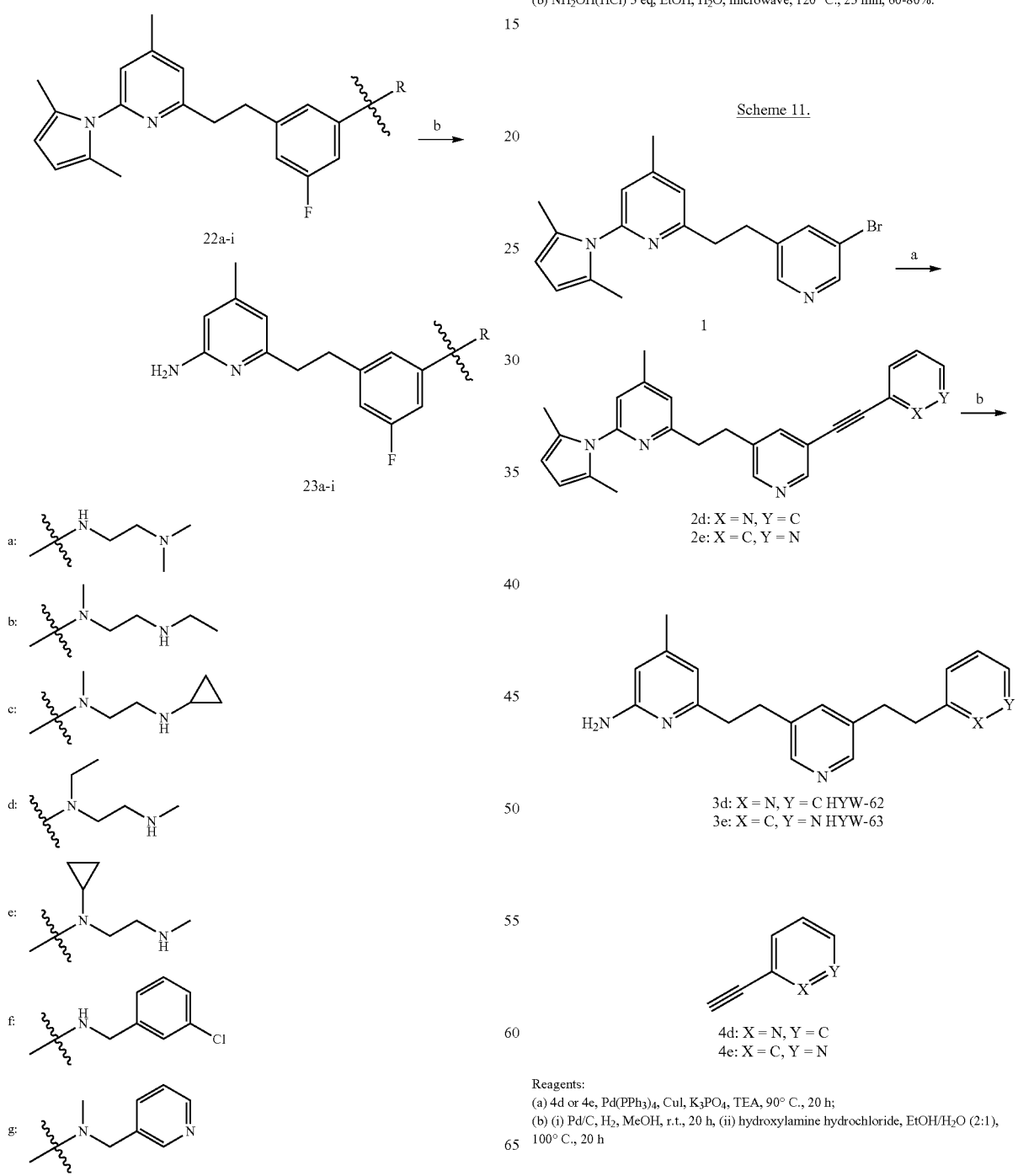
Reagents:
(a) 4d or 4e, Pd(PPh₃)₄, CuI, K₃PO₄, TEA, 90° C., 20 h;
(b) (i) Pd/C, H₂, MeOH, r.t., 20 h, (ii) hydroxylamine hydrochloride, EtOH/H₂O (2:1), 100° C., 20 h Scheme 12.

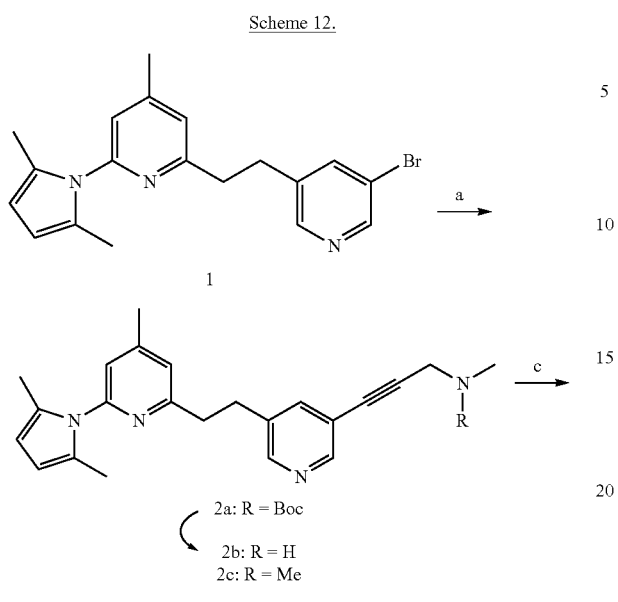

Reagents:
(a) 4a or 4c, Pd(PPh₃)₄, CuI, K₃PO₄, TEA, 90° C., 20 h;
(b) 20% TFA in DCM, r.t., 1 h; (i) Pd/C, H₂, MeOH, r.t., 20 h, (ii) hydroxylamine hydrochloride, EtOH/H₂O (2:1), 100° C., 20 h Scheme 13.

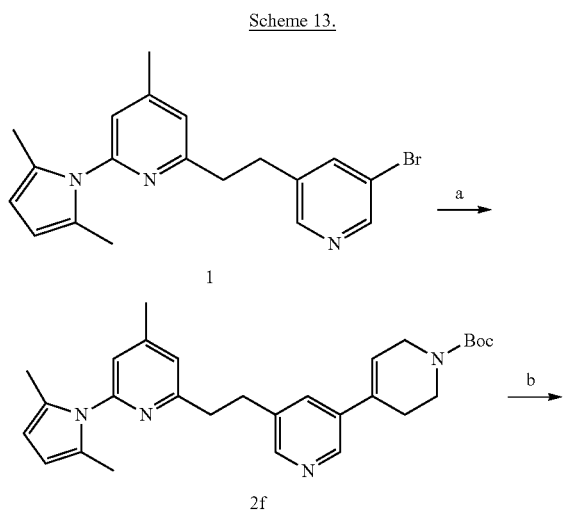

Reagents:
(a) 4f, Pd(OAc)₂, SPhos, K₃PO₄, toluene/H₂O (20:1), 100° C., 20 h, 68%;
(b) (i) Pd/C, H₂, MeOH, r.t., 20 h, (ii) LAH, THF, 0° C., to reflux, 1 h, (iii) hydroxylamine hydrochloride, EtOH/H₂O (2:1), 100° C., 20 h Scheme 14.

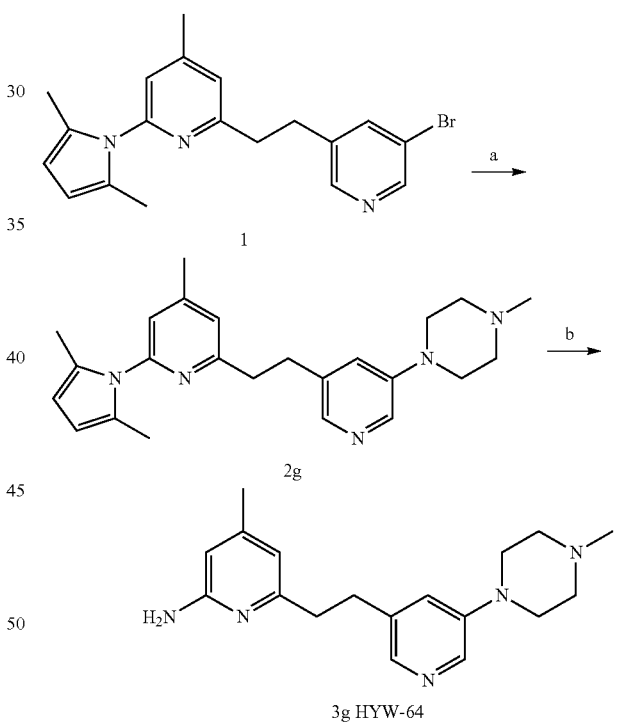

Reagents:
(a) (i) Piperazine, Pd₂(dba)₃, DavePhos, NaO$^t$Bu, dioxane, 100° C., 20 h, (ii) MeI, triethylamine, THF, r.t., 1 h;
(b) hydroxylamine hydrochloride, EtOH/H₂O (2:1), 100° C., 20 h Various other NOS inhibitor compounds, in accordance with certain non-limiting embodiments of this invention, can be prepared using well-known synthetic techniques, as would be understood by those skilled in the art made aware of this invention. Structural analogues of the compounds shown can be prepared using such techniques or straightforward variations thereof, such analogous compounds limited only by commercial or synthetic availability of corresponding starting materials and reagents, such techniques, variations, starting materials and reagents as would also be understood by those skilled in the art and made aware of this invention.

The oxyhemoglobin NO assays were performed with purified NOSs to measure $K_i$ values of the synthesized compounds, as previously described in the literature. Compounds 10a-d were found to have good potency for rat nNOS and modest isoform selectivity toward bovine eNOS and murine iNOS. Compounds 14a-b and 19a-c, having an N,N'-dimethylethylenediamine tail and a modified middle aromatic ring, were found to have good binding affinity to both rat and human nNOS as well as good selectivity (238-1040 of e/n, 122-166 of i/n). Inhibitory constants ($K_i$) for all of the synthesized molecules are shown in Table 9.

Table 9a. List of $K_i$ values and selectivity

| Name | structure | Ki (nM)* | | | | i/n | e/n |
| --- | --- | --- | --- | --- | --- | --- | --- |
| | | Rat nNOS | H nNOS | iNOS | eNOS | | |
| 10a | 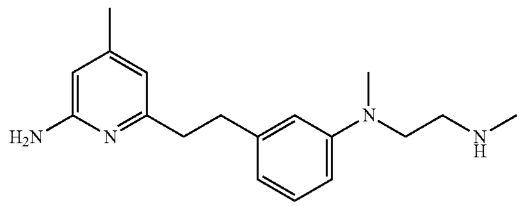 [SMILES: CNCCN(C)c1cccc(CCc2cc(C)cc(N)n2)c1] | 130 ± 10 | 98 ± 5 | 5,340 ± 336 | 20,240 ± 1032 | 41 | 156 |
| 10b | 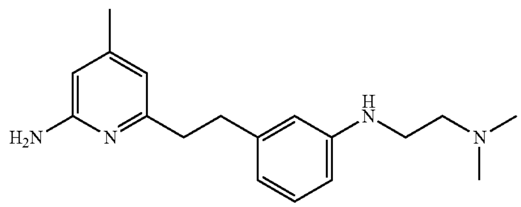 [SMILES: Cc1cc(N)nc(CCc2cccc(NCCN(C)C)c2)c1] | 190 ± 12 | 111 ± 9 | 5,430 ± 412 | 23,700 ± 1432 | 29 | 125 |
| 10c | 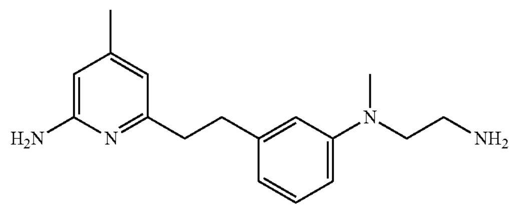 [SMILES: Cc1cc(N)nc(CCc2cccc(N(C)CCN)c2)c1] | 62 ± 4.1 | 56 ± 2 | 2,900 ± 187 | 10,675 ± 874 | 47 | 172 |
| 10d | 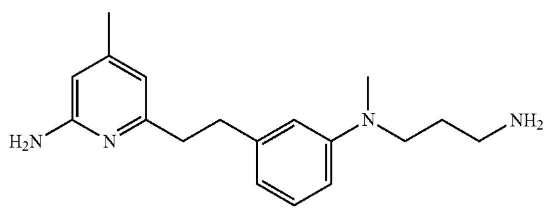 [SMILES: Cc1cc(N)nc(CCc2cccc(N(C)CCCN)c2)c1] | 430 ± 22 | 109 ± 3 | 4,640 ± 296 | 10,680 ± 886 | 11 | 25 |
| 14a | 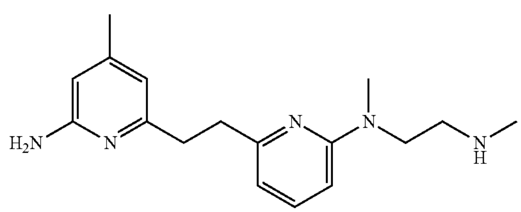 [SMILES: CNCCN(C)c1cccc(CCc2cc(C)cc(N)n2)n1] | 35 ± 2.0 | 64 ± 2.2 | 4,845 ± 310 | 17,742 ± 1244 | 138 | 507 |
| 14b | 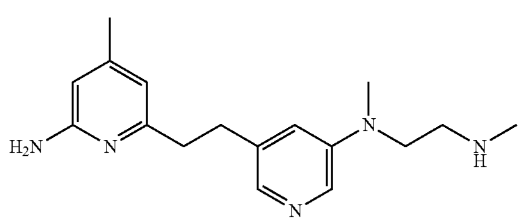 [SMILES: CNCCN(C)c1cncc(CCc2cc(C)cc(N)n2)c1] | 17 ± 1.6 | 59 ± 3.2 | 2,152 ± 129 | 12,910 ± 1008 | 127 | 759 |

| | | -continued | | | | | |
|---|---|---|---|---|---|---|---|
| 19a | (structure: 6-amino-4-methylpyridine linked via ethyl to 3-(N-methyl-N-(2-(methylamino)ethyl)amino)-5-trifluoromethylphenyl) | | 67 ± 3.3 | 189 ± 16 | 8,134 ± 760 | 15,940 ± 1266 | 122 | 238 |
| 19b | (structure: 6-amino-4-methylpyridine linked via ethyl to 3-(N-methyl-N-(2-(methylamino)ethyl)amino)-5-fluorophenyl) | | 34 ± 1.2 | 105 ± 8.1 | 5,559 ± 421 | 30,238 ± 2046 | 166 | 903 |
| 19c | (structure: 6-amino-4-methylpyridine linked via ethyl to 3-(N-methyl-N-(2-(methylamino)ethyl)amino)-5-cyanophenyl) | | 24 ± 1.1 | 55 ± 3.4 | 3,669 ± 223 | 24,950 ± 1684 | 153 | 1040 |

Table 9b. List of Ki values and selectivity

| Name | structure | Ki nNOS (nM) | H nNOS | Ki iNOS (nM) | Ki eNOS (nM) | i/n | e/n |
|---|---|---|---|---|---|---|---|
| 21a | (structure: 6-amino-4-methylpyridine linked via ethyl to 3-(N-methyl-N-(2-(ethylamino)ethyl)amino)-5-cyanophenyl) | 64 | 225 | 11469 | 37605 | 178.0 | 583.7 |
| 21b | (structure: 6-amino-4-methylpyridine linked via ethyl to 3-(N-methyl-N-(2-(isopropylamino)ethyl)amino)-5-cyanophenyl) | 125 | 357 | 45110 | 39944 | 361.5 | 320.1 |

-continued

| | | | | | | | |
|---|---|---|---|---|---|---|---|
| 21c | [structure] | 114 | 378 | 27992 | 31096 | 246.6 | 274.0 |
| 21d | [structure] | 1796 | N.D. | 45300 | N.D. | 33.7 | N.D. |
| 23a | [structure] | 70 | 758 | 3314 | 9582 | 47.3 | 136.9 |
| 23b | [structure] | 32 | 194 | 6381 | 17,870 | 199.4 | 558.4 |
| 23c | [structure] | 50 | 243 | 10892 | 6212 | 217.8 | 124.3 |
| 23d | [structure] | 46 | 139 | 5043 | 4288 | 109.6 | 93.2 |

| | | | | | | | |
|---|---|---|---|---|---|---|---|
| 23e | 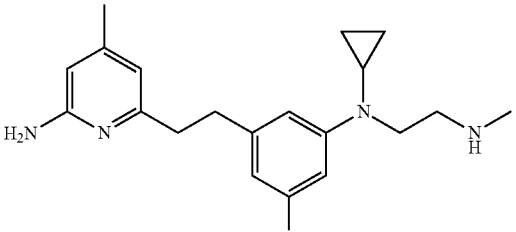 | 56 | 238 | 8328 | 7890 | 148.7 | 140.9 |
| 23f | 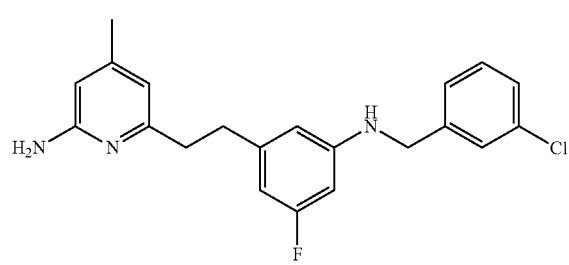 [SMILES: Cc1cc(N)nc(CCc2cc(F)cc(NCc3cccc(Cl)c3)c2)c1] | 27 | 2070 | 9562 | 7075 | 354.1 | 262.0 |
| 23g | 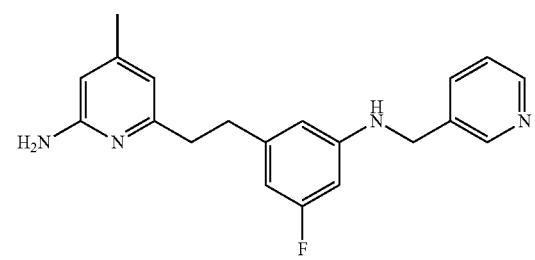 [SMILES: Cc1cc(N)nc(CCc2cc(F)cc(NCc3cccnc3)c2)c1] | 1026 | 255 | 10,978 | 10,270 | 10.7 | 10.0 |
| 23h | 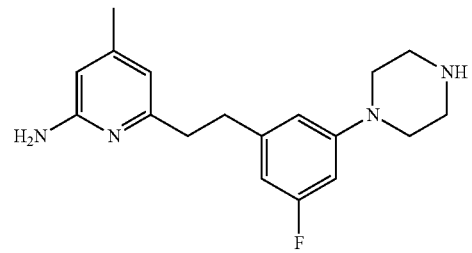 [SMILES: Cc1cc(N)nc(CCc2cc(F)cc(N3CCNCC3)c2)c1] | 58 | 161 | 3514 | 4836 | 60.2 | 82.8 |
| 23i | 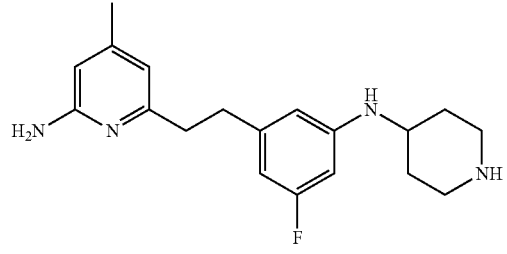 [SMILES: Cc1cc(N)nc(CCc2cc(F)cc(NC3CCNCC3)c2)c1] | 121 | 384 | 13511 | 4892 | 110.9 | 40.2 |

*$K_i$ for each compound was determined in triplicate using dose-response curves with nine concentration points (1 pM-3 mM). The calculated standard deviations (±S.D.) of the assays were less than 10% with all NOSs.

The $N^1,N^2$-dimethylethane-1,2-diamine side chain was chosen as the tail in the initial study after consideration that Buchwald amination with a symmetric diamine provides a better synthetic pathway than with asymmetric diamines. The inhibitory activities shown in Table 9 indicate that the terminal amine ($N^2$) has a better binding affinity when it is a primary amine (10c). Methylation of $N^2$ to make it a secondary (10a) or a tertiary (10b) amine results in a 2-3 fold drop in potency toward nNOS. Methylation of $N^1$ seems to have less of an effect on potency. Compound 10d, which has a one-carbon longer side chain compared to 10c, had a slightly lower binding affinity toward nNOS with poor selectivity over iNOS and eNOS. Although 10d also bears a primary amine like 10c, its one methylene longer linker pushes the amine away from a suitable position to make a hydrogen bond with heme propionate D, and, therefore, is the weakest binder among the four inhibitors (Table 9).

Crystal structures of 10a bound to nNOS and eNOS are shown in FIG. 16. In both structures, 10a uses its aminopyridine group to make hydrogen bonds with the active site Glu residue, Glu592 in nNOS or Glu363 in eNOS. The middle phenyl ring presses against the heme propionate from pyrrole ring D (propionate D), but the $N^1$ atom is only at van der Waals distance from the propionate. The three atoms in the tail of 10a are partially disordered in both nNOS and eNOS structures. In eNOS, the $N^2$ amine approaches heme propionate D close enough to make a hydrogen bond, but in nNOS the density for the tail is too poor to support a clear model. Nevertheless, the structural features found here explain why $N^1$ methylation does not affect the potency while the basicity of the $N^2$ amine contributes to binding. The primary $N^2$ amine in 10c is expected to make the tail more stable through a better hydrogen bond with heme propionate D.

Figure 17A:
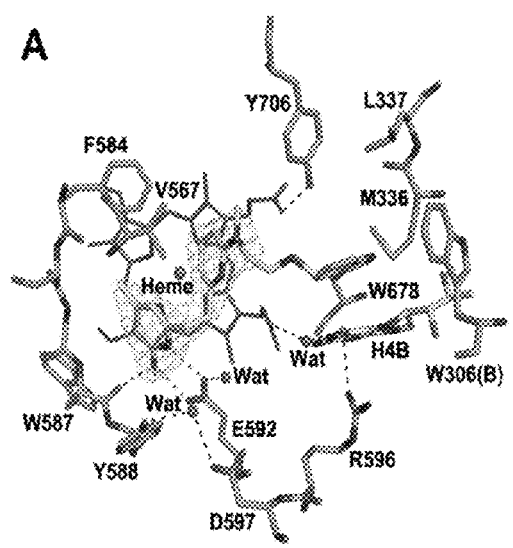
FIGS. 17A-B. Active site structure of nNOS with either 14a (A) or 14b (B) bound. The omit Fo-Fc electron density for the inhibitor is shown at the 2.5 σ contour level. Major hydrogen bonds are depicted with dashed lines.
Figure 17B:
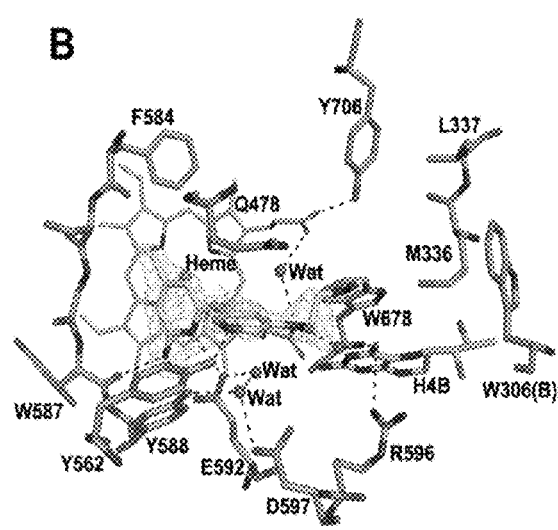

Compounds 14a and 14b, having a pyridine as the aromatic linker, improved the potency by 3- to 6-fold as well as improved selectivity against iNOS and eNOS. In addition, these two molecules show excellent potency (64 and 59 nM) for human nNOS. The binding mode of 14a closely resembles that of 10a, as shown in FIG. 17A, where the middle pyridine presses against heme propionate D but neither the ring nitrogen atom nor the $N^1$ amine is in hydrogen bonding distance to heme propionates. The tail $N^2$ secondary amine is partially disordered but is highly likely making a hydrogen bond with heme propionate D. The only difference in 14b from 14a is the position of the nitrogen atom in the middle pyridine ring, changing from the ortho-position relative to the other two substituents in 14a to the meta-position in 14b. This change brings in a binding mode to nNOS that is unprecedented with any other NOS inhibitors we have investigated. As seen in FIG. 17B, while the aminopyridine of 14b is still anchored by the Glu592 side chain, its middle pyridine ring takes an entirely different turn, going upward and making a hydrogen bond with Tyr562. For this to happen, the Gln478 side chain has to adopt an alternate rotamer position. With regard to the diamine tail, only the $N^1$ amine position is well defined, but the positions of the last three atoms are ambiguous with weaker density. In one subunit, the $N^2$ amino group can displace the water molecule that usually bridges between $H_4B$ and heme propionate A, but in the other subunit, the water molecule seems to be retained, and the tail of 14b steers away from it, which represents two possible tail positions.

Figure 18A:
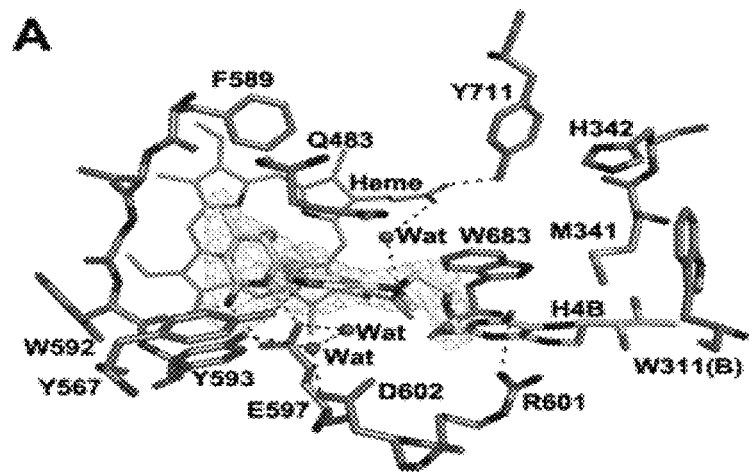
FIGS. 18A-C. Active site structure of human nNOS (A) or bovine eNOS (B) with 14b bound. The omit Fo-Fc electron density for the inhibitor is shown at the 2.5 σ contour level. Major hydrogen bonds are depicted with dashed lines. (C) The superimposition of two 14b positions found in human nNOS and bovine eNOS.
Figure 18B:
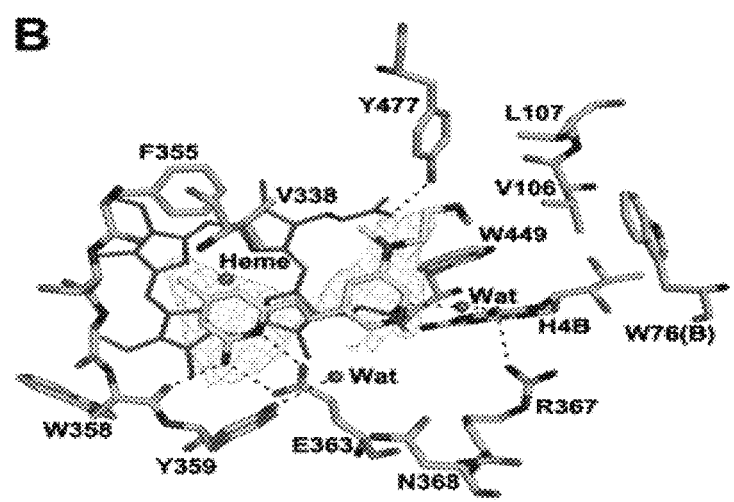
Figure 18C:
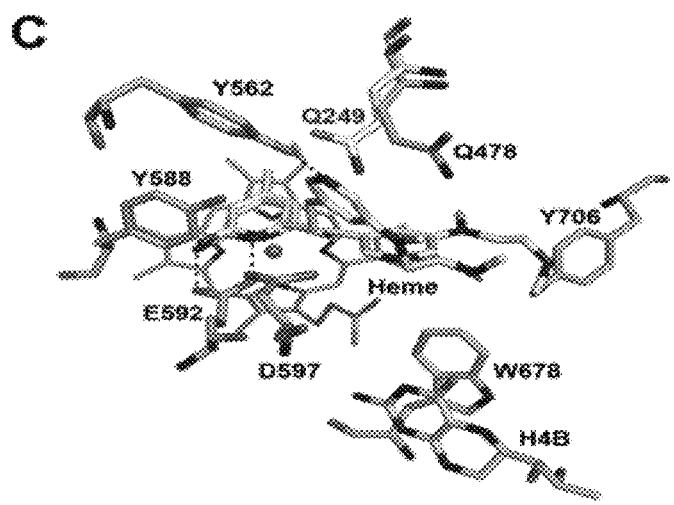

The crystal structure of human nNOS was also determined with 14b bound (FIG. 18A). The binding mode of 14b to human nNOS is essentially identical to that observed in rat nNOS. The only difference is that the diamine tail of 14b has displaced the bridging water molecule between the $H_4B$ and heme propionate A in human nNOS without any uncertainty. It is interesting that this upward binding mode of 14b found in nNOS does not repeat in the eNOS structure (FIG. 18B). The middle pyridine of 14b in eNOS sits on top of two heme propionates with only van der Waals contacts, while the aminopyridine ring is anchored to Glu363. The positions of the last three atoms in the tail are less certain. Overall, the upward binding mode of 14b seen in nNOS exhibits more favorite hydrogen bonding interactions than the "straight" binding mode in eNOS, even though it involves a rotamer change of Gln478 (FIG. 18C). The different binding preference for 14b provides a structural basis for the observed 759-fold selectivity for nNOS over eNOS. However, why 14b chooses two different binding modes in two NOS isoforms is not apparent, considering the residues making direct contacts with 14b are conserved.

Figure 19A:
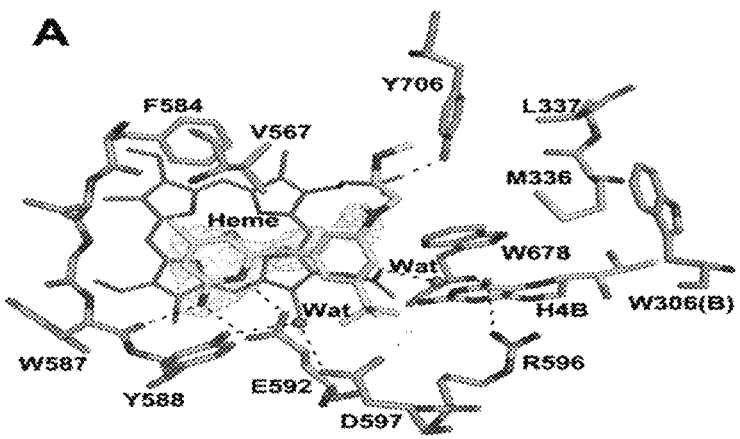
FIGS. 19A-C. Active site structures of (A) rat nNOS with 19a, (B) rat nNOS with 19b, and (C) bovine eNOS with 19b bound. The omit Fo-Fc electron density for the inhibitor is shown at the 2.5 σ contour level. Major hydrogen bonds are depicted with dashed lines.
Figure 19B:
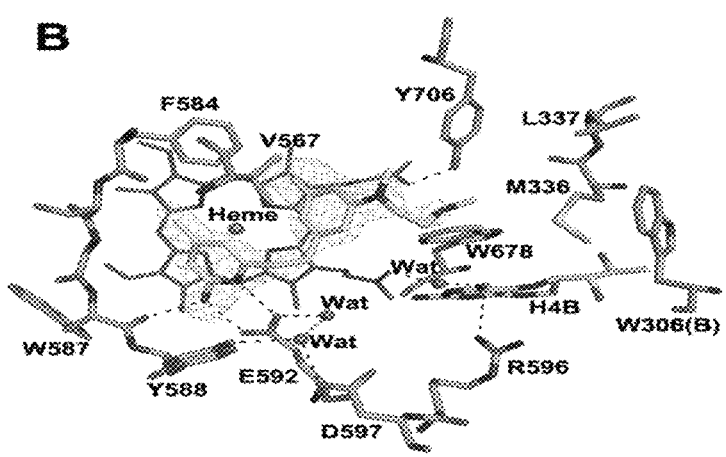
Figure 19C:
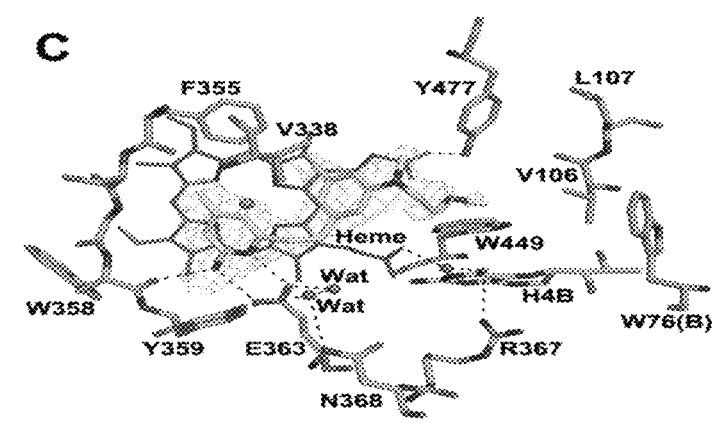

The binding mode variations observed with 14a and 14b encouraged further exploration of the properties of the middle aromatic ring. Compounds 19a, 19b, and 19c have a trifluoromethyl-phenyl ring, a fluorophenyl ring, or a benzonitrile, respectively, as the aromatic linker between the aminopyridine head and the ethylenediamine tail. The structure of 19a bound to rat nNOS (FIG. 19A) reveals a highly disordered trifluoromethyl phenyl ring, which likely fits into the open space defined by Glu592, Arg596, Asp597, and heme propionate A. There is no specific enzyme-inhibitor interaction other than more loose van der Waals contacts. The position of the tail amine also is not certain, but it may be in the vicinity of Asn569. The trifluoromethylphenyl ring is apparently too bulky to have a good fit with any other orientations in the nNOS active site. Although the diamine tail of 19b is partially disordered, the smaller fluorophenyl ring in 19b is well resolved. The fluorine closely interacts with heme pyrrole ring D at a distance shorter than 3.0 Å (FIG. 19B). These improved interactions very likely account for the 2-fold higher potency of 19b relative to 19a. The secondary $N^2$ amino group can interact with either heme propionate D or the bridging water molecule between the $H_4B$ and heme propionate A. Although 19b was found to have a 900-fold selectivity for rat nNOS over bovine eNOS, the binding mode observed in the eNOS structure (FIG. 19C) is almost identical to that seen in nNOS (FIG. 19B). As discussed in the past, the electrostatic environments of nNOS and eNOS are sufficiently different, mainly because of a one-residue variation (Asp597 in nNOS vs. Asn368 in eNOS), that they can have distinct impacts on the inhibitor binding affinity, even for those with identical binding conformations. (Kang, S.; Tang, W.; Li, H.; Chreifi, G.; Martásek, P.; Roman, L. J.; Poulos, T. L.; Silverman, R. B. Nitric oxide synthase inhibitors that interact with both heme propionate and $H_4B$ show high isoform selectivity. *J. Med. Chem.* 2014, 57, 4382-4396.)

Figure 20A:
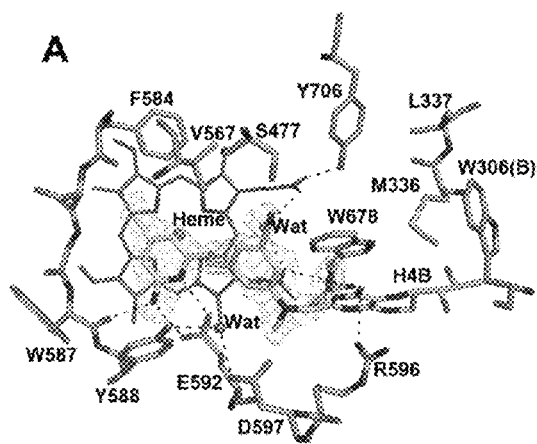
FIGS. 20A-D. Active site structures of rat nNOS (A), human nNOS (B), and bovine eNOS (C) with 19c bound. The omit Fo-Fc electron density for the inhibitor is shown at the 2.5 σ contour level. Major hydrogen bonds are depicted with dashed lines. (D) The superimposition of two 19c positions found in rat nNOS and bovine eNOS. The view is flipped from that in panel (A) in order to clearly show two different conformations of 19c in nNOS (yellow) and eNOS (orange).
Figure 20B:
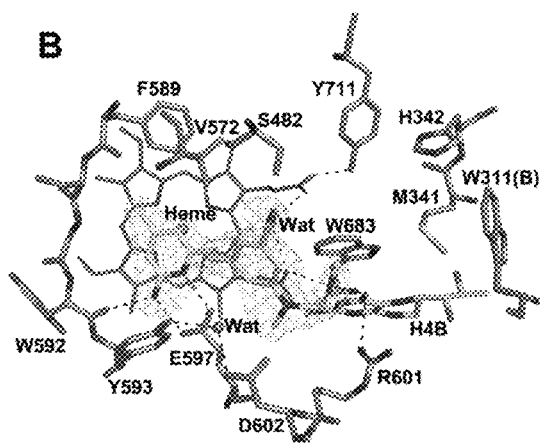
Figure 20C:
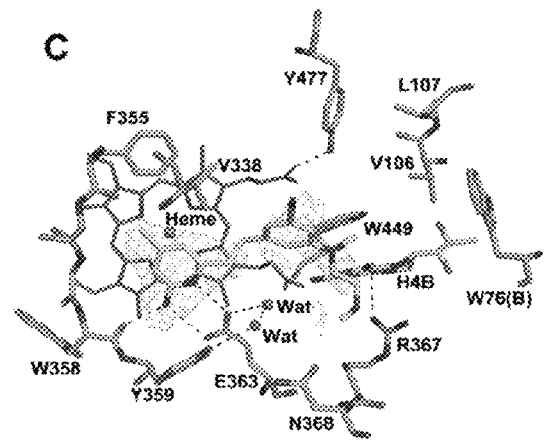
Figure 20D:
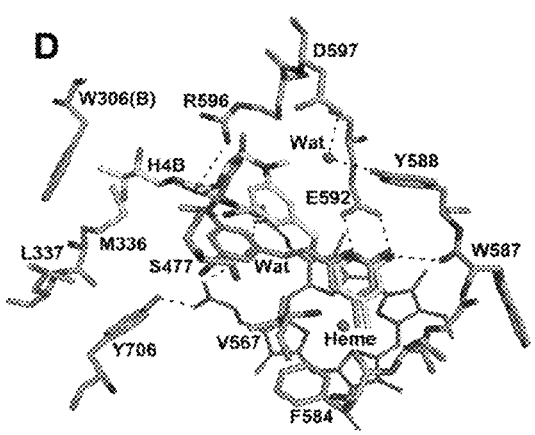

When the middle aromatic linker was changed to a benzonitrile, as in 19c, the inhibitor was the most potent and selective in this series with a $K_i$ of 24 nM and 1040-fold selectivity for nNOS over eNOS (Table 9). Despite the fact that the $N^1,N^2$-dimethylethane-1,2-diamine side chain of 19c does not reach the His342 pocket (Leu337 in rat nNOS), which was originally thought to be a good alkylamine target for human nNOS potency and selectivity, 19c has good binding affinity toward human nNOS ($K_i$ of 55 nM). For the bulky benzonitrile ring of 19c to have enough room (FIG. 20A), the middle aromatic ring rises upward from the plane of the aminopyridine ring so that the cyano nitrogen points toward Ser477, although without a strong hydrogen bond. The tail $N^2$ amino group can easily reach between the ketone oxygen atom of the $H_4B$ and heme propionate A, displacing the water molecule there. The same binding mode of 19c is conserved in human nNOS (FIG. 20B), leading to good potency (54 nM) for human nNOS as well as rat nNOS. The occupation of the water molecule site with an amino group has been implicated in the gain of nNOS over eNOS inhibitor selectivity with other aminopyridine compounds. (See, Kang, supra.) Here, a similar pattern was observed for 19c because the tail $N^2$ amino group of 19c in the eNOS structure does not directly displace the water molecule; rather, the water molecule is repelled by a methylene in the diamine tail (FIG. 20C). The different diamine tail position in eNOS results from a different position of the benzonitrile ring. The superimposition of the eNOS and nNOS structures with 19c bound illustrates this distinction (FIG. 20D). The middle aromatic ring in eNOS is packed directly against heme propionates (low-position), while in nNOS it is farther away (high-position). The cyano nitrogen atom of 19c in eNOS makes a hydrogen bond with Asn340, not with Ser248 (equivalent to Ser477 in nNOS).

Finally, the plasma pharmacokinetics and brain distribution of 19c in male BALB/c mice following a single intravenous and oral dose administration were carried out. Table 2 presents the pharmacokinetic parameters for 19c. At a single intravenous administration of 19c to male BALB/c mice at a 2 mg/kg dose, the compound showed high plasma clearance (184 mL/min/kg, the normal liver blood flow in mice=90 mL/min/kg) with an elimination half-life of 1.1 h. Following a single oral administration of 19c to male BALB/c mice at a dose of 10 mg/kg, plasma and brain concentrations were quantifiable up to 24 h with a $T_{max}$ of 0.25 h in plasma. Compound 19c was slowly cleared from brain (clearance=21 mL/min/kg) with appreciable brain concentrations detectable up to 24 h, and concentrations were approximately flat from 2 to 24 h. Compound 19c has a modest oral bioavailability of 18%.

TABLE 10

DMPK data in mice for compound 19c

| route | matrix | $T_{max}$ (hr) | [a]$C_0/C_{max}$ (ng/mL) | $AUC_{last}$ (hr*ng/mL) | $AUC_{inf}$ (hr*ng/mL) | $T_{1/2}$ (hr) | CL (mL/min/kg) | Vss (L/kg) | % F[b] |
|---|---|---|---|---|---|---|---|---|---|
| i.v. | plasma | — | 471.70 | 180.38 | 181.00 | 1.12 | 184.16 | 14.75 | — |
|  | brain[c] | — | 100.28 | 789.07 | NR[d] | 24.80 | 21.18 | 44.01 |  |
| p.o. | plasma | 0.25 | 50.75 | 162.43 | 182.46 | — | — | — | 18% |
|  | brain[c] | 4.00 | 39.31 | 673.67 | NR[d] | — | — | — |  |

[a]back extrapolated conc. for i.v. group.
[b]AUClast considered for calculating the bioavailability
[c]Brain concentrations and exposures are expressed as ng/g and h*ng/g, respectively. Density of brain homogenate was considered 1, which is equivalent to the plasma density.
[d]NR—not reported since $AUC_{inf}$ is 20% greater than $AUC_{last}$ The only structural difference that may affect the inhibitor binding between human and rat nNOS is in a peripheral binding pocket along the substrate access channel, His342 of human nNOS, which is larger and more polar than Leu337 in rat nNOS. In this work, 2-aminopyridine compounds were designed with a middle aromatic ring and a truncated tail so that none of the diamine tails of these compounds was long enough to reach the peripheral hydrophobic pocket, which thereby allowed for less differentiation between rat and human nNOS, resulting in binding constants that were comparable for rat and human nNOS. The introduction of substituents, such as a nitrile (19c) or fluorine atom (19b) in the middle aromatic linker was sufficient to increase nNOS binding affinity and iNOS/eNOS selectivity. The binding modes of 14b were unexpected, which induced side chain rotamer changes in Gln478 at the top of the active site; however, a different mode was observed in eNOS. Some good inhibitors in this series exhibit low nanomolar binding affinity to both rat and human nNOS, and >100-fold and >200-fold selectivity over iNOS and eNOS, respectively. Specifically 19c has a $K_i$ of 24 and 55 nM for rat and human nNOS, respectively, with 153-fold (iNOS) and 1040-fold (eNOS) selectivity, and this compound has 18% oral bioavailability. As designed, no binding mode difference was found between rat and human nNOS for this series of inhibitors, because the side chain does not reach the peripheral pocket where His342 in human nNOS replaces Leu337 in rat nNOS.

As relates to certain embodiments of this invention, compounds 1 and 2 (FIG. 21A), have been shown to be the most potent inhibitors for nNOS. These compounds are highlighted by excellent isoform selectivity (for 1) and easy synthesis (for 2). (Reference is made to Tables 13-14, schemes 15-18, examples 107-133, FIGS. 20-21 and the compounds separately numbered therein and discussed below.) Compound 1 has >700-fold selectivity against iNOS, and >3800-fold selectivity against eNOS. The X-ray crystal structures of 1 complexed with nNOS and eNOS reveal features of enzyme-inhibitor interactions that form the basis for high potency and selectivity (FIG. 21B): the aminopyridine of 1 interacts with a heme D-ring propionate via two H-bonds, as well as with Tyr706 in a π-π stacking interaction. The pyrrolidine nitrogen of 1 is located within hydrogen-bonding distances to both $H_4B$ and the heme A-ring propionate, replacing a water molecule, while the fluorophenyl ring stacks with the heme plane. Despite the excellent isoform selectivity of this molecule, the construction of the two unnaturally occurring chiral centers of 1 is not efficient and requires multiple steps with a relatively low overall yield. This limits the opportunities for optimizing the pharmacokinetic properties of the inhibitor and for carrying out in vivo studies. Compound 2, the other potent nNOS inhibitor ($K_i$=25 nM), is only moderately selective (i/n=58, e/n=107), but can be prepared from commercial starting materials in four chemical steps, in an excellent overall yield. The common feature of 1 and 2 is that both utilize one aminopyridine to make H-bonds with the heme D-ring propionate and to stack with Tyr706 (FIG. 21B). The additional H-bonds between the other aminopyridine of 2 and Glu592 of nNOS anchor the inhibitor to the substrate binding site above the heme in a double-headed mode. However, 2, in contrast to 1, does not directly interact with the $H_4B$ or with the propionate of the heme A-ring. The lack of these interactions may explain the moderate selectivity of 2 against iNOS and eNOS.

Figure 22:
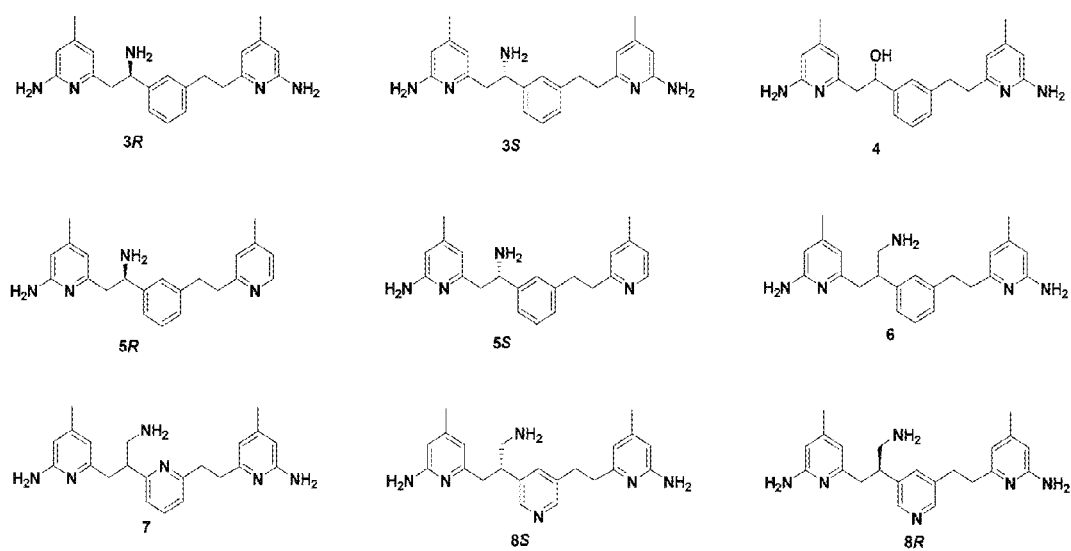
FIG. 22. Representative compounds of this invention and useful in conjunction with related methods of use, in accordance with various non-limiting embodiments thereof.

A strategy to confirm this structure-selectivity issue is to install a new functional group on molecule 2 to create an interaction with $H_4B$ and the heme A-ring propionate. This approach will allow an SAR study and confirm a chemotype design in which the molecules will be easy to prepare while still being highly isoform selective. From the structure overlay of 1 and 2 (FIG. 21B), it was thought that the pyrrolidine amine of 1 could be replaced by the addition of an amino group on the linker moiety of 2 (FIG. 21C), corresponding to $L^1$ as discussed above. The alignment of an amino group with an adapting position of the middle aromatic ring of 2, especially maintaining the structural similarity to the pyrrolidine amine of 1, was virtually performed using Surflex-Sim in the Sybyl-X program. Although the R-enantiomer of the α-amino derivative was predicted to interact with $H_4B$ and a propionate of the heme, the preparation of the other enantiomer was also desirable to confirm the stereo-activity relationship. After 2-amino-4-methylpyridine was selected as a head near the α-amino group, three different meta-substituted aromatic rings were adapted as linkers, and another 2-amino-4-methylpyridine or a 4-methylpyridine ring was chosen as the second head. The crystal structural information gathered with compounds bearing an α-amino group (3-5) led to the introduction of an aminomethyl group (6-8) to further improve the binding affinity and selectivity. FIG. 22 summarizes the compounds prepared and assayed as part of this study.

The synthesis of compounds 3R and 3S is shown in Scheme 15. Benzyl alcohol 11 was prepared by coupling of 3-bromomethylbenzaldehyde (9) with two equivalents of lithiated pyrrolyl-4,6-lutidine (10). The hydroxyl group of 11 was then converted to benzyl azide 12 via a Mitsunobu reaction with DPPA. Reduction of the azide with LiAlH$_4$ gave the free amine, which subsequently underwent amidation with (S)-camphanic chloride to give a separable diastereomeric mixture. Each pure diastereomer, 13a and 13b, was successfully isolated using general silica gel column chromatography. An asymmetric approach toward the target compounds using Ellman's chiral sulfinamide in the synthesis of 4R and 4S (Scheme 16) was not successful; only inseparable diastereomeric mixtures were produced. The (S)-camphanyl auxiliary and the two protecting groups on the aminopyridine rings were removed together by microwave-aided hydrolysis to give optically active 3R and 3S (Scheme 15).

Scheme 15. Synthesis of 3R and 3S.[a]

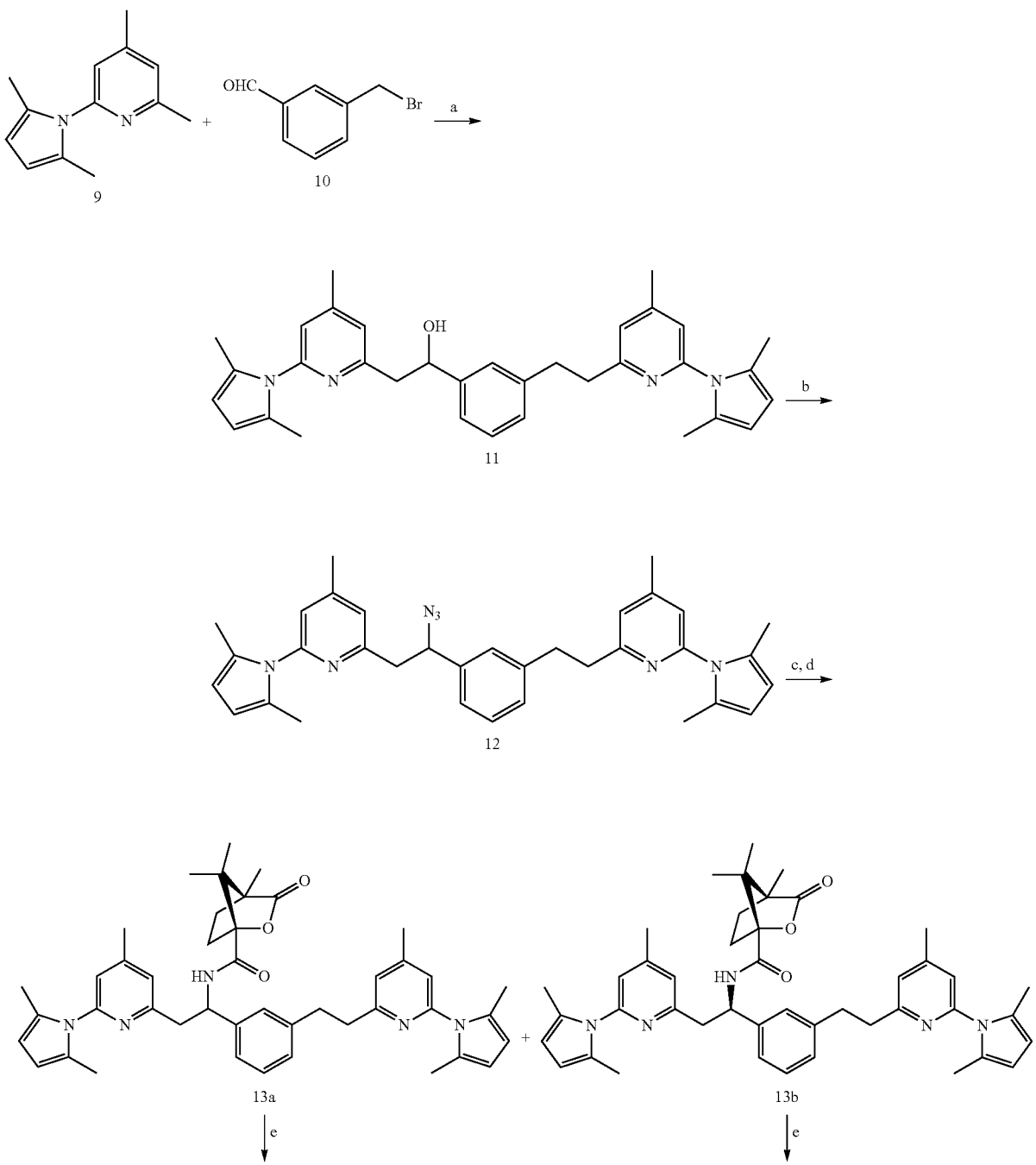

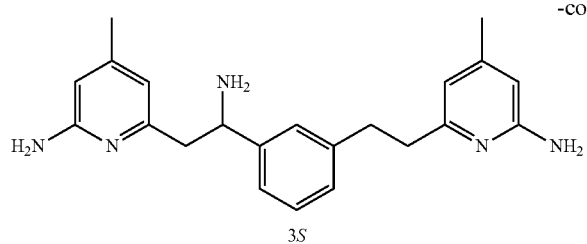

3S

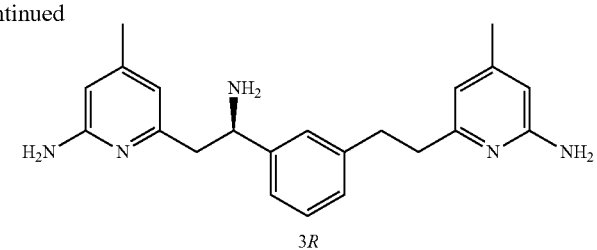

3R

*a*Reagents and condition:
(a) 9 (2.5 equiv), BuLi (2.5 equiv), THF, 0° C., to -78° C.;
(b) DEAD, DPPA, PPh₃, THF, room temp., 12 h;
(c) LialH₄;
(d) (i) (S)-camphamic chloride, TEA, CH₂Cl₂, room temp., (ii) chiral resolution on a silica gel column;
(e) conc HCl, AcOH, microwave, 150° C., 5 h.

Compounds 5R and 5S were prepared from 2,4-dimethyllutidine and 15 using a five-step procedure (Scheme 16). Lithiated 2,4-dimethyllutidine was coupled with benzyl bromide 15 to give nitrile 16. The cyano group of 16 was reduced to an aldehyde (17) using DIBAL, which then underwent condensation with Ellman's chiral sulfinamide to give (S)—N-tert-butanesulfinyl aldimine 18 in a moderate yield. This intermediate was coupled with lithiated pyrrolyl-4,6-lutidine 9 to give diastereomeric mixture 19a-b. Minor diasteromeric product 19b eluted first and major product 19a eluted second during silica gel column chromatography. Protecting groups on the aminopyridine and t-butyl sulfinamide of 19a and 19b were removed by microwave-aided acidic hydrolysis to give 5R and 5S in high yields.

Scheme 16. Synthesis of 5R and 5S.*a*

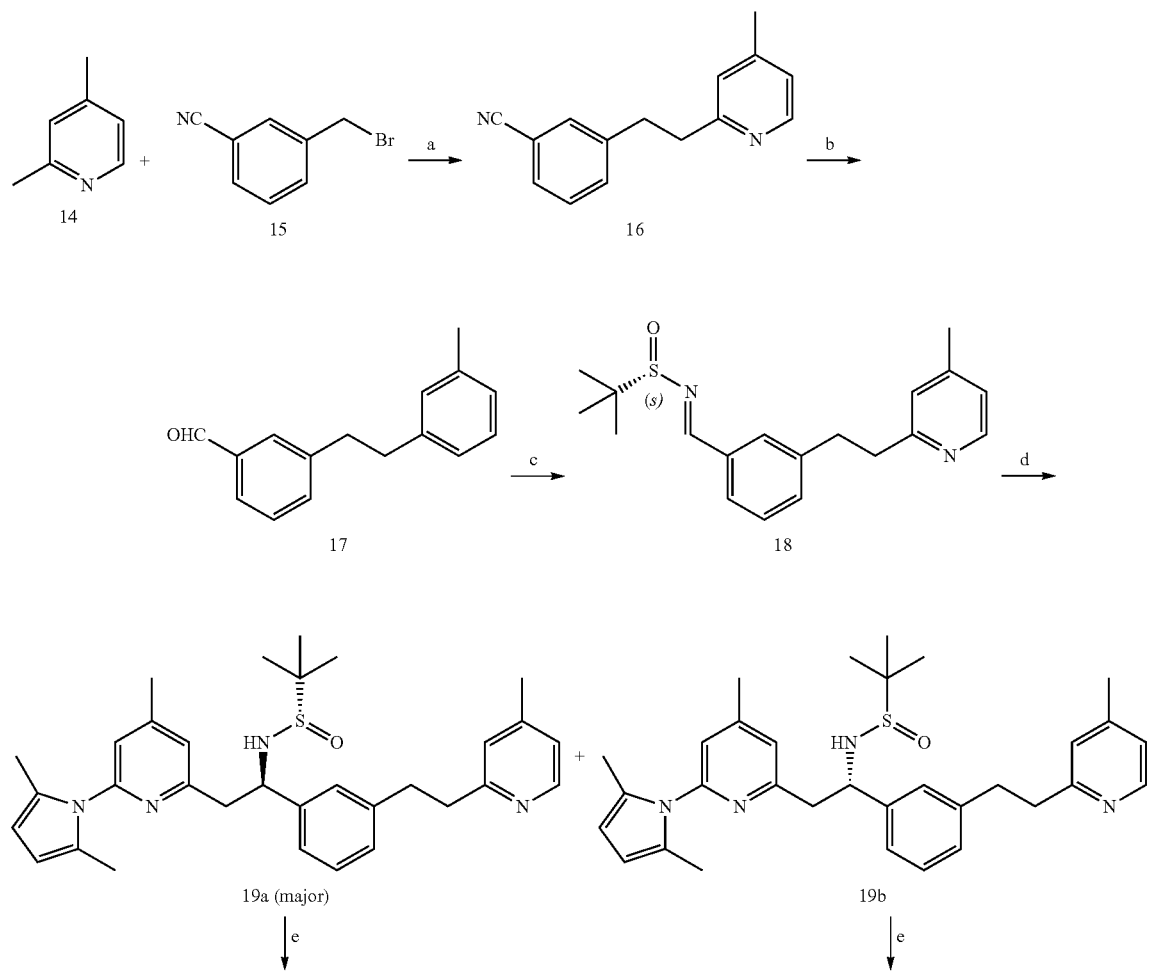

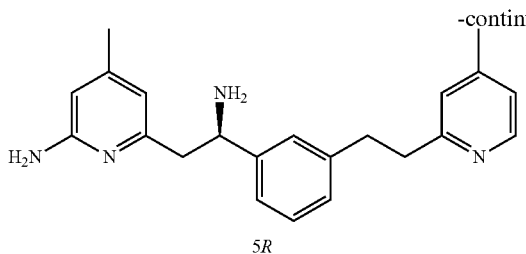 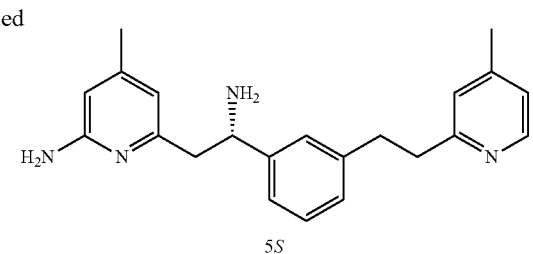

5R    5S

*Reagents and condition;
(a) BuLi, THF;
(b) DIBAL;
(c) (S)-t-butylsulfinamide, Ti(OEt)$_4$;
(d) 9, BuLi;
(e) conc HCl, EtOH, microwave, 120° C., 20 min.

Compound 6 was also prepared from benzyl bromide 15 using a six-step procedure (Scheme 17). Coupling of lithiated 9 with 15 gave nitrile 20, which was then reduced to aldehyde 21 by treatment with DIBAL. Condensation of 21 with nitromethane gave nitrovinyl compound 22 in a good yield. Michael addition of 22 with lithiated 9 produced nitro intermediate 23, which was reduced to amine 24 using Raney-Ni under a hydrogen atmosphere. Both aminopyridine protecting groups were removed by microwave-aided hydrolysis to give 6 in good yields.

Scheme 17. Synthesis of 5

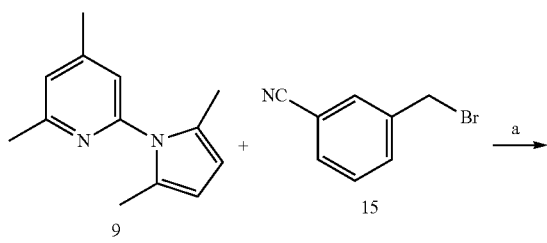

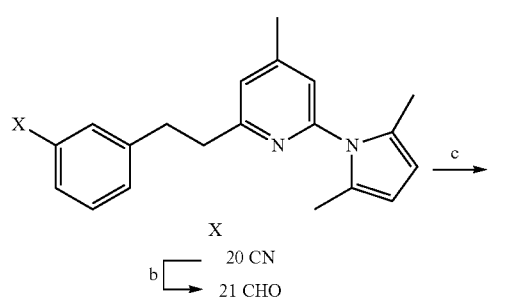

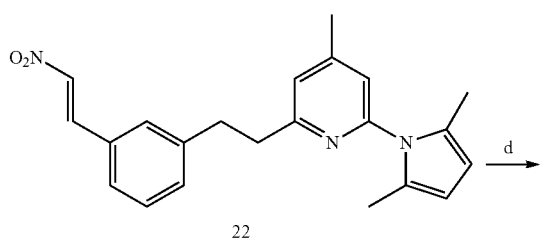

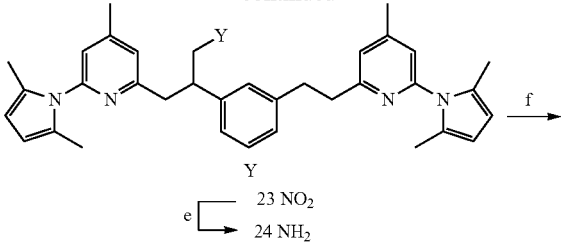

23 NO$_2$
e ⟶ 24 NH$_2$

6

*Reagents and condition:
(a) (i) 9, BuLi, THF; (ii): 15;
(b) DIBAL-H;
(c) (i) MeNO$_2$, TEA (ii) AcCl;
(d) 9, BuLi;
(e) LAH;
(f) conc HCl, EtOH, microwave, 120° C., 20 min.

Compounds 7 and 8 were prepared in five steps from commercially available brominated pyridinylaldehydes 25a-b (Scheme 18). Condensation of 25a-b with nitromethane in the presence of TEA and acetyl chloride, followed by Michael reaction with lithiated 4,6-dimethylpyridine, afforded 27a-b. Sonogashira coupling between 27a-b and alkyne 28, which was prepared from 6-bromo-2-aminopyridine and trimethylsilylacetylene, produced intermediate 29a-b. Raney nickel-mediated hydrogenation of 29a-b yielded reduced product 30a-b. Finally, the protecting groups on the aminopyridine rings were removed using microwave conditions to yield product 7 and 8. A portion of intermediate 30b was protected with Boc and then injected onto an OD-H chiral HPLC column to separate the enantiomers. Each enantiomerically pure compound was deprotected via microwave-assisted acidic hydrolysis to give optically active enantiomers 8S and 8R. A diverse approach for the chiral resolution of the final deprotected compound (8) using CrownPak CR-(+), Chiralcel OD-RH, and Whelk-O 1 chiral reverse phase HPLC columns, and Chiralcel OD-H chiral normal phase column with DEA, were not successful. Chiral derivatization of the final compound using Mosher's acid chloride, (S)-camphanyl chloride, and (S)-mandelic chloride also were not successful because the molecules have multiple reactive amines.

iNOS=8.2 µM; bovine eNOS=1.7 µM) for all three NOS isoforms using the following relationship: $K_i = IC_{50}/(1+[S]/K_M)$

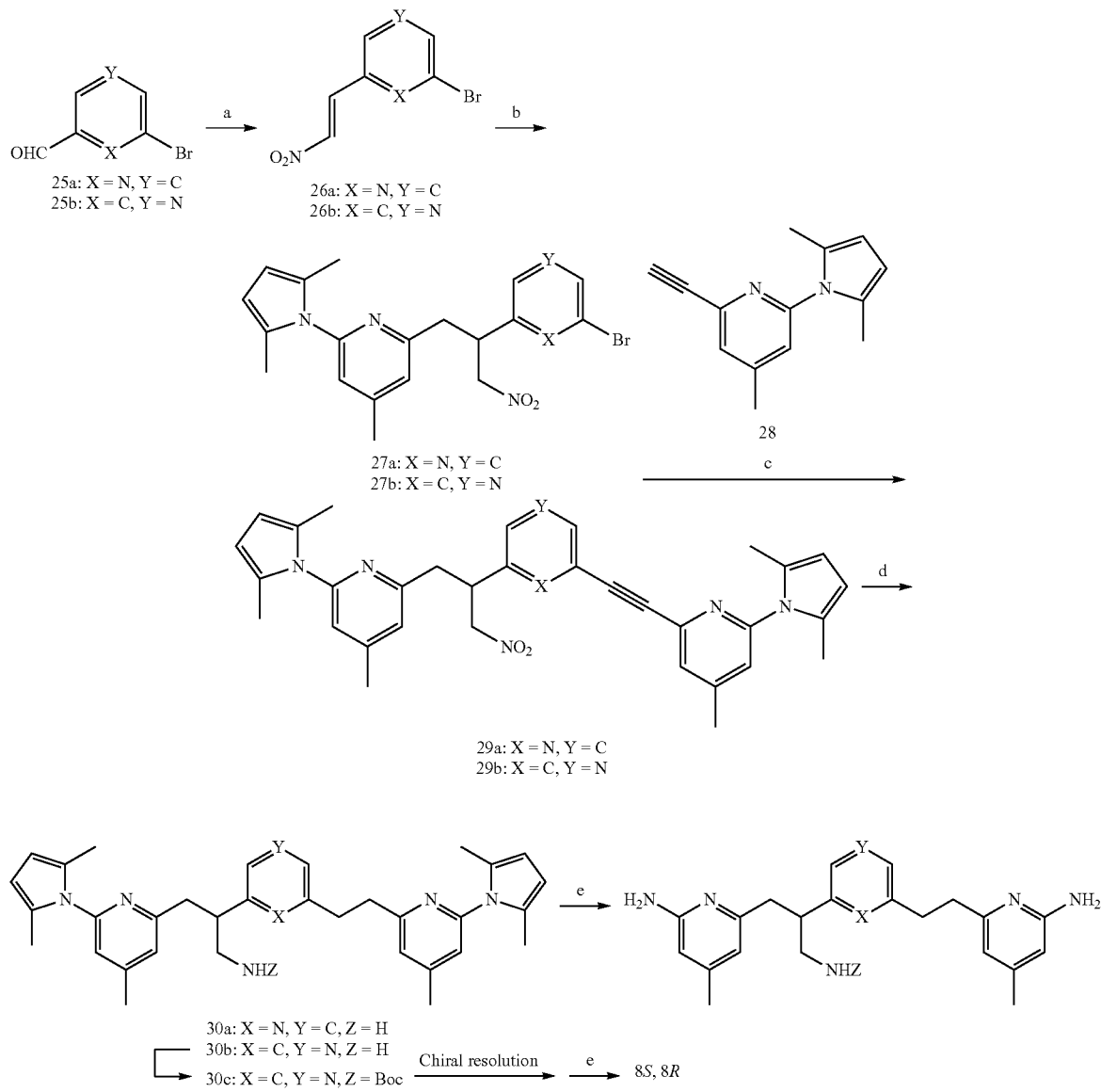

Scheme 18. Synthesis of 7 and 8

$^a$Reagents and conditions:
(a) (i) MeNO$_2$, TEA, (ii) AcCl;
(b) 9, BuLi;
(c) 28, Pd(PPh$_3$)$_2$Cl$_2$, CuI, PPh$_3$, DEA, DMF;
(d) Raney-Ni, H$_2$, MeOH/EtOH;
(e) conc HCl/EtOH (1/2), microwave, 120° C., 20 min.

The NOSs isoform assays involved subjecting 3-8 to an oxyhemoglobin NO capture assay using a Biotek Gen5™ microplate reader. IC$_{50}$ values for each compound were determined in duplicate or triplicate using dose-response curves with nine concentration points (1 pM-3 mM). The standard deviation of the assays were less than 15% with nNOS or iNOS, and less than 25% with eNOS. The inhibition constants (K$_i$) of these compounds were determined from the IC$_{50}$ and K$_m$ values (rat nNOS=1.3 µM; murine The selectivity of antagonism of nNOS relative to iNOS or eNOS was determined by calculating the ratios of the K$_i$ values with iNOS or eNOS to those with nNOS. Compounds 3-8, having various amino functional groups, were found to have moderate to excellent selectivity (50-2822 of e/n, 36-273 of i/n) and moderate to good binding affinity (24-4370 nM) to nNOS. All of the synthesized molecules as well as three reference molecules (31, 32, and 2; for comparative purpose), and their associated activities are shown in Table 13 and 14.

TABLE 13

List of K$_i$ values and selectivity of 3-8

| Name | structure | nNOS Ki (nM) | iNOS Ki (nM) | eNOS Ki (nM) | i/n | e/n |
|---|---|---|---|---|---|---|
| 3S | 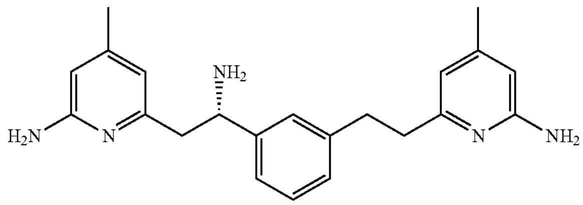 [SMILES: Cc1cc(N)nc(CCc2cccc([C@@H](N)Cc3cc(C)cc(N)n3)c2)c1] | 144 (±11) | 17,670 (±1,982) | 70,900 (±2,163) | 123 | 492 |
| 3R | 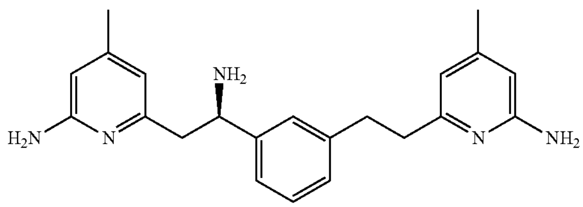 [SMILES: Cc1cc(N)nc(CCc2cccc([C@H](N)Cc3cc(C)cc(N)n3)c2)c1] | 122 (±9) | 15,620 (±1,210) | 14,390 (±1,053) | 128 | 118 |
| 4 | 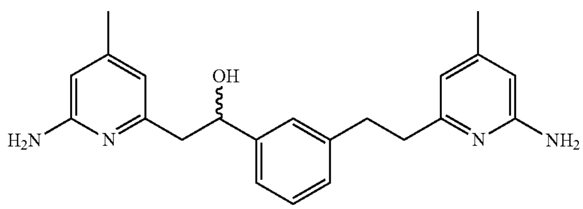 [SMILES: Cc1cc(N)nc(CCc2cccc(C(O)Cc3cc(C)cc(N)n3)c2)c1] | 70 (±4) | 5,990 (±563) | 3,610 (±320) | 86 | 52 |
| 5S | 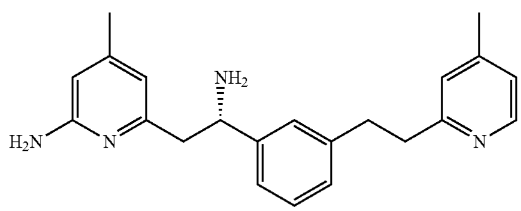 [SMILES: Cc1ccnc(CCc2cccc([C@@H](N)Cc3cc(C)cc(N)n3)c2)c1] | 903 (±81) | >100,000 | 328,000 (±25,000) | >110 | 363 |
| 5R | 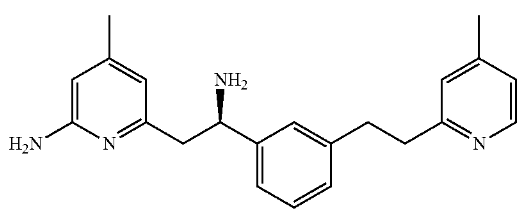 [SMILES: Cc1ccnc(CCc2cccc([C@H](N)Cc3cc(C)cc(N)n3)c2)c1] | 4,370 (±68) | >100,000 | 1049,000 (±31,000) | >22 | 240 |
| 6 | 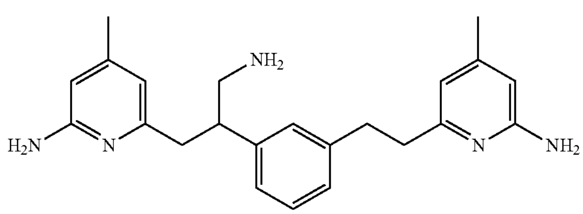 [SMILES: Cc1cc(N)nc(CCc2cccc(C(CN)Cc3cc(C)cc(N)n3)c2)c1] | 53 (±5) | 1,894 (±138) | 4,770 (±55) | 36 | 90 |
| 7 | 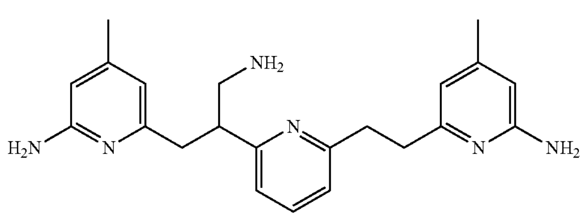 [SMILES: Cc1cc(N)nc(CCc2cccc(C(CN)Cc3cc(C)cc(N)n3)n2)c1] | 123 (±7) | 17,916 (±1,296) | 133,174 (±10,330) | 138 | 1072 |

TABLE 13-continued

List of K$_i$ values and selectivity of 3-8

| Name | structure | nNOS Ki (nM) | iNOS Ki (nM) | eNOS Ki (nM) | i/n | e/n |
|---|---|---|---|---|---|---|
| 8 | 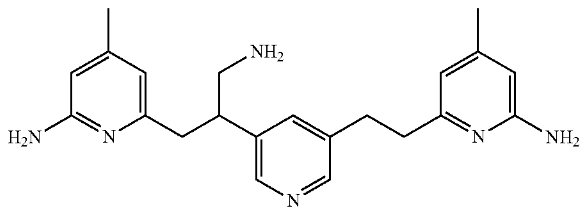 [SMILES: Cc1cc(N)nc(CCc2cncc(C(CN)Cc3cc(C)cc(N)n3)c2)c1] | 30 (±4) | 2,810 (±192) | 16,000 (±1,438) | 95 | 544 |
| 2[a] | 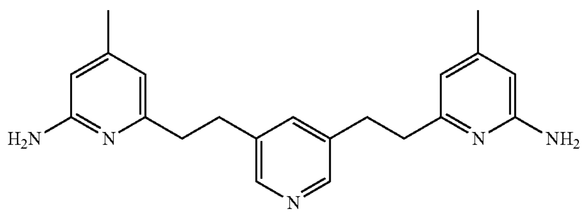 [SMILES: Cc1cc(N)nc(CCc2cncc(CCc3cc(C)cc(N)n3)c2)c1] | 25 | 1,450 | 2,680 | 58 | 107 |
| 31[a] | 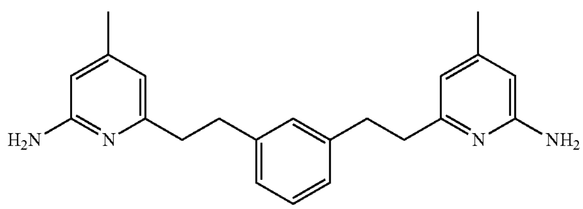 [SMILES: Cc1cc(N)nc(CCc2cccc(CCc3cc(C)cc(N)n3)c2)c1] | 49 | 682 | 1,410 | 14 | 29 |
| 32[a] | 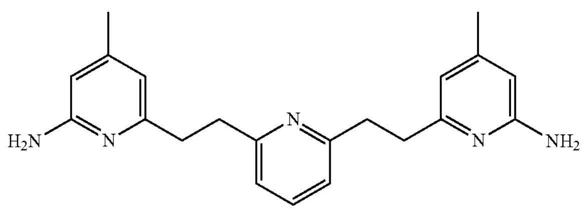 [SMILES: Cc1cc(N)nc(CCc2cccc(CCc3cc(C)cc(N)n3)n2)c1] | 99 | 4,750 | 9,400 | 48 | 95 |

[a]Reference molecules that were reported previously.

TABLE 14

K$_i$ values and selectivity of 8S and 8R

| Name | structure | nNOS Ki (nM) | iNOS Ki (nM) | eNOS Ki (nM) | i/n | e/n |
|---|---|---|---|---|---|---|
| 8S | 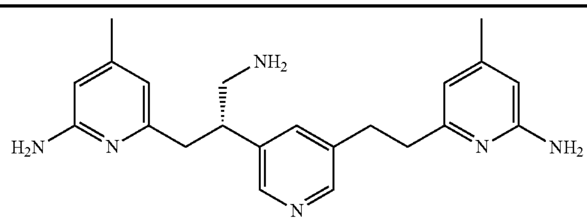 | 70 (±4) | 4,386 (±394) | 19,417 (±1,058) | 105 | 276 |
| 8R | 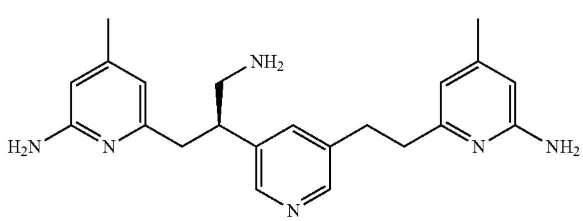 [SMILES: Cc1cc(N)nc(CCc2cncc([C@H](CN)Cc3cc(C)cc(N)n3)c2)c1] | 24 (±2) | 6,629 (±561) | 68,520 (±4,817) | 273 | 2,822 |

The compounds with an α-amino (or a hydroxyl) group and symmetric double heads, 3S, 3R, and 4, exhibited about a hundred nanomolar binding affinity to nNOS and modest selectivity against eNOS and iNOS, whereas 5R and 5S, having α-amino tailed asymmetric double heads, showed poor potency. Compounds 6-8, having an α-aminomethyl tail with two aminopyridine head groups, showed improved potency by 1- to 5-fold. The orientation of the nitrogen on the middle aromatic ring was important; compound 7 was a relatively less effective inhibitor of nNOS when the nitrogen was located in the narrow arc of the middle ring. Although the α-aminomethyl derivatives 6, 7, and 8 did not display improved binding affinity for nNOS compared with their parent molecules 31, 32, and 2, it is noteworthy that all of those α-aminomethyl derivatives have better selectivity (Table 13) against iNOS and eNOS. In general, the α-aminomethyl derivatives are 2- to 3-fold (i/n), and 3- to 10-fold (e/n) more selective than their parent molecules. To further explore the inhibition potency and selectivity of racemic 8, each enantiomer was prepared and assayed with the three NOS isoforms. Compound 8R, the (R)-enantiomer of 8, showed excellent potency ($K_i$=24 nM) for nNOS with a 273-fold selectivity over iNOS and a 2822-fold selectivity over eNOS, the best in the series.

Compound 8 was also assayed against human nNOS to explore whether the interactions are acceptable for the human isoform as well. As discussed above, human nNOS is very similar to rat nNOS, except that the hydrophobic pocket surrounded by Met336, Leu337, and Tyr706 in rat nNOS is replaced by Met340, His341, and Tyr710. This pocket is where the second head group of this series of double-headed inhibitors fits. The inhibitory potency of 8 for human nNOS is 90 nM, similar to that (70 nM) of compound 1, a most potent human nNOS inhibitor with potential selectivity over human iNOS and eNOS.

As demonstrated a series of α-amino functionalized aminopyridine derivatives (3-8) was designed based on the comparison and rationale that the pyrrolidine of lead 1, interacting with a heme propionate and $H_4B$, can promote isoform selectivity. An α-amino or aminomethyl group has been installed in the other lead (2) to probe the structure-selectivity relationship, while providing a substantially simple scaffold that retains selectivity. In general, the symmetric double-headed aminopyridine compounds (3 and 4) showed better potency than the asymmetric one (5) because the former can establish H-bonds through both head groups. Although a simple α-amino group installed on the side chain can stabilize the double-headed inhibitor binding mode, only the aminomethyl group is long enough to reach a water site. By replacing the water molecule, the inhibitor is able to make H-bonds with both the $H_4B$ and the propionate of the heme A-ring. These interactions seem to gain the isoform selectivity for the inhibitors. Compound 8R, the best inhibitor discovered and evaluated in this study, exhibits excellent nNOS potency (24 nM) and isoform selectivity (273-fold for i/n and 2822-fold for e/n). It also showed <100 nM potency for human nNOS. However, the crystal structures of 8R complexed with nNOS and eNOS share an almost identical binding mode, which is similar to what was observed with parent compound 1. A free energy calculation indicated that the different electrostatic environments in the active site of the two NOS isoforms give rise to the isoform distinct binding affinity, even for inhibitors that exhibit the same binding mode.

Methods of the present invention can also, as would be understood by those skilled in the art, be extended to or include methods using or in conjunction with a pharmaceutical composition comprising an inhibitor compound of the sort described herein and a physiologically or otherwise suitable formulation. In a some embodiments, the present invention includes one or more NOS inhibitors, as set forth above, formulated into compositions together with one or more physiologically tolerable or acceptable diluents, carriers, adjuvants or vehicles that are collectively referred to herein as carriers. Compositions suitable for such contact or administration can comprise physiologically acceptable sterile aqueous or nonaqueous solutions, dispersions, suspensions or emulsions. The resulting compositions can be, in conjunction with the various methods described herein, for administration or contact with a cellular medium, bacterium and/or a nitric oxide synthase expressed or otherwise present therein. Whether or not in conjunction with a pharmaceutical composition, "contacting" means that a nitric oxide synthase and one or more inhibitor compounds are brought together for purpose of binding and/or complexing such an inhibitor compound to the enzyme. Amounts of a compound effective to inhibit a nitric oxide synthase may be determined empirically, and making such determinations is within the skill in the art. Modulation, inhibition or otherwise affecting nitric oxide synthase activity includes both reduction and/or mitigation, as well as elimination of NOS activity and/or nitric oxide production.

It is understood by those skilled in the art that dosage amount will vary with the activity of a particular inhibitor compound, disease state, route of administration, duration of treatment, and like factors well-known in the medical and pharmaceutical arts. In general, a suitable dose will be an amount which is the lowest dose effective to produce a therapeutic or prophylactic effect. If desired, an effective dose of such a compound, pharmaceutically-acceptable salt thereof, or related composition may be administered in two or more sub-doses, administered separately over an appropriate period of time.

Methods of preparing pharmaceutical formulations or compositions include the step of bringing an inhibitor compound into association with a carrier and, optionally, one or more additional adjuvants or ingredients. For example, standard pharmaceutical formulation techniques can be employed, such as those described in Remington's Pharmaceutical Sciences, Mack Publishing Company, Easton, Pa.

Regardless of composition or formulation, those skilled in the art will recognize various avenues for medicament administration, together with corresponding factors and parameters to be considered in rendering such a medicament suitable for administration. Accordingly, with respect to one or more non-limiting embodiments, the present invention provides for use of one or more mammalian and/or bacterial nitric oxide synthase inhibitor compounds for the manufacture of a medicament for therapeutic use in the treatment of various disease states, in particular neurodegenerative diseases.

EXAMPLES OF THE INVENTION

The following non-limiting examples and data illustrate various aspects and features relating to the methods of the present invention. In comparison with the prior art, the present methods provide results and data which are surprising, unexpected and contrary thereto. While the utility of this invention is illustrated through the use of several NOS inhibitor compounds, and antimicrobial agents which can be optionally used therewith against certain bacteria, it will be understood by those skilled in the art that comparable results are obtainable with various other NOS compounds (and, as applicable with antimicrobial agents, against various other bacteria), as are commensurate with the scope of this invention.

Experimental Procedures for Examples 1-16

Bacterial Strains.

B. subtilis 168 was obtained from American Type Culture Collection (23857) and made competent by the Spizizen method (Anagnostopoulos, C. and Spizizen, J. Requirements for Transformation in *Bacillus Subtilis. Journal of Bacteriology* 81, 741 (1961)). NOS deletion vector, pTPJH046, was synthesized by Genscript to contain a spectinomycin resistance gene, adapted from pDG1728, flanked by two 400 BP fragments upstream and downstream of nos (yflM). B. subtilis ΔNOS was engineered by transforming pTPJH046 and selecting for spectinomycin resistance, as previously reported. Double recombination was checked by colony PCR. Spectinomycin was used at 100 µg/mL.

Example 1

Effect of Oxidative Stress and NOS inhibitor on *B. subtilis*. *B. subtilis* wt and Δnos were grown to an $OD_{600} \sim 1.0$ and diluted to $OD_{600}=0.6$. Cell stocks were treated with either nonselective NOS inhibitor $N^\omega$-nitro-L-arginine (L-NNA), compound 1, or compound 2 at 500 µM, 500 µM, and 250 µM, respectively, and either $H_2O_2$ or ACR at 2 mM and 1.25 mM, respectively, for 30 min at 30° C. Cells were serially diluted in M9 minimal media, plated on LB agar (with 0.5% glucose) and plates were incubated overnight at 37° C. Colony forming units (CFU) were counted the following day and % survival was calculated. For the *B. subtilis* growth assays wt and Δnos strains were grown in LB media to an $OD_{600} \sim 1.0$ and diluted into LB media until $OD_{600}=0.28$. The $OD_{600}=0.28$ cell stocks were then diluted 30 fold into a 96 well plate containing fresh LB media. Cells were pre-treated with NOS inhibitors 1 and 2 for 5 min, at 800 µM and 400 µM, respectively. ACR then was added to a final concentration of 5 µM, and growth was monitored at 600 nm for 14 h at 28° C. using a plate reader.

Example 2

Cloning and Mutagenesis. The *B. subtilis* NOS sequence was obtained from GenBank. The DNA sequence was codon optimized for bacterial expression, synthesized, and cloned into a pET28a vector (Novagen) using the NdeI and XhoI restriction sites by GenScript. Site directed mutagenesis was carried out using the QuikChange Lightning Site-Directed Mutagenesis Kit (Stratagene) to introduce surface mutations E25A/E26A/E316A.

Example 3

Protein Expression and Purification. *B. subtilis* NOS (bsNOS) was expressed and purified as previously reported. (Pant, K., Bilwes, A. M., Adak, S., Stuehr, D. J., & Crane, B. R. (2002) Structure of a nitric oxide synthase heme protein from *Bacillus subtilis Biochemistry* 41, 11071-11079.) Heme domains of nNOS and eNOS were also expressed and purified as previously reported. (Li, H., Shimizu, H., Flinspach, M., Jamal, J., Yang, W., Xian, M., Cai, T., Wen, E. Z., Jia, Q., Wang, P. G., et al. (2002) The novel binding mode of N-alkyl-N'-hydroxyguanidine to neuronal nitric oxide synthase provides mechanistic insights into NO biosynthesis *Biochemistry* 41, 13868-13875; Raman, C. S., Li, H., Martásek, P., Kral, V., Masters, B. S., & Poulos, T. L. (1998) Crystal structure of constitutive endothelial nitric oxide synthase: a paradigm for pterin function involving a novel metal center *Cell* 95, 939-950.)

Example 4

Imidazole Displacement. Coordination of imidazole to the heme iron generates a low spin spectrum with a Soret peak at 430 nm. NOS inhibitors displace the imidazole ligand and shift the heme to high-spin, resulting in a Soret maximum at 395 nm. This provides a convenient method for estimating the spectral dissociation constant, $K_s$. High spin ligands were titrated into a cuvette containing 2 µM NOS, 1 mM imidazole, 50 mM Tris (pH 7.6) and 100 µM DTT. An apparent $K_s$ ($K_{s,app}$) was calculated based on a non-linear regression analysis using Sigmaplot version 10.0 (Systat Software, Inc., San Jose Calif., USA) using equation 1:

$$A_{395} - A_{430} = \frac{B_{max} \cdot [I]}{K_{S,app} + [I]}.$$

Assuming $K_d$ of imidazole for bsNOS to be 384 µM, for nNOS to be 160 µM, and for eNOS to be 150 µM, the $K_S$ was calculated as previously reported. (See Table 4 for representative, non-limiting compounds which can be utilized in conjunction with this invention.)

Example 5

Crystallization. Crystals of bsNOS belonging to space group $P2_12_12$ were grown by vapor diffusion at 22° C. Initial crystals were obtained by mixing an equal volume of the crystallization reservoir and bsNOS at 25 mg/mL in 25 mM Tris pH 7.6, 150 mM NaCl, 1 mM DTT. The reservoir was composed of 60 mM Bis-Tris methane/40 mM citric acid pH 7.6 and 20% (v,v) polyethylene glycol (PEG) 3350. Crystal quality was further improved by introduction of surface entropy mutants E25A/E26A/E316A identified using the sERP server. Each glutamate was selected for mutation as a residue predicted to facilitate crystal packing and as a residue that did not contribute a stabilizing non-covalent interaction with nearby residues. Crystals of the E25A/E26A/E316A bsNOS were then seeded into an equal volume drop of reservoir containing 60 mM Bis-Tris methane/40 mM citric acid pH 7.6, 15% (v,v) PEG 3350, 1.9% (v/v) 1-propanol and protein containing E25A/E26A/E316A bsNOS at 18 mg/mL in 25 mM Bis-Tris methane pH 7.6, 150 mM NaCl, 1% (v/v) glycerol, 1% (w/v) PEG 3350, 1 mM DTT, and 500 µM imidazole. Enzyme-inhibitor-$H_4B$ complex crystals were prepared during the cryoprotection with 23% (v/v) glycerol by soaking at inhibitor and $H_4B$ concentrations of 7-10 mM and 2 mM, respectively, for 3-6 h. The heme domain of eNOS and nNOS were prepared and crystallized as described.

Example 6a

Data Collection and Structure Determination. High-resolution data were collected at the Stanford Synchrotron Radiation Lightsource (SSRL) beamline 7-1. Data frames were indexed, integrated, and scaled using HKL2000. Phases were determined by molecular replacement using Phaser with the PDB entry 2FBZ as the search model for bsNOS inhibitor bound structures. Inhibitor topology files were constructed using the online program PRODRG, protein and inhibitor were modeled in Coot and refined using REFMAC. Water molecules were added and checked by REFMAC and COOT, respectively. (Crystallographic data collection and refinement statistics are available but not shown.)

Example 6b

Data deposition: The atomic coordinates and structure factors have been deposited in the Protein Data Bank under the accession code 4LWB (bsNOS-1), 4LWA (bsNOS-2), 4LUW (eNOS-1), 4LUX (nNOS-1).

Example 7

Syntheses of Compound 1

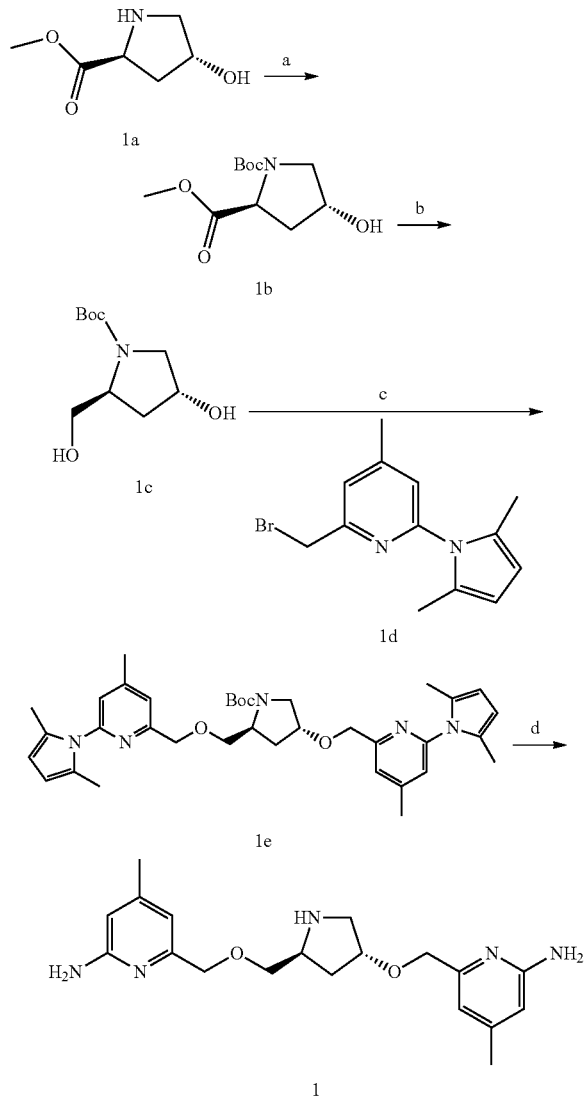

Reagents and conditions:
a) (i) (Boc)$_2$O, CH$_3$OH, 91%;
b) LiBH$_4$, THF, 94%;
c) NaH, DMF, compound 1d, 0° C., 86%;
d) NH$_2$OH—HCl, EtOH/H$_2$O (2/1); ii) 2M HCl in CH$_3$OH/dioxane (1/1), two steps, 68%.

Example 7a (2S,4R)-1-tert-butyl 2-methyl 4-hydroxypyrrolidine-1,2-dicarboxylate (1b). To a solution of 1a (200 mg, 1.38 mmol) in CH$_3$OH (15 mL) was added (Boc)$_2$O (331 mg, 1.52 mmol), and the resulting mixture was allowed to react at room temperature for 8 h. After the addition of 20 mL water, the mixture was extracted with ethyl acetate (3×15 mL), and the organic layer was dried over NaSO$_4$. The solvent was removed by rotary evaporation, and the residue was purified by flash chromatography (EtOAc/hexanes=1/4) to yield a white solid (308 mg, 64%); m.p. 89-91° C. $^1$H NMR (500 MHz, CDCl$_3$) δ 4.43 (br, 1H), 4.19-4.10 (m, 1H), 3.77 (s, 3H), 3.60-3.54 (m, 2H), 2.07-2.01 (m, 2H), 1.87-1.84 (m, 1H), 1.47 (s, 9H); $^{13}$C NMR (126 MHz, CDCl$_3$) δ 172.17, 157.35, 80.73, 69.49, 67.31, 58.89+55.85, 52.37, 37.70, 28.21 ppm; MS (ESI): 245.4 (M+H)$^+$.

Example 7b (2S,4R)-tert-butyl 4-hydroxy-2-(hydroxymethyl)pyrrolidine-1-carboxylate (1c): To a solution of 1b (300 mg, 1.22 mmol) in dry THF (15 mL) was added LiBH$_4$ (108 mg, 4.89 mmol), and the resulting mixture was allowed to react at room temperature overnight. After removing most of the THF and introducing 15 mL water, the mixture was extracted with ethyl ether (3×15 mL), and the organic layer was dried over NaSO$_4$. The solvent was removed by rotary evaporation, and a white solid was obtained in a yield of (249 mg, 94%). The product was used in the next step without further purification; m.p. 97-100° C.; $^1$H NMR (500 MHz, CDCl$_3$) δ 4.40 (br, 1H), 4.19-4.08 (m, 1H), 3.73 (br, 1H), 3.61-3.51 (m, 2H), 2.10-2.04 (m, 2H), 1.86-1.83 (m, 1H), 1.50 (s, 9H); $^{13}$C NMR (126 MHz, CDCl$_3$) δ 157.15, 80.70, 69.45, 67.26, 58.93, 55.89, 37.60, 28.44 ppm; MS (ESI): 218.2 (M+H)$^+$.

Example 7c (2S,4R)-tert-butyl 4-((6-(2,5-dimethyl-1H-pyrrol-1-yl)-4-methylpyridin-2-yl)methoxy)-2-(((6-(2,5-dimethyl-1H-pyrrol-1-yl)-4-methylpyridin-2-yl)methoxy)methyl)pyrrolidine-1-carboxylate (1e): To a solution of 1c (100 mg, 0.46 mmol) in dry DMF (10 mL) was added compound 1d (308 mg, 1.10 mmol), and the mixture was cooled to 0° C. After NaH (44 mg, 60% in mineral oil, 1.10 mmol) was introduced, the resulting mixture was allowed to react at 0° C. for 4 h. After removing most of the DMF under reduced pressure and introducing 15 mL water, the mixture was extracted with ethyl ether (3×15 mL), and the organic layer was dried over NaSO$_4$. The solvent was removed by rotary evaporation, and the residue was purified by flash chromatography (EtOAc/hexanes=1/4) to yield a colorless oil (242 mg, 86%); $^1$H NMR (500 MHz, CDCl$_3$) δ 8.24 (s, 1H), 7.29 (s, 1H), 7.23 (s, 1H), 6.95 (s, 2H), 5.88 (s, 4H), 4.62 (d, J=5.0 Hz, 4H), 4.32-4.29 (m, 1H), 4.21 (br, 1H), 3.74-3.56 (m, 3H), 3.55-3.52 (dd, J=11.5 Hz, J=5.0 Hz, 1H), 2.42 (s, 6H), 2.10 (s, 12H), 1.46+1.44 (s, 9H); $^{13}$C NMR (126 MHz, CDCl$_3$) δ 171.20, 158.05, 151.30+151.26, 150.15, 128.35, 121.22, 120.55+120.40, 106.76, 79.60, 73.77, 71.60, 60.42, 55.81, 53.43, 52.24+51.96, 35.42+34.55, 28.54, 21.27+21.21, 13.16 ppm; MS (ESI): 636.4 (M+Na)$^+$.

Example 7d 6-(((((3R,5S)-5-(((6-amino-4-methylpyridin-2-yl)methoxy)methyl)pyrrolidin-3-yl)oxy)methyl)-4-methylpyridin-2-amine (1): To a solution of 1e (120 mg, 0.195 mmol) in ethanol (6 mL) was added $NH_2OH$—HCl (271 mg, 3.90 mmol) and $H_2O$ (3 mL). The resulting mixture was allowed to react at 100° C. for 20 h. After adding 15 mL water, the mixture was extracted with ethyl ether (3×15 mL). The solvent was removed by rotary evaporation, and the yellow solid was mixed with 4 mL HCl (2M in $CH_3OH$/dioxane 1/1). The mixture was allowed to react at room temperature for 2 h before being treated with 2M NaOH (6 mL) and extracted with ethyl ether (3×15 mL). The organic layer was dried over $NaSO_4$, and the crude product was purified by preparative thin layer chromatography ($CH_3OH$/$CH_2Cl_2$ 1/15 with 0.5% $Et_3N$) to yield a pale yellow solid (47 mg, 68%); m.p. 124-126° C. $^1$H NMR (500 MHz, $CDCl_3$) δ 6.61 (s, 1H), 6.57 (s, 1H), 6.23 (s, 2H), 4.43 (q, J=10.0 Hz, J=5.0 Hz, 4H), 4.36 (d, J=5.0 Hz, 4H), 4.18-4.16 (m, 1H), 3.69-3.64 (m, 1H), 3.55-3.49 (m, 2H), 3.13-3.11 (m, 2H), 2.24 (s, 3H), 2.23 (s, 3H), 2.08 (dd, J=14.0 Hz, J=5.0 Hz, 1H), 1.73-1.67 (m, 1H); $^{13}$C NMR (126 MHz, $CDCl_3$) δ 158.27, 158.12, 156.39, 156.24, 149.58, 149.55, 113.10, 112.97, 107.86, 107.81, 80.30, 73.76, 71.63, 56.68, 52.02, 45.99, 34.96, 21.12 ppm; MS (ESI): 358.4 (M+H)$^+$. HRMS (ESI): calcd. 358.2234. Found: 358.2243.

Example 8

Synthesis of Compound 10

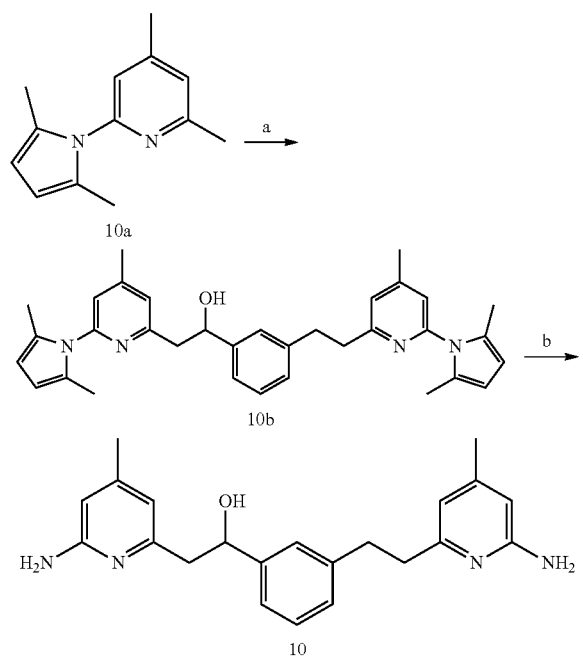

Reagents and conditions: (a) (i) n-BuLi, 0° C., 30 min, (ii) 3-(bromomethyl)benzaldehyde, -78° C., 20 min (b) $NH_2OH \cdot HCl$ μ-wave, 120° C., 25 min. EtOH/$H_2O$ (3:1)

Example 8a 2-(6-(2,5-Dimethyl-1H-pyrrol-1-yl)-4-methylpyridin-2-yl)-1-(3-(2-(6-(2,5-dimethyl-1H-pyrrol-1-yl)-4-methylpyridin-2-yl)ethyl)phenyl)ethanol (10b). To a solution of 10a (500 mg, 2.5 mmol) in THF (20 mL) was added n-BuLi (1.6 M solution in hexanes, 1.56 mL, 2.5 mmol), and the reaction was stirred for 30 min at 0° C. This mixture was transferred to a solution of 3-(bromomethyl)benzaldehyde (198.0 mg, 1.0 mmol) in THF (30 mL) at -78° C. via cannula. The reaction mixture was allowed to stir for an additional 20 min and then quenched with $H_2O$ (30 mL). After addition of ethyl acetate (50 mL), the organic layer was dried with $MgSO_4$ and concentrated by rotary evaporation. The resulting yellow oil was purified by flash chromatography (EtOAc/hexanes) to yield 2,5-dimethylpyrrole-protected product 10b as a yellow oil (332 mg, 64%). $^1$H NMR (500 MHz, $CDCl_3$) δ 7.33-7.25 (m, 3H), 7.14-7.09 (m, 1H), 6.99 (s, 1H), 6.95 (s, 2H), 6.89 (s, 1H), 5.93 (s, 2H), 5.91 (s, 2H), 5.15 (m, 1H), 3.17 (m, 2H), 3.10 (m, 4H), 2.42 (s, 3H), 2.40 (s, 3H), 2.18 (s, 6H), 2.16 (s, 6H); $^{13}$C NMR (126 MHz, $CDCl_3$) δ 161.01, 159.29, 151.62, 151.13, 150.28, 149.53, 143.99, 141.63, 128.56, 128.50, 128.40, 127.51, 125.97, 123.52, 123.46, 122.67, 120.77, 120.10, 106.93, 106.68, 73.25, 45.73, 39.78, 36.64, 35.98, 24.72, 21.10, 13.31

Example 8b 2-(6-Amino-4-methylpyridin-2-yl)-1-(3-(2-(6-amino-4-methylpyridin-2-yl)ethyl)phenyl)ethanol (10). To a 5 mL microwave vial was added compound 10b (130 mg, 0.25 mmol), hydroxylamine hydrochloride (350 mg, 5 mmol), ethanol (3 mL), and water (1 mL). The vial was shaken vigorously and then heated in the microwave irradiator for 25 min at 120° C. The reaction mixture was diluted with water (45 mL) and partitioned between ethyl acetate (30 mL) and 2 N aq NaOH (5 mL). After the aqueous layer was extracted with ethyl acetate (3×20 mL), the combined organic layers were dried over $MgSO_4$, filtered, and concentrated. The resulting yellow oil was purified by column chromatography using C-18 reverse phase silica (95-90% water in $CH_3CN$), to yield 10 as a pale yellow oil (50 mg, 55%). $^1$H NMR (500 MHz, $CD_3OD$) δ 7.33-7.23 (m, 3H), 7.14 (m, 1H), 6.35 (s, 1H), 6.33 (s, 1H), 6.23 (s, 1H), 6.19 (s, 1H), 5.04 (dd, J=9.1, 3.1 Hz, 1H), 4.54 (bs, 4H), 3.00 (m, 2H), 2.95-2.81 (m, 4H), 2.21 (s, 3H), 2.20 (s, 3H); $^{13}$C NMR (126 MHz, $CD_3OD$) δ 159.14, 158.05, 157.72, 157.58, 149.91, 149.50, 144.35, 141.83, 128.28, 127.35, 126.05, 123.47, 115.05, 114.41, 107.02, 106.67, 73.59, 45.35, 39.70, 36.14, 21.06, 21.04. LC-TOF (M+Na$^+$) calcd for $C_{22}H_{26}N_4NaO^+$ 385.2004. found 385.2008.

Example 9

General methods for synthesis and structure characterization. Experiments were conducted under anhydrous conditions in an atmosphere of argon. Reagents were obtained from Aldrich and TCI and were used without further purification. Solvents were purified by passage through a solvent column composed of activated alumina and a supported copper redox catalyst. Microwave irradiation was performed in a Biotage Initiator® Microwave with a 2-5 mL Biotage reaction vial. Flash column chromatography was carried out using an Agilent 971-FP purification system with a SuperFlash Si50 prepacked silica cartridge (normal phase) or a SF25 prepacked C18 cartridge. The purity of the final compounds was evaluated on a Beckman Gold HPLC system using a Phenomenex C18 reverse phase column with a linear gradient of 15% acetonitrile (0.1% TFA) in water (0.1% TFA) to 50% acetonitrile in water. Purities of the final compounds used for testing were >95% as determined by these conditions. ¹H NMR and ¹³C NMR data were obtained on a 500 MHz Bruker Avance-III spectrometer using CDCl₃ or CD₃OD solvents. The identity of each compound was verified by mass spectrometry using an Agilent 6210 LC-TOF spectrometer in the positive mode.

Data and results relating to the compounds of Examples 10-16 can be considered with respect to the following procedures and assays.

Site Directed Mutagenesis—

Active site mutations H128S and I218V were introduced using PfuTrubo (Agilent) on the bsNOS expression vector containing sERP mutations E24A/E25A/E316A described in Example 2, above.

Expression and Purification—

Isolation of recombinant *B. subtilis* NOS, bBiDomain, and YumC from *E. coli* were followed as previously reported in the literature (Holden, J. K., Lim, N., and Poulos, T. L. (2014) Identification of Redox Partners and Development of a Novel Chimeric Bacterial Nitric Oxide Synthase for Structure Activity Analyses, *J. Biol. Chem.*). The purification of mammalian NOS isoforms was also followed as previously reported.

Crystallization and Structure Determination— bsNOS crystals were prepared, cryoprotected, and soaked with inhibitor as described above for bsNOS-inhibitor complexes (Example 3). To obtain inhibitor bound crystal structures of compounds 5, 6, and 7, H₄B was removed from the cryosoak. X-ray data were collected at both the Stanford Synchotron Radiation Light (SSRL) source and the Advanced Light Source (ALS). Datasets were indexed and integrated with either imosflm or XDS. Aimless was used to scale the datasets Inhibitor restraints were constructed using PRODRG and datasets were refined using PHENIX.

Imidazole Displacement—

The transition from an imidazole bound low-spin to a ligand bound high-spin state was measured as described above (Example 4) using purified oxygenase domain of either bsNOS or iNOS. For trials that included H₄B, H₄B was added at 50 µM. The measured $K_{S,apparent}$ was used to calculate the $K_S$ using the bsNOS imidazole $K_D$ of 384 µM and iNOS imidazole $K_D$ of 158 µM.

Example 10

Inhibition Assay using bBiDomain. NADPH dependent *Bacillus subtilis* NOS activity/inhibition was evaluated using bBiDomain and the flavodoxin reductase YumC, as previously described, with varying concentrations of inhibitor. Nitrite levels were measured as a function of NOS activity and calculated by the Griess reaction using a standard curve.

Example 11

Molecular Dynamics. Starting coordinates for molecular dynamics simulations were generated from crystal structures of both bsNOS-7 and H128S-bsNOS-7. Since bsNOS is present as a dimer in solution, a second subunit was generated from the crystal structure monomer using a C2 rotation axis. Hydrogens were added to the protein, 7, and solvent using psfgen of VMD 1.9.1. Bulk water was added to each system using the solvate command of VMD to generate a 25 Å cushion of solvent. As both structures were identical in overall size, the same unit cell box dimensions of (122× 138×122) were used for each system. The final systems for bsNOS-7 and H128S-bsNOS-7 were composed of 194,372 and 192,503 atoms, respectively. Simulations were carried out on the Stampede supercomputer using NAMD 2.9. (Kale, L., Skeel, R., Bhandarkar, M., Brunner, R., Gursoy, A., Krawetz, N., Phillips, J., Shinozaki, A., Varadarajan, K., and Schulten, K. (1999) NAMD2: Greater scalability for parallel molecular dynamics, *J Comput Phys* 151, 283-312.) The CHARMM force fields employed to model the protein and heme were identical to those used in previous simulations. (Mackerell, A. D., Feig, M., and Brooks, C. L. (2004) Extending the treatment of backbone energetics in protein force fields: Limitations of gas-phase quantum mechanics in reproducing protein conformational distributions in molecular dynamics simulations, *J Comput Chem* 25, 1400-1415; Madrona, Y., Hollingsworth, S. A., Khan, B., and Poulos, T. L. (2013) P450cin active site water: implications for substrate binding and solvent accessibility, *Biochemistry* 52, 5039-5050.) The CHARMM force field of 7 was generated using ParamChem. (Vanommeslaeghe, K., Hatcher, E., Acharya, C., Kundu, S., Zhong, S., Shim, J., Darian, E., Guvench, O., Lopes, P., Vorobyov, I., and MacKerell, A. D. (2010) CHARMM General Force Field: A Force Field for Drug-Like Molecules Compatible with the CHARMM All-Atom Additive Biological Force Fields, *J Comput Chem* 31, 671-690.) The smooth partial Ewald mesh method was used in the calculation of Coulombic forces while a Langevin thermostat was employed for the constant temperature simulations. Nosé-Hoover-Langevin piston was employed for pressure control. All simulations were run at 300K and 1 atm with a time step of 1 fsec. All bonds involving hydrogen atoms were held fixed using the SHAKE algorithm. (Miyamoto, S., and Kollman, P. A. (1992) Settle—an Analytical Version of the Shake and Rattle Algorithm for Rigid Water Models, *J Comput Chem* 13, 952-962.) Each structure was minimized for 1000 fsec before the simulation was allowed to propagate. Positional restraints were placed on 7 during the first 4.5 nsec of the simulation, allowing the protein to equilibrate before the inhibitor restraints were removed. Analyses of the simulations were carried out using locally developed analysis tools and VMD. (Humphrey, W., Dalke, A., and Schulten, K. (1996) VMD: visual molecular dynamics, *Journal of molecular graphics* 14, 33-38, 27-38.)

Example 12

Effect of Antimicrobial Induced Stress and NOS Inhibitors on *B. subtilis*. Isolation and characterization of *B. subtilis* Δnos strain were much as previously described (Example 1). WT (American Type Culture Collection 23857) and Δnos *B. subtilis* strains were grown separately to an $OD_{600}≈1.0$ and diluted to $OD_{600}=0.6$ in LB media. From the diluted cell stock 80 µL, was aliquoted into a sterile 1.5 mL Eppendorf tube and diluted to a final volume of 100 µL, with M9 minimal media or a combination of either M9 minimal media, NOS inhibitor diluted in M9 minimal media, and/or acriflavine dissolved in M9 minimal media. Final concentrations of NOS inhibitor and acriflavine were 500 µM and 800 µM, respectively. Cells were treated for 30 min at 30° C. and then immediately serially diluted in M9 minimal media and plated on LB agar (supplemented with 0.5% glucose). Plates were incubated at 37° C. overnight. After overnight incubation colony-forming units were counted and percent survival was calculated relative to the untreated cells.

Example 13

Compounds 1, 2, 3, and 7 were prepared as previously described: for 1-3, see co-pending application Ser. No.

13/573,654 filed Oct. 1, 2012; and for 7 and various other thiophenecarboximidamide compounds and compositions, see co-pending application Ser. No. 14/285,927 filed May 23, 2014—each of which is incorporated herein by reference.

Example 14

To synthesize 4, Boc-protected 2-amino-4,6-dimethylpyridine (8) was treated with n-butyllithium and was mixed with 3,5-bis(bromomethyl)benzonitrile to give the corresponding intermediate (10). N-Methylation of 10 with 0.57 equivalents of iodomethane and NaH followed by deprotection of the Boc protecting group gave target compound 4 in a moderate yield.

Synthesis of Compound 4

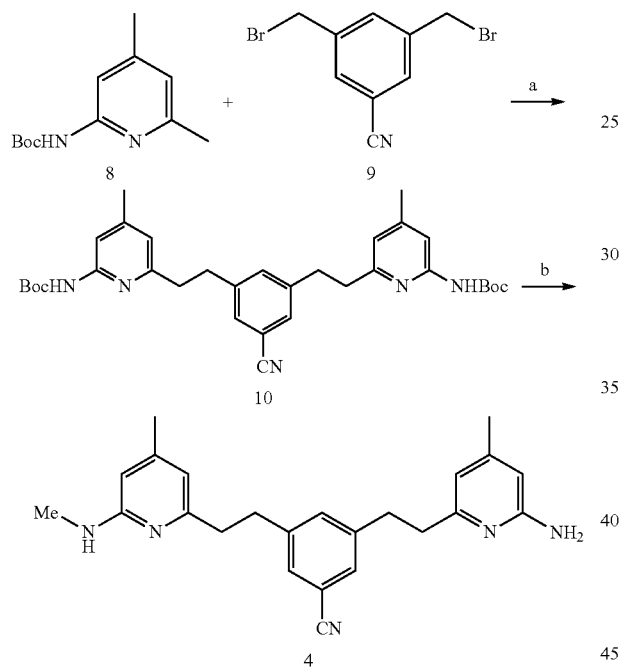

Reagents and conditions:
a) BuLi, THF, room temperature to −78° C., 42%;
b) (i) NaH, MeI, THF, room temperature, 12 h; (ii) HCl—MeOH, room temperature, 5 h, 51% (two steps).

Example 14a

Di-tert-butyl (((5-cyano-1,3-phenylene)bis(ethane-2,1-diyl))bis(4-methylpyridine-6,2-diyl))dicarbamate (10). To a solution of tert-butyl (4,6-dimethylpyridin-2-yl)carbamate (8, 889 mg, 4.0 mmol) in THF (25 mL) was added n-BuLi (1.6 M solution in hexanes, 5.0 mL, 8.0 mmol). The reaction mixture was stirred for 30 min at 0° C. and was then cooled to −78° C. To this solution, 3,5-bis(bromomethyl)benzonitrile (9, 578 mg, 2.0 mmol) in THF (2 mL) was added dropwise. After the mixture was stirred for an additional 10 min, it was quenched with $H_2O$ (50 mL). The organic layer was partitioned by addition of ethyl acetate (50 mL), dried with $MgSO_4$, and concentrated in vacuo. The resulting brown oil was purified by flash chromatography (EtOAc/hexanes) to yield 10 (480 mg, 42%) as a pale yellow oil. $^1$H NMR (500 MHz, $CDCl_3$) δ 7.64 (s, 2H), 7.50 (s, 2H), 7.29 (s, 2H), 7.19 (s, 1H), 6.57 (s, 2H), 2.96 (dd, J=9.3, 5.9 Hz, 4H), 2.90-2.80 (m, 4H), 2.30 (s, 6H), 1.52 (s, 18H); $^{13}$C NMR (126 MHz, $CDCl_3$) δ 158.25, 152.49, 151.52, 150.00, 143.03, 133.49, 129.65, 119.16, 118.81, 112.15, 110.34, 80.81, 38.99, 35.10, 28.27, 21.31; MS ESI $[M+H]^+=572.2$.

Example 14b 3-(2-(6-Amino-4-methylpyridin-2-yl)ethyl)-5-(2-(4-methyl-6-(methylamino)pyridin-2-yl)ethyl)benzonitrile (4). To a solution of Boc-protected aniline (400 mg, 0.70 mmol) in THF (2 mL), NaH (60% in oil, 17 mg, 0.4 mmol) was added at 0° C. The reaction mixture was stirred for 15 min at the same temperature, and then methyl iodide (57 mg, 0.4 mmol) was added. The mixture was stirred for an additional 12 h at room temperature, and then quenched with $H_2O$ (10 mL). After addition of ethyl acetate (10 mL), the organic layer was partitioned, dried with $MgSO_4$, and concentrated in vacuo. The resulting brown oil was mixed with 1 M HCl solution in MeOH, stirred for 5 h, and then concentrated in vacuo to give crude 4. The crude product was subjected to purification with a SiliaSep™ C18 flash cartridge (25 g, 40-63 μm/230-400 mesh, Pore Size 60 Å) using 5 to 80% MeOH to give pure 4 (131 mg, 51%) as a colorless gel. $^1$H NMR (500 MHz, MeOD) δ 7.42-7.37 (m, 2H), 7.35 (s, 1H), 6.39 (s, 1H), 6.34 (s, 1H), 6.30 (s, 1H), 6.28 (s, 1H), 3.05-2.95 (m, 4H), 2.90 (s, 3H), 2.88-2.80 (m, 4H), 2.23 (s, 3H), 2.22 (s, 3H); $^{13}$C NMR (126 MHz, MeOD) δ 160.36, 159.46, 157.59, 156.34, 153.29, 152.08, 144.59, 144.14, 134.97, 131.04, 130.88, 119.92, 114.82, 114.20, 113.14, 108.87, 106.37, 39.12, 38.68, 36.25, 36.18, 29.16, 21.32, 21.26; HRMS (ESI): calcd for $C_{24}H_{28}N_5$ $[M+H]^+$, 386.2339. found, 386.2333.

Example 15

The synthesis of 5 is shown below. Dibromophenethyl derivative 12 was prepared by coupling of 3,5-dibromobenzylbromide with lithiated pyrrolyl-4,6-lutidine (11). This intermediate underwent microwave-assisted Rosenmund-von Braun reaction with CuCN to replace one of the bromides by CN (13). A Buchwald-Hartwig reaction of 13 with 2-pyridinylethylamine using $Pd_2(dba)_3$ and Davephos gave the corresponding amine (14). The 2,5-dimethylpyrrole protecting group of 14 was removed with $NH_2OH.HCl$ using a microwave to generate 5.

Synthesis of Compound 5

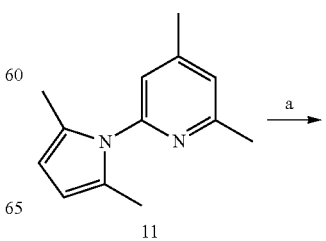

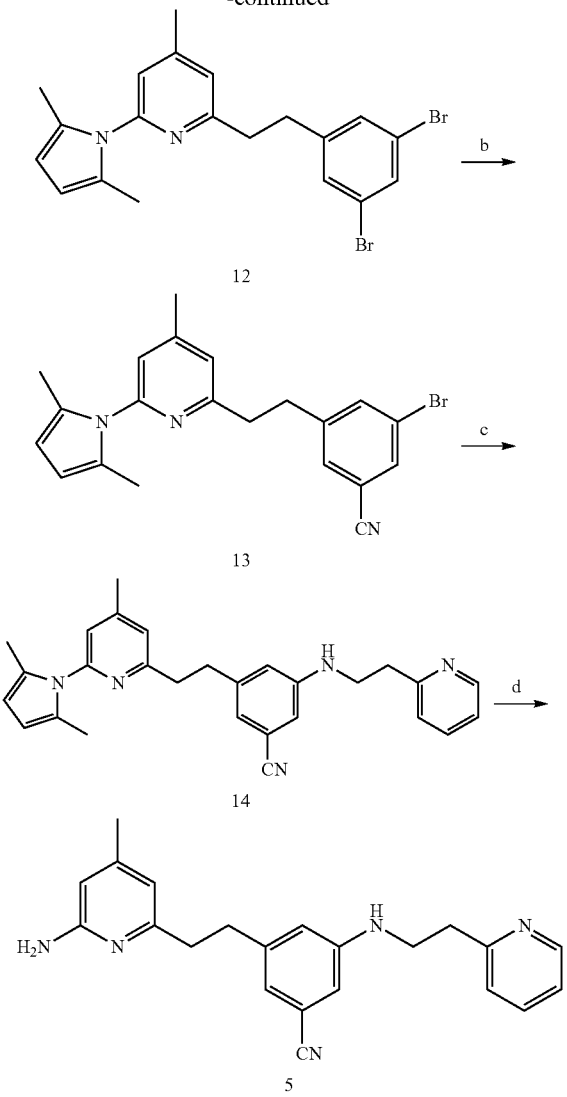

Reagents and conditions:
a) (i) BuLi, 0° C., THF, 30 min, (ii) 3,5-dibromobenzylbromide, -78° C. 20 min, 86%;
b) CuCN, DMF, 220° C., microwave, 15 min, 57%;
c) 2-pyridinylethylamine, Pd$_2$(dba)$_3$, Davephos, NaOtBu, THF-dioxane, 80° C., 72%;
d) NH$_2$OH(HCl), H$_2$O—EtOH, microwave, 30 min, 120° C., 76%

Example 15a 2-(3,5-Dibromophenethyl)-6-(2,5-dimethyl-1H-pyrrol-1-yl)-4-methylpyridine (12). To a solution of 11 (1.2 g, 6.0 mmol) in THF (25 mL) was added n-BuLi (1.6 M solution in hexanes, 3.75 mL, 6.0 mmol). The reaction mixture was stirred for 30 min at 0° C. and transferred to a solution of 3,5-dibromobenzylbromide (1.64 g, 5.0 mmol) in THF (25 mL) at −78° C. via cannula. The reaction mixture was allowed to stir for an additional 20 min and then quenched with H$_2$O (50 mL). After addition of ethyl acetate (50 mL), the organic layer was partitioned, dried with MgSO$_4$, and concentrated by rotary evaporation. The residue was purified by flash chromatography (EtOAc/hexanes) to yield 12 (86%) as a pale yellow oil; $^1$H NMR (500 MHz, CDCl3) δ 7.51 (s, 1H), 7.26 (ss, 2H), 6.91 (s, 2H), 5.92 (s, 2H), 3.06 (q, J=2.8 Hz, 4H), 2.40 (d, J=1.6 Hz, 3H), 2.15 (s, 6H); $^{13}$C NMR (126 MHz, CDCl$_3$) δ 159.76, 151.73, 149.72, 145.43, 131.65, 130.43, 128.48, 122.77, 122.74, 120.42, 106.76, 39.02, 34.89, 21.01, 13.27; MS ESI [M+H]$^+$=449.3.

Example 15b

3-Bromo-5-(2-(6-(2,5-dimethyl-1H-pyrrol-1-yl)-4-methylpyridin-2-yl)ethyl)benzonitrile (13). A mixture of 12 (448 mg, 1.0 mmol), CuCN (108 mg, 1.20 mmol), and DMF (4 mL) was heated at 220° C. for 20 min in the microwave cavity. The reaction mixture was then treated with dichloromethane (20 mL), filtered, and concentrated in vacuo. The residue was purified by flash chromatography to give the 13 (225 mg, 57%) as a pale yellow oil. $^1$H NMR (500 MHz, CDCl$_3$) δ 7.63 (s, 1H), 7.57 (s, 1H), 7.41 (s, 1H), 6.93 (ss, 2H), 5.92 (s, 2H), 3.19-3.03 (m, 4H), 2.41 (s, 3H), 2.13 (s, 6H); $^{13}$C NMR (126 MHz, CDCl$_3$) δ 159.27, 151.82, 149.88, 145.04, 136.39, 132.31, 130.76, 128.44, 122.77, 122.75, 120.59, 117.45, 113.92, 106.81, 38.69, 34.58, 21.01, 13.26; MS ESI [M+H]$^+$=394.5.

Example 15c 3-(2-(6-(2,5-Dimethyl-1H-pyrrol-1-yl)-4-methylpyridin-2-yl)ethyl)-5-((2-(pyridin-2-yl)ethyl)amino)benzonitrile (14). A mixture of 3-bromobenzonitrile 13 (200 mg, 0.5 mmol), 2-(2-pyridinyl)ethylamine (73 mg, 0.60 mmol), Pd$_2$(dba)$_3$ (23 mg, 0.025 mmol), Davephos (20 mg, 0.050 mmol), and NaOtBu (58 mg, 0.60 mmol) in THF (1.5 mL) and 1,4-dioxane (1.5 mL) was stirred at 80° C. for 12 h. The reaction mixture was then treated with diethyl ether (20 mL), filtered, and concentrated in vacuo. The residue was purified by flash chromatography (EtOAc/hexanes) to give 14 (157 mg, 72%) as a pale yellow oil. $^1$H NMR (500 MHz, CDCl$_3$) δ 8.62-8.55 (m, 1H), 7.65 (td, J=7.6, 1.9 Hz, 1H), 7.22-7.16 (m, 2H), 6.93 (s, 1H), 6.88 (s, 1H), 6.77 (s, 1H), 6.67 (s, 1H), 6.64 (s, 1H), 5.91 (s, 2H), 4.65 (t, J=5.6 Hz, 1H), 3.50 (q, J=5.8 Hz, 2H), 3.15-3.03 (m, 4H), 3.02-2.93 (m, 2H), 2.39 (s, 3H), 2.20 (s, 6H); $^{13}$C NMR (126 MHz, CDCl$_3$) δ 160.25, 159.34, 151.66, 149.62, 149.37, 148.54, 143.70, 136.75, 128.45, 123.39, 122.65, 121.73, 120.69, 120.25, 119.66, 117.48, 112.99, 112.70, 106.72, 43.09, 39.17, 36.83, 35.43, 21.01, 13.25; MS ESI [M+H]$^+$=436.5.

Example 15d 3-(2-(6-Amino-4-methylpyridin-2-yl)ethyl)-5-((2-(pyridin-2-yl)ethyl)amino)benzonitrile (5). To a 5 mL microwave vial was added protected aminopyridine 14 (131 mg, 0.3 mmol), hydroxylamine HCl (105 mg, 1.5 mmol), EtOH (1.5 mL), and H$_2$O (0.5 mL). After being sealed, the vial was shaken vigorously and then heated in the microwave irradiator for 30 min at 120° C. The reaction mixture was allowed to cool to room temperature and then concentrated in vacuo, and purified by flash column chromatography using a SiliaSep™ C18 flash cartridge (25 g, 40-63 μm/230-400 mesh, Pore Size 60 Å) with 5 to 80% MeOH in water to yield 5 (76%) as a pale yellow gel. $^1$H NMR (500 MHz, CDCl$_3$) δ 8.63-8.53 (m, 1H), 7.65 (td, J=7.7, 1.8 Hz, 1H), 7.20 (dd, J=7.6, 5.6 Hz, 2H), 6.81 (s, 1H), 6.67 (d, J=1.4 Hz, 2H), 6.32 (s, 1H), 6.20 (s, 1H), 4.60 (t, J=5.6 Hz, 1H), 3.51 (q, J=6.2 Hz, 2H), 3.09 (t, J=6.5 Hz, 2H), 2.91 (dd, J=9.5, 5.7 Hz, 2H), 2.82 (dd, J=9.5, 5.7 Hz, 2H), 2.20 (s, 3H); $^{13}$C NMR (126 MHz, CDCl$_3$) δ 159.38, 158.81, 158.22, 149.39, 149.27, 148.45, 144.12, 136.72, 123.39, 121.71, 120.89, 119.76, 117.54, 114.52, 112.88, 112.61, 106.68, 43.12, 39.34, 36.88, 35.68, 20.97; HRMS (ESI): calcd for $C_{22}H_{24}N_5$ [M+H]$^+$, 358.2026. found, 358.2024.

Example 16

Compound 6 was obtained using the synthetic pathway shown below. Sonogashira coupling between 13 and 15 using Pd(Ph$_3$)$_2$Cl$_2$ yielded 16. The produced alkyne of 16 underwent catalytic hydrogenation with Pd/C under hydrogen atmosphere. Microwave-assisted deprotection of the protecting groups on the aminopyridine ring with NH$_2$OH.HCl and Raney nickel mediated hydrogenation of the CN group yielded 6.

Synthesis of Compound 6

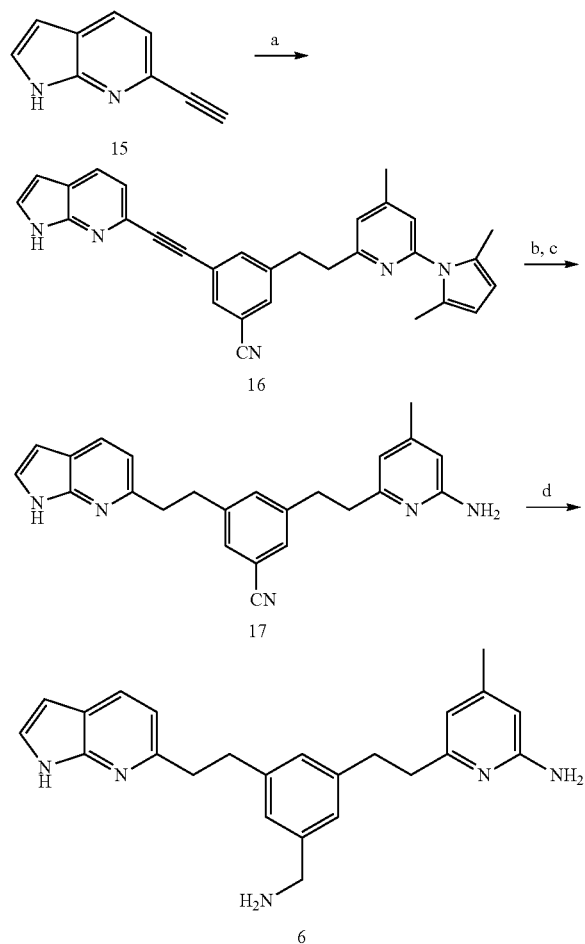

Reagents and conditions: a) 13, Pd(Ph$_3$)$_2$Cl$_2$, CuI, PPh$_3$, DEA—DMF, microwave, 120° C., 20 min, 89%; b) Pd/C, H$_2$, EtOH, 30 min, c) NH$_2$OH(HCl), H$_2$O—EtOH, microwave, 30 min, 120° C., 44% (two steps); d) Raney-Ni, H$_2$, NH$_3$, EtOH—MeOH, 87%.

Example 16a

6-Ethynyl-1H-pyrrolo[2,3-b]pyridine (15). Compound 15 was prepared as previously described (Minakata, S., Itoh, S., Komatsu, M., and Ohshiro, Y. (1992) Functionalization of 1h-Pyrrolo[2,3-B]Pyridine, *B Chem Soc Jpn* 65, 2992-2997; Minakata, S., Komatsu, M., and Ohshiro, Y. (1992) Regi- oselective Functionalization of 1h-Pyrrolo[2,3-B]Pyridine Via Its N-Oxide, *Synthesis-Stuttgart*, 661-663). The spectral data were in accordance with those previously reported.

Example 16b 3-((1H-Pyrrolo[2,3-b]pyridin-6-yl)ethynyl)-5-(2-(6-(2,5-dimethyl-1H-pyrrol-1-yl)-4-methylpyridin-2-yl)ethyl)benzonitrile (16). A mixture of 13 (394 mg, 1.0 mmol), 15 (156 mg, 1.1 mmol), Pd(PPh$_3$)$_2$Cl$_2$ (35 mg, 0.05 mmol), CuI (10 mg, 0.05 mmol), PPh$_3$ (52 mg, 0.20 mmol), diethylamine (2 mL), and DMF (2 mL) was heated at 120° C. for 20 min in the microwave cavity. Then the reaction mixture was treated with diethyl ether (20 mL), filtered, and concentrated in vacuo. The residue was purified by flash chromatography (EtOAc/hexanes) to give 16 (405 mg, 89%) as a pale yellow oil. $^1$H NMR (500 MHz, CDCl$_3$) δ 11.54 (s, 1H), 8.00 (d, J=8.0 Hz, 1H), 7.71 (t, J=1.6 Hz, 1H), 7.68 (t, J=1.7 Hz, 1H), 7.45 (dt, J=3.4, 2.1 Hz, 2H), 7.39 (d, J=8.0 Hz, 1H), 6.95 (d, J=1.3 Hz, 1H), 6.92 (d, J=1.3 Hz, 1H), 6.57 (dd, J=3.5, 1.9 Hz, 1H), 5.93 (s, 2H), 3.17 (h, J=2.6 Hz, 4H), 2.41 (s, 3H), 2.16 (s, 6H); $^{13}$C NMR (126 MHz, CDCl$_3$) δ 159.58, 151.80, 149.89, 148.47, 143.47, 136.14, 134.18, 132.66, 131.91, 129.07, 128.48, 127.35, 124.33, 122.78, 120.79, 120.56, 119.87, 118.16, 112.89, 106.82, 101.20, 91.73, 85.40, 38.75, 34.78, 21.04, 13.29. MS (ESI) e/z=456.3 [M+H]$^+$.

Example 16c 3-(2-(1H-Pyrrolo[2,3-b]pyridin-6-yl)ethyl)-5-(2-(6-amino-4-methylpyridin-2-yl)ethyl)benzonitrile (17). After stirring 16 (400 mg, 0.88 mmol) and Pd/C (10%, 200 mg) in EtOH (10 mL) for 30 min at ambient temperature under a hydrogen atmosphere, the reaction mixture was filtered through Celite and concentrated in vacuo. The residue was mixed with hydroxylamine HCl (308 mg, 4.4 mmol), EtOH (1.5 mL), and H$_2$O (0.5 mL) in a microwave vial. The vial was capped, shaken vigorously, and then heated in the microwave irradiator for 30 min at 120° C. After cooling the vial to room temperature, the reaction mixture was concentrated in vacuo, and purified using a SiliaSep™ C18 flash cartridge (25 g, 40-63 μm/230-400 mesh, Pore Size 60 Å) with 5 to 80% MeOH to give pure 17 (180 mg, 57%) as a pale brown gel. $^1$H NMR (500 MHz, MeOD) δ 7.89 (d, J=8.0 Hz, 1H), 7.39 (s, 1H), 7.35-7.31 (m, 2H), 7.27 (s, 1H), 6.91 (d, J=8.0 Hz, 1H), 6.46 (d, J=3.5 Hz, 1H), 6.28 (s, 1H), 6.21 (s, 1H), 3.10 (td, J=5.1, 4.0, 2.6 Hz, 4H), 2.92 (dd, J=9.1, 6.7 Hz, 2H), 2.72 (dd, J=9.1, 6.7 Hz, 2H), 2.17 (s, 3H); $^{13}$C NMR (126 MHz, MeOD) δ 160.67, 158.71, 154.78, 151.29, 149.18, 144.64, 144.53, 135.00, 130.88, 130.83, 130.58, 126.30, 120.33, 120.00, 116.62, 114.81, 113.01, 108.12, 101.30, 40.35, 39.87, 37.17, 36.50, 21.01; HRMS (ESI): calcd for $C_{24}H_{24}N_5$ [M+H]$^+$, 382.2026. found, 358.2027.

Example 16d 6-(3-(2-(1H-Pyrrolo[2,3-b]pyridin-6-yl)ethyl)-5-(aminomethyl)phenethyl)-4-methylpyridin-2-amine (6). A solution of 17 (100 mg, 0.28 mmol) in MeOH (10 mL) was stirred with Raney-Ni (50% in water, 0.2 mL) for 1 h at ambient temperature under a hydrogen atmosphere. The reaction mixture was filtered through Celite, concentrated in vacuo, and purified using prep-HPLC to yield 6 (63 mg, 62%). $^1$H NMR (500 MHz, MeOD) δ 8.31 (s, 2H), 7.74 (d, J=7.9 Hz, 1H), 7.18 (d, J=3.5 Hz, 1H), 7.05 (s, 1H), 7.02 (s, 1H), 6.93 (s, 1H), 6.80 (d, J=7.9 Hz, 1H), 6.77-6.67 (m, 1H), 6.35 (s, 1H), 6.31 (d, J=3.5 Hz, 1H), 6.27 (s, 1H), 3.92 (s, 2H), 2.98 (dd, J=8.7, 5.6 Hz, 2H), 2.92 (dd, J=8.6, 5.6 Hz, 2H), 2.81 (t, J=7.6 Hz, 2H), 2.72 (t, J=7.4 Hz, 2H), 2.13 (s, 3H); $^{13}$C NMR (126 MHz, MeOD) δ 157.84, 156.30, 155.35, 149.22, 144.46, 142.96, 134.90, 130.80, 130.53, 128.24, 127.83, 126.42, 120.45, 116.61, 115.67, 114.68, 110.01, 101.45, 44.42, 40.77, 37.78, 37.05, 36.31, 21.73; HRMS (ESI): calcd for $C_{24}H_{28}N_5$ $[M+H]^+$, 386.2339. found, 386.2338.

Experimental Procedures for Examples 17-39

Molecular Biology

Active site mutation I218V was introduced to *Bacillus subtilis* NOS (bsNOS) by site directed mutagenesis using PfuTrubo (Agilent). Both WT and I218V bsNOS were expressed and purified from *E. coli* as previously described for bsNOS. (Pant, K., Bilwes, A. M., Adak, S., Stuehr, D. J., and Crane, B. R. (2002) Structure of a nitric oxide synthase heme protein from *Bacillus subtilis*. *Biochemistry* 41, 11071-11079.) YumC and bBiDomain were also purified from *E. coli* and used for activity analysis. (Holden, J. K., Lim, N., and Poulos, T. L. (2014) Identification of Redox Partners and Development of a Novel Chimeric Bacterial Nitric Oxide Synthase for Structure Activity Analyses. *J. Biol. Chem.*) Recombinant rat nNOS, murine macrophage iNOS, and bovine eNOS were expressed in *E. coli* and isolated as reported. (Hevel, J. M., White, K. A., and Marletta, M. A. (1991) Purification of the inducible murine macrophage nitric oxide synthase. Identification as a flavoprotein. *J. Biol. Chem.* 266, 22789-22791. Roman, L. J., Sheta, E. A., Martásek, P., Gross, S. S., Liu, Q., and Masters, B. S.; (1995). High-level expression of functional rat neuronal nitric oxide synthase in *Escherichia coli*. *Proc. Natl. Acad. Sci. U.S.A.* 92, 8428-8432. Martásek, P., Liu, Q., Liu, J., Roman, L. J., Gross, S. S., Sessa, W. C., and Masters, B. S. (1996) Characterization of bovine endothelial nitric oxide synthase expressed in *E. coli*. *Biochemical and biophysical research communications* 219, 359-365.)

Bacterial NOS Activity Inhibition—

Reactions containing both bBiDomain (a chimera of bsNOS and redox partner YkuN) and YumC were initiated with NADPH and run for 4 min at 35° C. as described in the literature. Substrate N-omega-hydroxy-L-arginine (NOHA) and NOS inhibitor were included in each reaction at 200 μM and 30 μM, respectively. The Griess reaction was used to measure nitrite levels as a function of NOS activity. % Nitrite was calculated for each reaction as the concentration of nitrite detected in the presence of inhibitor divided by the concentration of nitrite detected without inhibitor present. Each reaction was measured in duplicate for three separate trials.

$K_i$ Determination—

The $K_i$ was calculated from the half maximal inhibitor concentration ($IC_{50}$) and $K_D$ of L-Arg using the Cheng-Prusoff equation. For bBidomain the $K_D$ of L-NOHA was approximated equal to the previously reported bsNOS L-Arg $K_D$ of 5.6 μM. $IC_{50}$ was measured for bsNOS using bBiDomain and YumC as previously described. $IC_{50}$ for mammalian NOS was determined using the oxyhemoglobin assay as described in the literature.

Crystallization and Structure Determination—

Crystals of bsNOS and I218V were prepared, cryo-protected and flash frozen at 100 K. Data was collected under cryogenic conditions on individual crystals at both the Advanced Light Source (Berkeley, Calif.) and Stanford Synchrotron Radiation Lightsource (Menlo Park, Calif.). The raw data frames were indexed and integrated using either iMOSFLM or XDS. The program Aimless was then used to scale the data sets. Datasets with high anisotropy were processed using the diffraction anisotropy server. Inhibitor bound structures were refined using phenix with inhibitor restraints built using PRODRG.

Imidazole Displacement—

Purified bsNOS was diluted to 2 μM into a buffered solution containing 50 mM Tris (pH 7.6), 10 mM NaCl, 100 μM dithiothreitol and 1 mM imidazole to generate a low spin heme. NOS inhibitors were titrated into the bsNOS-buffered solution and the conversion of the heme group from low spin to high spin was monitored using a Cary 3E UV-visible spectrophotometer. The $K_S$ was calculated as previously described from the $K_{S,app}$ using the bsNOS $K_D$ imidazole at 384 μM and the bsNOS-I218V $K_D$ imidazole at 506 μM.

Example 17

Effect of Antimicrobial Induced Stress and NOS Inhibitors on *S. Aureus*

Creation of the *S. aureus* UAMS1182 nos isogenic knock-out is described in a previous report. Parent (wild type, wt) and knockout (Δnos) were cultured in cation-adjusted Mueller Hinton broth (CAMHB). Prior to $H_2O_2$ assays, strains were cultured overnight at 37° C. then subcultured at a 1/20 dilution in fresh CAMHB. Strains were grown to mid-log phase ($OD_{600}$~0.4), pelleted by centrifugation, washed twice in CAMHB, and diluted in CAMHB to a predetermined concentration approximating $2\times10^7$ colony forming units per mL (CFU/mL). Volumes of 25 μL ($5\times10^5$ CFU) were dispensed to 96 well plates (Corning Life Sciences) into 200 μL aliquots of CAMHB, and CAMHB with amendments including 5 mM $H_2O_2$ (Sigma), 200 μM 19, 200 μM 27, and equivalent control volumes of 19/27 solvent. Plates were incubated at 37° C. with shaking Cultures were sampled at 30 min intervals by removing 25 μL for serial dilution in CAMHB and spot plating on Todd Hewitt agar (Becton Dickinson). Plates were incubated overnight and culture CFU/mL was calculated by enumerating counted colonies and multiplying back through the dilution factor. All conditions were sampled in triplicate; values presented are mean+standard deviation. Statistical analysis was performed in Excel (Microsoft) using the Student's t-test. The $K_S$ value are reported in Table 1.

Example 18

General procedure for coupling reaction of benzyl bromide with lithiated pyrrolyl-lutidine; Method A. n-BuLi (1.6 M solution in hexanes, 3.75 mL, 6.0 mmol) was added dropwise to a solution of 2-(2,5-dimethyl-1H-pyrrol-1-yl)-4,6-dimethylpyridine (1.2 g, 6.0 mmol) in THF (25 mL) at 0° C. After stirring 30 min at the same temperature, the mixture was transferred to a solution of benzylbromide (5.0 mmol) in THF (25 mL) at −78° C. via cannula. The reaction mixture was allowed to stir for an additional 20 min, and then quenched by an addition of $H_2O$ (50 mL) and ethyl acetate (50 mL). The organic layer was partitioned, dried with $MgSO_4$, and concentrated under vacuum. The residue was purified by flash chromatography (EtOAc/hexanes) to yield corresponding products.

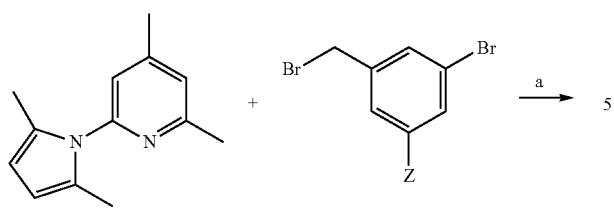

| Z |
|---|
| I Br |
| II F |

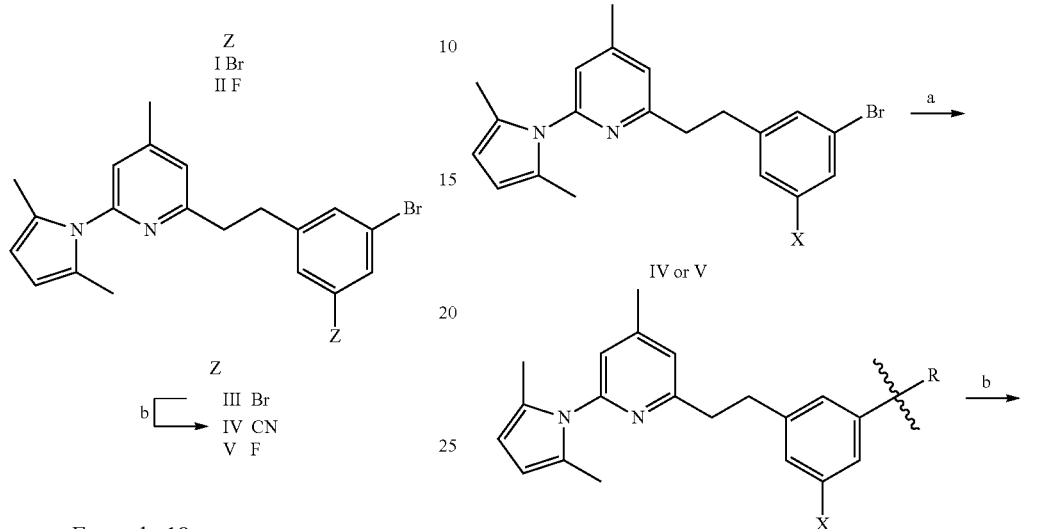

| Z |
|---|
| III Br |
| IV CN |
| V F |

Example 18a 2-(3,5-Dibromophenethyl)-6-(2,5-dimethyl-1H-pyrrol-1-yl)-4-methylpyridine (III). The title compound was prepared using the general method A from 3,5-dibromobenzylbromide (I). 86%; pale yellow oil; $^1$H NMR (500 MHz, CDCl3) δ 7.51 (s, 1H), 7.26 (ss, 2H), 6.91 (s, 2H), 5.92 (s, 2H), 3.06 (q, J=2.8 Hz, 4H), 2.40 (d, J=1.6 Hz, 3H), 2.15 (s, 6H); $^{13}$C NMR (126 MHz, CDCl$_3$) δ 159.76, 151.73, 149.72, 145.43, 131.65, 130.43, 128.48, 122.77, 122.74, 120.42, 106.76, 39.02, 34.89, 21.01, 13.27; MS ESI [M+H]$^+$=449.3.

Example 18b

3-Bromo-5-(2-(6-(2,5-dimethyl-1H-pyrrol-1-yl)-4-methylpyridin-2-yl)ethyl)benzonitrile (IV). To a 5 mL microwave vial equipped with a magnetic stir bar were added III (448 mg, 1.0 mmol), CuCN (108 mg, 1.20 mmol), and DMF (2 mL). After capped, the vial was heated in the microwave irradiator for 20 min at 220° C. After cooling, the reaction mixture was treated with dichloromethane (20 mL), filtered, and concentrated in vacuo. The residue was purified by flash chromatography to give the title compound (225 mg, 57%) as a pale yellow oil. $^1$H NMR (500 MHz, CDCl$_3$) δ 7.63 (s, 1H), 7.57 (s, 1H), 7.41 (s, 1H), 6.93 (ss, 2H), 5.92 (s, 2H), 3.19-3.03 (m, 4H), 2.41 (s, 3H), 2.13 (s, 6H); $^{13}$C NMR (126 MHz, CDCl$_3$) δ 159.27, 151.82, 149.88, 145.04, 136.39, 132.31, 130.76, 128.44, 122.77, 122.75, 120.59, 117.45, 113.92, 106.81, 38.69, 34.58, 21.01, 13.26; MS ESI [M+H]$^+$=394.5.

Example 18c 2-(3-Bromo-5-fluorophenethyl)-6-(2,5-dimethyl-1H-pyrrol-1-yl)-4-methylpyridine (V). The title compound was prepared using the general method A from 3-bromo-5-fluoro-benzylbromide (II). 81%; pale yellow oil; $^1$H NMR (500 MHz, CDCl$_3$) δ 7.15 (s, 1H), 7.10 (dt, J=8.2, 2.1 Hz, 1H), 6.95 (s, 1H), 6.92 (s, 1H), 6.87 (m, 1H), 5.94 (s, 2H), 3.16-3.03 (m, 4H), 2.42 (s, 3H), 2.17 (s, 6H); $^{13}$C NMR (126 MHz, CDCl$_3$) δ 162.60 (d, J=250.1 Hz), 159.89, 151.75, 149.71, 145.63 (d, J=7.8 Hz), 128.46, 127.56 (d, J=3.0 Hz), 122.74, 122.29 (d, J=10.2 Hz), 120.40, 116.69 (d, J=24.4 Hz), 114.42 (d, J=20.9 Hz), 106.79, 38.98, 35.04 (d, J=1.8 Hz), 21.01, 13.28; MS ESI [M+H]$^+$=387.2.

Example 19

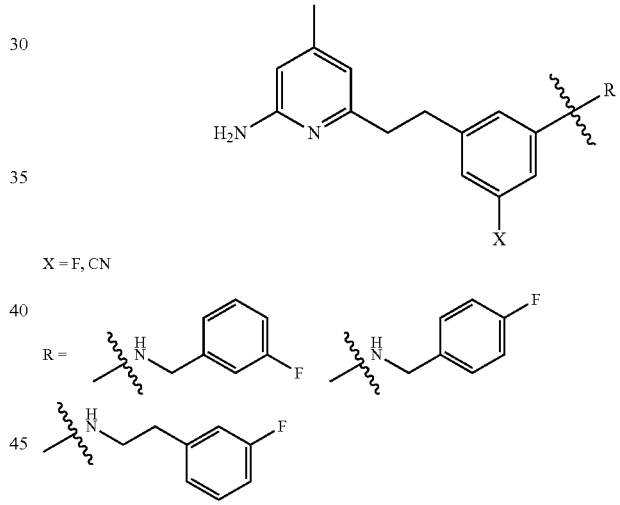

X = F, CN

General procedure for Buchwald Hartwig amination using Pd$_2$(dba)$_3$ and Davephos: Method B; The mixture of 3-bromobenzene (0.25 mmol), amine (0.30 mmol), Pd$_2$(dba)$_3$ (12 mg, 0.0125 mmol), Davephos (10 mg, 0.025 mmol), and NaOtBu (29 mg, 0.30 mmol) in THF (1.0 mL) and 1,4-dioxane (1.0 mL) was stirred at 80° C. for 12 h. The reaction mixture was then treated with diethyl ether (10 mL), filtered, and concentrated in vacuo. The residue was purified by flash chromatography (EtOAc/hexanes) to give the corresponding products.

Example 20

General procedure for deprotection of 2-(2,5-dimethyl-1H-pyrrol-1-yl)pyridine derivatives using microwave irradiation: Method C; To a 5 mL microwave vial equipped with a magnetic stir bar were added the protected aminopyridine (0.1~0.5 mmol), hydroxylamine HCl (5 eq), ethanol (2 mL), and water (1 mL). After capped, the vial was shaken vigorously and then heated in the microwave irradiator for 30 min at 120° C. The reaction mixture was concentrated in vacuo, and purified by flash column chromatography using C18 flash cartridge (12-25 g, 40-63 μm/230-400 mesh, Pore Size 60 Å) with 5 to 90% MeOH in water as the mobile phase. This method was applied to give pure (>95% by HPLC) final compounds (65%-80% yield).

Example 21a

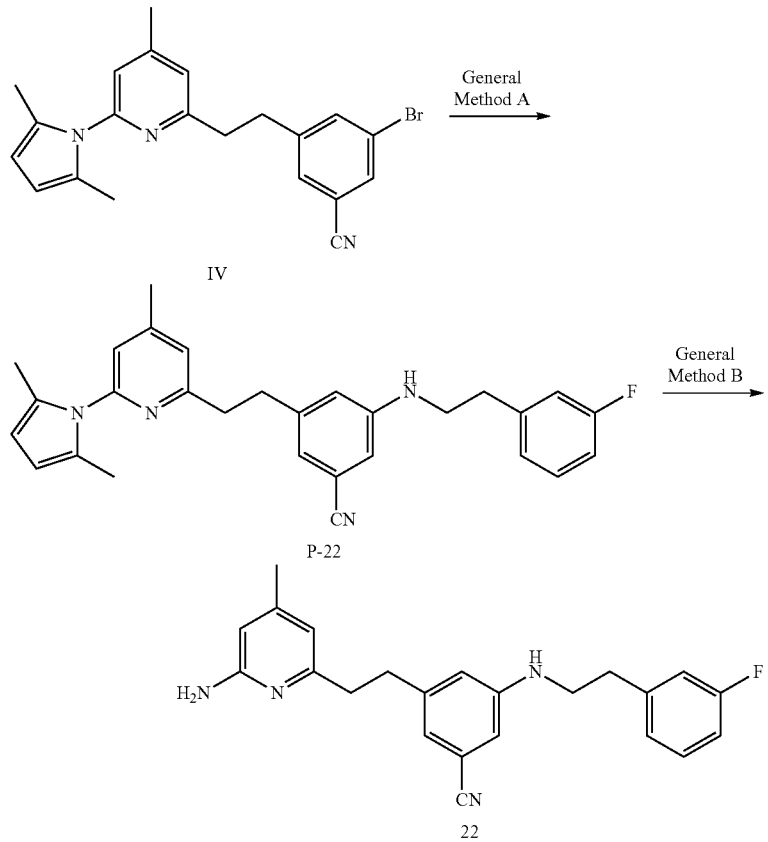

3-(2-(6-(2,5-Dimethyl-1H-pyrrol-1-yl)-4-methylpyridin-2-yl)ethyl)-5-((3-fluorophenethyl)amino)benzonitrile (P22). The title compound was prepared using the general method B from 2-(3-fluorophenyl)ethylamine. 86%, colorless gel; $^1$H NMR (500 MHz, CDCl$_3$) δ 7.37-7.28 (m, 1H), 7.01 (dt, J=7.6, 1.2 Hz, 1H), 7.00-6.92 (m, 3H), 6.90 (s, 1H), 6.81 (s, 1H), 6.66 (s, 1H), 6.63 (s, 1H), 5.92 (s, 2H), 3.96 (t, J=5.9 Hz, 1H), 3.38 (q, J=6.6 Hz, 2H), 3.11-3.05 (m, 2H), 3.05-2.99 (m, 2H), 2.92 (t, J=6.9 Hz, 2H), 2.41 (s, 3H), 2.15 (s, 6H); $^{13}$C NMR (126 MHz, CDCl$_3$) δ 163.98, 162.02, 160.21, 151.68, 149.70, 148.20, 143.91, 141.38, 141.32, 130.25, 130.19, 128.44, 124.45, 124.43, 122.69, 120.96, 120.29, 119.58, 117.45, 115.69, 115.53, 113.68, 113.51, 113.05, 112.81, 106.76, 44.34, 39.14, 35.40, 34.93, 21.01, 13.28; MS ESI [M+H]$^+$=453.7.

Example 21b 3-(2-(6-Amino-4-methylpyridin-2-yl)ethyl)-5-((3-fluorophenethyl)amino)benzonitrile (22). The title compound was prepared using the general method C from P22. 70%; pale yellow gel; $^1$H NMR (500 MHz, CDCl$_3$) δ 7.34-7.27 (m, 1H), 7.01-6.90 (m, 3H), 6.86 (s, 1H), 6.64 (s, 2H), 6.28 (s, 1H), 6.16 (s, 1H), 3.37 (q, J=6.7 Hz, 2H), 2.90 (dd, J=8.3, 5.4 Hz, 4H), 2.85-2.76 (m, 2H), 2.18 (s, 3H); $^{13}$C NMR (126 MHz, CDCl$_3$) δ 162.98 (d, J=246.1 Hz), 158.31 (d, J=22.4 Hz), 156.44, 149.67, 148.05, 144.22, 141.36 (d, J=7.2 Hz), 130.18 (d, J=8.4 Hz), 124.43 (d, J=2.7 Hz), 121.28, 119.68, 117.67, 115.61 (d, J=21.0 Hz), 114.12, 113.57 (d, J=21.2 Hz), 112.86, 112.70, 106.95, 44.37, 39.18, 35.81, 34.92 (d, J=1.7 Hz), 21.00; HRMS (ESI): calcd for C$_{23}$H$_{24}$FN$_4$ [M+H]$^+$, 375.1980. found, 375.1976.

Example 22a

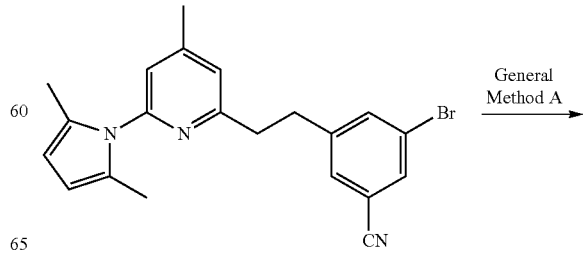

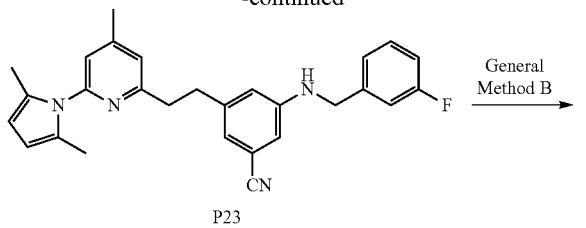

P23

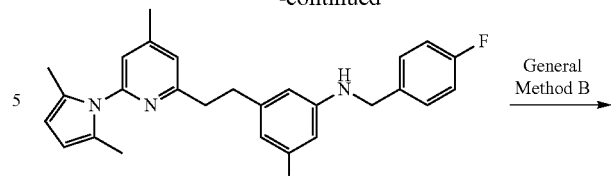

P24

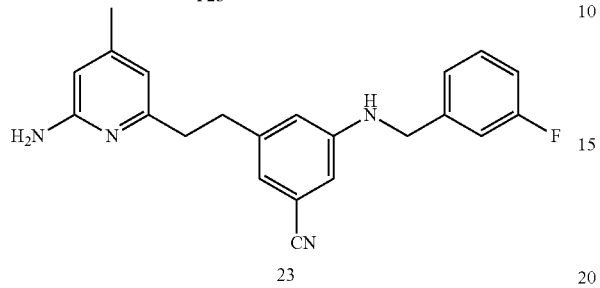

23

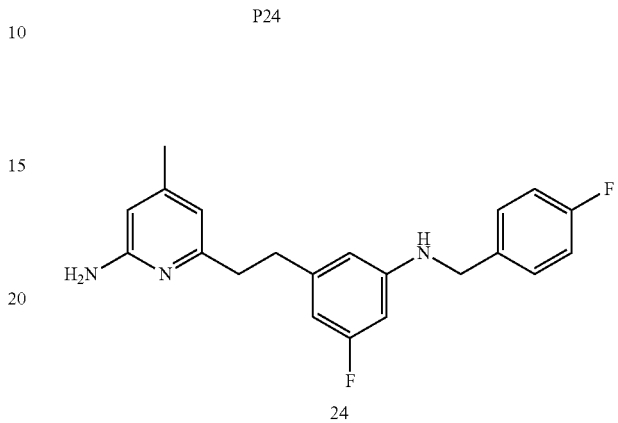

24

3-(2-(6-(2,5-Dimethyl-1H-pyrrol-1-yl)-4-methylpyridin-2-yl)ethyl)-5-((3-fluorobenzyl)amino)-benzonitrile (P23). The title compound was prepared using the general method B from 3-fluorobenzylamine. 69%; brown oil; $^1$H NMR (500 MHz, CDCl$_3$) δ 7.32-7.27 (m, 1H), 7.08 (d, J=7.6 Hz, 1H), 7.03-6.98 (m, 1H), 6.98-6.93 (m, 1H), 6.88 (s, 1H), 6.85 (s, 1H), 6.77 (ss, 1H), 6.62 (s, 1H), 6.60 (s, 1H), 5.87 (s, 2H), 4.35-4.30 (m, 1H), 4.29 (s, 2H), 3.10-2.89 (m, 4H), 2.36 (s, 3H), 2.09 (s, 6H); $^{13}$C NMR (126 MHz, CDCl$_3$) δ 163.16 (d, J=246.6 Hz), 160.14, 151.66, 149.67, 148.06, 143.90, 141.05 (d, J=6.8 Hz), 130.38 (d, J=8.2 Hz), 128.45, 122.69 (d, J=2.8 Hz), 122.64, 121.37, 120.28, 119.50, 117.57, 114.45 (d, J=21.1 Hz), 113.99 (d, J=21.8 Hz), 113.01, 112.83, 106.76, 47.28, 39.03, 35.32, 21.02, 13.26; MS ESI [M+H]$^+$=439.1.

Example 22b 3-(2-(6-Amino-4-methylpyridin-2-yl)ethyl)-5-((3-fluorobenzyl)amino)benzonitrile (23). The title compound was prepared using the general method C from P23. 78%; pale yellow gel; $^1$H NMR (500 MHz, MeOD) δ 7.35 (td, J=7.9, 5.8 Hz, 1H), 7.17 (d, J=7.6 Hz, 1H), 7.08 (dt, J=10.0, 2.0 Hz, 1H), 6.98 (td, J=8.5, 2.6 Hz, 1H), 6.75 (s, 1H), 6.68 (s, 2H), 6.31 (s, 1H), 6.26 (s, 1H), 4.33 (s, 2H), 2.84 (dd, J=8.8, 5.8 Hz, 2H), 2.76 (dd, J=8.8, 5.8 Hz, 2H), 2.18 (s, 3H); $^{13}$C NMR (126 MHz, MeOD) δ 164.54 (d, J=244.4 Hz), 160.10, 158.00, 156.10, 151.99, 150.43, 145.04, 143.86 (d, J=6.8 Hz), 131.30 (d, J=8.2 Hz), 123.90 (d, J=2.9 Hz), 121.07, 120.52, 118.34, 114.77, 114.60, 113.99, 113.39, 108.35, 47.38, 39.39, 36.71, 21.51; HRMS (ESI): calcd for C$_{22}$H$_{22}$FN$_4$ [M+H]$^+$, 361.1823. found, 361.1832.

Example 23a

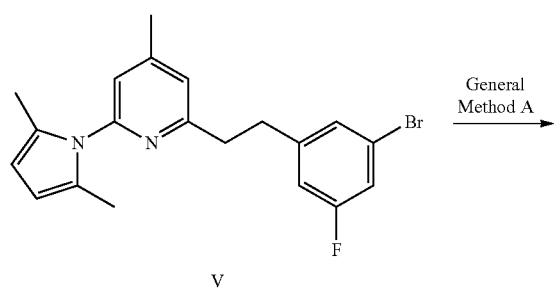

V 3-(2-(6-(2,5-Dimethyl-1H-pyrrol-1-yl)-4-methylpyridin-2-yl)ethyl)-5-fluoro-N-(4-fluorobenzyl)aniline (P24). The title compound was prepared using the general method B from V and 4-fluorobenzylamine. 75%; colorless oil; $^1$H NMR (500 MHz, CDCl$_3$) δ 7.37-7.31 (m, 2H), 7.10-7.01 (m, 2H), 6.95 (s, 1H), 6.89 (s, 1H), 6.31-6.24 (m, 2H), 6.16 (dt, J=11.2, 2.2 Hz, 1H), 5.92 (s, 2H), 4.27 (s, 2H), 3.10-3.01 (m, 2H), 3.01-2.92 (m, 2H), 2.40 (s, 3H), 2.15 (s, 6H); $^{13}$C NMR (126 MHz, CDCl$_3$) δ 164.04 (d, J=241.8 Hz), 161.13, 160.70, 151.61, 149.51, 149.41 (d, J=11.5 Hz), 144.56 (d, J=9.4 Hz), 134.51 (d, J=3.3 Hz), 129.02 (d, J=8.0 Hz), 128.47, 122.58, 120.11, 115.55 (d, J=21.6 Hz), 108.85, 106.71, 104.41 (d, J=21.4 Hz), 97.38 (d, J=25.7 Hz), 47.51, 39.30, 35.84 (d, J=1.9 Hz), 21.02, 13.26; MS ESI [M+H]$^+$=432.1.

Example 23b 6-(3-Fluoro-5-((4-fluorobenzyl)amino)phenethyl)-4-methylpyridin-2-amine (24). The title compound was prepared using the general method C from P24. 63%; pale yellow gel; $^1$H NMR (500 MHz, CDCl$_3$) δ 7.32 (dd, J=8.5, 5.5 Hz, 2H), 7.04 (t, J=8.7 Hz, 2H), 6.37-6.28 (m, 3H), 6.17 (s, 1H), 6.16-6.11 (m, 1H), 4.27 (d, J=5.3 Hz, 2H), 4.18 (t, J=5.7 Hz, 1H), 2.92-2.78 (m, 4H), 2.20 (s, 3H); $^{13}$C NMR (126 MHz, CDCl$_3$) δ 164.99 (d, J=242.4 Hz), 162.06 (d, J=245.1 Hz), 158.62, 158.22, 156.73 (d, J=55.5 Hz), 156.40, 149.72, 149.45 (d, J=11.3 Hz), 144.86 (d, J=9.5 Hz), 134.65 (d, J=3.1 Hz), 129.01 (d, J=8.1 Hz), 115.51 (d, J=21.4 Hz), 114.06, 108.96 (d, J=1.9 Hz), 106.86, 104.37 (d, J=21.5 Hz), 97.17 (d, J=25.6 Hz), 47.47, 39.15, 36.11, 21.04; HRMS (ESI): calcd for C$_{21}$H$_{22}$F$_2$N$_3$ [M+H]$^+$, 354.1776. found, 354.1782.

Example 24a

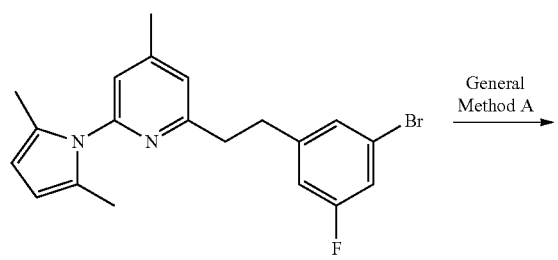

3-(2-(6-(2,5-Dimethyl-1H-pyrrol-1-yl)-4-methylpyridin-2-yl)ethyl)-5-fluoro-N-(3-fluorobenzyl)aniline (P25). The title compound was prepared using the general method B from 3-fluorobenzylamine. 71%; pale yellow oil; $^1$H NMR (500 MHz, CDCl$_3$) δ 7.36-7.31 (m, 1H), 7.17-7.11 (m, 1H), 7.10-7.06 (m, 1H), 7.02-6.96 (m, 1H), 6.94 (s, 1H), 6.89 (s, 1H), 6.31-6.25 (m, 2H), 6.15 (dt, J=11.1, 2.3 Hz, 1H), 5.92 (s, 2H), 4.32 (s, 2H), 3.05 (dd, J=9.3, 5.8 Hz, 2H), 2.97 (dd, J=9.2, 5.7 Hz, 2H), 2.40 (s, 3H), 2.15 (s, 6H); $^{13}$C NMR (126 MHz, CDCl$_3$) δ 164.55 (d, J=112.3 Hz), 162.61 (d, J=116.1 Hz), 160.69, 151.60, 149.52, 149.31 (d, J=11.4 Hz), 144.57 (d, J=9.3 Hz), 141.70 (d, J=6.8 Hz), 130.22 (d, J=8.4 Hz), 128.48, 122.76 (d, J=2.7 Hz), 122.60, 120.12, 114.25 (d, J=16.9 Hz), 114.08 (d, J=17.4 Hz), 108.87, 106.72 (d, J=4.7 Hz), 104.49 (d, J=21.4 Hz), 97.38 (d, J=25.8 Hz), 47.63, 39.28, 35.82 (d, J=1.9 Hz), 21.01, 13.25; MS ESI [M+H]$^+$=432.1.

Example 24b 6-(3-Fluoro-5-((3-fluorobenzyl)amino)phenethyl)-4-methylpyridin-2-amine (25). The title compound was prepared using the general method C from P29. 65%; pale yellow gel. $^1$H NMR (500 MHz, CDCl$_3$) δ 7.32 (td, J=7.9, 5.9 Hz, 1H), 7.13 (d, J=7.6 Hz, 1H), 7.07 (d, J=9.8 Hz, 1H), 6.98 (td, J=8.5, 2.7 Hz, 1H), 6.33 (dt, J=9.5, 1.7 Hz, 1H), 6.31-6.27 (m, 2H), 6.17 (s, 1H), 6.13 (dt, J=11.3, 2.2 Hz, 1H), 4.31 (d, J=4.6 Hz, 2H), 4.28 (d, J=5.5 Hz, 1H), 2.90-2.78 (m, 4H), 2.20 (s, 3H); $^{13}$C NMR (126 MHz, CDCl$_3$) δ 164.03 (d, J=242.1 Hz), 162.12 (d, J=247.0 Hz), 158.55, 158.23, 156.78 (d, J=52.3 Hz), 156.45, 149.77, 149.34 (d, J=11.3 Hz), 144.86 (d, J=9.5 Hz), 141.85 (d, J=6.8 Hz), 130.18 (d, J=8.2 Hz), 122.76 (d, J=2.8 Hz), 114.21 (d, J=8.1 Hz), 114.04 (t, J=4.3 Hz), 109.02 (d, J=1.9 Hz), 106.89, 104.45 (d, J=21.4 Hz), 97.15 (d, J=25.6 Hz), 47.59 (d, J=1.8 Hz), 39.11, 36.11 (d, J=1.9 Hz), 21.04; HRMS (ESI): calcd for C$_{21}$H$_{22}$F$_2$N$_3$ [M+H]$^+$, 354.1776. found, 354.1781.

Example 25

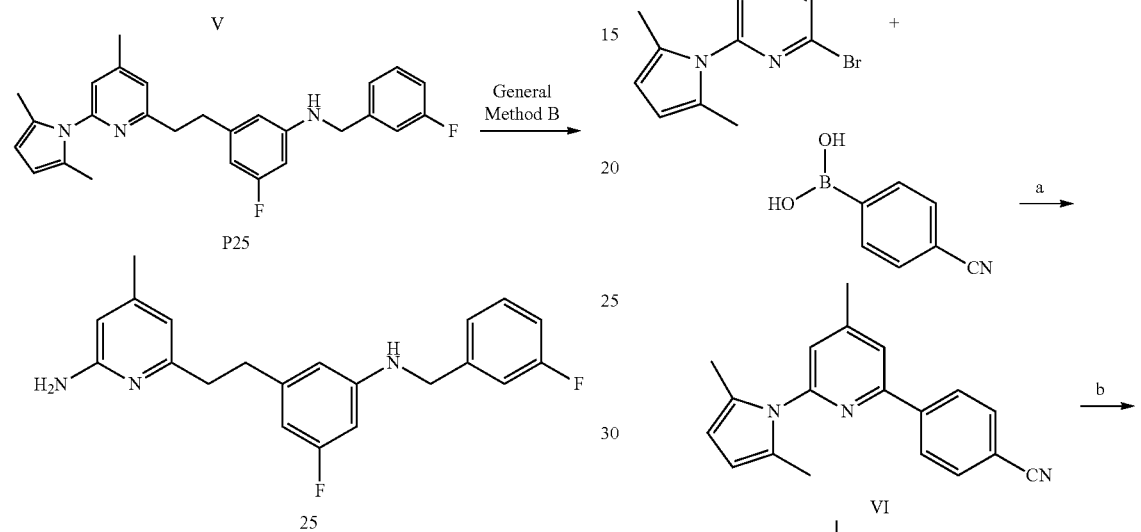

4-(6-(2,5-dimethyl-1H-pyrrol-1-yl)-4-methylpyridin-2-yl)benzonitrile (VI). (4-cyanophenyl)boronic acid (5.5 mmol) in 2M Na$_2$CO$_3$ (aqueous solution, 5 mL) and methanol (5 mL) was added to a stirred solution of 2-bromo-6-(2,5-dimethyl-1H-pyrrol-1-yl)-4-methylpyridine (5 mmol) and Pd(Ph$_3$)$_4$ (0.25 mmol) in toluene (20 mL) under a nitrogen atmosphere. The mixture was stirred at 100° C. for 24 h. After the solvent was removed under vacuum, the residue was partitioned between ethyl acetate (200 mL) and water (50 mL). The organic layer was dried (sodium sulfate), evaporated, and purified by column chromatography on silica gel cartridge, using hexanes/ethyl acetate (70/30, v/v) to give the title product as 71% yield. $^1$H NMR (500 MHz, CDCl$_3$) δ 8.32-8.08 (m, 2H), 7.86-7.72 (m, 2H), 7.64 (t, J=1.0 Hz, 1H), 7.08 (t, J=1.0 Hz, 1H), 5.96 (s, 2H), 2.55 (s, 3H), 2.23 (s, 6H); $^{13}$C NMR (126 MHz, CDCl$_3$) δ 154.43, 152.14, 150.49, 142.64, 132.54, 128.59, 127.49, 121.97, 120.10, 118.82, 112.62, 107.15, 21.36, 13.51; MS ESI [M+H]$^+$=288.1.

Example 26

4-(6-(2,5-dimethyl-1H-pyrrol-1-yl)-4-methylpyridin-2-yl)benzaldehyde (VII). A solution of DIBAL in hexane (1.0 M, 5.5 mL, 5.5 mmol) was added slowly to a solution of VI (5 mmol) in CH$_2$Cl$_2$ (20 mL). The solution was stirred at room temperature for 1 h and was then diluted with ethylether (20 mL). After careful addition of 1 N HCl (20 mL), the mixture was stirred for 15 min. The organic layer was washed with brine, dried over MgSO$_4$, and evaporated. Chromatography on silica gel gave the title product VII (51%). $^1$H NMR (500 MHz, CDCl$_3$) δ 10.10 (s, 1H), 8.33-8.16 (m, 2H), 8.04-7.91 (m, 2H), 7.68 (s, 1H), 7.07 (s, 1H), 5.96 (s, 2H), 2.54 (s, 3H), 2.24 (s, 6H); $^{13}$C NMR (126 MHz, CDCl$_3$) δ 192.02, 155.09, 152.08, 150.33, 144.08, 136.53, 130.12, 128.60, 127.53, 121.78, 120.33, 107.07, 21.34, 13.51; MS ESI [M+H]$^+$=291.8.

Example 27

General procedure for reductive amination: Method D; To a stirred solution of benzldehydes (1 mmol) and amines (1 mmol) in 10 mL of dichloromethane, acetic acid (1 mmol) and NaBH(OAc)$_3$ (1.1 mmol) were added and the resulting mixture was stirred at room temperature for 12 h. The organic materials were extracted by ethyl acetate and dried over anhydrous MgSO$_4$. After removal of the solvent with vacuum, the crude product was purified by flash column chromatography on silica gel cartridge to give the target compound.

Example 28a

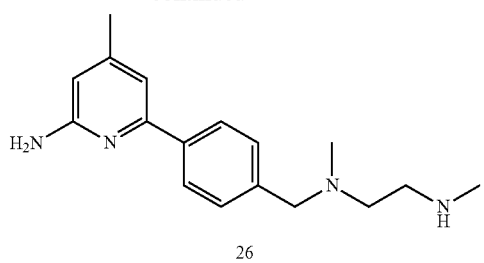

26

$N^1$-(4-(6-(2,5-dimethyl-1H-pyrrol-1-yl)-4-methylpyridin-2-yl)benzyl)-$N^1$,$N^2$-dimethylethane-1,2-diamine (P26). The title compound was prepared using the general method D from VII and $N^1$,$N^2$-dimethylethane-1,2-diamine. 62%; colorless gel; $^1$H NMR (500 MHz, CDCl$_3$) δ 8.03 (d, J=7.7 Hz, 2H), 7.59 (s, 1H), 7.43 (d, J=7.9 Hz, 2H), 6.98 (s, 1H), 5.94 (s, 2H), 3.61 (d, J=6.5 Hz, 2H), 3.40 (dt, J=39.9, 7.0 Hz, 2H), 2.87 (s, 3H), 2.67-2.53 (m, 2H), 2.51 (s, 3H), 2.30 (s, 3H), 2.24 (s, 6H); $^{13}$C NMR (126 MHz, CDCl$_3$) δ 156.51, 155.75, 151.76, 149.82, 140.25, 137.37, 129.21, 128.62, 126.88, 120.61, 119.41, 106.75, 62.34, 54.92, 46.93, 42.56, 34.59, 28.47, 21.33, 13.50; MS ESI [M+H]$^+$=363.0.

Example 28b

N1-(4-(6-amino-4-methylpyridin-2-yl)benzyl)-N1,N2-dimethylethane-1,2-diamine (26). The title compound was prepared using the general method B from P30. 60%; colorless gel; $^1$H NMR (500 MHz, MeOD) δ 7.98 (d, J=8.5 Hz, 2H), 7.93 (d, J=8.4 Hz, 2H), 7.16 (d, J=1.5 Hz, 1H), 6.88 (t, J=1.2 Hz, 1H), 4.77 (d, J=13.9 Hz, 1H), 4.52 (s, 1H), 3.75 (s, OH), 3.65 (d, J=6.2 Hz, 3H), 2.93 (s, 3H), 2.83 (s, 3H), 2.50 (d, J=1.0 Hz, 3H); $^{13}$C NMR (126 MHz, MeOD) δ 159.13, 156.41, 146.29, 134.90, 133.66, 133.42, 129.24, 114.58, 112.36, 60.83, 52.71, 44.41, 40.24, 33.95, 22.12; HRMS (ESI): calcd for C$_{17}$H$_{25}$N$_4$ [M+H]$^+$, 285.2074. found, 285.2078.

Example 29a

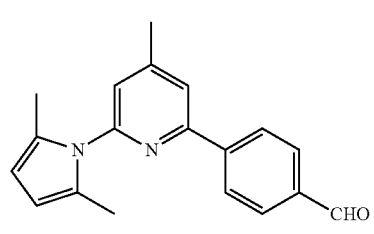

VII

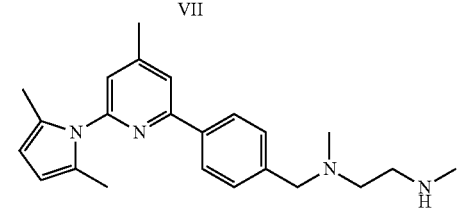

P26

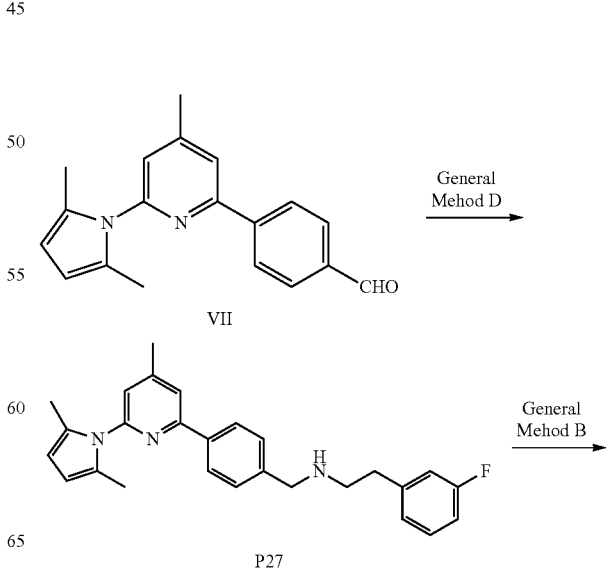

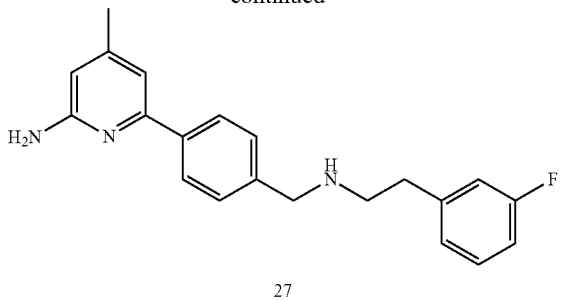

N-(4-(6-(2,5-Dimethyl-1H-pyrrol-1-yl)-4-methylpyridin-2-yl)benzyl)-2-(3-fluorophenyl)ethan-1-amine (P27) The title compound was prepared using the general method D from (3-fluorophenyl)ethylamine. 81%; white gel; $^1$H NMR (500 MHz, CDCl$_3$) δ 8.07-7.99 (m, 2H), 7.60-7.54 (m, 1H), 7.43-7.38 (m, 2H), 7.28-7.24 (m, 1H), 7.03-6.97 (m, 2H), 6.96-6.88 (m, 2H), 5.95 (s, 2H), 3.90 (s, 2H), 2.95 (dd, J=7.5, 6.0 Hz, 2H), 2.87 (t, J=6.7 Hz, 2H), 2.51 (s, 3H), 2.24 (s, 6H); $^{13}$C NMR (126 MHz, CDCl$_3$) δ 162.92 (d, J=245.7 Hz), 156.34, 151.78, 149.86, 142.26 (d, J=7.3 Hz), 140.43, 137.52, 129.93 (d, J=8.3 Hz), 128.63, 128.59, 127.10, 124.42 (d, J=2.7 Hz), 120.71, 119.42, 115.56 (d, J=20.9 Hz), 113.18 (d, J=20.9 Hz), 106.78, 53.18, 49.83, 35.74, 21.33, 13.50; MS ESI [M+H]$^+$=414.1

Example 29b 6-(4-(((3-Fluorophenethyl)amino)methyl)phenyl)-4-methylpyridin-2-amine (27). The title compound was prepared using the general method B from P30. 60%; colorless gel; $^1$H NMR (500 MHz, MeOD) δ 7.98-7.91 (m, 2H), 7.82-7.73 (m, 2H), 7.40 (td, J=7.9, 6.0 Hz, 1H), 7.14 (d, J=1.5 Hz, 1H), 7.11 (m, 2H), 7.08-7.01 (m, 1H), 6.86 (s, 1H), 4.39 (s, 2H), 3.37 (m, 2H), 3.18-3.05 (m, 2H), 2.49 (s, 3H); $^{13}$C NMR (126 MHz, MeOD) δ 164.49 (d, J=245.3 Hz), 159.05, 156.46, 146.57, 140.46 (d, J=7.4 Hz), 135.64, 134.42, 132.21, 131.83 (d, J=8.4 Hz), 129.10, 125.74 (d, J=2.9 Hz), 116.61 (d, J=21.8 Hz), 115.11 (d, J=21.1 Hz), 114.43, 112.18, 51.74, 49.63, 32.91, 22.09; HRMS (ESI): calcd for C$_{21}$H$_{23}$FN$_3$ [M+H]$^+$, 336.1871. found, 336.1876.

Example 30a

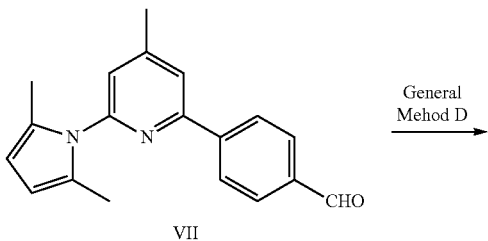

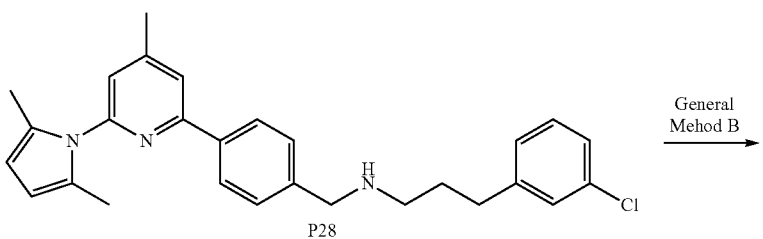

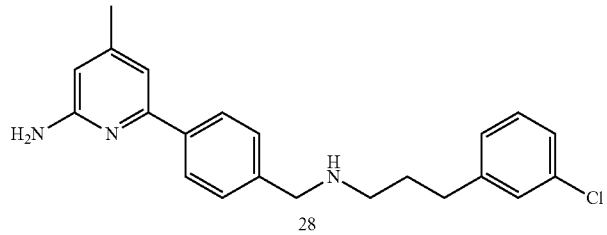

3-(3-Chlorophenyl)-N-(4-(6-(2,5-dimethyl-1H-pyrrol-1-yl)-4-methylpyridin-2-yl)benzyl)propan-1-amine (P28). The title compound was prepared using the general method D from 3-(3-fluorophenyl)propylamine. 81%; white gel; $^1$H NMR (500 MHz, CDCl$_3$) δ 8.10-7.98 (m, 2H), 7.62-7.56 (m, 1H), 7.46-7.39 (m, 2H), 7.26-7.15 (m, 3H), 7.08 (dt, J=7.3, 1.6 Hz, 1H), 6.99-6.95 (m, 1H), 5.94 (s, 2H), 3.86 (s, 2H), 2.69 (dt, J=12.8, 7.4 Hz, 4H), 2.51 (s, 3H), 2.24 (s, 6H), 1.95-1.78 (m, 2H). $^{13}$C NMR (126 MHz, CDCl$_3$) δ 156.45, 151.78, 149.83, 144.16, 141.41, 137.32, 134.05, 132.15, 132.07, 129.60, 128.63, 128.53, 128.48, 127.04, 126.62, 125.99, 120.65, 119.40, 106.76, 53.61, 48.61, 33.28, 31.44, 21.33, 13.50; MS ESI [M+H]$^+$=444.1.

Example 30b 6-(4-(((3-(3-Chlorophenyl)propyl)amino)methyl)phenyl)-4-methylpyridin-2-amine (28). The title compound was prepared using the general method B from P32. 70%; colorless gel; $^1$H NMR (500 MHz, MeOD) δ 7.95-7.91 (m, 2H), 7.74 (d, J=8.3 Hz, 2H), 7.35-7.28 (m, 2H), 7.25 (dt, J=8.4, 1.3 Hz, 1H), 7.21 (dd, J=7.6, 1.7 Hz, 1H), 7.12 (d, J=1.4 Hz, 1H), 6.82 (s, 1H), 4.33 (s, 2H), 3.18-3.05 (m, 2H), 2.76 (q, J=7.6 Hz, 2H), 2.48 (s, 3H), 2.13-2.03 (m, 2H); $^{13}$C NMR (126 MHz, MeOD) δ 159.16, 156.38, 146.45, 144.00, 135.78, 132.20, 132.12, 131.24, 129.50, 129.12, 129.06, 127.95, 127.62, 114.45, 112.22, 51.63, 48.30, 33.16, 28.68, 22.10; HRMS (ESI): calcd for C$_{21}$H$_{25}$ClN$_3$ [M+H]$^+$, 366.1732. found, 366.1737.

Example 31

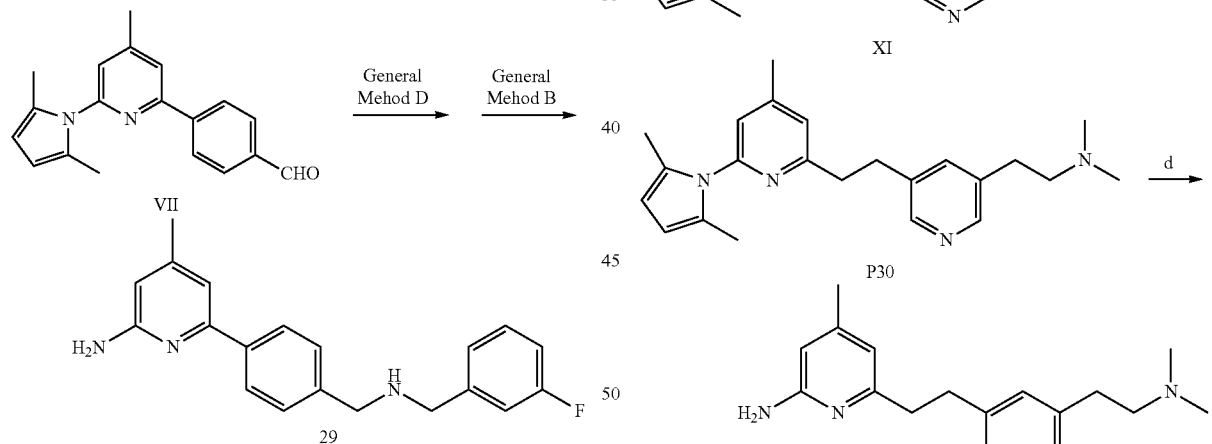

6-(4-(((3-Fluorobenzyl)amino)methyl)phenyl)-4-methylpyridin-2-amine (29). The title compound was prepared using the general method D and B from VII and (3-fluorophenyl)ethylamine. 39%; pale yellow gel; $^1$H NMR (500 MHz, MeOD) δ 7.95 (d, J=5.7 Hz, 2H), 7.73 (d, J=8.5 Hz, 2H), 7.52 (td, J=8.0, 5.8 Hz, 1H), 7.43-7.33 (m, 2H), 7.27-7.16 (m, 1H), 7.07 (s, 1H), 6.71 (s, 1H), 4.38 (s, 2H), 4.35 (s, 2H), 2.42 (s, 3H); $^{13}$C NMR (126 MHz, MeOD) δ 162.88 (d, J=246.4 Hz), 156.78, 154.79, 135.85, 133.66 (d, J=7.5 Hz), 133.11, 130.81 (d, J=8.3 Hz), 130.56, 130.48, 127.51, 125.75 (d, J=3.1 Hz), 116.62 (d, J=22.3 Hz), 116.10 (d, J=21.3 Hz), 112.48, 109.76, 50.35, 50.19, 20.36; HRMS (ESI): calcd for C$_{20}$H$_{21}$FN$_3$ [M+H]$^+$, 322.1714. found, 322.1723.

Example 32

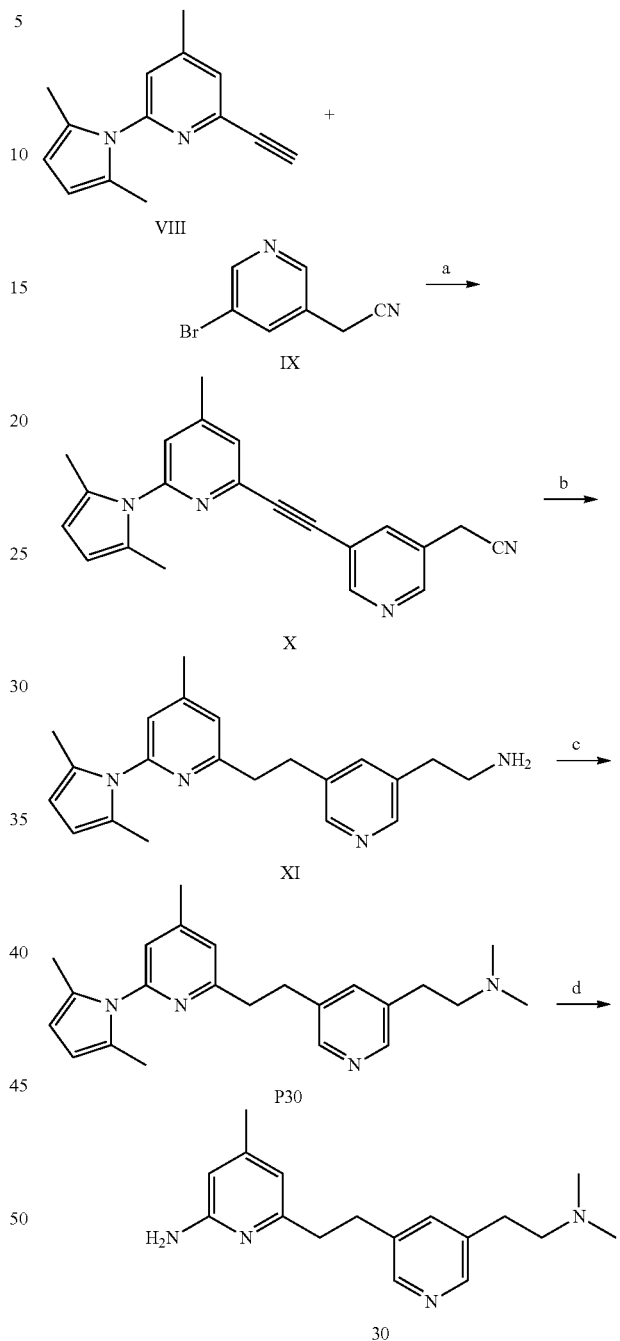

2-(5-((6-(2,5-Dimethyl-1H-pyrrol-1-yl)-4-methylpyridin-2-yl)ethynyl)pyridin-3-yl)acetonitrile (X). The reaction mixture of VIII (300 mg, 1.4 mmol), IX, (320 mg, 1.6 mmol), Pd(PPh$_3$)$_2$Cl$_2$ (45 mg, 0.070 mmol), CuI (11 mg, 0.070 mmol), PPh$_3$ (74 mg, 0.28 mmol), diethylamine (3 mL), and DMF (3 mL) were heated at 120° C. for 20 min in the microwave cavity. Then the reaction mixture was treated with diethyl ether (50 mL), filtered, and concentrated in vacuo. The residue was purified by flash chromatography (EtOAc/hexanes) to give the title compound (342 mg, 75%) as a pale yellow oil. $^1$H NMR (500 MHz, CDCl$_3$) δ 8.79 (s, 1H), 8.56 (s, 1H), 7.92 (s, 1H), 7.44 (s, 1H), 7.07 (s, 1H), 5.90 (s, 2H), 3.81 (s, 2H), 2.48 (s, 3H), 2.16 (s, 6H); $^{13}$C NMR (126 MHz, CDCl$_3$) δ 152.42, 152.15, 150.14, 148.46, 141.63, 138.28, 128.54, 127.09, 125.88, 123.02, 119.88, 116.44, 107.06, 92.31, 84.58, 21.03, 20.97, 13.22; MS ESI [M+H]$^+$=327.1.

Example 33

2-(5-(2-(6-(2,5-Dimethyl-1H-pyrrol-1-yl)-4-methylpyridin-2-yl)ethyl)pyridin-3-yl)ethan-1-amine (XI). A solution of X (300 mg, 0.92 mmol) in EtOH (10 mL) and MeOH (10 mL) was stirred with Raney-Ni (50% in water, 0.5 mL) for 1 hour at room temperature under a hydrogen atmosphere. The reaction mixture was filtered through a PTFE membrane filter (diam. 25 mm, pore size 0.2 μm) and concentrated in vacuo to give the crude title compound (300 mg). $^1$H NMR (500 MHz, CDCl$_3$) δ 8.30 (d, J=2.3 Hz, 1H), 8.31-8.26 (m, 2H), 5.90 (s, 2H), 3.09 (s, 3H), 2.95 (t, J=7.0 Hz, 2H), 2.71 (t, J=7.0 Hz, 2H), 2.38 (s, 3H), 2.12 (s, 5H); $^{13}$C NMR (126 MHz, CDCl$_3$) δ 160.09, 151.72, 149.69, 147.89, 147.82, 136.46, 136.43, 134.75, 128.43, 122.72, 120.33, 106.73, 43.22, 39.14, 37.01, 32.63, 20.99, 13.24; MS ESI [M+H]$^+$=335.2.

Example 34a 2-(5-(2-(6-(2,5-Dimethyl-1H-pyrrol-1-yl)-4-methylpyridin-2-yl)ethyl)pyridin-3-yl)-N,N-dimethylethane-1-amine (P30). To a primary amine XI (300 mg, ~0.9 mmol) solution in MeOH (10 mL) and CH$_2$Cl$_2$ (40 mL) was added aqueous formaldehyde (10 mL), and the reaction mixture was stirred for 30 min. After addition NaBH(OAc)$_3$ (1.27 g, 6.0 mmol), the reaction mixture was stirred for 20 h at room temperature. Then the reaction mixture was treated with CH$_2$Cl$_2$ (60 mL) and saturated NaHCO$_3$ solution (50 mL). The organic layer was partitioned, dried with MgSO$_4$, and concentrated in vacuo. The residue was purified by flash chromatography (CH$_2$Cl$_2$/MeOH) to give the title compound (231 mg, 71%) as a pale yellow oil. $^1$H NMR (500 MHz, CDCl$_3$) δ 8.17 (s, 1H), 8.14 (s, 1H), 7.19 (s, 1H), 6.78 (s, 1H), 6.75 (s, 1H), 5.77 (s, 2H), 3.01-2.88 (m, 4H), 2.68-2.55 (m, 2H), 2.40-2.34 (m, 2H), 2.25 (s, 3H), 2.17 (s, 6H), 1.99 (d, J=13.7 Hz, 6H); $^{13}$C NMR (126 MHz, CDCl$_3$) δ 160.14, 151.75, 149.62, 147.78, 147.68, 136.32, 136.21, 135.23, 128.43, 122.75, 120.30, 106.74, 60.99, 45.42, 39.23, 32.67, 31.29, 21.00, 13.27; MS ESI [M+H]$^+$=363.2.

Example 34b 6-(2-(5-(2-(dimethylamino)ethyl)pyridin-3-yl)ethyl)-4-methylpyridin-2-amine (30). The title compound was prepared using the general method B from P30. 61%, pale yellow gel; $^1$H NMR (500 MHz, MeOD) δ 8.88 (s, 1H), 8.83 (s, 1H), 8.80 (s, 1H), 6.76 (s, 1H), 6.72 (s, 1H), 3.62 (dd, J=9.9, 6.4 Hz, 2H), 3.42 (dd, J=10.0, 6.3 Hz, 2H), 3.36-3.33 (dd, J=10.0, 6.3 Hz, 2H), 3.20 (dd, J=9.6, 6.4 Hz, 2H), 3.04 (s, 6H), 2.40 (s, 3H); $^{13}$C NMR (126 MHz, MeOD) δ 159.09, 155.86, 149.20, 147.51, 147.26, 140.94, 138.48, 135.16, 115.04, 111.10, 62.82, 34.75, 33.80, 32.67, 30.18, 21.97; HRMS (ESI): calcd for C$_{17}$H$_{25}$FN$_4$ [M+H]$^+$, 285.2074. found, 285.2077.

Example 35

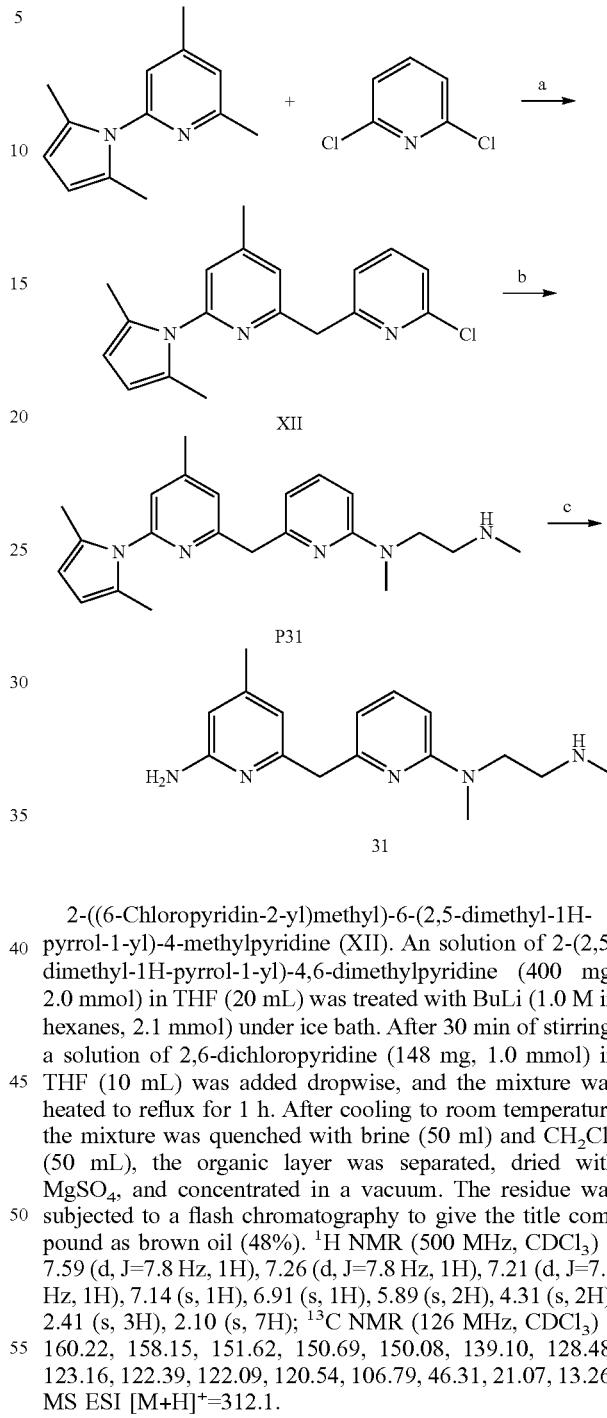

2-((6-Chloropyridin-2-yl)methyl)-6-(2,5-dimethyl-1H-pyrrol-1-yl)-4-methylpyridine (XII). An solution of 2-(2,5-dimethyl-1H-pyrrol-1-yl)-4,6-dimethylpyridine (400 mg, 2.0 mmol) in THF (20 mL) was treated with BuLi (1.0 M in hexanes, 2.1 mmol) under ice bath. After 30 min of stirring, a solution of 2,6-dichloropyridine (148 mg, 1.0 mmol) in THF (10 mL) was added dropwise, and the mixture was heated to reflux for 1 h. After cooling to room temperature the mixture was quenched with brine (50 ml) and CH$_2$Cl$_2$ (50 mL), the organic layer was separated, dried with MgSO$_4$, and concentrated in a vacuum. The residue was subjected to a flash chromatography to give the title compound as brown oil (48%). $^1$H NMR (500 MHz, CDCl$_3$) δ 7.59 (d, J=7.8 Hz, 1H), 7.26 (d, J=7.8 Hz, 1H), 7.21 (d, J=7.9 Hz, 1H), 7.14 (s, 1H), 6.91 (s, 1H), 5.89 (s, 2H), 4.31 (s, 2H), 2.41 (s, 3H), 2.10 (s, 7H); $^{13}$C NMR (126 MHz, CDCl$_3$) δ 160.22, 158.15, 151.62, 150.69, 150.08, 139.10, 128.48, 123.16, 122.39, 122.09, 120.54, 106.79, 46.31, 21.07, 13.26; MS ESI [M+H]$^+$=312.1.

Example 36a

N$^1$-(6-((6-(2,5-dimethyl-1H-pyrrol-1-yl)-4-methylpyridin-2-yl)methyl)pyridin-2-yl)-N$^1$,N$^2$-dimethylethane-1,2-diamine (P31). The title compound was prepared using the general method B from XII and N$^1$,N$^2$-dimethylethane-1,2-diamine. 55%, brown gel; $^1$H NMR (500 MHz, CDCl$_3$) δ 7.38 (t, J=8.5, 7.2 Hz, 1H), 7.14 (s, 1H), 6.87 (s, 1H), 6.52 (d, J=7.2 Hz, 1H), 6.38 (d, J=8.5 Hz, 1H), 5.89 (s, 2H), 4.16

(s, 2H), 3.72 (t, J=6.3 Hz, 2H), 3.06 (s, 3H), 2.82 (t, J=6.3 Hz, 2H), 2.44 (s, 3H), 2.38 (s, 3H), 2.12 (s, 6H); $^{13}$C NMR (126 MHz, CDCl$_3$) δ 159.99, 158.51, 157.33, 151.28, 149.31, 137.72, 128.49, 123.08, 120.04, 111.16, 106.60, 103.11, 49.94, 49.66, 47.05, 36.70, 36.54, 21.08, 13.23; MS ESI [M+H]$^+$=364.1.

Example 36b

N$^1$-(6-((6-Amino-4-methylpyridin-2-yl)methyl)pyridin-2-yl)-N$^1$,N$^2$-dimethylethane-1,2-diamine (31). The title compound was prepared using the general method C from P31. 63%, pale yellow gel; $^1$H NMR (500 MHz, MeOD) δ 7.68 (t, 1H), 6.82 (d, 1H), 6.76 (d, J=7.3 Hz, 1H), 6.71 (s, 1H), 6.69 (d, J=1.4 Hz, 1H), 4.20 (s, 2H), 4.00 (t, J=5.9 Hz, 2H), 3.31 (t, J=5.8 Hz, 2H), 3.15 (s, 3H), 2.74 (s, 3H), 2.38 (s, 3H); $^{13}$C NMR (126 MHz, MeOD) δ 159.14, 155.82, 115.55, 113.57, 111.19, 34.24, 21.97. HRMS (ESI): calcd for C$_{16}$H$_{24}$N$_5$ [M+H]$^+$, 286.2026. found, 286.2029.

Example 37

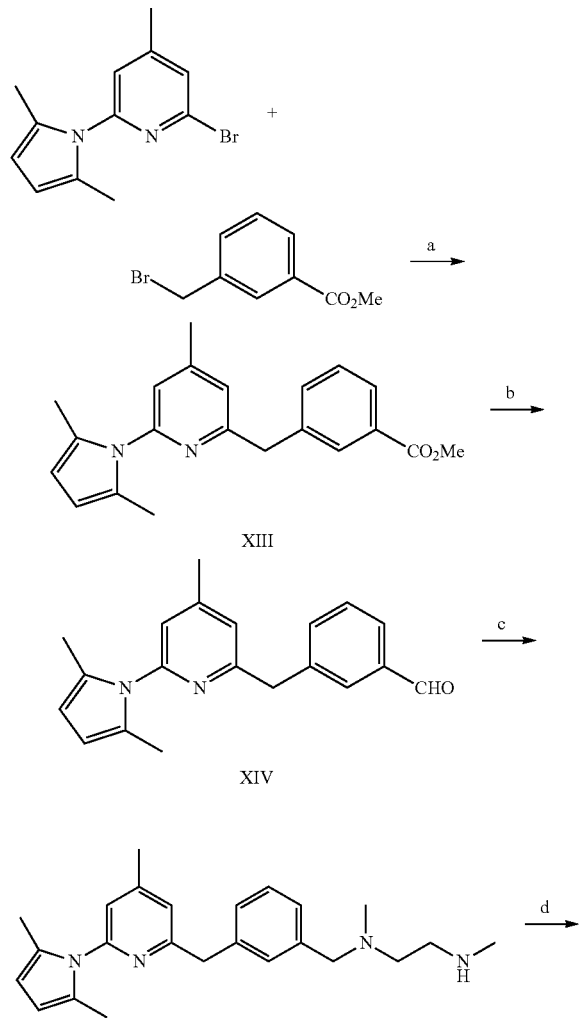

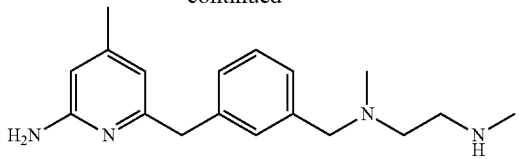

Methyl 3-((6-(2,5-dimethyl-1H-pyrrol-1-yl)-4-methylpyridin-2-yl)methyl)benzoate (XIII). A benzyl bromide (458 mg, 2.0 mmol) was added dropwise to a suspension of zinc dust (500 mg, 8.0 mmol) in dry THF. After stirring 15 min, the mixture was added to a solution of 2-bromo-6-(2,5-dimethyl-1H-pyrrol-1-yl)-4-methylpyridine (795 mg, 3.0 mmol) and Pd(PPh$_3$)$_4$ (50 mg, 0.4 mmol) in THF (20 mL). After stirring overnight the mixture was filtered using a short alumina column, and then concentrated in a vacuum. A column chromatography gave the title product as a colorless oil (68%). $^1$H NMR (500 MHz, CDCl$_3$) δ 7.99 (s, 1H), 7.93 (dt, J=7.7, 1.5 Hz, 1H), 7.53 (dt, J=7.7, 1.5 Hz, 1H), 7.40 (t, J=7.7 Hz, 1H), 6.96 (s, 1H), 6.90 (s, 1H), 5.90 (s, 2H), 4.20 (s, 2H), 3.93 (s, 3H), 2.38 (s, 3H), 2.11 (s, 6H); $^{13}$C NMR (126 MHz, CDCl$_3$) δ 167.10, 159.94, 151.63, 150.00, 139.80, 133.84, 130.36, 130.18, 128.61, 128.51, 127.74, 122.60, 120.33, 106.79, 52.14, 43.98, 21.08, 13.24; ESI MS m/z (M+H)$^+$=335.2.

Example 38

3-((6-(2,5-Dimethyl-1H-pyrrol-1-yl)-4-methylpyridin-2-yl)methyl)benzaldehyde (XIV). A solution of DIBAL-H in hexane (1.0 M, 1.4 mL, 1.4 mmol) was added slowly to a solution of XIII (400 mg, 1.2 mmol) in toluene (10 mL) at −78° C. The solution was stirred at the same temperature for 1 h and was then diluted with ethylether (20 mL). After careful addition of 1 N HCl (5 mL) at room temperature, the mixture was stirred for 10 min. The organic layer was washed with brine, dried over MgSO$_4$, and evaporated. Column chromatography with silica gel cartridge gave the title product XIV as a colorless oil (38%). $^1$H NMR (500 MHz, CDCl$_3$) δ 10.02 (s, 1H), 7.82 (d, J=1.8 Hz, 1H), 7.77 (dt, J=7.6, 1.5 Hz, 1H), 7.62 (dt, J=7.7, 1.5 Hz, 1H), 7.53-7.48 (m, 1H), 7.23 (td, J=7.7, 1.7 Hz, 1H), 7.00 (s, 1H), 6.91 (s, 1H), 5.90 (s, 2H), 4.24 (s, 2H); $^{13}$C NMR (126 MHz, CDCl$_3$) δ 192.46, 159.59, 151.72, 150.22, 140.58, 136.64, 133.45, 130.11, 128.50, 128.18, 128.04, 122.69, 120.52, 106.85, 43.78, 21.10, 13.23; ESI MS m/z (M+H)$^+$=305.1.

Example 39a

N$^1$-(3-((6-(2,5-Dimethyl-1H-pyrrol-1-yl)-4-methylpyridin-2-yl)methyl)benzyl)-N$^1$,N$^2$-dimethylethane-1,2-diamine (P32). The title compound was prepared using the general method D from XIV. 55%; brown oil; $^1$H NMR (500 MHz, CDCl$_3$) δ 7.28-7.23 (m, 2H), 7.23-7.14 (m, 2H), 6.96 (d, J=6.3 Hz, 1H), 6.87 (s, 1H), 5.90 (s, 2H), 4.14 (s, 2H), 3.60-3.47 (m, 2H), 3.45-3.27 (m, 3H), 2.84 (s, 3H), 2.61-2.46 (m, 2H), 2.37 (s, 3H), 2.25 (s, 4H), 2.12 (s, 6H); $^{13}$C NMR (126 MHz, CDCl$_3$) δ 160.73, 155.72, 151.48, 149.74, 139.43, 139.31, 129.64, 128.48, 127.83, 126.95, 122.59, 120.10, 106.69, 62.58, 54.94, 46.95, 44.23, 42.54, 34.56, 21.06, 13.25; ESI MS m/z (M+H)$^+$=377.1.

Example 39b

N$^1$-(3-((6-Amino-4-methylpyridin-2-yl)methyl)benzyl)-N$^1$,N$^2$-dimethylethane-1,2-diamine (32). The title compound was prepared using the general method C from P32. 75%; pale yellow gel; $^{1}$H NMR (500 MHz, MeOD) δ 7.74 (s, 1H), 7.57 (s, 1H), 7.52 (s, 1H), 7.47 (s, 1H), 6.71 (s, 1H), 6.69 (s, 1H), 4.63 (d, J=12.9 Hz, 1H), 4.40 (d, J=12.7 Hz, 1H), 4.16 (s, 2H), 3.80-3.66 (m, 3H), 3.62-3.55 (m, 1H), 2.89 (s, 3H), 2.81 (s, 3H), 2.39 (s, 3H); $^{13}$C NMR (126 MHz, MeOD) δ 159.30, 156.15, 148.59, 138.79, 133.28, 132.09, 131.71, 131.14, 131.11, 115.70, 111.31, 61.48, 52.41, 44.42, 40.21, 39.17, 33.91, 22.04; HRMS (ESI): calcd for $C_{18}H_{27}N_4$ [M+H]$^+$, 299.2230. found, 299.2234.

As shown, above, gene targeting experiments in pathogenic organisms including B. anthracis and S. aureus provided the basis for understanding bNOS function in mitigating antibiotic induced oxidative stress. In earlier work, it was found that a small handful of inhibitors developed for selective nNOS inhibition also improved the efficacy of antimicrobials, suggesting that bNOS might be a viable drug target. In the present study, two goals were achieved. The first goal was to identify bNOS-selective inhibitors with antimicrobial activity against the important human pathogen, MRSA. Of many compounds screened, two compounds were found to both bind well to bNOS and exhibit antimicrobial activity. Although 19 is only about 2-fold more selective for bNOS over nNOS, selectivity is about 100-fold and 400-fold over eNOS and iNOS, respectively. The second goal was to use crystallography to identify subtle differences between the bNOS and mNOS active sites that can be exploited in future inhibitor design. Ile-218 (Val in mNOS) is one such potentially important difference, since the Ile218Val mutant binds the two inhibitors used in this study with about a 6-fold lower affinity than wild type. Although this is a rather modest difference, it was also found that NOS inhibitors more readily bind to the pterin site in bNOS, given the lower of affinity of pterins for bNOS compared to mNOS. The Ile vs. Val active site difference together with the larger structural differences in the pterin site are structural features that can be exploited in future inhibitor design efforts.

Experimental Procedures for Examples 40-106

Materials, synthetic methods, and molecular characterization. All starting materials were purchased from Sigma-Aldrich and Matrix Scientific and were used without further purification. Solvents were purified by passage through a solvent column composed of activated alumina and a supported copper redox catalyst. All reactions were performed under an atmosphere of dry argon. A Biotage® Initiator microwave system was used for microwave-assisted deprotection. Thin-layer chromatography was carried out on Silicycle precoated silica gel 60 F254 plates. An Agilent 971-FP flash purification system with various SiliaSep™ (Silicycle, 40-63 μm, 60 Å) prepacked silica gel cartridges was used for flash column chromatography. $^1H$ NMR and $^{13}C$ NMR spectra were recorded in the indicated solvent on a Bruker Avance-III (500 MHz and 126 MHz for $^1H$ and $^{13}C$, respectively) spectrometer. Chemical shifts are reported as δ values in parts per million downfield from TMS (δ 0.0) as the internal standard in $CDCl_3$. MS was performed on a system consisting of an electrospray ionization (ESI) source in a Bruker amaZon SL mass spectrometer. High-resolution mass spectra were obtained using an Agilent 6210 LC-TOF spectrometer. The purity of the compounds was evaluated on a Beckman Gold reverse phase analytical HPLC system using an Phenonemex Gemini C-18 (4.6×250 mm, 5 μm) or Luna C-8 (4.6×250 mm, 5 μm) reverse phase columns with UV absorbance (254 nm). Purities of all compounds that were subjected to biological assay were >95%.

Example 40

General procedure for coupling reaction of aryl bromide with lithiated pyrrolyl-lutidine. Method A. To a solution of 7 (1.2 g, 6.0 mmol) in THF (25 mL) was added n-BuLi (1.6 M solution in hexanes, 3.75 mL, 6.0 mmol), and the reaction was stirred for 30 min at 0° C. This mixture was transferred to a solution of aryl bromide 8, 11a-b, or 15a-c (5.0 mmol) in THF (25 mL) at −78° C. via cannula. The reaction mixture was allowed to stir for an additional 20 min and then quenched with $H_2O$ (50 mL). After addition of ethyl acetate (50 mL), the organic layer was partitioned, dried with $MgSO_4$, and concentrated by rotary evaporation. The residue was purified by flash chromatography (EtOAc/hexanes) to yield products 9, 12a-b, 16a-c, respectively.

Example 41

2-(2,5-Dimethyl-1H-pyrrol-1-yl)-6-(3-iodophenethyl)-4-methylpyridine (9). The title compound was prepared using general method A from 3-iodobenzylbromide (8). 94%; colorless oil; $^1H$ NMR (500 MHz, $CDCl_3$) δ 7.57-7.51 (m, 2H), 7.17 (dt, J=7.7, 1.3 Hz, 1H), 7.02 (t, J=7.9 Hz, 1H), 6.91 (s, 1H), 6.89 (s, 1H), 5.92 (s, 2H), 3.06 (m, 4H), 2.40 (s, 3H), 2.15 (s, 6H); $^{13}C$ NMR (126 MHz, $CDCl_3$) δ 160.35, 151.69, 149.52, 143.95, 137.59, 135.03, 130.11, 128.48, 127.77, 122.70, 120.22, 106.71, 94.40, 39.45, 35.27, 21.02, 13.29; MS ESI $[M+H]^+$=417.5.

Example 42

2-(2-(6-Bromopyridin-2-yl)ethyl)-6-(2,5-dimethyl-1H-pyrrol-1-yl)-4-methylpyridine (12a). The title compound was prepared using general method A from 2-bromo-6-(bromomethyl)pyridine (11a). 91%; colorless oil; $^1H$ NMR (500 MHz, $CDCl_3$) δ 7.43 (t, J=7.6 Hz, 1H), 7.32 (d, J=7.9 Hz, 1H), 7.09 (d, J=7.2 Hz, 1H), 7.00 (s, 1H), 6.87 (s, 1H), 5.91 (s, 2H), 3.35-3.10 (m, 4H), 2.39 (s, 3H), 2.13 (s, 6H); $^{13}C$ NMR (126 MHz, $CDCl_3$) δ 162.82, 160.32, 151.58, 149.56, 141.57, 138.65, 128.47, 125.51, 122.80, 121.85, 120.20, 106.65, 37.30, 37.27, 21.01, 13.25; MS ESI $[M+H]^+$=370.3.

Example 43

2-(2-(5-Bromopyridin-3-yl)ethyl)-6-(2,5-dimethyl-1H-pyrrol-1-yl)-4-methylpyridine (12b). The title compound was prepared using general method A from 3-bromo-5-(bromomethyl)pyridine (11b). 89%; colorless oil; $^1H$ NMR (500 MHz, $CDCl_3$) δ 8.52 (d, J=2.2 Hz, 1H), 8.34 (d, J=1.9 Hz, 1H), 7.65 (t, J=2.1 Hz, 1H), 6.91 (dt, J=4.0, 1.2 Hz, 2H), 5.92 (s, 2H), 3.24-3.00 (m, 4H), 2.40 (s, 3H), 2.14 (s, 6H); $^{13}C$ NMR (126 MHz, $CDCl_3$) δ 159.46, 151.83, 149.79, 148.58, 148.08, 138.65, 138.61, 128.45, 122.79, 120.56, 120.51, 106.79, 38.80, 32.12, 21.01, 13.27; MS ESI $[M+H]^+$=370.5.

Example 44

2-(3-Bromo-5-(trifluoromethyl)phenethyl)-6-(2,5-dimethyl-1H-pyrrol-1-yl)-4-methylpyridine (16a). The title compound was prepared using general method A from 3-bromo-5-trifluoromethyl-benzylbromide (15a). 81%; colorless oil; $^1H$ NMR (500 MHz, $CDCl_3$) δ 7.61 (s, 1H), 7.53

(s, 1H), 7.33 (s, 1H), 6.92 (s, 1H), 6.91 (s, 1H), 5.94 (s, 2H), 3.35-3.03 (m, 4H), 2.40 (s, 3H), 2.16 (s, 6H); $^{13}$C NMR (126 MHz, CDCl$_3$) δ 159.59, 151.84, 149.79, 144.69, 135.05, 132.22 (q, J=32.7 Hz), 128.48, 126.11 (d, J=3.8 Hz), 124.15 (d, J=3.5 Hz), 123.17 (q, J=272.8 Hz), 122.85, 122.59, 120.49, 106.81, 39.03, 35.02, 20.97, 13.24; MS ESI [M+H]$^+$=437.2.

Example 45

2-(3-Bromo-5-fluorophenethyl)-6-(2,5-dimethyl-1H-pyrrol-1-yl)-4-methylpyridine (16b). The title compound was prepared using general method A from 3-bromo-5-fluorobenzylbromide (15b). 81%; pale yellow oil; $^1$H NMR (500 MHz, CDCl$_3$) δ 7.15 (s, 1H), 7.10 (dt, J=8.2, 2.1 Hz, 1H), 6.95 (s, 1H), 6.92 (s, 1H), 6.87 (m, 1H), 5.94 (s, 2H), 3.16-3.03 (m, 4H), 2.42 (s, 3H), 2.17 (s, 6H); $^{13}$C NMR (126 MHz, CDCl$_3$) δ 162.60 (d, J=250.1 Hz), 159.89, 151.75, 149.71, 145.63 (d, J=7.8 Hz), 128.46, 127.56 (d, J=3.0 Hz), 122.74, 122.29 (d, J=10.2 Hz), 120.40, 116.69 (d, J=24.4 Hz), 114.42 (d, J=20.9 Hz), 106.79, 38.98, 35.04 (d, J=1.8 Hz), 21.01, 13.28; MS ESI [M+H]$^+$=387.2.

Example 46

2-(3,5-Dibromophenethyl)-6-(2,5-dimethyl-1H-pyrrol-1-yl)-4-methylpyridine (16c). The title compound was prepared using general method A from 3,5-dibromobenzylbromide (15c). 86%; pale yellow oil; $^1$H NMR (500 MHz, CDCl$_3$) δ 7.51 (s, 1H), 7.29 (s, 1H), 7.26 (ss, 2H), 6.91 (s, 2H), 5.92 (s, 2H), 3.06 (q, J=2.8 Hz, 4H), 2.40 (d, J=1.6 Hz, 3H), 2.15 (s, 6H); $^{13}$C NMR (126 MHz, CDCl$_3$) δ 159.76, 151.73, 149.72, 145.43, 131.65, 130.43, 128.48, 122.77, 122.74, 120.42, 106.76, 39.02, 34.89, 21.01, 13.27; MS ESI [M+H]$^+$=449.2.

Example 47

3-Bromo-5-(2-(6-(2,5-dimethyl-1H-pyrrol-1-yl)-4-methylpyridin-2-yl)ethyl)benzonitrile (17). A mixture of 16c (448 mg, 1.0 mmol), CuCN (108 mg, 1.20 mmol), and DMF (4 mL) was heated at 220° C. for 20 min in the microwave cavity. Then the reaction mixture was treated with dichloromethane (20 mL), filtered, and concentrated in vacuo. The residue was purified by flash chromatography to give the title compound (225 mg, 57%) as a pale yellow oil. $^1$H NMR (500 MHz, CDCl$_3$) δ 7.63 (s, 1H), 7.57 (s, 1H), 7.41 (s, 1H), 6.93 (ss, 2H), 5.92 (s, 2H), 3.19-3.03 (m, 4H), 2.41 (s, 3H), 2.13 (s, 6H). $^{13}$C NMR (126 MHz, CDCl$_3$) δ 159.27, 151.82, 149.88, 145.04, 136.39, 132.31, 130.76, 128.44, 122.77, 122.75, 120.59, 117.45, 113.92, 106.81, 38.69, 34.58, 21.01, 13.26; MS ESI [M+H]$^+$=394.5.

Example 48

General procedure for Buchwald reaction and pyrrole deprotection for 10a-d; Method B. To a 5 mL microwave vial equipped with a magnetic stir bar was added aryl iodide 9 (0.5 mmol), an amine (1.0 mmol), Pd$_2$(dba)$_3$ (23 mg, 0.025 mmol), DavePhos (20 mg, 0.050 mmol), NaOtBu (58 mg, 0.60 mmol) in THF (1.5 mL) and 1,4-dioxane (1.5 mL). After being purged with dry argon, the reaction mixture were stirred for 5-10 h at 100° C. (oil bath). After being cooled to room temperature, the reaction mixture was passed through a silica gel pad (2 cm), washed with MeOH (10 mL), and concentrated in vacuo. After the residue was placed in a 5 mL microwave vial equipped with a magnetic stir bar, ethanol (2.5 mL) and concentrated hydrochloric acid (0.5 mL) were added. The vial was shaken vigorously and then heated in the microwave irradiator for 20 min at 120° C. (as recorded via the IR sensor of the microwave instrument). (Walia, A.; Kang, S.; Silverman, R. B. Microwave-assisted protection of primary amines as 2,5-dimethylpyrroles and their orthogonal deprotection. J. Org. Chem. 2013, 78, 10931-10937.) After being cooled to room temperature, the reaction mixture was concentrated in vacuo and purified by flash column chromatography using a SiliaSep™ C18 flash cartridge (25 g, 40-63 μm/230-400 mesh, Pore Size 60 Å) with 5-80% MeOH in water as the mobile phase.

Example 49

N$^1$-(3-(2-(6-Amino-4-methylpyridin-2-yl)ethyl)phenyl)-N$^1$,N$^2$-dimethylethane-1,2-diamine (10a). The title compound (64 mg, 43%) was prepared according to general method B using N,N-dimethylethane-1,2-diamine (88 mg, 1.0 mmol); pale yellow gel; $^1$H NMR (500 MHz, MeOD) δ 7.19 (dd, J=8.3, 7.5 Hz, 1H), 6.87 (s, 1H), 6.77-6.74 (m, 1H), 6.68-6.63 (m, 3H), 3.64 (t, J=6.4 Hz, 2H), 3.27 (t, J=6.4 Hz, 2H), 3.05-2.99 (m, 4H), 2.97 (s, 3H), 2.78 (s, 3H), 2.36 (s, 3H); $^{13}$C NMR (126 MHz, MeOD) δ 159.07, 155.72, 151.15, 150.27, 142.17, 130.57, 119.35, 115.07, 113.12, 110.67, 50.68, 47.95, 39.20, 36.31, 35.93, 34.08, 21.95; HRMS (ESI): calcd for C$_{18}$H$_{27}$N$_4$ [M+H]$^+$, 299.2230. found, 299.2236.

Example 50

N$^1$-(3-(2-(6-Amino-4-methylpyridin-2-yl)ethyl)phenyl)-N$^2$,N$^2$-dimethylethane-1,2-diamine (10b). The title compound (72 mg, 48%) was prepared according to general method B using N,N-dimethylethane-1,2-diamine (88 mg, 1.0 mmol); pale yellow gel; $^1$H NMR (500 MHz, MeOD) δ 7.10 (t, J=7.8 Hz, 1H), 6.70 (s, 1H), 6.66 (s, 1H), 6.64-6.56 (m, 3H), 3.55 (t, J=6.0 Hz, 2H), 3.40 (t, J=6.0 Hz, 2H), 3.06-2.98 (m, 4H), 2.96 (s, 6H), 2.35 (s, 3H); $^{13}$C NMR (126 MHz, MeOD) δ 159.00, 155.73, 150.29, 149.42, 142.11, 130.53, 119.19, 115.00, 114.22, 112.68, 110.66, 57.76, 43.73, 39.83, 36.11, 35.75, 21.95; HRMS (ESI): calcd for C$_{18}$H$_{27}$N$_4$ [M+H]$^+$, 299.2230. found, 299.2234.

Example 51

N$^1$-(3-(2-(6-Amino-4-methylpyridin-2-yl)ethyl)phenyl)-N$^1$-methylethane-1,2-diamine (10c). The title compound (49 mg, 35%) was prepared according to general method B using N$^1$-Boc-N$^2$-methylethane-1,2-diamine (174 mg, 1.0 mmol); brown gel; $^1$H NMR (500 MHz, MeOD) δ 7.14 (t, J=7.8 Hz, 1H), 6.77 (s, 1H), 6.70-6.64 (m, 3H), 6.62 (s, 1H), 3.52 (t, J=6.0 Hz, 2H), 3.27 (t, J=6.0 Hz, 2H), 3.04-2.94 (m, 4H), 2.77 (s, 3H), 2.36 (s, 3H); $^{13}$C NMR (126 MHz, MeOD) δ 159.03, 155.74, 150.20, 148.40, 142.25, 130.62, 120.16, 115.05, 115.00, 113.46, 110.70, 49.25, 41.72, 36.04, 35.68, 33.74, 21.95; HRMS (ESI): calcd for C$_{17}$H$_{25}$N$_4$ [M+H]$^+$, 285.2074. found, 285.2070.

Example 52

N$^1$-(3-(2-(6-Amino-4-methylpyridin-2-yl)ethyl)phenyl)-N$^1$-methylpropane-1,3-diamine (10d). The title compound (46 mg, 31%) was prepared according to general method B using N-Boc-N'-methylpropane-1,3-diamine (188 mg, 1.0 mmol); pale yellow gel; $^1$H NMR (500 MHz, MeOD) δ 7.09 (t, J=7.8 Hz, 1H), 6.69-6.64 (m, 2H), 6.62-6.55 (m, 3H), 3.27 (t, J=6.8 Hz, 2H), 3.19-3.10 (m, 2H), 3.01 (m, 2H), 2.95 (m, 2H), 2.73 (s, 3H), 2.36 (d, J=0.9 Hz, 3H), 2.03 (m, 2H); $^{13}$C NMR (126 MHz, MeOD) δ 158.98, 155.72, 150.46, 150.10, 141.87, 130.39, 118.38, 115.16, 114.18, 112.41, 110.67, 48.76, 41.82, 36.15, 35.86, 33.82, 26.92, 21.98; HRMS (ESI): calcd for $C_{18}H_{27}N_4$ [M+H]$^+$, 299.2230. found, 229.2227.

Example 53

General procedure for Buchwald reaction of an amine with an arylhalide; Method C. To a 5 mL microwave vial equipped with a magnetic stir bar was added an aryl halide (12a-b, 16a-b, or 17, 0.5 mmol), an amine (1.0 mmol), Pd$_2$(dba)$_3$ (23 mg, 0.025 mmol), DavePhos (20 mg, 0.050 mmol), NaOtBu (58 mg, 0.60 mmol) in THF (1.5 mL) and 1,4-dioxane (1.5 mL). After being purged with dry argon, the reaction mixture were stirred for 5-10 h at 100° C. (oil bath). The reaction mixture was treated with dichloromethane (20 mL), filtered, and concentrated in vacuo. The residue was purified by flash chromatography (dichloromethane/MeOH) to give the corresponding product.

Example 54

N$^1$-(6-(2-(6-(2,5-Dimethyl-1H-pyrrol-1-yl)-4-methylpyridin-2-yl)ethyl)pyridin-2-yl)-N$^1$,N$^2$-dimethylethane-1,2-diamine (13a). The title compound (172 mg, 91%) was prepared according to general method C using 12a (185 mg, 0.5 mmol) and N,N'-dimethylethane-1,2-diamine (88 mg, 1.0 mmol); pale yellow oil; $^1$H NMR (500 MHz, MeOD) δ 7.45 (dd, J=8.5, 7.3 Hz, 1H), 7.30 (s, 1H), 7.03 (s, 1H), 6.53 (dd, J=11.7, 7.9 Hz, 2H), 5.83 (s, 2H), 3.91-3.83 (m, 2H), 3.45-3.38 (m, 1H), 3.25 (dd, J=5.9, 4.8 Hz, 2H), 3.21-3.15 (m, 2H), 3.06 (s, 3H), 2.76-2.72 (m, 1H), 2.71 (s, 3H), 2.46 (s, 3H), 2.01 (s, 6H); $^{13}$C NMR (126 MHz, MeOD) δ 162.66, 160.36, 159.67, 153.03, 152.54, 139.58, 129.44, 124.64, 122.37, 113.28, 107.70, 105.17, 50.81, 45.03, 39.18, 38.11, 37.28, 34.29, 20.96, 13.06; MS ESI [M+H]$^+$=378.0.

Example 55

N$^1$-(5-(2-(6-(2,5-Dimethyl-1H-pyrrol-1-yl)-4-methylpyridin-2-yl)ethyl)pyridin-3-yl)-N$^1$,N$^2$-dimethylethane-1,2-diamine (13b). The title compound (164 mg, 87%) was prepared according to general method C using 12b (185 mg, 0.5 mmol) and N,N-dimethylethane-1,2-diamine (88 mg, 1.0 mmol); pale yellow gel; $^1$H NMR (500 MHz, CDCl$_3$) δ 8.18 (d, J=2.8 Hz, 1H), 7.84-7.72 (m, 1H), 7.15-6.97 (m, 2H), 6.88 (s, 1H), 5.87 (s, 2H), 3.89 (t, J=6.9 Hz, 2H), 3.24 (t, J=6.9 Hz, 2H), 3.16-3.03 (m, 2H), 3.03-2.97 (m, 2H), 2.96 (s, 3H), 2.75 (s, 3H), 2.40 (s, 3H), 2.08 (s, 6H); $^{13}$C NMR (126 MHz, CDCl$_3$) δ 160.16, 151.48, 150.05, 144.95, 137.98, 136.68, 131.67, 128.40, 122.93, 120.46, 106.72, 53.49, 48.45, 46.25, 39.05, 38.32, 33.55, 32.92, 21.05, 13.22; MS ESI [M+H]$^+$=378.5.

Example 56

N$^1$-(3-(2-(6-(2,5-Dimethyl-1H-pyrrol-1-yl)-4-methylpyridin-2-yl)ethyl)-5-(trifluoromethyl)phenyl)-N$^1$,N$^2$-dimethylethane-1,2-diamine (18a). The title compound (180 mg, 75%) was prepared according to general method C using 17a (219 mg, 0.5 mmol) and N,N-dimethylethane-1,2-diamine (88 mg, 1.0 mmol); pale yellow oil; $^1$H NMR (500 MHz, CDCl$_3$) δ 7.04 (s, 1H), 7.00 (s, 1H), 6.88 (s, 1H), 6.77 (s, 1H), 6.75 (s, 1H), 5.87 (s, 2H), 3.87 (t, J=7.1 Hz, 2H), 3.18-3.11 (m, 2H), 3.10-3.03 (m, 4H), 3.01 (s, 3H), 2.63 (s, 3H), 2.39 (s, 3H), 2.07 (s, 6H); $^{13}$C NMR (126 MHz, CDCl$_3$) δ 160.74, 151.37, 149.98, 148.88, 143.49, 131.44 (q, J=31.3 Hz), 128.47, 124.35 (d, J=273.5 Hz), 123.05, 120.41, 116.09, 114.33 (d, J=3.9 Hz), 106.88 (d, J=4.1 Hz), 106.67, 48.84, 46.24, 39.36, 39.00, 36.08, 33.55, 20.99, 13.10; ESI [M+H]$^+$=445.1.

Example 57

N$^1$-(3-(2-(6-(2,5-Dimethyl-1H-pyrrol-1-yl)-4-methylpyridin-2-yl)ethyl)-5-fluorophenyl)-N$^1$,N$^2$-dimethylethane-1,2-diamine (18b). The title compound (160 mg, 80%) was prepared according to general method C using 17 (193 mg, 0.5 mmol) and N,N-dimethylethane-1,2-diamine (88 mg, 1.0 mmol); pale yellow oil; $^1$H NMR (500 MHz, CDCl$_3$) δ 7.01-6.95 (m, 1H), 6.92-6.86 (m, 1H), 6.36 (dd, J=2.3, 1.3 Hz, 1H), 6.32-6.24 (m, 2H), 5.91 (s, 2H), 3.46 (t, J=6.6 Hz, 2H), 3.11-3.05 (m, 2H), 3.03-2.98 (m, 2H), 2.94 (s, 3H), 2.81 (t, J=6.5 Hz, 2H), 2.50 (s, 3H), 2.40 (s, 3H), 2.15 (s, 6H); $^{13}$C NMR (126 MHz, CDCl$_3$) δ 164.15 (d, J=241.5 Hz), 160.87, 151.61, 150.97 (d, J=11.3 Hz), 149.52, 144.30 (d, J=9.6 Hz), 128.48, 122.65, 120.10, 107.93, 106.70, 103.08 (d, J=21.5 Hz), 96.99 (d, J=26.1 Hz), 52.54, 49.12, 39.59, 38.85, 36.49, 36.30, 21.02, 13.25; MS ESI [M+H]$^+$=395.2.

Example 58

3-(2-(6-(2,5-Dimethyl-1H-pyrrol-1-yl)-4-methylpyridin-2-yl)ethyl)-5-(methyl(2-(methylamino)ethyl)amino)benzonitrile (18c). The title compound (145 mg, 72%) was prepared according to general method C using 17 (197 mg, 0.5 mmol) and N,N-dimethylethane-1,2-diamine (88 mg, 1.0 mmol); colorless gel; $^1$H NMR (500 MHz, MeOD) δ 7.22 (s, 1H), 7.01 (s, 1H), 6.95 (s, 1H), 6.91 (s, 1H), 6.83 (s, 1H), 5.82 (s, 2H), 3.57 (t, J=6.8 Hz, 2H), 3.13-3.06 (m, 2H), 3.06-3.00 (m, 2H), 2.98 (s, 3H), 2.97-2.92 (m, 2H), 2.58 (s, 3H), 2.44 (s, 3H), 2.02 (s, 6H); $^{13}$C NMR (126 MHz, MeOD) δ 161.95, 152.83, 152.78, 150.99, 145.02, 129.42, 124.79, 122.41, 121.36, 120.54, 118.38, 114.18, 113.79, 107.63, 51.32, 48.45, 39.86, 38.89, 37.05, 35.29, 20.94, 13.13; MS ESI [M+H]$^+$=402.3.

Example 59

General procedure for deprotection of 2-(2,5-dimethyl-1H-pyrrol-1-yl)pyridine derivatives using microwave irradiation; Method D. To a 5 mL microwave vial equipped with a magnetic stir bar was added the protected aminopyridine (0.5 mmol), hydroxylamine HCl (173.75 mg), ethanol (2 mL), and water (1 mL). After being capped, the vial was shaken vigorously and then heated in the microwave irradiator for 30 min at 120° C. The reaction mixture was concentrated in vacuo, and purified by flash column chromatography using a SiliaSep™ C18 flash cartridge (25 g, 40-63 μm/230-400 mesh, Pore Size 60 Å) with 5 to 80% MeOH in water as the mobile phase. This method applied to give the products in 62%-81% yields.

Example 60

N$^1$-(6-(2-(6-Amino-4-methylpyridin-2-yl)ethyl)pyridin-2-yl)-N$^1$,N$^2$-dimethylethane-1,2-diamine (14a). The title compound (97 mg, 65%) was prepared according to general method D; pale yellow gel; $^1$H NMR (500 MHz, MeOD) δ 8.37 (s, 2H), 7.53-7.45 (m, 1H), 6.58 (s, 1H), 6.57 (s, 1H), 6.55 (s, 2H), 3.91 (q, J=5.6 Hz, 2H), 3.31 (d, J=5.5 Hz, 2H), 3.07 (s, 3H), 3.05-2.98 (m, 4H), 2.77 (s, 3H), 2.32 (s, 3H); $^{13}$C NMR (126 MHz, MeOD) δ 160.30, 158.78, 157.34, 157.02, 152.23, 139.68, 114.39, 113.10, 110.20, 105.39, 50.22, 47.99, 38.11, 37.07, 34.37, 34.23, 21.73; HRMS (ESI): calcd for $C_{17}H_{26}N_5$ [M+H]$^+$, 300.2183. found, 300.2189.

Example 61

$N^1$-(5-(2-(6-Amino-4-methylpyridin-2-yl)ethyl)pyridin-3-yl)-$N^1$,$N^2$-dimethylethane-1,2-diamine (14b). The title compound (105 mg, 70%) was prepared according to general method D; pale brown gel; $^1$H NMR (500 MHz, MeOD) δ 8.22 (s, 2H), 8.10 (s, 1H), 6.78 (s, 1H), 6.71 (s, 1H), 3.93 (t, J=6.9 Hz, 2H), 3.39-3.35 (m, 2H), 3.29-3.22 (m, 2H), 3.20 (s, 3H), 3.19-3.14 (m, 2H), 2.81 (s, 3H), 2.40 (s, 3H); $^{13}$C NMR (126 MHz, MeOD) δ 159.18, 155.84, 148.79, 148.67, 141.90, 129.47, 128.91, 124.88, 115.15, 111.28, 46.78, 38.92, 34.62, 34.12, 32.77, 21.99; HRMS (ESI): calcd for $C_{17}H_{26}N_5$ [M+H]$^+$, 300.2183. found, 300.2188.

Example 62

$N^1$-(3-(2-(6-Amino-4-methylpyridin-2-yl)ethyl)-5-(trifluoromethyl)phenyl)-$N^1$,$N^2$-dimethylethane-1,2-diamine (19a). The title compound (148 mg, 81%) was prepared according to general method D; colorless gel; $^1$H NMR (500 MHz, MeOD) δ 7.22 (s, 1H), 6.91 (s, 1H), 6.89 (s, 1H), 6.69 (ss, 2H), 3.77 (t, J=6.7 Hz, 2H), 3.30 (t, J=6.7 Hz, 2H), 3.09 (d, J=3.1 Hz, 4H), 3.05 (s, 3H), 2.80 (s, 3H), 2.37 (s, 3H); $^{13}$C NMR (126 MHz, MeOD) δ 159.07, 155.75, 151.14, 149.78, 143.60, 132.76 (q, J=31.3 Hz), 126.96 (q, J=271.8 Hz), 117.77, 115.17, 115.03 (d, J=4.0 Hz), 110.85, 108.46 (d, J=4.0 Hz), 50.12, 47.60, 38.98, 36.13, 35.75, 34.16, 21.99; HRMS (ESI): calcd for $C_{19}H_{25}F_3N_4$ [M+H]$^+$, 367.2104. found, 367.2111.

Example 63

$N^1$-(3-(2-(6-Amino-4-methylpyridin-2-yl)ethyl)-5-fluorophenyl)-$N^1$,$N^2$-dimethylethane-1,2-diamine (19b). The title compound (120 mg, 76%) was prepared according to general method D; colorless gel; $^1$H NMR (500 MHz, MeOD) δ 6.73 (s, 1H), 6.70 (s, 1H), 6.67 (s, 1H), 6.45 (dt, J=12.5, 2.3 Hz, 1H), 6.40 (dt, J=9.3, 1.6 Hz, 1H), 3.72 (t, J=6.7 Hz, 2H), 3.26 (t, J=6.7 Hz, 2H), 3.07-3.00 (m, 4H), 2.99 (s, 3H), 2.78 (s, 3H), 2.36 (s, 3H); $^{13}$C NMR (126 MHz, MeOD) δ 165.55 (d, J=241.2 Hz), 159.03, 155.76, 152.21 (d, J=11.0 Hz), 149.92, 144.33 (d, J=9.7 Hz), 115.09, 110.83, 110.28, 105.19 (d, J=22.1 Hz), 99.28 (d, J=26.6 Hz), 50.22, 47.60, 39.16, 36.16, 35.65, 34.15, 22.05; HRMS (ESI): calcd for $C_{18}H_{25}FN_4$[M+H]$^+$, 317.2136. found, 317.2142.

Example 64

3-(2-(6-Amino-4-methylpyridin-2-yl)ethyl)-5-(methyl(2-(methylamino)ethyl)amino)benzonitrile (19c). The title compound (100 mg, 62%) was prepared according to general method D; pale yellow gel; $^1$H NMR (500 MHz, MeOD) δ 7.22 (s, 1H), 7.02 (s, 1H), 6.98 (s, 1H), 6.68 (ss, 2H), 3.73 (t, J=6.7 Hz, 2H), 3.27 (t, J=6.7 Hz, 2H), 3.12-3.05 (m, 4H), 3.04 (s, 3H), 2.79 (s, 3H), 2.38 (s, 3H); $^{13}$C NMR (126 MHz, MeOD) δ 159.11, 155.80, 151.08, 149.67, 143.98, 121.71, 120.26, 118.78, 115.03, 114.97, 114.23, 110.89, 49.93, 47.50, 38.85, 35.79, 35.48, 34.10, 21.95; HRMS (ESI): calcd for $C_{19}H_{26}N_5$ [M+H]$^+$, 324.2183. found, 324.2187.

Example 65

3-(2-(6-(2,5-Dimethyl-1H-pyrrol-1-yl)-4-methylpyridin-2-yl)ethyl)-5-((2-(ethylamino)ethyl)(methyl)amino)benzonitrile (20a). The title compound (187 mg, 90%) was prepared according to the general method B using 17 (197 mg, 0.5 mmol) and N-ethyl-N'-methylethane-1,2-diamine (102 mg, 1.0 mmol). Colorless gel; $^1$H NMR (500 MHz, CDCl$_3$) δ 7.04 (s, 1H), 7.01 (s, 1H), 6.91 (s, 1H), 6.88 (s, 1H), 6.78 (s, 1H), 5.88 (s, 2H), 3.95 (t, J=7.6 Hz, 2H), 3.09 (m, 9H), 3.00 (s, 3H), 2.40 (s, 3H), 2.07 (s, 6H), 1.46 (t, J=7.2 Hz, 3H); $^{13}$C NMR (126 MHz, CDCl$_3$) δ 160.45, 151.45, 149.87, 148.56, 143.99, 128.44, 122.88, 120.73, 120.41, 119.67, 116.99, 113.17, 112.81, 106.65, 48.41, 43.72, 43.57, 39.13, 38.73, 35.70, 21.04, 13.17, 11.75.

Example 66

3-(2-(6-(2,5-Dimethyl-1H-pyrrol-1-yl)-4-methylpyridin-2-yl)ethyl)-5-((2-(isopropylamino)ethyl)(methyl)amino) benzonitrile (20b). The title compound (178 mg, 83%) was prepared according to the general method B using 17 (197 mg, 0.5 mmol) and N-isopropyl-N-methylethane-1,2-diamine (116 mg, 1.0 mmol). Colorless gel; $^1$H NMR (500 MHz, MeOD) δ 7.27 (s, 1H), 7.05 (s, 1H), 7.03 (s, 1H), 6.96 (s, 1H), 6.87 (s, 1H), 5.82 (s, 2H), 3.69 (t, J=7.1 Hz, 2H), 3.41-3.36 (m, 1H), 3.18 (t, J=7.1 Hz, 2H), 3.13-3.08 (m, 2H), 3.08-3.03 (m, 2H), 3.01 (s, 3H), 2.45 (s, 3H), 2.02 (s, 6H), 1.36 (d, J=6.6 Hz, 6H); $^{13}$C NMR (126 MHz, MeOD) δ 161.94, 152.91, 152.76, 150.80, 145.23, 129.41, 124.81, 122.45, 121.89, 120.42, 118.64, 114.42, 113.90, 107.62, 54.87, 52.23, 42.94, 39.89, 38.87, 37.04, 20.94, 19.60, 13.10.

Example 67

3-((2-(Cyclopropylamino)ethyl)(methyl)amino)-5-(2-(6-(2,5-dimethyl-1H-pyrrol-1-yl)-4-methylpyridin-2-yl)ethyl) benzonitrile. (20c) The title compound (148 mg, 69%) was prepared according to the general method B using 17 (197 mg, 0.5 mmol) and N-cyclopropyl-N'-methylethane-1,2-diamine (114 mg, 1.0 mmol). Colorless gel; $^1$H NMR (500 MHz, MeOD) δ 7.24 (s, 1H), 7.21 (s, 1H), 7.17 (s, 1H), 7.03 (s, 1H), 6.91 (s, 1H), 5.82 (s, 2H), 3.70 (t, J=7.4 Hz, 2H), 3.17-3.08 (m, 2H), 3.07-2.97 (m, 4H), 2.64 (s, 3H), 2.57 (tt, J=6.7, 3.7 Hz, 1H), 2.45 (s, 3H), 2.01 (s, 6H), 0.96 (dt, J=6.8, 3.4 Hz, 2H), 0.62 (dt, J=7.0, 3.5 Hz, 2H); $^{13}$C NMR (126 MHz, MeOD) δ 160.50, 151.47, 151.34, 149.33, 143.47, 127.99, 123.33, 121.28, 121.02, 119.00, 118.89, 114.79, 112.23, 106.21, 46.33, 38.37, 35.59, 33.35, 31.42, 29.41, 19.52, 11.68, 8.58.

Example 68

3-(2-(6-(2,5-Dimethyl-1H-pyrrol-1-yl)-4-methylpyridin-2-yl)ethyl)-5-((3-fluorophenethyl)(methyl)amino)benzonitrile (20d). To a solution of p20d (190 mg, 0.42 mmol) in THF (15 ml) was added NaH (20 mg, 0.5 mmol) and stirred for 15 min at 0° C. After addition of MeI (71 mg, 0.5 mmol) and stirred for 12 h at room temperature, the reaction mixture was quenched by addition of water (20 mL) and ethyl acetate (20 mL). The organic layer was partitioned, dried with MgSO$_4$, concentrated in vacuo, and purified using flash column chromatography to give the title compound (120 mg, 61%) as a pale yellow gel. $^1$H NMR (500 MHz, MeOD) δ 7.30 (td, J=7.8, 6.1 Hz, 1H), 7.01 (dt, J=7.5, 1.2 Hz, 1H), 6.99-6.89 (m, 2H), 6.80 (d, J=1.4 Hz, 1H), 6.74 (dd, J=2.6, 1.4 Hz, 1H), 6.70 (dd, J=2.6, 1.4 Hz, 1H), 6.28 (d, J=1.3 Hz, 1H), 6.25 (s, 1H), 3.61 (t, J=7.1 Hz, 2H), 2.91 (dd, J=8.8, 6.6 Hz, 2H), 2.84 (s, 3H), 2.83-2.76 (m, 4H), 2.16 (s, 3H); $^{13}$C NMR (126 MHz, MeOD) δ 164.37 (d, J=244.3 Hz), 160.76, 159.18, 151.10, 150.44, 145.23, 143.81 (d, J=7.3 Hz), 131.20 (d, J=8.3 Hz), 125.99 (d, J=2.8 Hz), 120.76, 120.39, 117.88, 116.73 (d, J=21.1 Hz), 114.90, 114.00 (d, J=21.2 Hz), 113.59, 113.40, 108.03, 54.82, 40.19, 38.78, 37.13, 33.71, 21.01.

Example 69

Compounds 21a-e were provided by pyrrole deprotection, as described in Example 20.

Example 70

$N^1$-(3-(2-(6-(2,5-Dimethyl-1H-pyrrol-1-yl)-4-methylpyridin-2-yl)ethyl)-5-fluorophenyl)-$N^1$,$N^2$-dimethylethane-1,2-diamine (22a). The title compound (160 mg, 80%) was prepared according to the general method B using 16b (193 mg, 0.5 mmol) and N,N'-dimethylethane-1,2-diamine (88 mg, 1.0 mmol). Pale yellow oil; $^1$H NMR (500 MHz, CDCl$_3$) δ 7.01-6.95 (m, 1H), 6.92-6.86 (m, 1H), 6.36 (dd, J=2.3, 1.3 Hz, 1H), 6.32-6.24 (m, 2H), 5.91 (s, 2H), 3.46 (t, J=6.6 Hz, 2H), 3.11-3.05 (m, 2H), 3.03-2.98 (m, 2H), 2.94 (s, 3H), 2.81 (t, J=6.5 Hz, 2H), 2.50 (s, 3H), 2.40 (s, 3H), 2.15 (s, 6H); $^{13}$C NMR (126 MHz, CDCl$_3$) δ 164.15 (d, J=241.5 Hz), 160.87, 151.61, 150.97 (d, J=11.3 Hz), 149.52, 144.30 (d, J=9.6 Hz), 128.48, 122.65, 120.10, 107.93, 106.70, 103.08 (d, J=21.5 Hz), 96.99 (d, J=26.1 Hz), 52.54, 49.12, 39.59, 38.85, 36.49, 36.30, 21.02, 13.25.

Example 71

$N^1$-(3-(2-(6-(2,5-Dimethyl-1H-pyrrol-1-yl)-4-methylpyridin-2-yl)ethyl)-5-fluorophenyl)-$N^2$,$N^2$-dimethylethane-1,2-diamine (22b). The title compound (187 mg, 93%) was prepared according to the general method B using 16 (193 mg, 0.5 mmol) and N,N-dimethylethane-1,2-diamine (88 mg, 1.0 mmol). Pale yellow oil; $^1$H NMR (500 MHz, CDCl$_3$) δ 6.96 (s, 1H), 6.89 (s, 1H), 6.29-6.22 (m, 2H), 6.18 (dt, J=11.5, 2.2 Hz, 1H), 5.92 (s, 2H), 3.16-3.10 (m, 2H), 3.07 (dd, J=9.2, 5.9 Hz, 2H), 2.98 (dd, J=9.3, 6.0 Hz, 2H), 2.59 (t, J=5.8 Hz, 2H), 2.40 (s, 3H), 2.29 (s, 6H), 2.16 (s, 6H); $^{13}$C NMR (126 MHz, CDCl$_3$) δ 164.09 (d, J=241.9 Hz), 160.84, 151.61, 150.07 (d, J=11.3 Hz), 149.50, 144.38 (d, J=9.5 Hz), 128.50, 122.63, 120.09, 108.78, 106.68, 103.79 (d, J=21.6 Hz), 97.22 (d, J=25.3 Hz), 57.72, 45.09, 40.86, 39.39, 35.91, 21.02, 13.26; MS ESI [M+H]$^+$=395.2.

Example 72

$N^1$-(3-(2-(6-(2,5-Dimethyl-1H-pyrrol-1-yl)-4-methylpyridin-2-yl)ethyl)-5-fluorophenyl)-$N^2$-ethyl-$N^1$-methylethane-1,2-diamine (22b) and $N^1$-(3-(2-(6-(2,5-Dimethyl-1H-pyrrol-1-yl)-4-methylpyridin-2-yl)ethyl)-5-fluorophenyl)-$N^1$-ethyl-$N^2$-methylethane-1,2-diamine (22d). The title compounds 22b (102 mg, 55%) and 22d (61 mg, 30%) were separated after Buchawald reaction (Method B). 16b (193 mg, 0.5 mmol) and N-ethyl-N'-methylethane-1,2-diamine (102 mg, 1.0 mmol) were used. 22b: $^1$H NMR (500 MHz, CDCl$_3$) δ 7.05 (s, 1H), 6.87 (s, 1H), 6.52 (s, 1H), 6.33 (d, J=12.3 Hz, 1H), 6.26 (d, J=9.1 Hz, 1H), 5.88 (s, 3H), 3.87 (t, J=7.5 Hz, 2H), 3.11-2.97 (m, 8H), 2.96 (s, 3H), 2.40 (s, 3H), 2.09 (s, 6H), 1.43 (t, J=7.2 Hz, 3H); $^{13}$C NMR (126 MHz, CDCl$_3$) δ 164.07 (d, J=241.8 Hz), 160.91, 151.39, 149.94 (d, J=11.3 Hz), 149.87, 144.54 (d, J=9.5 Hz), 128.51, 122.91, 120.32, 108.28, 106.60, 104.09 (d, J=21.6 Hz), 97.44 (d, J=26.3 Hz), 48.65, 43.86, 43.52, 39.39, 38.90, 36.24 (d, J=2.0 Hz), 21.03, 13.14, 11.69; 22d: $^1$H NMR (500 MHz, CDCl$_3$) δ 7.02 (s, 1H), 6.87 (s, 1H), 6.48-6.44 (m, 1H), 6.32 (dt, J=12.3, 2.3 Hz, 1H), 6.26 (dt, J=9.3, 1.5 Hz, 1H), 5.89 (s, 2H), 3.84-3.66 (m, 2H), 3.10-3.06 (m, 2H), 3.03-2.96 (m, 4H), 2.95 (s, 3H), 2.94-2.88 (m, 2H), 2.40 (s, 3H), 2.11 (s, 6H), 1.34 (t, J=7.2 Hz, 3H); $^{13}$C NMR (126 MHz, CDCl$_3$) δ 164.11 (d, J=241.8 Hz), 160.89, 151.49, 150.26 (d, J=11.0 Hz), 149.65, 144.49 (d, J=9.8 Hz), 128.48, 122.76, 120.19, 108.11, 106.62, 103.70 (d, J=21.5 Hz), 97.24 (d, J=26.2 Hz), 49.97, 44.66, 43.61, 39.46, 38.84, 36.24, 21.02, 13.19, 12.80.

Example 73

$N^1$-Cyclopropyl-$N^2$-(3-(2-(6-(2,5-dimethyl-1H-pyrrol-1-yl)-4-methylpyridin-2-yl)ethyl)-5-fluorophenyl)-$N^2$-methylethane-1,2-diamine (22c) and $N^1$-Cyclopropyl-$N^1$-(3-(2-(6-(2,5-dimethyl-1H-pyrrol-1-yl)-4-methylpyridin-2-yl)ethyl)-5-fluorophenyl)-$N^2$-methylethane-1,2-diamine (22e). The title compounds 22c (95 mg, 45%) and 22e (59 mg, 28%) were separated after Buchawald reaction (Method B). 16b (193 mg, 0.5 mmol) and N-cyclopropyl-N-methylethane-1,2-diamine (114 mg, 1.0 mmol) were used. 22c: $^1$H NMR (500 MHz, CDCl$_3$) δ 6.99 (s, 1H), 6.88 (s, 1H), 6.64 (t, J=1.7 Hz, 1H), 6.59 (dt, J=12.4, 2.3 Hz, 1H), 6.32 (dt, J=9.3, 1.7 Hz, 1H), 5.90 (s, 2H), 3.61 (t, J=7.2 Hz, 2H), 3.12-3.05 (m, 2H), 3.04-2.98 (m, 2H), 2.85 (t, J=7.2 Hz, 2H), 2.51 (s, 3H), 2.49-2.43 (m, 1H), 2.40 (s, 3H), 2.13 (s, 6H), 0.89-0.81 (m, 2H), 0.64-0.60 (m, 2H); $^{13}$C NMR (126 MHz, CDCl$_3$) δ 163.82 (d, J=241.2 Hz), 160.90, 151.52, 150.82 (d, J=10.9 Hz), 149.61, 143.99 (d, J=9.3 Hz), 128.47, 122.69, 120.14, 109.77, 106.70, 104.33 (d, J=21.6 Hz), 99.06 (d, J=26.0 Hz), 49.93, 48.24, 39.45, 36.22 (d, J=2.2 Hz), 35.71, 32.12, 21.02, 13.22, 9.31; 22e: $^1$H NMR (500 MHz, CDCl$_3$) δ 6.98 (s, 1H), 6.89 (s, 1H), 6.34 (s, 1H), 6.32-6.28 (m, 1H), 6.27 (s, 1H), 5.92 (s, 2H), 3.43 (t, J=6.8 Hz, 2H), 3.09 (dd, J=10.2, 6.4 Hz, 2H), 3.01 (dd, J=9.3, 5.6 Hz, 2H), 2.94 (s, 3H), 2.91 (t, J=6.8 Hz, 2H), 2.41 (s, 3H), 2.18 (dd, J=6.7, 3.5 Hz, 1H), 2.16 (s, 6H), 0.48 (dt, J=6.4, 3.1 Hz, 2H), 0.42-0.34 (m, 2H); $^{13}$C NMR (126 MHz, CDCl$_3$) δ 164.15 (d, J=241.2 Hz), 160.85, 151.62, 150.98 (d, J=11.2 Hz), 149.50, 144.25 (d, J=9.7 Hz), 128.47, 122.63, 120.08, 107.88 (d, J=1.7 Hz), 106.70, 102.92 (d, J=21.6 Hz), 96.92 (d, J=26.1 Hz), 52.76, 46.62, 44.00, 39.61, 38.76, 36.31 (d, J=2.1 Hz), 30.48, 21.02, 13.26, 6.43.

Example 74

N-(3-Chlorobenzyl)-3-(2-(6-(2,5-dimethyl-1H-pyrrol-1-yl)-4-methylpyridin-2-yl)ethyl)-5-fluoroaniline (22f). The title compound (202 mg, 90%) was prepared according to the general method B using 16b (197 mg, 0.5 mmol) and 3-chlorobenzylamine (142 mg, 1.0 mmol). Pale yellow oil; $^1$H NMR (500 MHz, CDCl$_3$) δ 7.37 (d, J=1.9 Hz, 1H), 7.33-7.22 (m, 3H), 6.95 (s, 1H), 6.89 (s, 1H), 6.32-6.23 (m, 2H), 6.15 (dt, J=11.2, 2.2 Hz, 1H), 5.93 (s, 2H), 4.30 (s, 2H), 3.06 (dd, J=9.2, 5.8 Hz, 2H), 2.98 (dd, J=9.2, 5.8 Hz, 2H), 2.41 (s, 3H), 2.16 (s, 6H); $^{13}$C NMR (126 MHz, CDCl$_3$) δ 164.04 (d, J=242.5 Hz), 160.69, 151.60, 149.54, 149.30 (d, J=11.3 Hz), 144.58 (d, J=9.4 Hz), 141.15, 134.58, 130.00, 128.49, 127.54, 127.35, 125.39, 122.62, 120.13, 108.88 (d, J=1.8 Hz), 106.72, 104.51 (d, J=21.6 Hz), 97.38 (d, J=25.7 Hz), 47.60, 39.29, 35.83 (d, J=2.0 Hz), 21.03, 13.27.

Example 75

3-(2-(6-(2,5-Dimethyl-1H-pyrrol-1-yl)-4-methylpyridin-2-yl)ethyl)-5-fluoro-N-(pyridin-3-ylmethyl)aniline (22 g). The title compound (135 mg, 65%) was prepared according to the general method B using 16b (197 mg, 0.5 mmol) and pyridin-3-ylmethanamine (108 mg, 1.0 mmol). Colorless oil; $^1$H NMR (500 MHz, CDCl$_3$) δ 8.59 (s, 1H), 8.51 (s, 1H), 7.65 (d, J=8.0 Hz, 1H), 7.26 (dd, J=7.8, 4.8 Hz, 1H), 6.90 (s, 1H), 6.83 (s, 1H), 6.27-6.22 (m, 2H), 6.11 (dt, J=11.1, 2.2 Hz, 1H), 5.86 (s, 2H), 4.29 (s, 2H), 3.05-2.95 (m, 2H), 2.95-2.86 (m, 2H), 2.35 (s, 3H), 2.09 (s, 6H); $^{13}$C NMR (126 MHz, CDCl$_3$) δ 164.02 (d, J=242.8 Hz), 160.65, 151.60, 149.54, 149.15 (d, J=11.3 Hz), 148.96, 148.75, 144.69 (d, J=9.5 Hz), 135.21, 134.47, 128.46, 123.67, 122.59, 120.13, 108.89 (d, J=1.9 Hz), 106.71, 104.70 (d, J=21.5 Hz), 97.47 (d, J=25.6 Hz), 45.66, 39.28, 35.81 (d, J=2.0 Hz), 21.02, 13.26.

Example 76 tert-Butyl 4-(3-(2-(6-(2,5-dimethyl-1H-pyrrol-1-yl)-4-methylpyridin-2-yl)ethyl)-5-fluorophenyl)piperazine-1-carboxylate (22h). The title compound (157 mg, 64%) was prepared according to the general method B using 16b (197 mg, 0.5 mmol) and N-Boc-piperazine (186.26 mg, 1.0 mmol). Colorless oil; $^1$H NMR (500 MHz, CDCl$_3$) δ 6.90 (s, 1H), 6.85 (s, 1H), 6.49 (t, J=1.8 Hz, 1H), 6.44-6.36 (m, 2H), 5.87 (s, 2H), 3.53 (t, J=5.1 Hz, 4H), 3.16-3.04 (m, 4H), 3.04-2.93 (m, 4H), 2.35 (s, 3H), 2.11 (s, 6H), 1.46 (d, J=9.0 Hz, 9H); $^{13}$C NMR (126 MHz, CDCl$_3$) δ 163.77 (d, J=243.0 Hz), 160.56, 154.69, 152.60 (d, J=10.1 Hz), 151.6, 149.53, 144.38 (d, J=9.2 Hz), 128.43, 122.66, 120.13, 112.01 (d, J=2.3 Hz), 106.75, 106.53, 100.93 (d, J=25.0 Hz), 80.03, 48.92, 39.44, 36.02 (d, J=2.1 Hz), 28.43 (d, J=3.1 Hz), 21.01, 13.28.

Example 77 tert-Butyl 4-((3-(2-(6-(2,5-dimethyl-1H-pyrrol-1-yl)-4-methylpyridin-2-yl)ethyl)-5-fluorophenyl)amino)piperidine-1-carboxylate (22i). The title compound (182 mg, 72%) was prepared according to the general method B using 16b (197 mg, 0.5 mmol) and N-Boc-4-aminopiperidine (200 mg, 1.0 mmol). Colorless oil; $^1$H NMR (500 MHz, CDCl$_3$) δ 6.92 (s, 1H), 6.84 (s, 1H), 6.21 (dt, J=9.5, 1.8 Hz, 1H), 6.18 (t, J=1.7 Hz, 1H), 6.10 (dt, J=11.3, 2.3 Hz, 1H), 5.87 (s, 2H), 4.12-3.83 (m, 2H), 3.67 (s, 1H), 3.33 (tt, J=10.2, 3.9 Hz, 1H), 3.06-2.98 (m, 2H), 2.97-2.79 (m, 4H), 2.36 (s, 3H), 2.01-1.91 (m, 2H), 1.45 (s, 9H), 1.34-1.23 (m, 2H); $^{13}$C NMR (126 MHz, CDCl$_3$) δ 164.12 (d, J=242.3 Hz), 160.73, 154.75, 151.62, 149.54, 148.30 (d, J=11.3 Hz), 144.67 (d, J=9.5 Hz), 128.44, 122.61, 120.11, 109.06, 106.74, 104.04 (d, J=21.5 Hz), 97.65 (d, J=25.3 Hz), 79.68, 50.10, 39.39, 35.90 (d, J=2.1 Hz), 32.23, 28.46, 21.01, 13.28.

Example 78

Compounds 23a-i were provided by pyrrole deprotection, as described in Example 9.

Example 79

N$^1$-(3-(2-(6-Amino-4-methylpyridin-2-yl)ethyl)-5-fluorophenyl)-N$^2$,N$^2$-dimethylethane-1,2-diamine (23a). $^1$H NMR (500 MHz, MeOD) δ 6.68 (s, 1H), 6.64 (s, 1H), 6.52 (s, 1H), 6.38-6.30 (m, 2H), 3.56 (t, J=6.1 Hz, 2H), 3.40 (t, J=6.1 Hz, 2H), 3.08-2.99 (m, 2H), 2.98 (s, 6H), 2.96 (m, 2H), 2.36 (s, 3H); $^{13}$C NMR (126 MHz, MeOD) δ 165.54 (d, J=241.5 Hz), 159.05, 155.77, 151.10 (d, J=11.5 Hz), 149.94, 144.24 (d, J=9.6 Hz), 115.02, 110.81, 110.09, 105.26 (d, J=22.0 Hz), 99.08 (d, J=25.7 Hz), 57.50, 43.77, 39.70, 35.86, 35.38, 21.98; HRMS (ESI): calcd for C$_{18}$H$_{26}$FN$_4$ [M+H]$^+$, 317.2136. found, 317.2144.

Example 80

N$^1$-(3-(2-(6-Amino-4-methylpyridin-2-yl)ethyl)-5-fluorophenyl)-N$^2$-ethyl-N$^1$-methylethane-1,2-diamine (23b). $^1$H NMR (500 MHz, MeOD) δ 6.71 (s, 1H), 6.70-6.59 (m, 2H), 6.45 (d, J=12.5 Hz, 1H), 6.39 (d, J=8.8 Hz, 1H), 3.70 (t, J=6.7 Hz, 2H), 3.24 (t, J=7.0 Hz, 2H), 3.15 (q, J=7.3 Hz, 2H), 3.07-3.01 (m, 4H), 3.00 (s, 3H), 2.37 (s, 3H), 1.44-1.30 (m, 3H); $^{13}$C NMR (126 MHz, MeOD) δ 165.59 (d, J=241.3 Hz), 159.08, 155.77, 152.12 (d, J=11.2 Hz), 149.95, 144.32 (d, J=9.7 Hz), 115.08, 110.80, 110.15, 105.07 (d, J=21.9 Hz), 99.16 (d, J=26.7 Hz), 50.12, 45.40, 44.61, 39.10, 36.17, 35.67, 21.99, 11.63; HRMS (ESI): calcd for C$_{19}$H$_{28}$FN$_4$ [M+H]$^+$, 331.2293. found, 331.2300.

Example 81

N$^1$-(3-(2-(6-Amino-4-methylpyridin-2-yl)ethyl)-5-fluorophenyl)-N$^2$-cyclopropyl-N$^1$-methylethane-1,2-diamine (23c). $^1$H NMR (500 MHz, MeOD) δ 6.71 (s, 1H), 6.68-6.64 (m, 2H), 6.45 (d, J=12.4 Hz, 1H), 6.40 (d, J=9.3 Hz, 1H), 3.70 (t, J=6.8 Hz, 2H), 3.36 (t, J=6.9 Hz, 2H), 3.10-3.00 (m, 4H), 2.99 (s, 3H), 2.87-2.80 (m, 1H), 2.37 (s, 3H), 1.04-0.99 (m, 2H), 0.98-0.91 (m, 2H); $^{13}$C NMR (126 MHz, MeOD) δ 165.59 (d, J=241.2 Hz), 159.10, 155.79, 152.35 (d, J=11.0 Hz), 149.98, 144.28 (d, J=9.5 Hz), 115.03, 110.78, 110.20, 105.06 (d, J=22.1 Hz), 99.26 (d, J=26.6 Hz), 49.92, 46.48, 38.97, 36.15, 35.63, 31.73, 21.95, 4.20; HRMS (ESI): calcd for C$_{20}$H$_{28}$FN$_4$ [M+H]$^+$, 343.2293. found, 343,2298.

Example 82

N$^1$-(3-(2-(6-Amino-4-methylpyridin-2-yl)ethyl)-5-fluorophenyl)-N$^1$-ethyl-N$^2$-methylethane-1,2-diamine (23d). $^1$H NMR (500 MHz, CD$_3$OD) δ 6.88 (s, 1H), 6.68 (s, 2H), 6.61 (d, J=12.1 Hz, 1H), 6.53 (d, J=9.1 Hz, 1H), 3.76 (t, J=6.8 Hz, 2H), 3.26 (t, J=6.8 Hz, 2H), 3.15 (q, J=7.2 Hz, 2H), 3.10-2.99 (m, 7H), 2.37 (s, 3H), 1.38 (t, J=7.1 Hz, 3H); $^{13}$C NMR (126 MHz, CD$_3$OD) δ 165.43 (d, J=242.7 Hz), 159.09, 155.79, 150.82 (d, J=10.3 Hz), 149.85, 144.71 (d, J=10.3 Hz), 115.10, 111.41, 110.86, 107.04 (d, J=22.1 Hz), 100.54 (d, J=26.5 Hz), 50.83, 45.10, 44.64, 40.17, 36.08, 35.54, 22.01, 11.63; HRMS (ESI): calcd for C$_{19}$H$_{28}$FN$_4$ [M+H]$^+$, 331.2293. found, 331.2299.

Example 83

N$^1$-(3-(2-(6-amino-4-methylpyridin-2-yl)ethyl)-5-fluorophenyl)-N$^1$-cyclopropyl-N$^2$-methylethane-1,2-diamine (23e). $^1$H NMR (500 MHz, MeOD) δ 6.85 (s, 1H), 6.71 (d, J=12.4 Hz, 1H), 6.66 (s, 2H), 6.44 (d, J=9.2 Hz, 1H), 3.77 (t, J=7.4 Hz, 2H), 3.21 (t, J=7.5 Hz, 2H), 3.12-2.98 (m, 4H), 2.77 (s, 3H), 2.57 (tt, J=6.8, 3.7 Hz, 1H), 2.37 (s, 3H), 0.95 (td, J=6.8, 4.8 Hz, 2H), 0.67-0.62 (m, 2H); $^{13}$C NMR (126 MHz, MeOD) δ 165.32 (d, J=241.4 Hz), 159.09, 155.79, 151.91 (d, J=10.9 Hz), 149.98, 144.07 (d, J=9.4 Hz), 115.05, 111.57, 110.79, 105.90 (d, J=22.1 Hz), 100.91 (d, J=26.4

Hz), 48.27, 47.17, 36.17, 35.66, 34.07, 33.10, 21.96, 9.91; HRMS (ESI): calcd for $C_{20}H_{28}FN_4$ $[M+H]^+$, 343.2293. found, 343.2297.

Example 84

6-(3-((3-Chlorobenzyl)amino)-5-fluorophenethyl)-4-methylpyridin-2-amine (23o). $^1$H NMR (500 MHz, MeOD) δ 7.35 (s, 1H), 7.34-7.19 (m, 3H), 6.53 (s, 1H), 6.42 (s, 1H), 6.24 (s, 1H), 6.23-6.10 (m, 2H), 4.29 (s, 2H), 2.97-2.70 (m, 4H), 2.27 (s, 3H); $^{13}$C NMR (126 MHz, MeOD) δ 165.52 (d, J=240.7 Hz), 157.06, 156.77, 152.56, 151.77 (d, J=11.6 Hz), 144.20 (d, J=9.7 Hz), 143.88, 135.44, 131.06, 128.06, 127.99, 126.54, 114.94, 110.01, 109.64, 104.05 (d, J=22.2 Hz), 98.41 (d, J=25.7 Hz), 47.64, 36.66, 36.24, 21.72; HRMS (ESI): calcd for $C_{21}H_{22}ClFN_3$ $[M+H]^+$, 370.1481. found, 370.1486.

Example 85

6-(3-Fluoro-5-((pyridin-3-ylmethyl)amino)phenethyl)-4-methylpyridin-2-amine (23 g). $^1$H NMR (500 MHz, MeOD) δ 8.55 (s, 1H), 8.43 (s, 1H), 7.84 (d, J=7.9 Hz, 1H), 7.42 (dd, J=7.9, 4.6 Hz, 1H), 6.29 (s, 1H), 6.27 (s, 1H), 6.26 (s, 1H), 6.20 (d, J=9.7 Hz, 1H), 6.15 (d, J=11.6 Hz, 1H), 4.37 (s, 2H), 2.84-2.67 (m, 4H), 2.18 (s, 3H); $^{13}$C NMR (126 MHz, MeOD) δ 164.03 (d, J=240.5 Hz), 159.07, 157.82, 149.95 (d, J=11.2 Hz), 149.93, 147.81, 147.09, 144.38 (d, J=9.6 Hz), 136.41, 135.91, 123.80, 113.22, 108.36, 106.60, 102.98 (d, J=21.8 Hz), 96.71 (d, J=25.8 Hz), 44.29, 38.63, 35.88, 19.63; HRMS (ESI): calcd for $C_{20}H_{22}FN_4$ $[M+H]^+$, 337.1823. found, 337.1822.

Example 86

6-(3-Fluoro-5-(piperazin-1-yl)phenethyl)-4-methylpyridin-2-amine (23h). $^1$H NMR (500 MHz, MeOD) δ 6.80 (t, J=1.71 Hz, 1H), 6.69 (t, J=1.19 Hz, 1H), 6.65 (dt, J=2.28, 11.85 Hz, 1H), 6.62 (d, J=1.45 Hz, 1H), 6.57 (dt, J=1.74, 9.16 Hz, 1H), 3.48 (dd, J=3.81, 6.71 Hz, 4H), 3.39 (dd, J=3.73, 6.73 Hz, 4H), 3.03 (s, 4H), 2.36 (s, 3H); $^{13}$C NMR (126 MHz, MeOD) δ 163.81 (d, J=242.61 Hz), 157.60, 154.36, 151.94 (d, J=10.50 Hz), 148.35, 142.92 (d, J=9.27 Hz), 113.62, 111.99 (d, J=2.17 Hz), 109.44, 106.78 (d, J=21.94 Hz), 101.29 (d, J=25.57 Hz), 45.78, 43.17, 34.50, 33.98, 20.56; HRMS (ESI): calcd for $C_{18}H_{24}FN_4$ $[M+H]^+$, 315.1980. found, 315.1978.

Example 87

6-(3-Fluoro-5-(piperidin-4-ylamino)phenethyl)-4-methylpyridin-2-amine (23i). $^1$H NMR (500 MHz, MeOD) δ 6.69 (s, 1H), 6.60 (s, 1H), 6.45 (t, J=1.6 Hz, 1H), 6.30 (dt, J=11.6, 2.2 Hz, 1H), 6.26 (dt, J=9.5, 1.8 Hz, 1H), 3.71-3.58 (m, 1H), 3.53-3.40 (m, 2H), 3.25-3.14 (m, 2H), 3.05-2.97 (m, 2H), 2.96-2.84 (m, 2H), 2.35 (s, 3H), 2.26-2.17 (m, 2H), 1.77-1.65 (m, 2H); $^{13}$C NMR (126 MHz, MeOD) δ 164.17 (d, J=240.8 Hz), 157.57, 154.33, 148.98 (d, J=11.6 Hz), 148.53, 142.60 (d, J=9.7 Hz), 113.64, 109.36, 108.71, 102.95 (d, J=22.1 Hz), 97.66 (d, J=25.6 Hz), 46.67, 42.73, 34.48 (d, J=2.1 Hz), 34.05, 28.40, 20.58; HRMS (ESI): calcd for $C_{19}H_{26}FN_4$ $[M+H]^+$, 329.2136. found, 329.2132.

Examples 49-62 relate to the preparation of compounds 3b-f outlined in Schemes 6-9.

Example 88

General Procedure A: Sonagashira coupling (preparation of 2a, 2c, 2d, and 2e). A microwave vial was charged with Pd(PPh$_3$)$_4$ (5 mol %), CuI (5 mol %), 2-(2-(5-bromopyridin-3-yl)ethyl)-6-(2,5-dimethyl-1H-pyrrol-1-yl)-4-methylpyridine (1) (1 equiv.). The mixtures were diluted with triethylamine (TEA) to form a 0.16 M solution followed by addition of the alkyne (1.5 equiv.). The microwave vial was then capped and the reaction mixture was stirred at 90° C. for 20 h. At this time, the cap was removed, and the reaction was diluted with ethyl acetate. The crude product was washed with water, ammonium chloride, and brine. The organic layer was dried over MgSO$_4$ and concentrated under reduced pressure. The crude product mixture was purified by chromatography.

Example 89

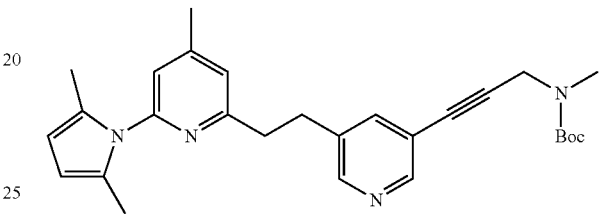

tert-butyl-3-(5-(2-(6-(2,5-dimethyl-1H-pyrrol-1-yl)-4-methylpyridin-2-yl)ethyl)pyridin-3-yl)prop-2-ynyl(methyl) carbamate (2a). 2a was synthesized according to general procedure A using 1 (184.6 mg, 0.50 mmol), Pd(PPh$_3$)$_4$ (28.8 mg), CuI (4.8 mg), tert-butyl methyl(prop-2-ynyl)carbamate (126.8 mg, 0.75 mmol), and triethylamine (3 ml). 2a was isolated as brown oil (171.9 mg, 75%) after chromatography (methanol:DCM 1:20). $^1$H NMR (500 MHz, CDCl$_3$): δ 8.44 (s, 1H), 8.29 (s, 1H), 7.50 (s, 1H), 6.86 (s, 1H), 6.84 (s, 1H), 5.86 (s, 2H), 4.26 (s, 2H), 3.05-3.04 (m, 4H), 2.94 (s, 3H), 2.33 (s, 3H), 2.08 (s, 6H), 1.46 (s, 9H); $^{13}$C NMR (125 MHz, CDCl$_3$): δ 159.7, 151.8, 150.1, 149.7, 149.0, 148.6, 148.1, 138.6, 128.4, 122.7, 120.4, 119.6, 106.8, 88.0, 80.3, 80.2, 38.9, 38.8, 33.6, 32.3, 28.4, 21.0, 13.2.

Example 90

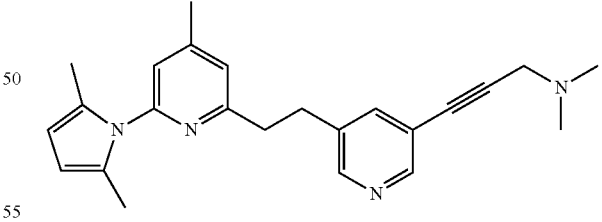

3-(5-(2-(6-(2,5-dimethyl-1H-pyrrol-1-yl)-4-methylpyridin-2-yl)ethyl)pyridin-3-yl)-N,N-dimethylprop-2-yn-1-amine (2c). 2c was synthesized according to general procedure A using 1 (185 mg, 0.50 mmol), Pd(PPh$_3$)$_4$ (28.8 mg), CuI (4.8 mg), N,N-dimethylprop-2-yn-1-amine (62.3. mg, 0.75 mmol), and triethylamine (3 ml). 2c was isolated as brown oil (166.6 mg, 90%) after chromatography (methanol:DCM 1:10). $^1$H NMR (500 MHz, CDCl$_3$): δ 8.45 (s, 1H), 8.27 (s, 1H), 7.49 (s, 1H), 6.85 (s, 1H), 6.83 (s, 1H), 5.85 (s, 2H), 3.43 (s, 2H), 3.05-3.04 (m, 4H), 2.33 (s, 6H), 2.32 (s, 3H), 2.08 (s, 6H); $^{13}$C NMR (125 MHz, CDCl$_3$): δ 159.8, 151.8, 150.1, 149.7, 148.8, 138.6, 136.2, 128.4, 122.7, 120.4, 119.9, 106.7, 88.0, 82.1, 48.6, 44.3, 38.9, 32.3, 21.0, 13.2.

Example 91

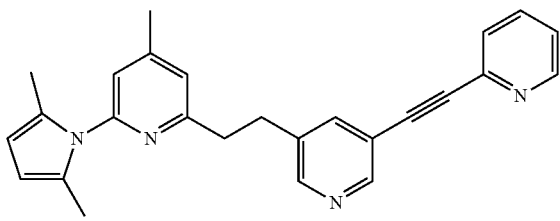 [SMILES: Cc1cc(CCc2cncc(C#Cc3ccccn3)c2)nc(-n2c(C)ccc2C)c1]

2-(2,5-dimethyl-1H-pyrrol-1-yl)-4-methyl-6-(2-(5-(pyridin-2-ylethynyl)pyridin-3-yl)ethyl)pyridine (2d). 2d was synthesized according to general procedure A using 1 (185 mg, 0.50 mmol), Pd(PPh$_3$)$_4$ (28.8 mg), CuI (4.8 mg), 2-ethynylpyridine (77.3 mg, 0.75 mmol), and triethylamine (3 ml). 2d was isolated as brown oil (111.7 mg, 57%) after chromatography (methanol:ethyl acetate 1:20). $^1$H NMR (500 MHz, CDCl$_3$): δ 8.61-8.59 (m, 2H), 8.33 (s, 1H), 7.67 (s, 1H), 7.50 (d, J=3.5 Hz, 1H), 7.44-7.40 (m, 1H), 7.25-7.22 (m, 1H), 6.85 (s, 1H), 6.83 (s, 1H), 5.85 (s, 2H), 3.08-3.07 (m, 4H), 2.32 (s, 3H), 2.08 (s, 6H); $^{13}$C NMR (125 MHz, CDCl$_3$): δ 159.7, 150.3, 150.2, 149.7, 149.6, 138.8, 136.4, 136.3, 132.2, 132.1, 128.6, 128.4, 127.3, 123.2, 122.8, 120.4, 106.8, 91.5, 85.7, 38.7, 32.2, 21.0, 13.2.

Example 92

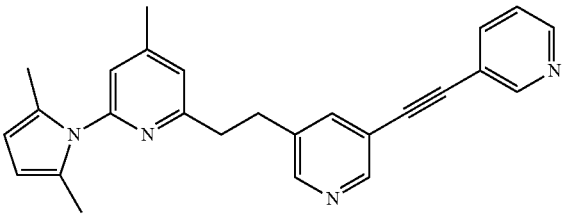 [SMILES: Cc1cc(CCc2cncc(C#Cc3cccnc3)c2)nc(-n2c(C)ccc2C)c1]

2-(2,5-dimethyl-1H-pyrrol-1-yl)-4-methyl-6-(2-(5-(pyridin-3-ylethynyl)pyridin-3-yl)ethyl)pyridine (2e). 2e was synthesized according to general procedure A using 1 (108.9 mg, 0.30 mmol), Pd(PPh$_3$)$_4$ (17.3 mg), CuI (2.9 mg), 3-ethynylpyridine (46.4 mg, 0.45 mmol), and triethylamine (1.8 ml). 2e was isolated as brown oil (54.3 mg, 47%) after chromatography (methanol:ethyl acetate 1:20). $^1$H NMR (500 MHz, CDCl$_3$): δ 8.72 (s, 1H), 8.55-8.52 (m, 2H), 8.32 (s, 1H), 7.76 (d, J=3.5 Hz, 1H), 7.61 (s, 1H), 7.27-7.24 (m, 1H), 6.86 (s, 1H), 6.83 (s, 1H), 5.84 (s, 2H), 3.07-3.06 (m, 4H), 2.32 (s, 3H), 2.07 (s, 6H); $^{13}$C NMR (125 MHz, CDCl$_3$): δ 159.7, 152.2, 151.8, 149.9, 149.7, 149.4, 149.0, 138.5, 136.4, 128.5, 128.4, 123.1, 122.7, 120.4, 119.8, 119.3, 106.8, 89.3, 89.0, 38.8, 32.2, 21.0, 13.2.

Example 93

General Procedure B: Pd/C hydrogenation and 2,5-dimethylpyrrole deprotection. A scintillation vial was charged with 10% wt. Pd/C and 2b (or 2c-2e). The mixtures were diluted with methanol to form a 0.1 M solution. The reaction mixture was stirred at room temp. for 20 h under hydrogen gas. The crude product was filtered through Celite, and the filtrate was concentrated under reduced pressure. The crude product was subjected to 2,5-dimethylpyrrole deprotection without purification. A microwave vial was charged with the hydrogenation crude product (1 equiv.) and NH$_2$OH.HCl (4 equiv.). The mixtures were diluted with EtOH/water (2:1) to form a 0.16 M solution. The microwave vial was then capped and the reaction mixture was stirred at 100° C. for 20 h. The cap was removed, and the reaction mixture was concentrated under reduced pressure. The crude product mixture was purified by chromatography to give inhibitors HYW-62, HYW-63, HYW-66, and HYW-67 (compounds 3d, 3e, 3b and 3c, respectively.

Example 94

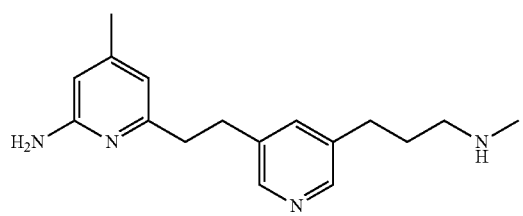 [SMILES: CNCCCc1cncc(CCc2cc(C)cc(N)n2)c1]

4-methyl-6-(2-(5-(3-(methylamino)propyl)pyridin-3-yl)ethyl)pyridin-2-amine (3b, HYW66). 2a (171.9, 0.38 mmol) was diluted with DCM (3.8 ml) to form a 0.1 M solution followed by addition of TFA (1.4 ml). The reaction mixture was allowed to stir at room temp. for 1 h. At this time, the crude was concentrated under reduced pressure. The crude product was diluted with DCM and washed with sat. NaHCO$_3$. The organic layer was dried over MgSO$_4$ and concentrated. The crude product was used for further steps without purification. The crude product was treated with 10% wt. Pd/C (56.1 mg), and NH$_2$OH.HCl (52.2 mg) according to general procedure B. Inhibitor HYW-67 was isolated as a brown oil (63.8 mg, 60%) after chromatography (methanol:DCM 4:6).

$^1$H NMR (500 MHz, Methanol-d$_4$): δ 8.79 (s, 1H), 8.78 (s, 1H), 8.68 (s, 1H), 6.75 (s, 2H), 3.35-3.32 (m, 2H), 3.21-3.18 m, 2H), 3.14-3.11 (m, 2H), 3.04-3.01 (m, 2H), 2.75 (s, 6H), 2.38 (s, 3H), 2.20-2.14 (m, 2H); $^{13}$C NMR (125 MHz, Methanol-d$_4$): δ 157.8, 154.5, 147.1, 147.0, 141.2, 140.4, 139.4, 139.2, 113.9, 110.0, 48.1, 32.7, 32.4, 31.1, 28.8, 26.3, 20.7.

Example 95

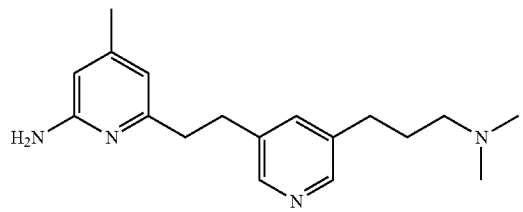 [SMILES: Cc1cc(N)nc(CCc2cncc(CCCN(C)C)c2)c1]

6-(2-(5-(3-(dimethylamino)propyl)pyridin-3-yl)ethyl)-4-methylpyridin-2-amine (3c, HYW67). Inhibitor HYW-67 was synthesized according to general procedure B using 2c (166.6 mg, 0.45 mmol), 10% wt. Pd/C (131.2 mg), and NH$_2$OH.HCl (79.2 mg) Inhibitor HYW-67 was isolated as a brown oil (118.5 mg, 89%) after chromatography (methanol: DCM 4:6). $^1$H NMR (500 MHz, Methanol-d$_4$): δ 8.80 (s, 2H), 8.71 (s, 1H), 6.76 (s, 2H), 3.36-3.33 (m, 2H), 3.31-3.28 (m, 2H), 3.22-3.19 (m, 2H), 3.03-3.00 (m, 2H), 2.95 (s, 6H), 2.38 (s, 3H), 2.27-2.21 (m, 2H); $^{13}$C NMR (125 MHz, Methanol-d$_4$): δ 157.8, 154.5, 147.1, 147.0, 141.1, 140.4, 139.4, 139.1, 113.9, 110.0, 56.5, 42.2, 32.7, 31.1, 28.7, 24.8, 20.7.

Example 96

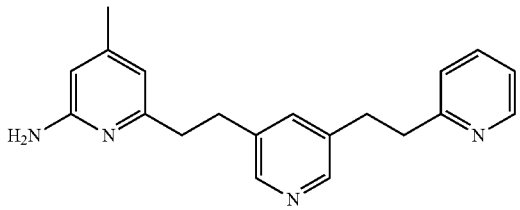 [SMILES: Cc1cc(N)nc(CCc2cncc(CCc3ccccn3)c2)c1]

4-methyl-6-(2-(5-(2-(pyridin-2-yl)ethyl)pyridin-3-yl) ethyl)pyridin-2-amine (3d, HYW62). Inhibitor HYW-62 was synthesized according to general procedure B using 2d (111.7 mg, 0.28 mmol), 10% wt. Pd/C (89.0 mg), and NH$_2$OH.HCl (35.3 mg). Inhibitor HYW-62 was isolated as a brown oil (37.7 mg, 42%) after chromatography (methanol:DCM 4:6). $^1$H NMR (500 MHz, methanol-d$_4$): δ 8.71-8.70 (m, 3H), 8.43 (s, 1H), 8.34 (s, 1H), 7.89 (s, 1H), 7.78 (s, 1H), 6.72 (s, 1H), 6.71 (s, 1H), 3.45-3.44 (m, 2H), 3.35-3.34 (m, 2H), 3.26-3.25 (m, 2H), 3.14-3.13 (m, 2H), 2.36 (s, 3H); $^{13}$C NMR (125 MHz, Methanol-d$_4$): δ 157.7, 156.6, 154.5, 147.3, 147.2, 144.3, 144.2, 143.6, 143.5, 141.8, 126.6, 124.4, 124.3, 113.9, 110.0, 35.0, 33.1, 31.7, 31.3, 20.8.

Example 97

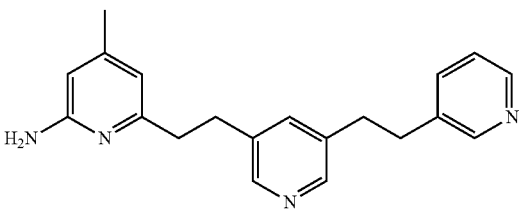 [SMILES: Cc1cc(N)nc(CCc2cncc(CCc3cccnc3)c2)c1]

4-methyl-6-(2-(5-(2-(pyridin-3-yl)ethyl)pyridin-3-yl) ethyl)pyridin-2-amine (3e, HYW63). Inhibitor HYW-63 was synthesized according to general procedure B using 2e (129.9 mg, 0.33 mmol), 10% wt. Pd/C (105.1 mg), and NH$_2$OH.HCl (83.9 mg). Inhibitor HYW-63 was isolated as a brown oil (51.7 mg, 49%) after chromatography (methanol:DCM 4:6). $^1$H NMR (500 MHz, Methanol-d$_4$): δ 8.94 (s, 1H), 8.78-8.77 (m, 3H), 8.70 (s, 1H), 8.66-8.65 (m, 1H), 8.08-8.07 (m, 1H), 6.73 (s, 1H), 6.70 (s, 1H), 3.35-3.29 (m, 6H), 3.17-3.16 (m, 2H), 2.38 (s, 3H); $^{13}$C NMR (125 MHz, Methanol-d$_4$): δ 157.8, 154.7, 154.6, 147.1, 146.8, 141.7, 141.0, 140.7, 140.3, 139.9, 139.8, 139.7, 127.1, 113.8, 110.0, 32.8, 32.6, 32.5, 31.1, 20.7.

Example 98

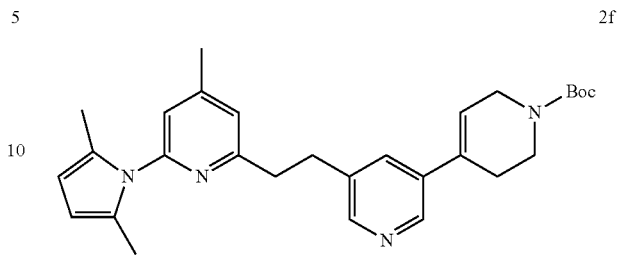

tert-butyl-4-(5-(2-(6-(2,5-dimethyl-1H-pyrrol-1-yl)-4-methylpyridin-2-yl)ethyl)pyridin-3-yl)-5,6-dihydropyridine-1(2H)-carboxylate (2f). A microwave vial was charged with Pd(OAc)$_2$ (13.4 mg), SPhos (41.1), K$_3$PO$_4$ (849.1 mg), boronic acid 4f (459.2 mg), and 1 (364 mg, 1.0 mmol). The mixtures were diluted with toluene/water (20:1) to form a 0.13 M solution. The microwave vial was then capped, and the reaction mixture was stirred at 100° C. for 20 h. The cap was removed, and the reaction mixture was diluted with ethyl acetate. The crude product was filtered, and the filtrate was dried over MgSO$_4$ and concentrated under reduced pressure. The crude product mixture was purified by chromatography (ethyl acetate:hexane 1:1) to give 2f (316.2 mg, 68%). $^1$H NMR (500 MHz, CDCl$_3$): δ 8.43 (s, 1H), 8.27 (s, 1H), 7.44 (s, 1H), 6.87 (s, 1H), 6.84 (s, 1H), 6.02-6.01 (m, 1H), 5.86 (s, 2H), 4.07-4.05 (m, 2H), 3.62-3.60 (m, 2H), 3.08-3.07 (m, 4H), 2.45-2.43 (m, 2H), 2.34 (s, 3H), 2.08 (s, 6H), 1.47 (s, 9H); $^{13}$C NMR (125 MHz, CDCl$_3$): δ 159.9, 154.8, 151.8, 149.7, 148.3, 148.2, 144.1, 136.4, 135.8, 132.7, 132.6, 128.4, 122.7, 120.3, 106.8, 79.9, 39.1, 39.0, 32.6, 32.5, 28.5, 27.1, 21.0, 13.2.

Example 99

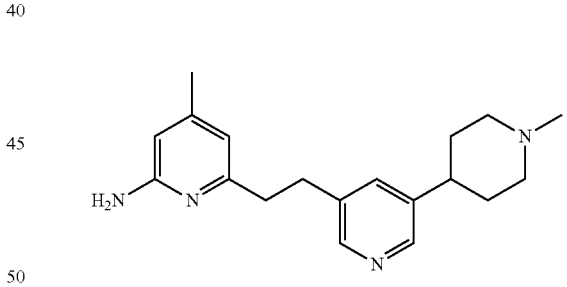

4-methyl-6-(2-(5-(1-methylpiperidin-4-yl)pyridin-3-yl) ethyl)pyridin-2-amine (3f, HYW65). 2f (316.2, 0.67 mmol) was treated with 10% wt. Pd/C (235.2 mg) and diluted with MeOH to form a 0.1 M solution. The reaction mixture was stirred at room temp. for 20 h under hydrogen gas. The crude product was filtered through Celite, and the filtrate was concentrated under reduced pressure. The crude product (298.9 mg) was subjected to tert-butyl carbamate reduction without purification. A round-bottom flask was charged with lithium aluminum hydride (126.1 mg). The hydrogenated crude product solution in THF (0.1M) was slowly added to the round-bottom flask at 0° C. under N$_2$. The reaction mixture was allowed to warm up to room temp. then reflux for 1 h. The reaction was quenched and worked-up to give the crude tert-butyl carbamate reduction product (136.6 mg). The crude product was treated with NH$_2$OH.HCl (99.7 mg)

and diluted with EtOH/water (2:1) to form a 0.16 M solution. The reaction mixture was stirred at 100° C. for 20 h. The reaction was concentrated under reduced pressure. The crude product mixture was purified by chromatography to give inhibitor HYW-65 (74.4 mg, 36%). $^1$H NMR (500 MHz, Methanol-$d_4$): δ 8.35 (s, 1H), 8.32 (s, 1H), 7.74 (s, 1H), 6.60 (s, 1H), 6.54 (s, 1H), 3.62-3.60 (m, 2H), 3.22-3.20 (m, 3H), 3.08-3.07 (m, 2H), 3.04-2.98 (m, 4H), 2.93 (s, 3H), 2.88-2.86 (m, 2H), 2.29 (s, 3H); $^{13}$C NMR (125 MHz, Methanol-$d_4$): δ 155.8, 155.6, 150.1, 147.4, 145.8, 139.7, 136.5, 135.4, 113.7, 109.0, 54.1, 48.5, 42.5, 34.7, 31.6, 29.9, 20.4.

Example 100

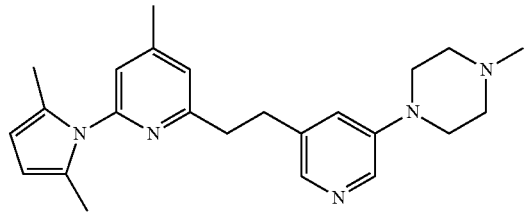 [SMILES: Cc1cc(CCc2cncc(N3CCN(C)CC3)c2)nc(-n2c(C)ccc2C)c1]

1-(5-(2-(6-(2,5-dimethyl-1H-pyrrol-1-yl)-4-methylpyridin-2-yl)ethyl)pyridin-3-yl)-4-methylpiperazine (2 g). A microwave vial was charged with Pd$_2$(dba)$_3$ (28.1 mg), DavePhos (24.1 mg), NaO$^t$Bu (70.7 mg), piperazine (79.1 mg), and (1) (226.2 mg, 0.61 mmol). The mixtures were diluted with dioxane to form a 0.16 M solution. The microwave vial was then capped and the reaction mixture was stirred at 100° C. for 20 h. At this time, the cap was removed, and the reaction was filtered through a silica pad. The filtrate was concentrated under reduced pressure. The crude product was subjected to methylation without purification. A scintillation vial was charged with the crude product (1 equiv.). The crude product was diluted with THF to form a 0.1 M solution followed by addition of triethylamine (1.5 equiv.) and MeI (1 equiv.). The reaction mixture was allowed to stir at room temp. for 1 h. At this time, the crude product was diluted with DCM and washed with water and brine. The organic layer was dried over MgSO$_4$ and concentrated under reduced pressure. The crude product mixture was purified by chromatography to give 2 g (34.6 mg, 15%). $^1$H NMR (500 MHz, CDCl$_3$): δ 8.09 (s, 1H), 7.89 (s, 1H), 7.42 (s, 1H), 6.07 (s, 1H), 6.87 (s, 1H), 6.83 (s, 1H), 5.84 (s, 2H), 3.20 (t, J=5.0 Hz, 4H), 3.04-2.99 (m, 4H), 2.60 (t, J=5.0 Hz, 4H), 2.36 (s, 3H), 2.33 (s, 3H), 2.08 (s, 6H); $^{13}$C NMR (125 MHz, CDCl$_3$): δ 160.2, 151.7, 149.6, 146.6, 140.9, 136.8, 136.3, 128.4, 122.8, 122.7, 120.3, 106.8, 54.7, 48.1, 45.9, 39.2, 32.9, 21.0, 13.2.

Example 101

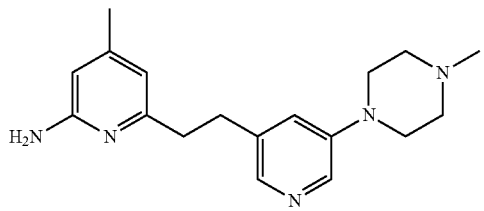 [SMILES: Cc1cc(N)nc(CCc2cncc(N3CCN(C)CC3)c2)c1]

4-methyl-6-(2-(5-(4-methylpiperazin-1-yl)pyridin-3-yl)ethyl)pyridin-2-amine (3 g, HYW64). A microwave vial was charged with 2 g (34.6 mg, 0.09 mmol) and NH$_2$OH.HCl (25.1 mg). The mixtures were diluted with EtOH/water (2:1) to form a 0.16 M solution. The microwave vial was then capped, and the reaction mixture was stirred at 100° C. for 20 h. The cap was removed, and the reaction was concentrated under reduced pressure. The crude product mixture was purified by chromatography (methanol:DCM 4:6) to give inhibitor HYW-64 (18.0 mg, 65%). $^1$H NMR (500 MHz, Methanol-$d_4$): δ 8.16 (s, 1H), 7.92 (s, 1H), 7.42 (s, 1H), 6.59 (s, 1H), 6.55 (s, 1H), 3.51-3.49 (m, 4H), 3.28-3.26 (m, 4H), 3.05-2.98 (m, 4H), 2.84 (s, 3H), 2.31 (s, 3H); $^{13}$C NMR (125 MHz, Methanol-$d_4$): δ 156.2, 155.3, 149.8, 146.3, 140.1, 136.6, 135.7, 123.9, 113.6, 109.1, 53.3, 46.1, 42.8, 34.5, 31.6, 20.4.

Example 102

Oxyhemoglobin assays. The oxyhemoglobin NO assays were performed with purified NOSs using a Biotek Gen5™ microplate reader as previously reported. (Labby, K. J.; Xue, F.; Kraus, J. M.; Ji, H.; Mataka, J.; Li, H.; Martásek, P.; Roman, L. J.; Poulos, T. L.; Silverman, R. B. Intramolecular hydrogen bonding: A potential strategy for more bioavailable inhibitors of neuronal nitric oxide synthase. *Bioorg. Med. Chem.* 2012, 20, 2435-2443; Hevel, J. M.; Marletta, M. A. Nitric-oxide synthase assays. *Methods Enzymol.* 1994, 233, 250-258.) The following were included in the assay: 10 μM L-arginine, 100 μM NADPH, 10 μM tetrahydrobiopterin, 1 mM CaCl$_2$, 11.6 μg/mL calmodulin, 3.0 μM oxyhemoglobin, and 100 mM HEPES buffer (10% glycerol; pH 7.4). For iNOS, calmodulin and CaCl$_2$ were omitted because iNOS is calcium independent. All NOS isozymes were used at a concentration of approximately 100 nM. IC$_{50}$ for each compound was determined in triplicate using dose-response curves with nine concentration points (1 pM-3 mM). The calculated standard deviations of the assays were less than 10% with all NOSs. The inhibition constants ($K_i$) were calculated from the IC$_{50}$ and $K_m$ (human nNOS: 1.6 μM; rat nNOS: 1.3 μM; murine iNOS=8.2 μM; bovine eNOS=1.7 μM) for all NOSs using the general equation: $K_i$=IC$_{50}$/(1+ [S]/$K_m$). The selectivity of antagonism of nNOS was determined by calculating the ratios of the $K_i$ values with iNOS or eNOS to those with rat nNOS.

Example 103

Pharmacokinetic study. A group of forty-eight male mice were divided into two groups: Group 1 (2 mg/kg; i.v.) and Group 2 (10 mg/kg; p.o.) with each group comprising twenty-four mice. Animals in Group 1 were administered intravenously with a 19c solution in saline at a 2 mg/kg dose, and animals in Group 2 were administered orally with a 10 mg/kg solution of 19c in saline. Blood samples (approximately 100 μL) were collected from the retro orbital plexus under light isoflurane anesthesia; samples were obtained at 0.08, 0.25, 0.5, 1, 2, 4, 8 and 24 h (i.v.) and 0.25, 0.5, 1, 2, 4, 6, 8 and 24 h (p.o.). The blood samples were collected from a set of three mice at each time point in labeled micro centrifuge tubes containing K2EDTA as anticoagulant. Plasma samples were separated by centrifugation of whole blood and stored below −70° C. until bioanalysis. Immediately after collection of blood, brain samples were collected from each mouse at 0.08, 0.25, 0.5, 1, 2, 4, 8 and 24 h (i.v.) and 0.25, 0.5, 1, 2, 4, 6, 8 and 24 h (p.o.). Tissue samples were homogenized using ice-cold phosphate buffer saline (pH 7.4) and homogenates were stored below −70° C. until analyzed. The total homogenate volume was three times that of the tissue weight. All samples were processed for analysis by protein precipitation using acetonitrile (ACN) and analyzed with a fit for purpose LC/MS/MS method (LLOQ: 2.02 ng/mL for plasma and 3.03 ng/g for brain). Specific LC-MS/MS and MRM conditions are described below. Pharmacokinetic parameters were calculated using the non-compartmental analysis tool of Phoenix WinNonlin (Version 6.3).

TABLE 11

HPLC and MS Conditions for DMPK study

| Chromatographic Mode: | LC/MS/MS |
|---|---|
| MS System Used: | AB Sciex API-4000 |
| Software Version: | Analyst 1.5 |
| Scan Type: | MRM |
| Polarity: | Positive |
| Ion Source: | Turbospray |
| Mobile Phase: | A: 0.1% Formic Acid in Water |
| | B: 0.1% Formic Acid in Acetonitrile |
| Flow Rate (mL/min): | 0.8 |
| Needle Stroke: | 52 |
| Splitter: | Approximately 75% out |
| Probe Position: | 5 mm vertical, and 5 mm horizontal |
| Injection Volume (µL): | 5 |
| Auto Sampler Temperature (° C.): | 4 |
| Column Oven Temperature (° C.): | 40 |
| Column Used (length × width in mm, Particle size): | WATERS Xterra, MX C18, (50 × 3.0, 5 µ) |
| Retention Time (in min): | 19c: 1.11 |
| Glipizide (IS): | 1.44 |
| Run Time (in min): | 3.20 |

Example 104

Inhibitor Complex Crystal Preparation. The preparations of rat nNOS, bovine eNOS, and human nNOS heme domains used for crystallographic studies were carried out using the procedures described previously. (Li, H.; Jamal, J.; Plaza, C.; Pineda, S. H.; Chreifi, G.; Jing, Q.; Cinelli, M. A.; Silverman, R. B.; Poulos, T. L. Structures of human constitutive nitric oxide Synthases. *Acta Crystallogr.* 2014. D70, 2667-2674.) The heme domain samples of rat nNOS (at 9 mg/mL containing 20 mM histidine) and bovine eNOS (10 mg/mL containing 2 mM imidazole) were used for the sitting drop vapor diffusion crystallization setup under conditions reported. Human nNOS crystals were obtained with the triple K301R/R354A/G357D mutant heme domain sample at 10 mg/mL. By slightly modifying the original conditions where the monoclinic C2 crystals grew, a new crystal form was obtained. (Li, H.; Jamal, J.; Delker, S.; Plaza, C.; Ji, H.; Jing, Q.; Huang, H.; Kang, S.; Silverman, R. B.; Poulos, T. L. The mobility of a conserved tyrosine residue controls isoform-dependent enzyme-inhibitor interactions in nitric oxide synthases. *Biochemistry* 2014, 53, 5272-5279; Li, H.; Jamal, J.; Plaza, C.; Pineda, S. H.; Chreifi, G.; Jing, Q.; Cinelli, M. A.; Silverman, R. B.; Poulos, T. L. Structures of human constitutive nitric oxide Synthases. *Acta Crystallogr.* 2014. *D*70, 2667-2674.) Long plate crystals were grown at 4° C. with the sitting drop setup against a well solution of 8-9% PEG3350, 40 mM citric acid, 60 mM Bis-Tris-Propane, pH 6.2, 10% glycerol, and 5 mM TCEP. New crystals belong to the orthorhombic $P2_12_12_1$ space group with cell dimensions of a=52.3 Å b=122.7 Å c=165.0 Å with one homodimer in the asymmetric unit, which closely resemble the cell dimensions of rat nNOS crystal. Fresh crystals were first passed stepwise through cryoprotectant solutions and then soaked with 10 mM inhibitor for 4-6 h at 4° C. before being flash cooled with liquid nitrogen.

Example 105

X-ray Diffraction Data Collection, Data Processing, and Structural Refinement. The cryogenic (100 K) X-ray diffraction data were collected remotely at the Stanford Synchrotron Radiation Lightsource (SSRL) or Advanced Light Source (ALS) using the data collection control software Blu-Ice with a crystal mounting robot. (McPhillips, T. M.; McPhillips, S. E.; Chiu, H. J.; Cohen, A. E.; Deacon, A. M.; Ellis, P. J.; Garman, E.; Gonzalez, A.; Sauter, N. K.; Phizackerley, R. P.; Soltis, S. M.; Kuhn, P. Blu-Ice and the Distributed Control System: software for data acquisition and instrument control at macromolecular crystallography beamlines. *J. Synchrotron Radiat.* 2002, 9, 401-406.) When a Q315r CCD detector was used, 90-100° of data were typically collected with 0.5° per frame. If a Pilatus pixel array detector was used, 140-160° of fine-sliced data were collected with 0.2° per frame. Raw CCD data frames were indexed, integrated, and scaled using HKL2000 or MOSFLM, but the pixel array data were processed with XDS and scaled with Scala (Aimless). (Otwinowski, Z.; Minor, W. Processing of X-ray diffraction data collected in oscillation mode. *Methods Enzymol.* 1997, 276, 307-326; Leslie, A. G. W.; Powell, H. R. Processing diffraction data with Mosflm. *In Evolving Methods for Macromolecular crystallography* 2007, 245, 41-51, Springer, Dordrecht; Kabsch, W. XDS. *Acta Crystallogr.* 2010, D66, 125-132; Evans, P. R. Scaling and assessment of data quality. *Acta Crystallogr.* 2006, D62, 72-82.) The binding of inhibitors was detected by the initial difference Fourier maps calculated with REFMAC. (Murshudov, G. N.; Vagin, A. A.; Dodson, E. J. Refinement of macromolecular structures by the maximum-likelihood method. *Acta Crystallogr.* 1997, *D*53, 240-255.) The inhibitor molecules were then modeled in COOT and refined using REFMAC or PHENIX. (Emsley, P.; Cowtan, K. Coot: model-building tools for molecular graphics. *Acta Crystallogr.* 2004, D60, 2126-2132; Adams, P. D.; Afonine, P. V.; Bunkóczi, G.; Chen, V. B.; Davis, I. W.; Echols, N.; Headd, J. J.; Hung, L.-W.; Kapral, G. J.; Grosse-Kunstleve, R. W.; McCoy, A. J.; Moriarty, N. W.; Oeffner, R.; Read, R. J.;

Richardson, D. C.; Richardson, J. S.; Terwilliger, T. C.; Zwart, P. H. PHENIX: a comprehensive Python-based system for macromolecular structure solution. *Acta Crystallogr.* 2010, D66, 213-221.) Water molecules were added in REFMAC or PHENIX and checked manually in COOT. The TLS protocol was implemented in the final stage of refinements with each subunit as one TLS group. ((Winn, M. D.; Isupov, M. N.; Murshudov, G. N. Use of TLS parameters to model anisotropic displacements in macromolecular refinement. *Acta Crystallogr.* 2001, D57, 122-133.) The omit Fo-Fc density maps were calculated by removing inhibitor coordinates from the input PDB file before running one more round of TLS refinement in REFMAC or in PHENIX (simulated annealing protocol with a 2000 K initial temperature). The resulting map coefficients DELFWT and PHDELWT were used to generate maps. The refined structures were validated in COOT before deposition in the protein data bank. The crystallographic data collection and structure refinement statistics, with the PDB accession codes, are summarized in Table 12.

TABLE 12

Crystallographic data collection and refinement statistics.

| Data set [1] | nNOS-10a | nNOS-14a | nNOS-14b | nNOS-19a |
|---|---|---|---|---|
| *Data collection* | | | | |
| PDB code | 4UGZ | 4UH0 | 4UH1 | 4UH2 |
| Space group | $P2_12_12_1$ | $P2_12_12_1$ | $P2_12_12_1$ | $P2_12_12_1$ |
| Cell dimensions a, b, c (Å) | 51.8 111.2 164.9 | 52.2 111.7 165.6 | 52.2 111.1 164.1 | 51.7 111.0 164.4 |
| Resolution (Å) | 2.08 (2.11-2.08) | 2.03 (2.07-2.03) | 1.80 (1.83-1.80) | 1.99 (2.02-1.99) |
| Rmerge | 0.096 (>1.00) | 0.063 (0.392) | 0.058 (0.458) | 0.096 (0.931) |
| Rpim | 0.061 (0.721) | 0.037 (0.456) | 0.034 (0.285) | 0.039 (0.577) |
| CC 1/2 | n/a (0.575) | n/a (0.933) | n/a (0.925) | n/a (0.871) |
| I/σI | 16.5 (0.8) | 25.7 (2.0) | 28.4 (1.8) | 23.3 (1.0) |
| No. unique reflections | 57,430 | 61,372 | 88,754 | 64,181 |
| Completeness (%) | 99.1 (94.5) | 98.0 (93.3) | 99.5 (99.2) | 97.9 (91.0) |
| Redundancy | 3.5 (3.0) | 3.8 (3.7) | 3.9 (3.4) | 5.2 (3.2) |
| *Refinement* | | | | |
| Resolution (Å) | 2.08 | 2.04 | 1.80 | 1.99 |
| No. reflections used | 57,220 | 61,196 | 88,343 | 63,889 |
| $R_{work}/R_{free}$ [2] | 0.190/0.227 | 0.181/0.224 | 0.200/0.234 | 0.179/0.216 |
| *No. atoms* | | | | |
| Protein | 6673 | 6660 | 6671 | 6659 |
| Ligand/ion | 173 | 183 | 173 | 181 |
| Water | 256 | 377 | 456 | 297 |
| *R.m.s. deviations* | | | | |
| Bond lengths (Å) | 0.008 | 0.008 | 0.015 | 0.007 |
| Bond angles (deg) | 1.14 | 1.13 | 1.76 | 1.14 |

| Data set [1] | nNOS-19b | nNOS-19c | HnNOS-14b | HnNOS-19c |
|---|---|---|---|---|
| *Data collection* | | | | |
| PDB code | 4UH3 | 4UH4 | 4UH5 | 4UH6 |
| Space group | $P2_12_12_1$ | $P2_12_12_1$ | $P2_12_12_1$ | $P2_12_12_1$ |
| Cell dimensions a, b, c (Å) | 51.7 110.6 164.6 | 52.1 111.5 165.2 | 52.4 122.6 164.0 | 52.3 122.7 165.0 |
| Resolution (Å) | 2.03 (2.07-2.03) | 1.95 (1.98-1.95) | 1.98 (2.05-1.98) | 1.98 (2.05-1.98) |
| Rmerge | 0.079 (0.982) | 0.088 (0.882) | 0.095 (1.710) | 0.077 (0.922) |
| Rpim | 0.040 (0.874) | 0.040 (0.395) | 0.086 (1.555) | 0.070 (0.828) |
| CC 1/2 | n/a (0.874) | n/a (0.932) | 0.995 (0.335) | 0.996 (0.398) |
| I/σI | 24.1 (1.6) | 28.5 (2.5) | 5.3 (0.4) | 8.2 (1.1) |
| No. unique reflections | 62,031 | 69,615 | 71,749 | 71,459 |
| Completeness (%) | 99.6 (99.6) | 99.4 (99.9) | 97.0 (90.1) | 96.3 (91.8) |
| Redundancy | 4.8 (4.2) | 6.0 (5.9) | 3.9 (3.6) | 4.1 (4.0) |
| *Refinement* | | | | |
| Resolution (Å) | 2.03 | 1.95 | 1.98 | 1.98 |
| No. reflections used | 61,974 | 66,076 | 71,655 | 71,391 |
| $R_{work}/R_{free}$ [2] | 0.185/0.234 | 0.191/0.224 | 0.195/0.247 | 0.173/0.213 |
| *No. atoms* | | | | |
| Protein | 6686 | 6665 | 6735 | 6716 |
| Ligand/ion | 175 | 177 | 167 | 171 |
| Water | 226 | 280 | 297 | 512 |
| *R.m.s. deviations* | | | | |
| Bond lengths (Å) | 0.017 | 0.011 | 0.007 | 0.008 |
| Bond angles (deg) | 1.85 | 1.96 | 1.15 | 1.18 |

TABLE 12-continued

Crystallographic data collection and refinement statistics.

| Data set [1] | eNOS-10a | eNOS-14b | eNOS-19b | eNOS-19c |
|---|---|---|---|---|
| Data collection | | | | |
| PDB code | 4UH7 | 4UH8 | 4UH9 | 4UHA |
| Space group | $P2_12_12_1$ | $P2_12_12_1$ | $P2_12_12_1$ | $P2_12_12_1$ |
| Cell dimensions a, b, c (Å) | 58.0 106.4 157.2 | 57.9 106.3 156.9 | 58.2 106.8 157.9 | 57.9 106.3 156.5 |
| Resolution (Å) | 2.24 (2.28-2.24) | 2.30 (2.34-2.30) | 2.14 (2.23-2.14) | 2.20 (2.30-2.20) |
| Rmerge | 0.057 (0.660) | 0.060 (0.738) | 0.069 (1.063) | 0.102 (1.741) |
| Rpim | 0.033 (0.374) | 0.035 (0.431) | 0.034 (0.614) | 0.091 (1.531) |
| CC 1/2 | n/a (0.815) | n/a (0.725) | 0.999 (0.535) | 0.995 (0.346) |
| I/σI | 29.9 (2.3) | 26.8 (1.9) | 14.8 (1.2) | 7.6 (0.8) |
| No. unique reflections | 47,727 | 43,858 | 54,517 | 49,840 |
| Completeness (%) | 99.6 (99.9) | 99.6 (100.0) | 98.5 (98.5) | 99.7 (98.4) |
| Redundancy | 4.0 (4.0) | 3.9 (3.9) | 4.9 (3.6) | 4.0 (4.0) |
| Refinement | | | | |
| Resolution (Å) | 2.24 | 2.30 | 2.14 | 2.20 |
| No. reflections used | 47,588 | 43,089 | 54,405 | 49,581 |
| $R_{work}/R_{free}$ [2] | 0.159/0.211 | 0.161/0.217 | 0.174/0.227 | 0.181/0.240 |
| No. atoms | | | | |
| Protein | 6431 | 6438 | 6418 | 6408 |
| Ligand/ion | 234 | 191 | 234 | 213 |
| Water | 338 | 294 | 243 | 233 |
| R.m.s. deviations | | | | |
| Bond lengths (Å) | 0.008 | 0.007 | 0.017 | 0.008 |
| Bond angles (deg) | 1.16 | 1.18 | 1.90 | 1.20 |

[1] See FIG. 3 for the inhibitor chemical formula.
[2] $R_{free}$ was calculated with the 5% of reflections set aside throughout the refinement. The set of reflections for the $R_{free}$ calculation were kept the same for all data sets of each isoform according to those used in the data of the starting model.

Experimental Procedures for Examples 107-133

Materials, synthetic methods, and molecular characterization. All starting reagents and solvents were purchased from Sigma-Aldrich, TCI America, and Matrix Scientific and were used without further purification. Solvents were purified by passage through a solvent column composed of activated alumina and a supported copper redox catalyst. Moisture or oxygen-sensitive reactions were performed under an atmosphere of dry $N_2$ or argon. Biotage® Initiator microwave system was used for microwave-assisted reactions. Thin-layer chromatography was carried out on E. Merck precoated silica gel 60 F254 plates. An Agilent 971-FP flash purification system with various SiliaSep™ (Silicycle, 40-63 μm, 60 Å) prepacked silica gel cartridges was used for flash column chromatography. $^1$H NMR and $^{13}$C NMR spectra were recorded in the indicated solvent on a Bruker Avance-III (500 MHz and 126 MHz for $^1$H and $^{13}$C, respectively) spectrometer. Chemical shifts are reported as δ values in parts per million downfield from TMS (δ 0.0) as the internal standard in $CDCl_3$. MS was performed on a system consisting of an electrospray ionization (ESI) source in a Thermo Finnigan LCQ and Bruker amaZon SL mass spectrometer. High-resolution mass spectra were obtained using an Agilent 6210 LC-TOF spectrometer. The purity of the compounds was evaluated on an Beckman Gold reverse phase analytical HPLC system using an Phenonemex Gemini C-18 (4.6×250 mm, 5 μm) or Luna C-8 (4.6×250 mm, 5 μm) reverse phase columns with UV absorbance and evaporative light scattering detection. Purities of all compounds that were subjected to biological assay were >95%. The direct chiral resolutions of racemic 8R and 8S were performed on a Beckman Gold HPLC system using a Chiralcel OD-H HPLC column (Daicel, 250×4.6 mm i.d., 5 mm). Hexanes and isopropanol (85-92% hexanes) were used as the mobile phases. The operation temperature was 25° C., and the flow rate was 0.8 ml/min with 254 nm UV detection. Optical rotations were measured on a PerkinElmer Model 341 digital readout polarimeter.

Computational Methods. The MM-PBSA method, as implemented in Amber 9.0 used in previous work, was used to calculate free energies of binding. In this method the total free energy of the NOS-inhibitor complex is taken as the sum of the following energy terms:

$$G = E_{MM} + G_{solv} + G_{np} - TS_{solute}$$

where $E_{MM}$=the total molecular mechanics energy computed with the Sander module in Amber 9.0, $G_{solv}$ is the solvation free energy estimated from the Poisson-Boltzmann equation, $G_{np}$=the nonpolar solvation energy estimated from the solvent accessible surface area, and $TS_{solute}$=the solute entropy. From a single energy minimized structure the free energy is computed for the NOS-inhibitor complex, NOS alone with the inhibitor removed, and the inhibitor alone. The overall free energy of binding is computed from the following equation:

$$\Delta G_{bind} = (G_{complex} - G_{receptor} - G_{inhibitor})$$

As others have done, the solute entropy is ignored. Given that the inhibitors used for these calculations are exactly the same, ignoring entropy introduces little error. Parameters for the inhibitor and heme were the same as described previously in the literature.

Enzyme Assay Methods. All of the NOS isoforms were overexpressed and purified, and enzyme kinetics data were determined using the hemoglobin capture assay (HCA) at 37° C. in a high-throughput method using 96-well plates. A typical assay mixture for nNOS and eNOS contained various concentrations of the test compound, 10 M L-Arg, 1.0 mM $CaCl_2$, 300 units/mL calmodulin (Sigma, P-2277), 100 M NADPH, 0.125 mg/mL hemoglobin-A° (ferrous form, Sigma, H0267), 10 M H$_4$B, in 100 mM HEPES (pH 7.5). A typical assay mixture for iNOS contained various concentrations of the test compound, 100 M NADPH, 0.125 mg/mL hemoglobin-A° (ferrous form), 10 M H$_4$B, in 100 mM HEPES (pH 7.5). All assays were in a final volume of 100 L and were initiated by addition of enzyme (approximately 100 nM final concentration). Nitric oxide-mediated oxidation of hemoglobin-A0 was monitored at 401 nm for 1 min on a Synergy H1 reader by Biotek. Curves were fitted using the Michaelis-Menten equation in GraphPad Prism 5.0 (GraphPad Software, Inc.). For K$_i$ determinations, IC$_{50}$ values were calculated using nonlinear regressions (dose-response inhibition, four-parameter variable slope). Subsequent K$_i$ values were calculated using the Cheng-Prusoff relationship: K$_i$=IC$_{50}$/(1+[S]/K$_m$) (K$_m$ values used for rat nNOS, murine iNOS, bovine eNOS and human nNOS were 1.3, 8.3, 1.7 and 1.6 M respectively).

Example 107

General procedure for deprotection of 2-(2,5-dimethyl-1H-pyrrol-1-yl)pyridine derivatives using microwave irradiation. (Walia, A.; Kang, S.; Silverman, R. B. Microwave-assisted protection of primary amines as 2,5-dimethylpyrroles and their orthogonal deprotection. *J. Org. Chem.* 2013, 78, 10931-10937.) Method A. To a 5 mL microwave vial equipped with a magnetic stir bar was added the protected aminopyridine (1.0 mmol), ethanol (2.5 mL), concentrated hydrochloric acid (0.5 mL). After being capped, the vial was shaken vigorously and then heated in the microwave irradiator for 20 min at 120° C. (as recorded via the IR sensor of the microwave instrument). After being cooled to room temperature, the reaction mixture was concentrated in vacuo and purified by flash column chromatography using a SiliaSep™ C18 flash cartridge (25 g, 40-63 μm/230-400 mesh, Pore Size 60 Å) with 5 to 80% MeOH in water as the mobile phase.

Example 108

(S)-6-(2-Amino-2-(3-(2-(6-amino-4-methylpyridin-2-yl)ethyl)phenyl)ethyl)-4-methylpyridin-2-amine (3S) and (R)-6-(2-Amino-2-(3-(2-(6-amino-4-methylpyridin-2-yl)ethyl)phenyl)ethyl)-4-methylpyridin-2-amine (3R). The title compounds were synthesized using General Method A. 3S (55 mg, 58%) was prepared as a pale yellow gel from 13a (180 mg, 0.26 mmol), and 3R (50 mg, 60%) was prepared as a pale yellow gel from 13b (160 mg, 0.23 mmol). 3S: [α]$^{20}_D$=+72.1° (c 3 g/L, MeOH); 3R: [α]$^{20}_D$=−79.2° (c 2 g/L, MeOH). $^1$H NMR (500 MHz, MeOD) δ 7.22-7.17 (m, 1H), 7.14 (qt, J=2.9, 1.9, 1.4 Hz, 2H), 7.05 (dt, J=7.4, 1.6 Hz, 1H), 6.25 (s, 1H), 6.24 (ss, 2H), 6.18 (s, 1H), 4.21 (t, J=7.1 Hz, 1H), 2.89 (dd, J=9.6, 6.4 Hz, 2H), 2.81 (d, J=7.1 Hz, 2H), 2.79-2.71 (m, 2H), 2.13 (s, 3H), 2.11 (s, 3H); $^{13}$C NMR (126 MHz, MeOD) δ 160.86, 160.70, 159.73, 157.35, 151.03, 150.86, 145.85, 143.10, 129.46, 128.35, 127.82, 125.18, 115.89, 114.67, 108.22, 107.92, 57.15, 48.09, 40.64, 37.32, 21.08, 21.05; HRMS (ESI): calcd for C$_{22}$H$_{28}$N$_5$ [M+H]$^+$, 362.2339. found, 362.2338.

Example 109

(R)-6-(2-Amino-2-(3-(2-(4-methylpyridin-2-yl)ethyl)phenyl)ethyl)-4-methylpyridin-2-amine (5R) and (S)-6-(2-Amino-2-(3-(2-(4-methylpyridin-2-yl)ethyl)phenyl)ethyl)-4-methylpyridin-2-amine (5S). Method A was used to prepare 5R (153 mg, 65%, colorless gel) from 19a (360 mg, 0.682 mmol) and 5S (22 mg, 60%, colorless gel) from 19b (55 mg, 0.104 mmol). 5S: [α]$^{20}_D$=−20.0° (c 2 g/L, MeOH); 5R: [α]$^{20}_D$=+19.2° (c 2 g/L, MeOH); $^1$H NMR (500 MHz, MeOD) δ 8.54 (d, J=6.0 Hz, 1H), 7.79 (s, 1H), 7.68 (d, J=5.9 Hz, 1H), 7.63 (s, 1H), 7.51-7.37 (m, 2H), 7.36-7.29 (m, 1H), 6.68 (s, 2H), 4.87 (d, J=7.8 Hz, 1H), 3.51 (dd, J=14.7, 7.9 Hz, 1H), 3.42-3.34 (m, 3H), 3.21-3.14 (m, 2H), 2.62 (s, 3H), 2.34 (s, 3H); $^{13}$C NMR (126 MHz, MeOD) δ 162.50, 158.89, 156.51, 156.12, 143.95, 142.17, 141.24, 137.24, 131.02, 130.88, 129.16, 128.68, 127.00, 126.98, 116.76, 112.22, 55.32, 38.40, 35.76, 22.36, 21.96; HRMS (ESI): calcd for C$_{22}$H$_{27}$N$_4$ [M+H]$^+$, 347.2230. found, 347.2229.

Example 110

6-(3-Amino-2-(3-(2-(6-amino-4-methylpyridin-2-yl)ethyl)phenyl)propyl)-4-methylpyridin-2-amine (6). Method A was used to prepare 6 (144 mg, 43%, pale yellow gel) from 24 (475 mg, 0.89 mmol). $^1$H NMR (500 MHz, MeOD) δ 7.43 (s, 1H), 7.32 (t, J=7.6 Hz, 1H), 7.21 (dt, J=7.5, 1.8 Hz, 2H), 6.68 (s, 2H), 6.62 (s, 1H), 6.50 (s, 1H), 3.60-3.51 (m, 1H), 3.40-3.34 (m, 2H), 3.29 (dd, J=14.3, 6.1 Hz, 1H), 3.07-3.00 (m, 5H), 2.38 (s, 3H), 2.28 (s, 3H); $^{13}$C NMR (126 MHz, MeOD) δ 159.08, 158.70, 155.78, 150.00, 147.22, 142.47, 139.40, 130.61, 129.59, 129.31, 127.58, 116.07, 114.88, 111.16, 110.83, 44.87, 44.69, 37.99, 35.93, 35.61, 22.01, 21.91; HRMS (ESI): calcd for C$_{23}$H$_{30}$N$_5$ [M+H]$^+$, 376.2496. found, 376.2502.

Example 111

6-(3-Amino-2-(6-(2-(6-amino-4-methylpyridin-2-yl)ethyl)pyridin-2-yl)propyl)-4-methylpyridin-2-amine (7). Method A was used to prepare 7 (87 mg, two step 43%, pale yellow gel) from crude 30a (300 mg). $^1$H NMR (500 MHz, MeOD) δ 7.83 (m, 1H), 7.38 (m, 1H), 7.33 (m, 1H), 6.73 (s, 1H), 6.70 (s, 1H), 6.65 (s, 1H), 6.45 (s, 1H), 3.80 (s, 1H), 3.61 (dd, J=12.9, 9.0 Hz, 1H), 3.37 (t, J=4.7 Hz, 1H), 3.23 (m, 6H), 2.39 (s, 3H), 2.29 (s, 3H); $^{13}$C NMR (126 MHz, MeOD) δ 160.66, 159.10, 158.71, 157.66, 155.90, 155.79, 149.94, 146.66, 124.54, 124.02, 115.82, 114.76, 111.48, 110.92, 44.82, 43.32, 37.01, 36.55, 32.91, 21.99, 21.89; HRMS (ESI): calcd for C$_{22}$H$_{29}$N$_6$ [M+H]$^+$, 377.2448. found, 377.2455.

Example 112

(S)-6-(3-Amino-2-(5-(2-(6-amino-4-methylpyridin-2-yl)ethyl)pyridin-3-yl)propyl)-4-methylpyridin-2-amine (8S) and (R)-6-(3-amino-2-(5-(2-(6-amino-4-methylpyridin-2-yl)ethyl)pyridin-3-yl)propyl)-4-methylpyridin-2-amine (8R). Method A was used to prepare 8 (45 mg, 41%) from racemic 30b (180 mg), 8S (21 mg, 69%) from enantiomer 30c-1 (43 mg), and 8R (15 mg, 79%) from enantiomer 30c-2 (32 mg). 8S:[α]$^{20}_D$=−85.3° (c 4 g/L, MeOH); 8R:[α]$^{20}_D$=+84.9° (c 3 g/L, MeOH). $^1$H NMR (500 MHz, MeOD) δ 8.44 (s, 2H), 8.20 (d, J=2.2 Hz, 1H), 6.74 (s, 1H), 6.71 (s, 1H), 6.65 (s, 1H), 6.58 (s, 1H), 3.75-3.66 (m, 1H), 3.50 (dd, J=13.1, 9.9 Hz, 1H), 3.42 (dd, J=13.1, 5.3 Hz, 1H), 3.39-3.34 (m, 1H), 3.13 (td, J=9.8, 9.4, 5.6 Hz, 5H), 2.39 (s, 3H), 2.31 (s, 3H); $^{13}$C NMR (126 MHz, MeOD) δ 159.12, 158.75, 155.95, 155.84, 149.33, 147.89, 146.49, 138.99, 138.68, 136.11, 116.10, 114.96, 111.51, 111.08, 44.14, 42.24, 37.57, 34.83, 32.89, 21.99, 21.89; HRMS (ESI): calcd for C$_{22}$H$_{29}$N$_6$ [M+H]$^+$, 377.2448. found, 377.2454.

Example 113

2-(6-(2,5-Dimethyl-1H-pyrrol-1-yl)-4-methylpyridin-2-yl)-1-(3-(2-(6-(2,5-dimethyl-1H-pyrrol-1-yl)-4-methylpyridin-2-yl)ethyl)phenyl)ethanol (11). To a solution of 9 (1.0 g, 5.0 mmol) in THF (25 mL) was added n-BuLi (1.6 M solution in hexanes, 3.12 mL, 5.0 mmol), and the reaction was stirred for 30 min at 0° C. This mixture was transferred to a solution of 3-(bromomethyl)benzaldehyde (10, 396 mg, 2.0 mmol) in THF (25 mL) at −78° C. via cannula. The reaction mixture was allowed to stir for an additional 20 min, and then quenched with $H_2O$ (50 mL). After addition of ethyl acetate (50 mL), the organic layer was partitioned, dried with $MgSO_4$, and concentrated by rotary evaporation. The resulting yellow oil was purified by flash chromatography (EtOAc/hexanes) to yield 2,5-dimethylpyrrole-protected product 11 as a yellow oil (663 mg, 64%). $^1$H NMR (500 MHz, $CDCl_3$) δ 7.33-7.25 (m, 3H), 7.14-7.09 (m, 1H), 6.99 (s, 1H), 6.95 (s, 2H), 6.89 (s, 1H), 5.93 (s, 2H), 5.91 (s, 2H), 5.15 (m, 1H), 3.17 (m, 2H), 3.10 (m, 4H), 2.42 (s, 3H), 2.40 (s, 3H), 2.18 (s, 6H), 2.16 (s, 6H); $^{13}$C NMR (126 MHz, $CDCl_3$) δ 161.01, 159.29, 151.62, 151.13, 150.28, 149.53, 143.99, 141.63, 128.56, 128.50, 128.40, 127.51, 125.97, 123.52, 123.46, 122.67, 120.77, 120.10, 106.93, 106.68, 73.25, 45.73, 39.78, 36.64, 35.98, 24.72, 21.10, 13.31; MS (ESI) m/z 519.32 $[M+H]^+$.

Example 114

2-(2-Azido-2-(3-(2-(6-(2,5-dimethyl-1H-pyrrol-1-yl)-4-methylpyridin-2-yl)ethyl)phenyl)ethyl)-6-(2,5-dimethyl-1H-pyrrol-1-yl)-4-methylpyridine (12). To a stirred solution of triphenylphosphine (314 mg, 1.2 mmol) and diethylazodicarboxylate (210 mg, 1.2 mmol) in dry THF (15 mL), diphenylphosphonyl azide (331 mg, 1.2 mmol) was added dropwise followed by a THF solution of 11 (518 mg, 1.0 mmol). After stirring 1 h at room temp, the reaction mixture was concentrated in vacuo and purified by flash column chromatography to yield the title compound (522 mg, 96%) as a colorless oil. $^1$H NMR (500 MHz, $CDCl_3$) δ 7.30 (t, J=7.9 Hz, 2H), 7.22-7.15 (m, 3H), 6.99 (s, 1H), 6.94 (s, 1H), 6.92 (s, 1H), 6.89 (s, 1H), 5.94 (s, 2H), 5.92 (s, 2H), 5.12 (t, J=7.3 Hz, 1H), 3.16 (d, J=7.4 Hz, 2H), 3.10 (s, 4H), 2.38 (s, 3H), 2.16 (ss, 12H); $^{13}$C NMR (126 MHz, $CDCl_3$) δ 160.66, 157.25, 151.78, 151.67, 149.86, 149.52, 142.22, 139.42, 128.84, 128.52, 128.48, 126.94, 124.55, 123.86, 122.67, 120.85, 120.13, 106.80, 106.70, 65.75, 44.75, 39.66, 35.79, 21.05, 20.99, 13.29, 13.25; MS (ESI) m/z 544.21 $[M+H]^+$.

Example 115

(1S,4S)—N—((S)-2-(6-(2,5-dimethyl-1H-pyrrol-1-yl)-4-methylpyridin-2-yl)-1-(3-(2-(6-(2,5-dimethyl-1H-pyrrol-1-yl)-4-methylpyridin-2-yl)ethyl)phenyl)ethyl)-4,7,7-trimethyl-3-oxo-2-oxabicyclo[2.2.1]heptane-1-carboxamide (13a). and (1S,4S)—N—((R)-2-(6-(2,5-dimethyl-1H-pyrrol-1-yl)-4-methylpyridin-2-yl)-1-(3-(2-(6-(2,5-dimethyl-1H-pyrrol-1-yl)-4-methylpyridin-2-yl)ethyl)phenyl)ethyl)-4,7,7-trimethyl-3-oxo-2-oxabicyclo[2.2.1]heptane-1-carboxamide (13b). To the solution of 12 (500 mg, 0.92 mmol) in THF (25 mL) was added dropwise a 1.0 M solution of $LiAlH_4$ in THF (1.4 mL, 1.4 mmol) at 0° C. After being stirred for 3 h at the same temperature, the reaction mixture was allowed to warm to room temp, and the reaction was quenched by sequential addition of i-PrOH (1 mL), water (15 mL), and then 1 M NaOH aq. (10 mL). The organic materials were extracted with ethyl acetate (25 mL) three times, and the combined organic layers were washed with brine, dried over anhydrous $MgSO_4$, and then concentrated in vacuo to yield a crude amine (2-(6-(2,5-Dimethyl-1H-pyrrol-1-yl)-4-methylpyridin-2-yl)-1-(3-(2-(6-(2,5-dimethyl-1H-pyrrol-1-yl)-4-methylpyridin-2-yl)ethyl)phenyl)ethan-1-amine). To the solution of the produced amine in dichloromethane (25 mL) was added (S)-camphanic chloride (325 mg, 1.5 mmol) and triethylamine (0.279 mL, 2.0 mmol) at 0° C. After being stirred for 12 h at room temp, the reaction mixture was quenched with $H_2O$ (50 mL). After addition of dichloromethane (25 mL), the organic layer was partitioned, dried with $MgSO_4$, concentrated by rotary evaporation, and purified by flash chromatography (EtOAc/hexanes) to yield diastereomeric pure compounds 13 (180 mg, 28%) and 13b (161 mg, 25%) as a pale yellow oil. 13a: $^1$H NMR (500 MHz, $CDCl_3$) δ 7.19 (t, J=7.6 Hz, 1H), 7.14 (t, J=1.8 Hz, 1H), 7.11 (dt, J=7.6, 1.5 Hz, 1H), 7.06 (dt, J=7.5, 1.4 Hz, 1H), 6.98 (d, J=8.4 Hz, 1H), 6.93 (s, 1H), 6.92 (s, 1H), 6.84 (ss, 2H), 5.87 (s, 2H), 5.86 (s, 2H), 5.51 (td, J=8.7, 5.8 Hz, 1H), 3.26 (dd, J=14.0, 5.9 Hz, 1H), 3.17 (dd, J=14.0, 9.0 Hz, 1H), 3.01 (q, J=2.5, 1.8 Hz, 4H), 2.40 (ddd, J=13.4, 10.4, 4.1 Hz, 1H), 2.36 (s, 3H), 2.31 (s, 3H), 2.11 (s, 6H), 2.06 (s, 6H), 1.90-1.73 (m, 2H), 1.61 (ddd, J=12.7, 8.9, 4.2 Hz, 1H), 1.04 (s, 3H), 0.97 (s, 3H), 0.57 (s, 3H); $^{13}$C NMR (126 MHz, $CDCl_3$) δ 178.24, 165.99, 160.78, 157.36, 151.82, 151.54, 149.74, 142.05, 141.27, 128.80, 128.51, 128.49, 127.75, 126.68, 124.04, 123.29, 122.58, 120.64, 120.12, 106.85, 106.73, 92.49, 55.28, 53.72, 53.23, 44.37, 39.63, 35.88, 30.27, 29.03, 21.04, 20.95, 16.61, 16.18, 13.36, 13.30, 9.72; MS (ESI) m/z 720.36 $[M+Na]^+$; 13b: $^1$H NMR (500 MHz, $CDCl_3$) δ 7.16 (t, J=7.6 Hz, 1H), 7.14-7.09 (m, 2H), 7.06 (dd, J=7.7, 1.6 Hz, 1H), 7.03 (dt, J=7.6, 1.4 Hz, 1H), 6.89 (s, 2H), 6.84 (s, 2H), 5.87 (s, 2H), 5.84 (s, 2H), 5.44 (td, J=8.2, 6.1 Hz, 1H), 3.27 (dd, J=14.0, 6.1 Hz, 1H), 3.20 (dd, J=14.0, 8.3 Hz, 1H), 2.98 (d, J=2.0 Hz, 4H), 2.40-2.34 (m, 4H), 2.32 (s, 3H), 2.11 (s, 6H), 2.04 (s, 6H), 1.85 (ddd, J=13.0, 10.8, 4.2 Hz, 1H), 1.67 (ddd, J=13.0, 9.3, 4.1 Hz, 1H), 1.59 (ddd, J=13.2, 9.3, 3.8 Hz, 1H), 1.04 (s, 3H), 0.98 (s, 3H), 0.74 (s, 3H); $^{13}$C NMR (126 MHz, $CDCl_3$) δ 178.22, 166.28, 160.74, 157.33, 151.67, 149.73, 141.92, 141.45, 128.66, 128.49, 127.63, 126.64, 124.05, 123.42, 122.51, 120.77, 120.12, 106.75, 106.70, 92.30, 55.25, 54.01, 53.37, 43.95, 39.64, 35.87, 30.23, 29.06, 21.04, 21.01, 16.69, 16.43, 13.30, 13.24, 9.69; MS (ESI) m/z 720.37 $[M+Na]^+$.

Example 116

3-(2-(4-Methylpyridin-2-yl)ethyl)benzonitrile (16). To a solution of 14 (0.804 g, 7.5 mmol) in dry THF (30 mL) was added n-BuLi (1.6 M solution in hexanes, 4.68 mL, 7.5 mmol), and the reaction was stirred for 30 min at 0° C. This solution (red color) was added dropwise to a solution of 3-(bromomethyl)benzonitrile (15, 1.16 g, 6.0 mmol) in THF (20 mL) at −78° C. using a cannula, until the solution became pale red. The reaction mixture was allowed to stir for an additional 20 min, and then quenched with $H_2O$ (50 mL). After addition of ethyl acetate (100 mL), the organic layer was partitioned, dried with $MgSO_4$, and concentrated in vacuo. The resulting yellow oil was purified by flash chromatography (EtOAc/hexanes) to yield the title compound as a yellow oil (680 mg, 51%). $^1$H NMR (500 MHz, $CDCl_3$) δ 8.40 (d, J=5.0 Hz, 1H), 7.52-7.39 (m, 3H), 7.36 (t, J=7.6 Hz, 1H), 6.96 (dd, J=5.1, 1.5 Hz, 1H), 6.89 (d, J=1.6 Hz, 1H), 3.19-2.94 (m, 4H), 2.30 (s, 3H); $^{13}$C NMR (126 MHz, $CDCl_3$) δ 159.85, 149.15, 147.57, 143.05, 133.15, 132.02, 129.78, 129.12, 123.96, 122.49, 119.04, 112.24, 39.44, 35.32, 20.97; MS (ESI) m/z 222.97 [M+H]+.

Example 117

3-(2-(4-Methylpyridin-2-yl)ethyl)benzaldehyde (17). To a solution of 16 (660 mg, 2.94 mmol) in dichloromethane (30 mL) was added 1.0 M solution of DIBAL in toluene (8.8 mL, 8.8 mmol) at 0° C., and stirred 3 h. The reaction mixture was then quenched with MeOH (3 mL) and water (25 mL). The mixture was warmed to ambient temperature, stirred for 30 min, and diluted with CH$_2$Cl$_2$ (50 mL). The organic layer was washed with Rochelle's solution and brine, dried over MgSO$_4$, and concentrated in vacuo. The resulting residue was purified by flash chromatography (EtOAc/hexanes) to yield the title compound as a yellow oil (350 mg, 53%). $^1$H NMR (500 MHz, CDCl$_3$) δ 10.01 (s, 1H), 8.44 (d, J=5.0 Hz, 1H), 7.77-7.68 (m, 2H), 7.52-7.42 (m, 2H), 6.98 (dd, J=5.2, 1.6 Hz, 1H), 6.93 (s, 1H), 3.21-3.13 (m, 2H), 3.13-3.05 (m, 2H), 2.32 (s, 3H); $^{13}$C NMR (126 MHz, CDCl$_3$) δ 192.58, 160.31, 149.17, 147.49, 142.80, 136.55, 134.81, 129.59, 129.03, 127.69, 123.94, 122.39, 39.79, 35.61, 21.00.

Example 118

(S,E)-2-Methyl-N-(3-(2-(4-methylpyridin-2-yl)ethyl) benzylidene)propane-2-sulfinamide (18). To a solution of (S)-tert-butanesulfinamide (0.210 g, 1.7 mmol) in THF (5 mL) was added 17 (350 mg, 1.55 mmol) followed by Ti(OEt)$_4$ (0.70 g, 3 mmol). The reaction solution was stirred overnight at room temp (16 h), and then the reaction was quenched by the slow addition of saturated aqueous NaHCO$_3$ (10 mL). The resulting mixture was diluted with EtOAc (20 mL), filtered through Celite, and the Celite pad was washed with EtOAc (20 mL). The organic layers were partitioned, dried over MgSO$_4$, and concentrated in vacuo. The residue was purified by silica gel chromatography (EtOAc:hexanes) to give the title compound (361 mg, 71% yield) as a pale yellow solid. $^1$H NMR (500 MHz, CDCl$_3$) δ 8.56 (s, 1H), 8.43 (d, J=5.0 Hz, 1H), 7.70 (d, J=1.6 Hz, 1H), 7.67 (dt, J=6.9, 1.8 Hz, 1H), 7.43-7.34 (m, 2H), 6.96 (dd, J=5.0, 1.6 Hz, 1H), 6.94 (s, 1H), 3.16-3.00 (m, 4H), 2.31 (s, 3H), 1.28 (s, 9H); $^{13}$C NMR (126 MHz, CDCl$_3$) δ 162.85, 160.44, 149.12, 147.45, 142.62, 134.13, 132.75, 129.08, 128.98, 127.46, 123.95, 122.36, 57.77, 39.87, 35.75, 22.63, 20.99; MS (ESI) m/z 329.35 [M+H]+.

Example 119

(S)—N—((R)-2-(6-(2,5-Dimethyl-1H-pyrrol-1-yl)-4-methylpyridin-2-yl)-1-(3-(2-(4-methylpyridin-2-yl)ethyl) phenyl)ethyl)-2-methylpropane-2-sulfinamide (19a down, major) and (S)—N—((S)-2-(6-(2,5-Dimethyl-1H-pyrrol-1-yl)-4-methylpyridin-2-yl)-1-(3-(2-(4-methylpyridin-2-yl) ethyl)phenyl)ethyl)-2-methylpropane-2-sulfinamide (19b). To a solution of 9 (250 mg, 1.25 mmol) in dry THF (15 mL) was added n-BuLi (1.6 M solution in hexanes, 0.781 mL, 1.25 mmol), and the reaction was stirred for 30 min at 0° C. This solution was added dropwise to a solution of sulfonamide (18, 350 mg, 1.07 mmol) in THF (15 mL) at −78° C. using a cannula. After being stirred for an additional 20 min, the reaction mixture was quenched with H$_2$O (20 mL) and diluted with EtOAc (25 mL). The organic layer was partitioned, dried with MgSO$_4$, and concentrated in vacuo. The resulting yellow oil was purified by flash chromatography (EtOAc/hexanes) to yield title compounds 19a (367 mg, 65%) and 19b (62 mg, 11%). The minor product (19b) eluted first. 19a: pale brown oil; $^1$H NMR (500 MHz, CDCl$_3$) δ 8.43 (dd, J=4.9, 0.9 Hz, 1H), 7.25-7.17 (m, 3H), 7.14-7.09 (m, 1H), 6.97-6.94 (m, 2H), 6.88 (s, 1H), 6.87 (s, 1H), 5.89 (s, 2H), 4.92-4.82 (m, 1H), 4.33 (d, J=4.8 Hz, 1H), 3.47-3.34 (m, 1H), 3.20 (dd, J=13.9, 6.1 Hz, 1H), 3.02 (s, 3H), 2.35 (s, 3H), 2.32 (s, 3H), 2.08 (s, 6H), 1.10 (s, 9H); $^{13}$C NMR (126 MHz, CDCl$_3$) δ 160.87, 158.06, 151.49, 149.57, 149.03, 147.43, 142.08, 141.84, 128.64, 128.44, 127.94, 127.34, 124.90, 123.91, 123.87, 122.24, 120.59, 106.67, 59.49, 56.09, 45.43, 40.14, 36.09, 22.47, 22.13, 21.01, 20.97, 13.26; MS (ESI) m/z 551.15 [M+H]+. 19b: pale brown oil; $^1$H NMR (500 MHz, CDCl$_3$) δ 8.44 (d, J=5.1 Hz, 1H), 7.30-7.19 (m, 3H), 7.15 (dt, J=7.5, 1.6 Hz, 1H), 6.97 (dd, J=5.1, 1.5 Hz, 1H), 6.95 (s, 1H), 6.94 (s, 2H), 5.88 (s, 2H), 4.76 (ddd, J=9.3, 4.1, 1.9 Hz, 1H), 3.21-3.09 (m, 2H), 3.04 (p, J=2.8 Hz, 4H), 2.40 (s, 3H), 2.33 (s, 3H), 2.14 (s, 6H), 1.09 (s, 9H); $^{13}$C NMR (126 MHz, CDCl$_3$) δ 160.89, 158.28, 151.28, 150.35, 149.07, 147.41, 142.17, 141.93, 128.58, 128.48, 127.83, 127.62, 125.13, 123.89, 123.57, 122.25, 120.91, 106.50, 57.95, 55.45, 45.58, 40.14, 36.12, 22.59, 21.08, 21.03, 13.27; MS (ESI) m/z 551.22 [M+Na]+.

Example 120

3-(2-(6-(2,5-Dimethyl-1H-pyrrol-1-yl)-4-methylpyridin-2-yl)ethyl)benzonitrile (20). The title compound (785 mg, 83%) was prepared according to a similar procedure described in the synthesis of 16 using n-BuLi (1.6 M, 2.34 mL, 3.75 mmol), 9 (750 mg, 3.75 mmol), and 15 (0.582 g, 3.0 mmol). Colorless oil; $^1$H NMR (500 MHz, CDCl$_3$) δ 7.54-7.43 (m, 3H), 7.39 (d, J=15.3 Hz, 1H), 6.93 (s, 1H), 6.91 (s, 1H), 5.92 (s, 2H), 3.22-3.00 (m, 4H), 2.40 (s, 3H), 2.14 (s, 6H); $^{13}$C NMR (126 MHz, CDCl$_3$) δ 159.86, 151.76, 149.72, 142.92, 133.17, 132.00, 129.85, 129.18, 128.45, 122.69, 120.41, 119.00, 112.32, 106.77, 39.05, 35.05, 21.02, 13.26; MS (ESI) m/z 632.34 [2M+H]+.

Example 121

3-(2-(6-(2,5-Dimethyl-1H-pyrrol-1-yl)-4-methylpyridin-2-yl)ethyl)benzaldehyde (21). The title compound (615 mg, 78%) was prepared according to a similar procedures described in the synthesis of 17 using DIBAL (1M, 7.5 mL, 7.5 mmol) and 20 (780 mg, 2.48 mmol). Pale yellow oil; $^1$H NMR (500 MHz, CDCl$_3$) δ 10.00 (s, 1H), 7.79-7.69 (m, 2H), 7.52-7.42 (m, 2H), 6.94 (s, 1H), 6.90 (s, 1H), 5.92 (s, 2H), 3.19 (ddd, J=8.4, 5.9, 2.1 Hz, 2H), 3.14 (ddd, J=8.9, 6.0, 2.1 Hz, 2H), 2.39 (s, 3H), 2.14 (s, 6H); $^{13}$C NMR (126 MHz, CDCl$_3$) δ 192.52, 160.27, 151.71, 149.62, 142.62, 136.56, 134.81, 129.50, 129.07, 128.46, 127.79, 122.68, 120.28, 106.73, 39.34, 35.33, 21.01, 13.27.

Example 122

2-(2,5-Dimethyl-1H-pyrrol-1-yl)-4-methyl-6-(3-(2-nitrovinyl)phenethyl)pyridine (22). Compound 21 (600 mg, 1.88 mmol), nitromethane (0.151 mL, 2.83 mmol), and triethylamine (0.524 mL, 3.76 mmol) were dissolved in dichloromethane and stirred at room temp for 2 h. After the solvent was removed under reduced pressure, the organic residue was redissolved in dichloromethane and then mixed with acetyl chloride (0.134 mL, 3.76 mmol) and triethylamine (0.655 mL, 4.7 mmol). After being stirred at room temp for 1 h, the mixture was concentrated in vacuo and purified by column chromatography to give the title compound (577 mg, 85%) as a yellow solid. $^1$H NMR (500 MHz, CDCl$_3$) δ 8.00 (d, J=13.7 Hz, 1H), 7.58 (d, J=13.6 Hz, 1H), 7.45-7.34 (m, 4H), 6.97 (s, 1H), 6.91 (s, 1H), 5.92 (s, 2H), 3.14 (h, J=3.0 Hz, 4H), 2.41 (s, 3H), 2.15 (s, 6H); $^{13}$C NMR (126 MHz, CDCl$_3$) δ 151.74, 149.66, 142.97, 139.23, 137.00, 132.50, 130.11, 129.45, 129.28, 128.47, 128.44, 126.97, 122.67, 120.31, 120.07, 106.79, 106.63, 39.36, 35.36, 21.03, 13.28, 13.25; MS (ESI) m/z 362.45 [M+H]$^+$.

Example 123

2-(2,5-Dimethyl-1H-pyrrol-1-yl)-6-(3-(1-(6-(2,5-dimethyl-1H-pyrrol-1-yl)-4-methylpyridin-2-yl)-3-nitropropan-2-yl)phenethyl)-4-methylpyridine (23). The title compound (531 mg, 61%) was prepared according to a similar procedures described in the synthesis of 19a-b using n-BuLi (1.6 M, 1.21 mL, 1.94 mmol), 9 (387 mg, 1.94 mmol), and 22 (560 mg, 1.55 mmol). Yellow oil; $^1$H NMR (500 MHz, CDCl$_3$) δ 7.21 (t, J=7.84 Hz, 1H), 7.09-7.02 (m, 3H), 6.90 (s, 1H), 6.89 (s, 1H), 6.88 (s, 2H), 5.92 (s, 4H), 4.74-4.57 (m, 2H), 4.12-4.02 (m, 1H), 3.15 (d, J=7.69 Hz, 2H), 3.04 (s, 4H), 2.38 (s, 3H), 2.37 (s, 3H), 2.16 (s, 6H), 2.11 (s, 6H); $^{13}$C NMR (126 MHz, CDCl$_3$) δ 160.60, 157.76, 151.80, 151.57, 149.94, 149.68, 142.17, 139.19, 128.90, 128.53, 128.47, 127.89, 127.66, 125.05, 123.37, 122.71, 120.84, 120.15, 106.83, 106.71, 79.79, 44.04, 41.34, 39.62, 35.77, 21.00, 20.99, 13.28, 13.24; MS (ESI) m/z 562.29 [M+H]$^+$.

Example 124

3-(6-(2,5-Dimethyl-1H-pyrrol-1-yl)-4-methylpyridin-2-yl)-2-(3-(2-(6-(2,5-dimethyl-1H-pyrrol-1-yl)-4-methylpyridin-2-yl)ethyl)phenyl)propan-1-amine (24). A solution of 23 (500 mg, 0.89 mmol) in EtOH (5 mL) and MeOH (5 mL) was stirred with Raney-Ni (50% in water, 0.4 mL) for 1 h at ambient temperature under a hydrogen atmosphere. The reaction mixture was filtered through Celite and concentrated in vacuo to yield the title compound (475 mg, 99%). $^1$H NMR (500 MHz, CDCl$_3$) δ 7.22 (t, J=7.9 Hz, 1H), 7.08-7.01 (m, 3H), 6.93 (s, 1H), 6.89 (s, 1H), 6.83 (ss, 2H), 5.91 (s, 2H), 5.90 (s, 2H), 3.21 (td, J=7.9, 5.0 Hz, 1H), 3.13 (dd, J=13.5, 7.4 Hz, 1H), 3.07-2.98 (m, 5H), 2.92 (qd, J=12.9, 6.9 Hz, 2H), 2.39 (s, 3H), 2.33 (s, 3H), 2.15 (s, 6H), 2.10 (s, 6H). 13C NMR (126 MHz, CDCl3) δ 160.93, 159.89, 151.63, 151.49, 149.51, 149.32, 142.58, 141.77, 128.60, 128.47, 128.43, 128.18, 126.78, 125.66, 123.35, 122.56, 120.20, 120.07, 106.71, 106.58, 49.54, 47.14, 42.21, 39.83, 35.94, 21.01, 20.96, 13.28, 13.20; MS (ESI) m/z 532.27 [M+H]$^+$.

Example 125

2-Bromo-6-(2-nitrovinyl)pyridine (26a). The title compound (295 mg, 65%) was prepared according to a similar procedure described in the synthesis of 22 using MeNO$_2$ (0.160 mL, 3.0 mmol) and 25a (372 mg, 2.0 mmol). Yellow solid; $^1$H NMR (500 MHz, CDCl$_3$) δ 8.05 (d, J=13.07 Hz, 1H), 7.85 (d, J=13.10 Hz, 1H), 7.67 (t, J=7.71 Hz, 1H), 7.59 (dd, J=0.92, 7.98 Hz, 1H), 7.45 (dd, J=0.88, 7.45 Hz, 1H); $^{13}$C NMR (126 MHz, CDCl$_3$) δ 150.37, 143.04, 141.72, 139.27, 135.26, 130.34, 125.09; MS (ESI) m/z 455.77 [2M+H]$^+$.

Example 126

3-Bromo-5-(2-nitrovinyl)pyridine (26b). The title compound (390 mg, 86%) was prepared according to a similar procedure described in the synthesis of 22 using MeNO$_2$ (0.160 mL, 3.0 mmol) and 25b (372 mg, 2.0 mmol). Yellow solid; $^1$H NMR (500 MHz, CDCl$_3$) δ 8.80 (d, J=2.2 Hz, 1H), 8.74 (t, J=2.7 Hz, 1H), 8.05 (t, J=2.1 Hz, 1H), 7.97 (d, J=13.8 Hz, 1H), 7.64 (d, J=13.8 Hz, 1H); $^{13}$C NMR (126 MHz, CDCl$_3$) δ 153.48, 148.10, 139.35, 137.53, 133.83, 128.15, 121.42; MS (ESI) m/z 455.98 [2M+H]$^+$.

Example 127

2-(2-(6-Bromopyridin-2-yl)-3-nitropropyl)-6-(2,5-dimethyl-1H-pyrrol-1-yl)-4-methylpyridine (27a). The title compound (329 mg, 60%) was prepared according to a similar procedure described in the synthesis of 19a-b using n-BuLi (1.6 M, 1.00 mL, 1.60 mmol), 9 (320 mg, 1.60 mmol), and 26a (290 mg, 1.28 mmol). Pale brown oil; $^1$H NMR (500 MHz, CDCl$_3$) δ 7.43 (t, J=7.67 Hz, 1H), 7.36 (d, J=7.92 Hz, 1H), 7.10 (d, J=7.40 Hz, 1H), 6.90 (s, 1H), 6.88 (s, 1H), 5.93 (s, 2H), 5.04 (dd, J=9.68, 13.55 Hz, 1H), 4.66 (dd, J=4.52, 13.58 Hz, 1H), 4.35-4.24 (m, 1H), 3.24 (dd, J=7.27, 14.09 Hz, 1H), 3.19-3.07 (m, 1H), 2.38 (s, 3H), 2.13 (s, 6H); $^{13}$C NMR (126 MHz, CDCl$_3$) δ 160.51, 157.17, 151.93, 150.09, 142.07, 138.94, 128.43, 126.95, 123.59, 122.75, 120.94, 106.91, 106.84, 77.55, 44.24, 40.14, 21.00, 13.27; MS (ESI) m/z 450.96 [M+Na]$^+$.

Example 128

2-(2-(5-Bromopyridin-3-yl)-3-nitropropyl)-6-(2,5-dimethyl-1H-pyrrol-1-yl)-4-methylpyridine (27b). The title compound (375 mg, 51%) was prepared according to a similar procedure described in the synthesis of 19a-b using n-BuLi (1.6 M, 1.34 mL, 2.15 mmol), 9 (430 mg, 2.15 mmol), and 26b (390 mg, 1.72 mmol). $^1$H NMR (500 MHz, CDCl$_3$) δ 8.59 (s, 1H), 8.42 (s, 1H), 6.92 (ss, 2H), 5.93 (s, 2H), 4.79 (dd, J=13.1, 5.6 Hz, 1H), 4.70 (dd, J=13.1, 9.2 Hz, 1H), 4.22 (dtd, J=9.3, 7.6, 5.5 Hz, 1H), 3.23 (dd, J=14.2, 7.7 Hz, 1H), 3.16 (dd, J=14.2, 7.6 Hz, 1H), 2.39 (s, 3H), 2.10 (s, 6H); $^{13}$C NMR (126 MHz, CDCl$_3$) δ 156.39, 152.04, 150.42, 150.35, 147.36, 137.72, 136.59, 128.44, 123.47, 121.32, 120.94, 106.98, 78.82, 40.86, 40.55, 21.02, 13.25; MS (ESI) m/z 450.98 [M+Na]$^+$.

Example 129

2-(2,5-Dimethyl-1H-pyrrol-1-yl)-6-((6-(1-(6-(2,5-dimethyl-1H-pyrrol-1-yl)-4-methylpyridin-2-yl)-3-nitropropan-2-yl)pyridin-2-yl)ethynyl)-4-methylpyridine (29a). The reaction mixture of 27a (300 mg, 0.70 mmol), Pd(PPh$_3$)$_2$Cl$_2$ (23 mg, 0.035 mmol), CuI (6 mg, 0.035 mmol), PPh$_3$ (37 mg, 0.14 mmol), 28 (167 mg, 0.80 mmol), diethylamine (1.5 mL), and DMF (1.5 mL) were heated at 120° C. for 20 min in the microwave cavity. Then the reaction mixture was treated with diethyl ether (20 mL), filtered, and concentrated in vacuo. The residue was purified by flash chromatography (EtOAc/hexanes) to give the title compound (306 mg, 78%) as a pale yellow oil. $^1$H NMR (500 MHz, CDCl$_3$) δ 7.58 (t, J=7.77 Hz, 1H), 7.53 (s, 1H), 7.47 (dd, J=1.03, 7.76 Hz, 1H), 7.11 (d, J=7.74 Hz, 1H), 7.08 (s, 1H), 6.90 (s, 1H), 6.85 (s, 1H), 5.93 (s, 2H), 5.91 (s, 2H), 5.16 (dd, J=9.67, 13.66 Hz, 1H), 4.70 (dd, J=4.66, 13.62 Hz, 1H), 4.33 (m, 1H), 3.26 (dd, J=7.45, 14.02 Hz, 1H), 3.19 (dd, J=7.75, 14.02 Hz, 1H), 2.49 (s, 3H), 2.36 (s, 3H), 2.18 (s, 6H), 2.13 (s, 6H); $^{13}$C NMR (126 MHz, CDCl$_3$) δ 159.78, 157.45, 152.39, 151.91, 150.01, 142.40, 141.88, 136.77, 128.57, 128.45, 127.37, 126.61, 123.82, 123.57, 123.00, 120.87, 106.95, 106.87, 88.03, 87.44, 44.65, 40.38, 20.98, 20.96, 13.28, 13.22; MS (ESI) m/z 559.24 [M+H]$^+$.

Example 130

2-(2,5-Dimethyl-1H-pyrrol-1-yl)-6-((5-(1-(6-(2,5-dimethyl-1H-pyrrol-1-yl)-4-methylpyridin-2-yl)-3-nitropropan-2-yl)pyridin-3-yl)ethynyl)-4-methylpyridine (29b). The title compound (355 mg, 74%) was prepared using the same procedure described in the synthesis of 29a from 27b (370 mg, 0.86 mmol) and 28 (207 mg, 0.98 mmol). $^1$H NMR (500 MHz, CDCl$_3$) δ 8.71 (s, 1H), 8.45 (s, 1H), 7.43 (s, 1H), 7.07 (s, 1H), 6.91 (ss, 2H), 5.92 (ss, 4H), 4.80 (dd, J=13.0, 5.6 Hz, 1H), 4.71 (dd, J=13.0, 9.2 Hz, 1H), 4.25 (m, 1H), 3.25 (dd, J=14.2, 7.6 Hz, 2H), 3.16 (dd, J=14.2, 7.7 Hz, 1H), 2.49 (s, 3H), 2.38 (s, 3H), 2.17 (s, 6H), 2.10 (s, 6H); $^{13}$C NMR (126 MHz, CDCl$_3$) δ 156.52, 152.43, 152.01, 151.80, 150.37, 150.09, 148.99, 141.78, 137.74, 134.50, 128.55, 128.46, 126.97, 123.47, 122.94, 121.27, 107.01, 106.93, 91.87, 85.09, 78.96, 40.96, 40.56, 21.02, 20.98, 14.23, 13.25, 13.22; MS (ESI) m/z 559.17 [M+H]$^+$.

Example 131

3-(6-(2,5-Dimethyl-1H-pyrrol-1-yl)-4-methylpyridin-2-yl)-2-(6-(2-(6-(2,5-dimethyl-1H-pyrrol-1-yl)-4-methylpyridin-2-yl)ethyl)pyridin-2-yl)propan-1-amine (30a). A solution of 29a (300 mg, 0.54 mmol) in EtOH (5 mL) and MeOH (5 mL) was stirred with Raney-Ni (50% in water, 0.5 mL) for 7 h at ambient temperature under a hydrogen atmosphere. The reaction mixture was filtered through a PTFE membrane filter (diam. 25 mm, pore size 0.2 μm) and concentrated in vacuo to give the crude title compound (300 mg). $^1$H NMR (500 MHz, MeOD) δ 7.50 (t, J=7.7 Hz, 1H), 7.14 (s, 1H), 7.02 (d, J=7.4 Hz, 1H), 6.99 (s, 1H), 6.97 (s, 1H), 6.95 (d, J=7.5 Hz, 1H), 6.92 (s, 1H), 5.82 (s, 3H), 5.81 (s, 2H), 3.60-3.43 (m, 1H), 3.37 (s, 2H), 3.27-3.14 (m, 7H), 3.07 (dd, J=12.9, 8.0 Hz, 1H), 2.93 (dd, J=12.9, 5.4 Hz, 1H), 2.40 (s, 3H), 2.31 (s, 3H), 2.05 (s, 7H), 2.00 (s, 6H); $^{13}$C NMR (126 MHz, MeOD) δ 162.44, 162.33, 161.77, 161.33, 152.85, 152.74, 152.53, 152.24, 138.13, 129.41, 129.39, 125.28, 124.53, 122.59, 122.34, 122.17, 122.12, 107.65, 107.57, 46.94, 41.38, 38.69, 38.12, 25.32, 20.97, 20.87, 13.25, 13.21; MS (ESI) m/z 533.19 [M+H]$^+$.

Example 132

3-(6-(2,5-Dimethyl-1H-pyrrol-1-yl)-4-methylpyridin-2-yl)-2-(6-(2-(6-(2,5-dimethyl-1H-pyrrol-1-yl)-4-methylpyridin-2-yl)ethyl)pyridin-2-yl)propan-1-amine (30b). The crude title compound (330 mg) was prepared using the same procedure described in the synthesis of 30a from 27b (350 mg, 0.63 mmol). $^1$H NMR (500 MHz, CD$_3$Cl) δ 8.26 (s, 1H), 8.17 (s, 1H), 7.62 (s, 1H), 7.03 (s, 1H), 6.89 (s, 1H), 6.88 (s, 1H), 6.79 (s, 1H), 5.87 (s, 2H), 5.80 (s, 2H), 3.80-3.71 (m, 1H), 3.54-3.44 (m, 1H), 3.24-3.14 (m, 1H), 3.10-2.95 (m, 4H), 2.96-2.77 (m, 2H), 2.39 (s, 3H), 2.27 (s, 3H), 2.09 (s, 6H), 1.99 (s, 6H); $^{13}$C NMR (126 MHz, CDCl$_3$) δ 160.26, 157.89, 151.45, 151.31, 150.51, 150.27, 148.37, 147.03, 137.22, 136.23, 134.99, 128.55, 128.53, 124.19, 122.87, 121.01, 120.55, 106.91, 106.74, 44.00, 41.31, 40.72, 38.72, 32.72, 21.06, 20.96, 13.21, 13.11; MS (ESI) m/z 533.30 [M+H]$^+$.

Example 133

N-Boc-3-(6-(2,5-Dimethyl-1H-pyrrol-1-yl)-4-methylpyridin-2-yl)-2-(6-(2-(6-(2,5-dimethyl-1H-pyrrol-1-yl)-4-methylpyridin-2-yl)ethyl)pyridin-2-yl)propan-1-amine (30c). To a portion of the crude product of 30b (~0.27 mmol, 150 mg) in 10 mL of dichloromethane was added Boc$_2$O (109 mg, 0.5 mmol) and triethylamine (70 μL, 0.5 mmol), and stirred for 12 h. The reaction mixture was concentrated in vacuo and then purified by flash chromatography (EtOAc/hexanes) to give the title compound (110 mg, 62%) as a colorless oil. The chiral resolution of racemic 30c was performed using an OD-H chiral column with an auto-collector equipped HPLC system; 30c (100 mg) was dissolved in 2 mL of EtOH, and then 0.1 mL of the solution per time was injected until the parent solution was all consumed. The separated enantiomers were collected and concentrated in vacuo to give 30c-1 (43 mg, R$_t$=16.1 min, ee=98%) and 30c-2 (32 mg, R$_t$=23.1 min, ee=97%). $^1$H NMR (500 MHz, CDCl$_3$) δ 8.27 (s, 1H), 8.22 (s, 1H), 7.42 (s, 1H), 6.93 (s, 1H), 6.90 (s, 1H), 6.84 (s, 2H), 5.91 (s, 2H), 5.89 (s, 2H), 4.64 (d, J=6.7 Hz, 1H), 3.55-3.37 (m, 3H), 3.35-3.24 (m, 1H), 3.24-3.14 (m, 1H), 3.06-2.93 (m, 3H), 2.39 (s, 3H), 2.33 (s, 3H), 2.15 (s, 6H), 2.07 (s, 6H), 1.40 (s, 9H); $^{13}$C NMR (126 MHz, CDCl$_3$) δ 160.02, 158.72, 155.74, 151.75, 151.64, 149.74, 149.69, 148.28, 147.32, 137.04, 136.73, 135.32, 128.42, 123.41, 122.64, 120.54, 120.33, 106.79, 106.67, 79.38, 45.18, 43.46, 41.36, 39.13, 32.69, 28.35, 21.02, 20.98, 13.30, 13.21; MS (ESI) m/z 654.56 [M+Na]$^+$.

We claim:
1. A compound of a formula

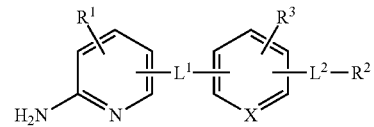

wherein R$^1$ is selected from H, alkyl and amino moieties; L$^1$ is a divalent linker moiety selected from a covalent bond, alkylene and substituted alkylene moieties, said alkylene substituents selected from hydroxy, amino, aminoalkyl, aza (—NH—), alkyl (R) substituted aza (—NR—) and amino substituents and combinations thereof; R$^3$ is selected from H, alkyl, halo, haloalkyl, cyano and amino moieties and combinations thereof; X is selected from CH, CR$^3$ and N; L$^2$ is an alkylamino moiety or a cycloalkylamino moiety; and R$^2$ is selected from amino, substituted amino and optionally-substituted cycloalkyl, heterocycloalkyl, aryl and heteroaryl moieties, said substituents selected from amino, halo, alkyl, cycloalkyl and heterocycloalkyl substituents and divalent alkylene and heteroatom-substituted alkylene substituents, or a salt thereof.

2. The compound of claim 1 of a formula

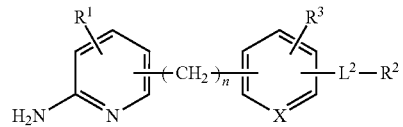

wherein n is 1-3.

3. The compound of claim 2 wherein n is 2, L$^2$ is selected from —NH(CH$_2$)$_m$— and —N(R)(CH$_2$)$_m$— moieties, where m is 0-4; R is selected from alkyl and cycloalkyl moieties; and R$_2$ is selected from amine, alkyl- and cycloalkyl-substituted amine moieties and optionally-substituted aryl and heteroaryl moieties.

4. The compound of claim 1 of a formula

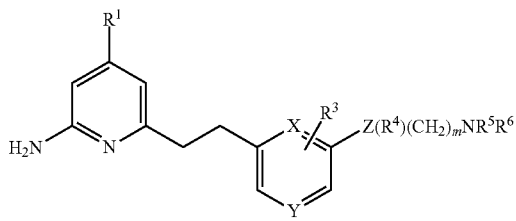

wherein R¹ is selected from H and methyl moieties; X and Y are independently selected from CH, CR³ and N, providing both X and Y are not N; Z is selected from N and NH; m is an integer selected from 0-3; and R⁴ is selected from H, alkyl, cycloalkyl and divalent alkylene moieties; and R⁵ and R⁶ are independently selected from H, alkyl, cycloalkyl, optionally substituted aryl and heteroaryl moieties and divalent alkylene moieties, providing where m is 0, R⁶ is selected from H and alkyl and R⁴ and R⁵ are independently selected from divalent alkylene moieties to provide together with NR⁶ and Z, respectively, a heterocycloalkyl moiety.

5. The compound of claim 4 wherein Z is selected from N and NH; m is 0; and R⁴ and R⁵ are independently divalent alkylene moieties to provide a said heterocycloalkyl moiety.

6. The compound of claim 5 wherein Z is N and said heterocycloalkyl moiety is a piperazinyl moiety.

7. The compound of claim 5 wherein Z is NH and said heterocycloalkyl moiety is a piperidinyl moiety.

8. The compound of claim 4 wherein one of X and Y is N; R³ is H; Z is N; R⁴ is selected from H, alkyl and cycloalkyl; m is 2-3; R⁵ and R⁶ are independently selected from H, alkyl and cycloalkyl moieties.

9. The compound of claim 4 wherein X is CH and Y is CR³, where R³ is selected from fluoro, trifluoromethyl and cyano substituents; R⁴ is selected from H and alkyl; m is 2-3; R⁵ and R⁶ are independently selected from H, alkyl and cycloalkyl moieties.

10. The compound of claim 3 wherein n is 2; L² is —NH(CH₂)ₘ—, where m is selected from 1 and 2; and R² is selected from pyridinyl and substituted phenyl moieties.

11. A compound of a formula

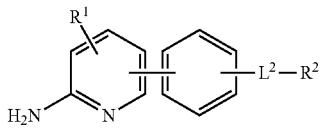

wherein R¹ is selected from H, alkyl and amino moieties; R³ is H; L² is an alkylamino moiety or a cycloalkylamino moiety; and R² is selected from amino, substituted amino and optionally-substituted cycloalkyl, heterocycloalkyl, aryl and heteroaryl moieties, said substituents selected from amino, halo, alkyl, cycloalkyl and heterocycloalkyl substituents and divalent alkylene and heteroatom-substituted alkylene substituents, or a salt thereof.

12. The compound of claim 11 of a formula

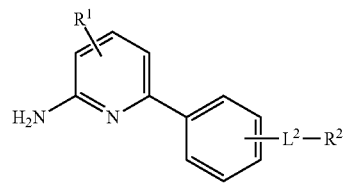

wherein L² is an aza-substituted alkylene moiety, said substituent selected from —NH— and —NR— where R is alkyl; and R² is selected from halo-substituted phenyl and alkyl-substituted amino moieties.

13. The compound of claim 12 wherein said aza-substituted alkylene moiety is selected from CH₂NH(CH₂)₂—, CH₂N(CH₃)(CH₂)₂—, —CH₂NH(CH₂)₃—, —CH₂NHCH₂— and N(CH₃)(CH₂)₂— moieties.

14. The compound of claim 1 wherein L¹ is selected from alkylene moieties; X is N; L² is an aza-substituted alkylene moiety; and R² is selected from alkyl-substituted amino moieties.

15. The compound of claim 14 wherein said aza-substituted alkylene moiety is selected from —CH₂NH(CH₂)₂—, CH₂N(CH₃)(CH₂)₂—, —CH₂NH(CH₂)₃—, CH₂N(CH₃)(CH₂)₃—, —CH₂NHCH₂— and N(CH₃)(CH₂)₂— moieties.

16. A compound of a formula

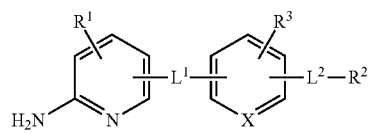

wherein R¹ is selected from H, alkyl and amino moieties; L¹ is a divalent linker moiety selected from substituted alkylene moieties, said alkylene substituents selected from amino and aminoalkyl substituents; R³ is selected from H, alkyl, halo, haloalkyl, cyano and amino moieties and combinations thereof; X is selected from CH, CR³ and N; L² is an alkylamino moiety or a cycloalkylamino moiety; and R² is selected from amino, substituted amino and optionally-substituted cycloalkyl, heterocycloalkyl, aryl and heteroaryl moieties, said substituents selected from amino, halo, alkyl, cycloalkyl and heterocycloalkyl substituents and divalent alkylene and heteroatom-substituted alkylene substituents, or a salt thereof.

* * * * *